US006548788B2

(12) United States Patent
Kellogg et al.

(10) Patent No.: US 6,548,788 B2
(45) Date of Patent: Apr. 15, 2003

(54) DEVICES AND METHODS FOR USING CENTRIPETAL ACCELERATION TO DRIVE FLUID MOVEMENT IN A MICROFLUIDICS SYSTEM

(75) Inventors: Gregory Kellogg, Somerville, MA (US); Stephen G. Kieffer-Higgins, Dorchester, MA (US); Bruce L. Carvalho, Watertown, MA (US); Gene A. Davis, Lexington, MA (US); John P. Willis, Shirley Center, MA (US); Ted Minior, Bedford, MA (US); Laura L. Chapman, Somerville, MA (US); Mikayla Kob, Allston, MA (US); Sarah D. Oeltjen, Somerville, MA (US); Shari Ommert, Medford, MA (US); Alec Mian, Cambridge, MA (US)

(73) Assignee: Tecan Trading AG, Baar (CH)

( * ) Notice: Subject to any disclaimer, the term of this patent is extended or adjusted under 35 U.S.C. 154(b) by 28 days.

(21) Appl. No.: 09/981,007

(22) Filed: Oct. 16, 2001

(65) Prior Publication Data

US 2002/0027133 A1 Mar. 7, 2002

Related U.S. Application Data

(62) Division of application No. 09/526,496, filed on Mar. 15, 2000, now Pat. No. 6,302,134, which is a division of application No. 09/083,678, filed on May 22, 1998, now Pat. No. 6,063,589.
(60) Provisional application No. 60/047,488, filed on May 23, 1997.

(51) Int. Cl.[7] .............................. H05B 3/16; C12M 1/00
(52) U.S. Cl. ................. 219/543; 435/283.1; 435/286.4; 435/285.2; 435/287.1
(58) Field of Search ....................... 219/543; 435/283.1, 435/286.4, 285.2, 287.1

(56) References Cited

U.S. PATENT DOCUMENTS 3,528,449 A    9/1970  Witte et al.

(List continued on next page.)

FOREIGN PATENT DOCUMENTS

DE    4410224    9/1995
EP    322657     7/1989

(List continued on next page.)

OTHER PUBLICATIONS

Anderson, (1968), *Anal. Biochem.*, 28: 545–562.
Renoe et al., (1974), Clin. Chem., 20/8: 955–960.
Burtis et al., (1974), Clin. Chem., 20: 932–941.
Fritsche et al., (1975), Clin Biochem., 8: 240–246.
Burtis et al., (1975), Clin. Chem., 21/9: 1225–1233.
Hadjiioannou et al., (1976), Clin. Chem., 22/6: 802–805.
Lee et al., (1978), Clin. Chem., 24/8: 1361–1365.
Cho et al., (1982), Clin. Chem., 28/9: 1961–1965.

(List continued on next page.)

*Primary Examiner*—Teresa Walberg
*Assistant Examiner*—Vinod D. Patel
(74) *Attorney, Agent, or Firm*—McDonnell Boehnen Hulbert & Berghoff

(57) ABSTRACT

This system provides methods and apparatus for performing microanalytic and microsynthetic analyses and procedures. Specifically, the system provides a microsystem platform for use with a micromanipulation device to manipulate the platform by rotation, thereby utilizing the centripetal force resulting from rotation of the platform to motivate fluid movement through microchannels embedded in the microplatform. The microsystem platforms of the system are also provided having microfluidics components, resistive heating elements, temperature sensing elements, mixing structures, capillary and sacrificial valves, and methods for using these microsystems platforms for performing biological, enzymatic, immunological and chemical assays. An electronic spindle designed rotor capable of transferring electrical signals to and from the microsystem platforms of the system is also provided.

8 Claims, 111 Drawing Sheets

U.S. PATENT DOCUMENTS

| | | |
|---|---|---|
| 3,679,367 A | 7/1972 | Negersmith et al. |
| 3,713,062 A | 1/1973 | Butler et al. |
| 3,952,116 A | 4/1976 | Trenkler et al. |
| 4,030,834 A | 6/1977 | Bauer et al. |
| 4,154,793 A | 5/1979 | Guigan |
| 4,258,740 A | 3/1981 | Kaartinen et al. |
| 4,279,862 A | 7/1981 | Bertaudiere |
| 4,381,291 A | 4/1983 | Ekins |
| 4,515,889 A | 5/1985 | Klose |
| 4,612,959 A | 9/1986 | Costello et al. |
| 4,676,952 A | 6/1987 | Edelmann |
| 4,722,853 A | 2/1988 | Batliwalla et al. |
| 4,729,862 A | 3/1988 | Salatiello et al. |
| 4,745,072 A | 5/1988 | Ekins |
| 4,872,821 A | 10/1989 | Weiss |
| 4,940,527 A | 7/1990 | Kazlauskas et al. |
| 5,006,749 A | 4/1991 | White |
| 5,061,381 A | 10/1991 | Burd |
| 5,122,284 A | 6/1992 | Braynin et al. |
| 5,160,702 A | 11/1992 | Kopf-Sill et al. |
| 5,171,533 A | 12/1992 | Fine et al. |
| 5,171,695 A | 12/1992 | Ekins |
| 5,173,193 A | 12/1992 | Schembri |
| 5,173,262 A | 12/1992 | Burtis et al. |
| 5,186,844 A | 2/1993 | Burd et al. |
| 5,242,606 A | 9/1993 | Braynin et al. |
| 5,242,803 A | 9/1993 | Burtis et al. |
| 5,252,294 A | 10/1993 | Kroy et al. |
| 5,275,016 A | 1/1994 | Chatterjee et al. |
| 5,304,348 A | 4/1994 | Burd et al. |
| 5,304,487 A | 4/1994 | Wilding et al. |
| 5,336,181 A | 8/1994 | Nakao |
| 5,368,704 A | 11/1994 | Madou et al. |
| 5,403,415 A | 4/1995 | Schembri |
| 5,409,665 A | 4/1995 | Burd |
| 5,413,009 A | 5/1995 | Ekins |
| 5,413,732 A | 5/1995 | Buhl et al. |
| 5,426,032 A | 6/1995 | Phillips et al. |
| 5,431,303 A | 7/1995 | Miskell |
| 5,432,009 A | 7/1995 | Tabata et al. |
| 5,457,053 A | 10/1995 | Burd et al. |
| 5,472,603 A | 12/1995 | Schembri |
| 5,478,750 A | 12/1995 | Bernstein et al. |
| 5,496,520 A | 3/1996 | Kelton et al. |
| 5,518,930 A | 5/1996 | Burd |
| 5,590,052 A | 12/1996 | Kopf-Sill et al. |
| 5,591,643 A | 1/1997 | Schembri |
| 5,599,411 A | 2/1997 | Schembri |
| 5,622,819 A | 4/1997 | Herman |
| 5,624,597 A | 4/1997 | Buhl et al. |
| 5,639,428 A | 6/1997 | Cottingham |
| 5,693,233 A | 12/1997 | Schembri |
| 5,821,116 A | 10/1998 | Herman |
| 6,063,589 A | 5/2000 | Kelogg |
| 6,302,134 B1 | 10/2001 | Kellogg |
| 6,399,361 B2 * | 6/2002 | Brotherston et al. ..... 435/283.1 |

FOREIGN PATENT DOCUMENTS

| | | |
|---|---|---|
| EP | 0 408 207 A2 | 6/1990 |
| EP | 417305 | 3/1991 |
| EP | 305210 | 12/1993 |
| EP | 616218 | 9/1994 |
| EP | 0637367 B1 | 12/1997 |
| FR | 1 292 407 | 3/1962 |
| GB | 1 307 628 | 2/1973 |
| WO | WO 93/22053 | 11/1993 |
| WO | WO 93/22058 | 11/1993 |
| WO | WO 94/26414 | 11/1994 |
| WO | WO 95/33986 | 12/1995 |
| WO | WO 97/08556 | 3/1997 |
| WO | WO97/21090 | 6/1997 |

OTHER PUBLICATIONS

Bertrand et al., (1982), Clinica Chimica Acta, 119: 275–284.
Schembri et al., (1992), Clin. Chem., 38/9: 1665–1670.
Columbus et al., (1987), Clin. Chem., 33/9: 1531–1537.
Ekins et all., (1992), Ann. Biol. Clin., 50: 337–353.
Wilding et al., (1994), Clin. Chem., 40/1: 43–47.
Ikada, (1994), Biomaterials, 15/10: 725–736.
Nakagawa et al., (Apr. 1990), Proc. IEEE Workshop of Micro Electro Mechanical Systems, pp. 89.
Glass et al., (Jun. 1987), Appl. Optics, 26/11: 2181–2187.
Haab et al., (1995), Anal. Chem., 67: 3253–3260.
Rosenzweig et al., (1994), Anal. Chem., 66: 1771–1776.
Reijenga et al., (1983), J. Chromatography, 260: 241–254.
Aoki et al., (1990), Anal. Chem. 62: 2206–2210.
Linliu et al., (1994), Rev. Sci. Instrum., 65/12: 3823–3828.
Esashi et al., (Jul. 1992), Proc. Micro. Electro Mechanical Systems, 11: 43–48.
Ballantine et al., (Jun. 1989), Anal. Chem., 6/11: 704–715.
Collison et al., (Apr. 1990), Anal. Chem., 62/7: 425–437.
Lamture et al., (1994), Nucleic Acids Res., 22/11: 2121–2125.
Burtis et al., (1974), Clin. Chem., 20/8: 932–941.
Foucault, (1991), Anal. Chem., 63: page ?.
Poole et al., (Jan. 1994), Anal. Chem. 66/1: 27A–37A.
Shoji & Esashi, (1992), Sensors and Actuators, B8: 205.
Bor Fuh et al., (1995), Biotechnol. Prog., 11: 14–20.
Heineman, (1993), App. Biochem. Biotech., 41: 87–97.
Arquint et al., (Sep. 1994), Clinical Chemistry, vol. 40, No. 9, pp. 1805–1809.
Blackburn et al., (1991), Clin. Chem., 37: 1534–1539.
Cho et al., (1982) Clin. Chem. 38/9:1961–1965.
Huff et al., (1994) 7th International COnference of Solid-State Sensors and Actuators pp. 98–101.
Enclopedia of Polmer Science & Technology, 2nd Edition, 1989, vol. 3, pp. 421–430.

* cited by examiner

DEVICES AND METHODS FOR USING CENTRIPETAL ACCELERATION TO DRIVE FLUID MOVEMENT IN A MICROFLUIDICS SYSTEM This application is a divisional of U.S. Ser. No. 09/526,496, filed Mar. 15, 2000, now U.S. Pat. No. 6,302,134, issued Oct. 16, 2001, which is a divisional of U.S. Ser. No. 09/083,678, filed May 22, 1998, now U.S. Pat. No. 6,063,589, issued May 16, 2000, which claims priority to U.S. Serial No. 60/047,488, filed May 23, 1997.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and chemical processes related to analysis, synthesis and purification. Specifically, the invention provides a microsystem platform and a micromanipulation device to manipulate the platform by rotation, thereby utilizing the centripetal forces resulting from rotation of the platform to motivate fluid movement through microchannels embedded in the microplatform. The microsystem platforms of the invention are also provided having microfluidics components, resistive heating elements, temperature sensing elements, mixing structures, capillary and sacrificial valves, and methods for using these microsystems platforms for performing biological, enzymatic, immunological and chemical assays. A slip ring designed rotor capable of transferring electrical signals to and from the microsystem platforms of the invention is also provided.

2. Summary of the Related Art

In the field of medical, biological and chemical assays, mechanical and automated fluid handling systems and instruments are known in the prior art.

U.S. Pat. No. 4,279,862, issued Jul. 21, 1981 to Bertaudiere et al. disclose a centrifugal photometric analyzer.

U.S. Pat. No. 4,381,291, issued Apr. 26, 1983 to Ekins teach analytic measurement of free ligands.

U.S. Pat. No. 4,515,889, issued May 7, 1985 to Klose et al. teach automated mixing and incubating reagents to perform analytical determinations.

U.S. Pat. No. 4,676,952, issued Jun. 30, 1987 to Edelmann et al. teach a photometric analysis apparatus.

U.S. Pat. No. 4,745,072, issued May 17, 1998 to Ekins discloses immunoassay in biological fluids.

U.S. Pat. No. 5,061,381, issued Oct. 29, 1991 to Burd discloses a centrifugal rotor for performing blood analyses.

U.S. Pat. No. 5,122,284, issued Jun. 16, 1992 to Braynin et al. discloses a centrifugal rotor comprising a plurality of peripheral cuvettes.

U.S. Pat. No. 5,160,702, issued Nov. 3, 1993 to Kopf-Sill and Zuk discloses rotational frequency-dependent "valves" using capillary forces and siphons, dependent on "wettablility" of liquids used to prime said siphon.

U.S. Pat. No. 5,171,695, issued Dec. 15, 1992 to Ekins discloses determination of analyte concentration using two labelling markers.

U.S. Pat. No. 5,173,193, issued Dec. 22, 1992 to Schembri discloses a centrifugal rotor for delivering a metered amount of a fluid to a receiving chamber on the rotor.

U.S. Pat. No. 5,242,803, issued Sep. 7, 1993 to Burtis et al. disclose a rotor assembly for carrying out an assay.

U.S. Pat. No. 5,409,665, issued Apr. 25, 1995 to Burd discloses a cuvette filling in a centrifuge rotor.

U.S. Pat. No. 5,413,009, issued Jul. 11, 1995 to Ekins discloses a method for analyzing analytes in a liquid.

U.S. Pat. No. 5,472,603, issued Dec. 5, 1995 to Schembri discloses an analytical rotor comprising a capillary passage having an exit duct wherein capillary forces prevent fluid flow at a given rotational speed and permit flow at a higher rotational speed.

Anderson, 1968, *Anal. Biochem.* 28: 545–562 teach a multiple cuvette rotor for cell fractionation.

Renoe et al., 1974 *Clin. Chem.* 20: 955–960 teach a "minidisc" module for a centrifugal analyzer.

Burtis et al., 1975, *Clin. Chem.* 20: 932–941 teach a method for a dynamic introduction of liquids into a centrifugal analyzer.

Fritsche et al., 1975, *Clin. Biochem.* 8: 240–246 teach enzymatic analysis of blood sugar levels using a centrifugal analyzer.

Burtis et al., 1975, *Clin Chem.* 21: 1225–1233 teach a multipurpose optical system for use with a centrifugal analyzer.

Hadjiioannou et al., 1976, *Clin. Chem.* 22: 802–805 teach automated enzymatic ethanol determination in biological fluids using a miniature centrifugal analyzer.

Lee et al., 1978, *Clin. Chem.* 24: 1361–1365 teach a automated blood fractionation system.

Cho et al., 1982, *Clin. Chem.* 28: 1956–1961 teach a multichannel electrochemical centrifugal analyzer.

Bertrand et al., 1982, *Clinica Chimica Acta* 119: 275–284 teach automated determination of serum 5'-nucleotidase using a centrifugal analyzer.

Schembri et al., 1992, *Clin Chem.* 38: 1665–1670 teach a portable whole blood analyzer.

Walters et al., 1995, *Basic Medical Laboratory Technologies* 3rd ed., Delmar Publishers: Boston teach a variety of automated medical laboratory analytic techniques.

Recently, microanalytical devices for performing select reaction pathways have been developed.

U.S. Pat. No. 5,006,749, issued Apr. 9, 1991 to White disclose methods apparatus for using ultrasonic energy to move microminiature elements.

U.S. Pat. No. 5,252,294, issued Oct. 12, 1993 to Kroy et al. teach a micromechanical structure for performing certain chemical microanalyses.

U.S. Pat. No. 5,304,487, issued Apr. 19, 1994 to Wilding et al. teach fluid handling on microscale analytical devices.

U.S. Pat. No. 5,368,704, issued Nov. 29, 1994 to Madou et al. teach microelectrochemical valves.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Columbus et al., 1987, *Clin. Chem.* 33: 1531–1537 teach fluid management of biological fluids.

Ekins et al., 1994 *Ann. Biol. Clin.* 50:337–353 teach a multianalytic microspot immunoassay.

Wilding et al., 1994, *Clin. Chem.* 40: 43–47 disclose manipulation of fluids on straight channels micromachined into silicon.

One drawback in the prior art microanalytical methods and apparati has been the difficulty in designing systems for moving fluids on microchips through channels and reservoirs having diameters in the 10–100 μm range. Microfluidic systems require precise and accurate control of fluid flow and valving to control chemical reactions and analyte detection. Conventional pumping and valving mechanisms have been difficult to incorporate into microscale structures due to inherent conflicts-of-scale. These conflicts of scale arise in part due to the fact that molecular interactions arising out of mechanical components of such components, which are negligible in large (macroscopic) scale devices, become very significant for devices built on a microscopic scale.

Systems that use centripetal force to effect fluid movement in microstructures address the need for a pumping mechanism to effect fluid flow, but cannot alone solve these scale-related drawbacks of conventional fluidics reduced to microfluidics scale. There remains a need for a simple, flexible, reliable, rapid and economical microanalytic and microsynthetic reaction platform for performing biological, biochemical and chemical analyses and syntheses that can move fluids within the structural components of a microsystems platform. Such a platform should be able to move nanoliter-to microliter amounts of fluid, including reagents and reactants, at rapid rates to effect the proper mixing of reaction components, removal of reaction side products, and isolation of desired reaction products and intermediates. There remains a need in the art for centripetally-motivated microfluidics platforms capable of precise and accurate control of flow and metering of fluids in both microchip-based and centrifugal microplatform-based technologies.

SUMMARY OF THE INVENTION

This invention provides microsystems platforms as disclosed in co-owned and co-pending U.S. Ser. No. 08/761,063, filed Dec. 5, 1996 and incorporated by reference herein. Specifically, this invention provides microfluidics components, resistive heating elements, temperature sensing elements, mixing structures, capillary and sacrificial valves, and methods for using these microsystems platforms for performing biological, enzymatic, immunological and chemical assays.

It is an advantage of the centrifugal rotors and microsystems platforms of the invention that an imprecise amount of a fluid comprising a biological sample can be applied to the rotor or platform and a precise volumetric amount of the biological sample is delivered to a fluid reservoir comprising a reaction vessel or other component of the rotor of platform for performing chemical, biochemical, immunological or other analyses. It is an advantage of the centrifugal rotors and microsystems platforms of the invention that metering of said precise amount of a biological fluid sample, for example, a drop of blood, is provided as an intrinsic property of the metering capillary channel of the rotor or platform, thereby avoiding variability introduced by centripetal metering of the sample into a reaction reservoir. It is a further advantage of the centrifugal rotors and microsystems platforms of the invention that an operator can avoid having to precisely measure an amount of a fluid comprising a biological sample for application to the rotor or microsystem platform, thereby permitting end-users, including consumers, having a lower level of sophistication to use a medically diagnostic or other embodiment of the rotor or microsystem platform of the invention.

It is an advantage of the centrifugal rotors and microsystems platforms of the invention that fluid movement into and out of fluid reservoirs on the rotor or platform is precisely determined by displacement of a first fluid, such as biological sample, from a fluid reservoir by a second fluid contained in a second reservoir on the rotor or platform. It is also an advantage of the centrifugal rotors and microsystems platforms of the invention that approximately complete replacement of the volumetric capacity of a first reservoir can be achieved by using fluid displacement as disclosed herein, thereby providing for maximum recovery of a first fluid sample upon displacement by a second fluid, or maximum delivery and replacement of the first fluid by the second fluid. This aspect of the invention is advantageous for providing sequential chemical or biochemical reaction steps wherein mixing of the reagents is not desired.

Specific preferred embodiments of the present invention will become evident from the following more detailed description of certain preferred embodiments and the claims.

DETAILED DESCRIPTION OF PREFERRED EMBODIMENTS

Figure 1:
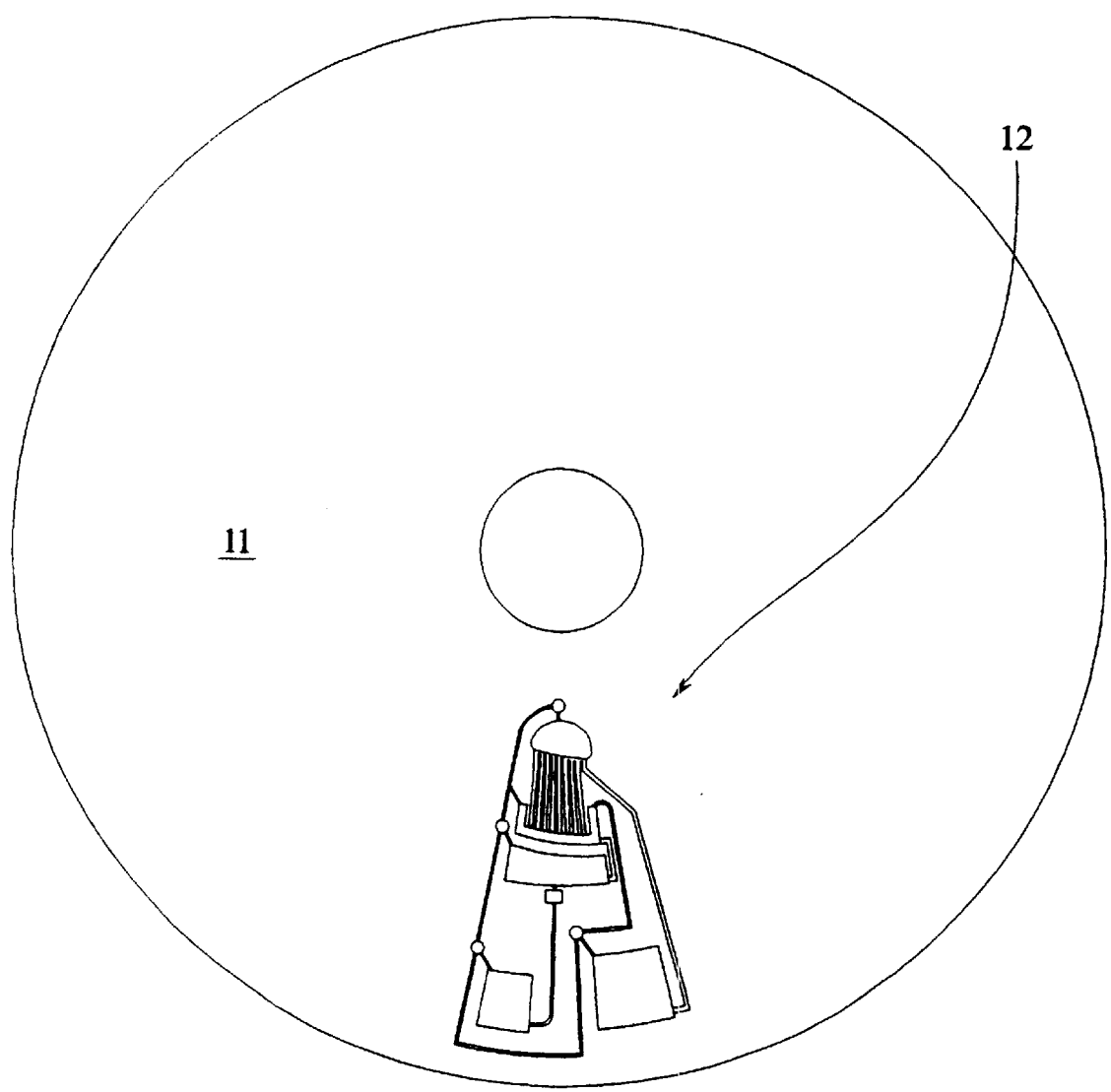
FIGS. 1 through 3 illustrate the microfluidics array of the microsystem platform described in Example 1.

The present invention provides centrifugal rotors and microsystems platforms for providing centripetally-motivated fluid micromanipulation.

For the purposes of this invention, the term "sample" will be understood to encompass any fluid, solution or mixture, either isolated or detected as a constituent of a more complex mixture, or synthesized from precursor species.

For the purposes of this invention, the term "in fluid communication" or "fluidly connected" is intended to define components that are operably interconnected to allow fluid flow between components. In preferred embodiments, the platform comprises a rotatable platform, more preferably a disk, whereby fluid movement on the disk is motivated by centripetal force upon rotation of the disk.

For the purposes of this invention, the term "a centripetally motivated fluid micromanipulation apparatus" is intended to include analytical centrifuges and rotors, microscale centrifugal separation apparati, and most particularly the microsystems platforms and disk handling apparati of International Application No. WO97/21090.

For the purposes of this invention, the term "microsystems platform" is intended to include centripetally-motivated microfluidics arrays as disclosed in International Application No. WO97/21090.

For the purposes of this invention, the terms "capillary", "microcapillary" and "microchannel" will be understood to be interchangeable and to be constructed of either wetting or non-wetting materials where appropriate.

For the purposes of this invention, the term "fluid chamber" will be understood to mean a defined volume on a rotor or microsystems platform of the invention comprising a fluid.

For the purposes of this invention, the term "entry port" will be understood to mean a defined volume on a rotor or microsystems platform of the invention comprising a means for applying a fluid to the rotor or platform.

For the purposes of this invention, the term "capillary junction" will be understood to mean a junction of two components wherein one or both of the lateral dimensions of the junction are larger than the corresponding dimensions the capillary. In wetting or wettable systems, the such junctions are where capillary valving occurs, because fluid flow through the capillaries is stopped at such junctions. In non-wetting or non-wettable junctions, the exit from the chamber or reservoir is where the capillary junction occurs. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

For the purposes of this invention, the term "biological sample" or "biological fluid sample" will be understood to mean any biologically-derived analytical sample, including but not limited to blood, plasma, serum, lymph, saliva, tears, cerebrospinal fluid, urine, sweat, plant and vegetable extracts, semen, and ascites fluid.

For the purposes of this invention, the term "air displacement channels" will be understood to include ports in the surface of the platform that are contiguous with the components (such as chambers and reservoirs) on the platform, and that comprise vents and microchannels that permit displacement of air from components of the platforms and rotors by fluid movement.

For the purposes of this invention, the term "capillary action" will be understood to mean fluid flow in the absence of rotational motion or centripetal force applied to a fluid on a rotor or platform of the invention.

For the purposes of this invention, the term "capillary microvalve" will be understood to mean a capillary comprising a capillary junction whereby fluid flow is impeded and can be motivated by the application of pressure on a fluid, typically by centripetal force created by rotation of the rotor or platform of the invention.

The microplatforms of the invention (preferably and hereinafter collectively referred to as "disks"; for the purposes of this invention, the terms "microplatform", "microsystems platform" and "disk" are considered to be interchangeable), are provided to comprise one or a multiplicity of microsynthetic or microanalytic systems. Such microsynthetic or microanalytic systems in turn comprise combinations of related components as described in further detail herein that are operably interconnected to allow fluid flow between components upon rotation of the disk. These components can be fabricated as described below either integral to the disk or as modules attached to, placed upon, in contact with or embedded in the disk. The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in International Application WO97/21090.

Fluid (including reagents, samples and other liquid components) movement is controlled by centripetal acceleration due to rotation of the platform. The magnitude of centripetal acceleration required for fluid to flow at a rate and under a pressure appropriate for a particular microsystem is determined by factors including but not limited to the effective radius of the platform, the position angle of the structures on the platform with respect to the direction of rotation and the speed of rotation of the platform.

The capillary junctions and microvalves of the invention are based on the use of rotationally-induced fluid pressure to overcome capillary forces. Fluids which completely or partially wet the material of the microchannels (or reservoirs, reaction chambers, detection chambers, etc.) which contain them experience a resistance to flow when moving from a microchannel of narrow cross-section to one of larger cross-section, while those fluids which do not wet these materials resist flowing from microchannels (or reservoirs, reaction chambers, detection chambers, etc.) of large cross-section to those with smaller cross-section. This capillary pressure varies inversely with the sizes of the two microchannels (or reservoirs, reaction chambers, detection chambers, etc., or combinations thereof), the surface tension of the fluid, and the contact angle of the fluid on the material of the microchannels (or reservoirs, reaction chambers, detection chambers, etc.) Generally, the details of the cross-sectional shape are not important, but the dependence on cross-sectional dimension results in microchannels of dimension less than 500 µm exhibit significant capillary pressure. By varying the intersection shapes, materials and cross-sectional areas of the components of the microsystems platform of the invention, "valve" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the microsystem platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate. The theoretical principles underlying the use of capillary junctions and microvalves are disclosed in International Patent Application, Publication No. WO97/21090.

The instant invention provides microsystems platforms comprising microfluidics components, heating elements, temperature sensing elements, capillary valves, sacrificial valves and a rotor design for transmitting electrical signals to and from the microsystems platforms of the invention. The invention provides fluidics components for capillary metering of precise amounts of a volume of a fluid sample from the application of a less precise volume of a fluid sample at an entry port on the microsystem platform. These embodiments of the invention provide for delivery of precise amounts of a sample such as a biological fluid sample without requiring a high degree of precision or accuracy by the operator or end-user in applying the fluid to the platform, and is advantageous in embodiments of the microsystems platforms of the invention that are used by consumers and other relatively unsophisticated users. The invention also provides laminar flow-dependent replacement of a fluid in a first chamber by a second displacement fluid in a second chamber on the platform. These embodiments of the invention provide approximately complete replacement of a fluid in one chamber on the platform with fluid from another, and thereby provide means for practicing sequential chemical reactions and other sequential processes on the platform under conditions wherein mixing of the two fluids is disadvantageous. The invention also provides turbulent flow mixing components, which permit thorough mixing of different fluid components on the platform. In particular, the invention provides mixing chambers fluidly connected with fluid reservoirs containing equal amounts of two or more different fluids or unequal amounts of two or more different fluids. In addition, the invention provides fluid reservoirs fluidly connected with mixing chamber of the invention and shaped to determine the relative rate of flow of each of the different fluids into the mixing chamber. In these embodiments, gradients of two fluids differing in viscosity, solute concentration or concentration of suspended particulates can be produced using the mixing chambers of the invention. Such gradients can be transferred to reservoirs on the platform for further analytical manipulations, and can form the basis for controlled testing of concentration-dependent effects of various catalysts, drugs, toxins or other biological or chemical agents.

Platforms of the invention such as disks and the components comprising such platforms are advantageously provided having a variety of composition and surface coatings appropriate for a particular application. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly (methylmethacrylate) (PMMA), acetonitrile-butadiene-styrene (ABS), polycarbonate, polyethylene, polystyrene, polyolefins, polypropylene and metallocene. These may be used with unmodified or modified surfaces. Surface properties of these materials may be modified for specific applications. Surface modification can be achieved by silanization, ion implantation and chemical treatment with inert-gas plasmas (i.e., gases through which electrical currents are passed to create ionization). Also provided by the invention are platforms made of composites or combinations of these materials, for example, platforms manufactures of a plastic material having embedded therein an optically transparent glass surface comprising for example the detection chamber of the platform. Microplatform disks of the invention are preferably fabricated from thermoplastics such as teflon, polyethylene, polypropylene, methylmethacrylates and polycarbonates, among others, due to their ease of molding, stamping and milling. Alternatively, the disks can be made of silica, glass, quartz or inert metal. A fluid handling system is built by sequential application of one or more of these materials laid down in stepwise fashion onto the thermoplastic substrate. Disks of the invention are fabricated with an injection molded, optically-clear base layer having optical pits in the manner of a conventional compact disk (CD). The disk is a round, polycarbonate disk 120 mm in diameter and 100 pm thick. The optical pits provide means for encoding instrument control programming, user interface information, graphics and sound specific to the application and driver configuration. The driver configuration depends on whether the micromanipulation device is a hand-held, benchtop or floor model, and also on the details of external communication and other specifics of the hardware configuration. This layer is then overlaid with a reflective surface, with appropriate windows for external detectors, specifically optical detectors, being left clear on the disk. Other layers of polycarbonate of varying thickness are laid down on the disk in the form of channels, reservoirs, reaction chambers and other structures, including provisions on the disk for valves and other control elements. These layers can be pre-fabricated and cut with the appropriate geometries for a given application and assembled on the disk. Layers comprising materials other than polycarbonate can also be incorporated into the disk. The composition of the layers on the disk depend in large part on the specific application and the requirements of chemical compatibility with the reagents to be used with the disk. Electrical layers can be incorporated in disks requiring electric circuits, such as electrophoresis applications and electrically-controlled valves. Control devices, such as integrated circuits, laser diodes, photodiodes and resistive networks that can form selective heating areas or flexible logic structures can be incorporated into appropriately wired recesses, either by direct fabrication of modular installation onto the disk. Reagents that can be stored dry can be introduced into appropriate open chambers by spraying into reservoirs using means similar to inkjet printing heads, and then dried on the disk. A top layer comprising access ports and air vents, ports or shafts is then applied. Liquid reagents are then injected into the appropriate reservoirs, followed by application of a protective cover layer comprising a thin plastic film.

The platforms of the invention are preferably provided with a multiplicity of components, either fabricated directly onto the platform, or placed on the platform as prefabricated modules. In addition to the integral components, certain devices and elements can be located external to the platform, optimally positioned on a device of the invention in relation to the platform, or placed in contact with the platform either while rotating or when at rest. Components optimally comprising the platforms of the invention or a controlling device in combination therewith include detection chambers, reservoirs, valving mechanisms, detectors, sensors, temperature control elements, filters, mixing elements, and control systems.

This invention provides microsystems platforms comprising the following components.

1. Microfluidics Components

The platforms of the invention are provided comprising microfluidics handling structures in fluidic contract with one another. In preferred embodiments, fluidic contact is provided by capillary or microchannels comprising the surface of the platforms of the invention. Microchannel sizes are optimally determined by specific applications and by the amount of delivery rates required for each particular embodiment of the platforms and methods of the invention. Microchannel sizes can range from 0.1 m to a value close to the 1 mm thickness of the platform. Microchannel shapes can be trapezoid, circular or other geometric shapes as required. Microchannels preferably are embedded in a platform having a thickness of about 0.1 to 100 mm, wherein the cross-sectional dimension of the microchannels across the thickness dimension of the platform is less than 500 $\mu$m and from 1 to 90 percent of said cross-sectional dimension of the platform. In these embodiments, which is based on the use of rotationally-induced fluid pressure to overcome capillary forces, it is recognized that fluid flow is dependent on the orientation of the surfaces of the components. Fluids which completely or partially wet the material of the microchannels, reservoirs, detection chambers, etc. (i.e., the components) of the platforms of the invention which contain them experience a resistance to flow when moving from a component of narrow cross-section to one of larger cross-section, while those fluids which do not wet these materials resist flowing from components of the platforms of the invention of large cross-section to those with smaller cross-section. This capillary pressure varies inversely with the sizes of the two components, or combinations thereof, the surface tension of the fluid, and the contact angle of the fluid on the material of the components. Generally, the details of the cross-sectional shape are not important, but the dependence on cross-sectional dimension results in microchannels of dimension less than 500 $\mu$m exhibit significant capillary pressure. By varying the intersection shapes, materials and cross-sectional areas of the components of the platform of the invention, "valves" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate.

Figure 2:
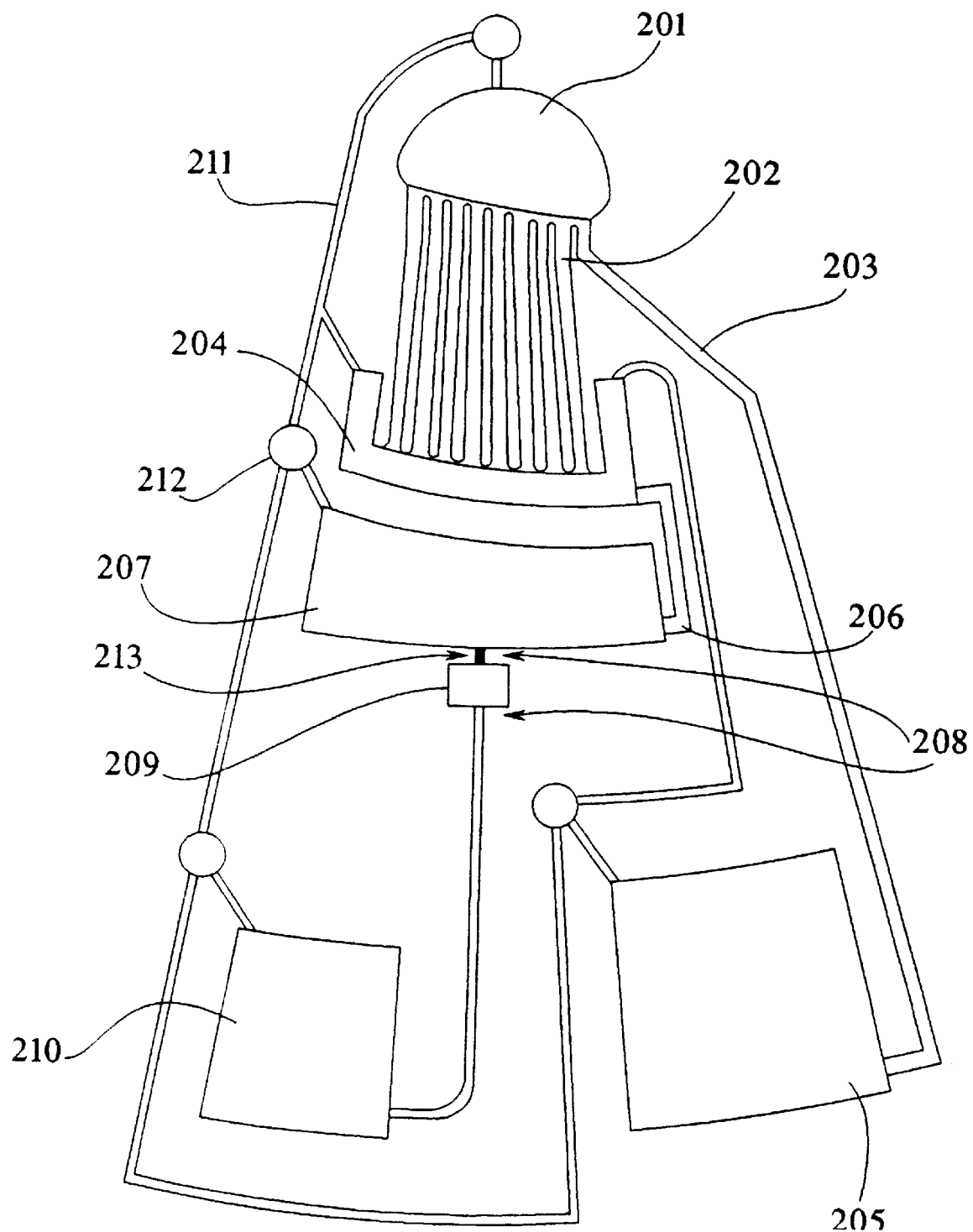

A first example of the microfluidics arrays provided by this invention is shown in FIGS. 1 through 3. A microsystems platform is provided by the invention that is specifically designed for performing two-step assays. These Figures illustrate an array advantageously used for any two-step analytic process; an antibiotic detection assay is illustrated herein.

Such a microsystem platform is illustrated in FIG. 1. In the Figure, the arrangement of one assay array 12 on a disk 11 is shown; a multiplicity of such arrays can be advantageously arranged on a microsystems platform, most preferably a disk, of the invention, to provide a multi-use or multi-assay platform.

The components of the antibiotic assay array are shown in greater detail in FIG. 2. It will be understood by a comparison of FIGS. 1 and 2 that the center of the platform 11 is at the top of FIG. 2, and the edge or lateral extent of the platform is at the bottom of FIG. 2, illustrated by a curved line. Rotation of the antibiotic array on platform disks of the invention can be in either direction, although rotation in a consistent, particular direction is preferred. Disc embodiments of the platforms of the invention were fashioned from machined acrylic and injection-molded polycarbonate. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction with reagents was about 1–150 $\mu$L.

The components of the antibiotic array are as follows. An entry port 201 having a depth in the platform surface ranging from about 0.25 mm to about 6 mm and lateral dimensions of from about 0.2 cm to about 2 cm is constructed on the platform, and designed to accommodate a volume of about 5–100 $\mu$L. This entry port is fluidly connected with an array of metering capillaries 202 having a square cross-sectional diameter ranging from about 0.02 mm to about 1 mm and proximal ends rounded with respect to entry port 201; the length of this metering capillary array was sufficient to contain a total volume of about 10–50 $\mu$L. The entry port is also constructed to be fluidly connected with an overflow capillary 203 having a cross-sectional diameter of from about 0.02 mm to about 1 mm and proximal ends rounded with respect to entry port 201. The overflow capillary is fluidly connected with an overflow chamber 205 having a depth in the platform surface ranging from about 0.02 mm to about 5 mm, provided that the depth of the overflow chamber 205 is greater than the depth of the overflow capillary 203. Metering capillary 202 is fluidly connected to fluid chamber 204 having a depth in the platform surface ranging from about 0.02 mm to about 1 mm, provided that the depth of the fluid chamber 204 is greater than the depth of the metering capillary 202. Each of the overflow and fluid chambers is also connected with air ports or air channels, such as 211, that have dimensions ranging from about 0.02 mm to about 1 mm and permit venting of air displaced by fluid movement on the platform. A capillary junction 212 that is about 0.75 mm to 1 mm deep is present in the air channel to prevent fluid flow into the air channel. For the purposes of the description of these microfluidics structures, a "capillary junction" is defined in a hydrophilic support material as a pocket, depression or chamber that has a greater depth (vertically within the platform) and/or a greater width (horizontally within the platform) that the fluid channel to which it is fluidly connected. For liquid with a contact angle less than 90° (such as aqueous solutions on platforms made with most plastics, glass and silica), flow is impeded as the channel cross-section increases at the interface of the capillary junction. The force hindering flow is produced by capillary pressure, which is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned and co-pending U.S. patent application, Ser. No. 08/910,726, filed Aug. 12, 1997, incorporated by reference in its entirety herein.

Entry port 201 is positioned on the platform from 1 cm to 20 cm from the center of rotation. Metering capillary 202 extends from entry port 201 from about 0.2 cm to about 20 cm. The extent of the length of overflow capillary 203 is at least about 20% greater than the extent of the length of metering capillary 202. The position of fluid chamber 204 is from about 0.5 cm to about 10 cm from the center of rotation, and the position of overflow chamber 205 is thus from about 1.5 cm to about 11.5 cm from the axis of rotation.

The fluid chamber 204 acts as a capillary barrier that prevents fluid flow from metering capillary 202 at a first, non-zero rotational speed $f_1$ sufficient to permit fluid flow comprising overflow from the entry port 201 through overflow capillary 203 and into overflow chamber 205. The capillary boundary of fluid chamber 204 is constructed to be overcome at a second rotational speed $f_2$ (where $f_2 > f_1$). Fluid chamber 204 is fluidly connected to capillary 206 that is from about 0.02 mm to about 1 mm deep and has a cross-sectional diameter ranging from about 0.02 mm to about 1 mm. Capillary 206 extends from about 0.1 cm to about 20 cm from fluid chamber 204 and is connected to holding chamber 207. Holding chamber 207 has a depth in the platform surface from about 0.02 mm to about 1 mm and greater than the depth of capillary 206. Filling of fluid chamber 204 is motivated by centripetal acceleration and is accompanied by fluid flow through capillary 206 into holding chamber 207. Holding chamber 207 is fluidly connected by way of capillary 208, having a cross-sectional diameter of from about 0.1 mm to about 1 mm and extending from about 0.2 cm to about 10 cm from holding chamber 207 and is further connected with read chamber 210. Read chamber 210 has a depth in the platform surface of from about 0.02 mm to about 5 mm. For optical detection methods, read chamber 210 is of sufficient optical quality to prevent excessive scattering for a diffusely-reflecting medium such as milk. For transparent samples, read chamber 210 comprises a reflector, for example. This may be a diffuse reflector on the side of the chamber opposite to that upon which light is incident or a mirror-like surface. In the case of a diffuse reflector such as paint, a porous material, or any other material which causes diffuse reflection because of its rough surface or porous nature, light incident at a given angle is emitted over a hemisphere with a well-known cosine dependence on angle. In this way the detector may be aligned at an angle not equal to the incident angle, so that specular reflection from the plastic window of the chamber does not enter the detector. Alternatively, the mirror-like surface reflects light at an angle equal to the incident angle.

In certain embodiments, a sacrificial valve 213 (as described herein below) is placed as shown in the channel 209.

Figure 3A:
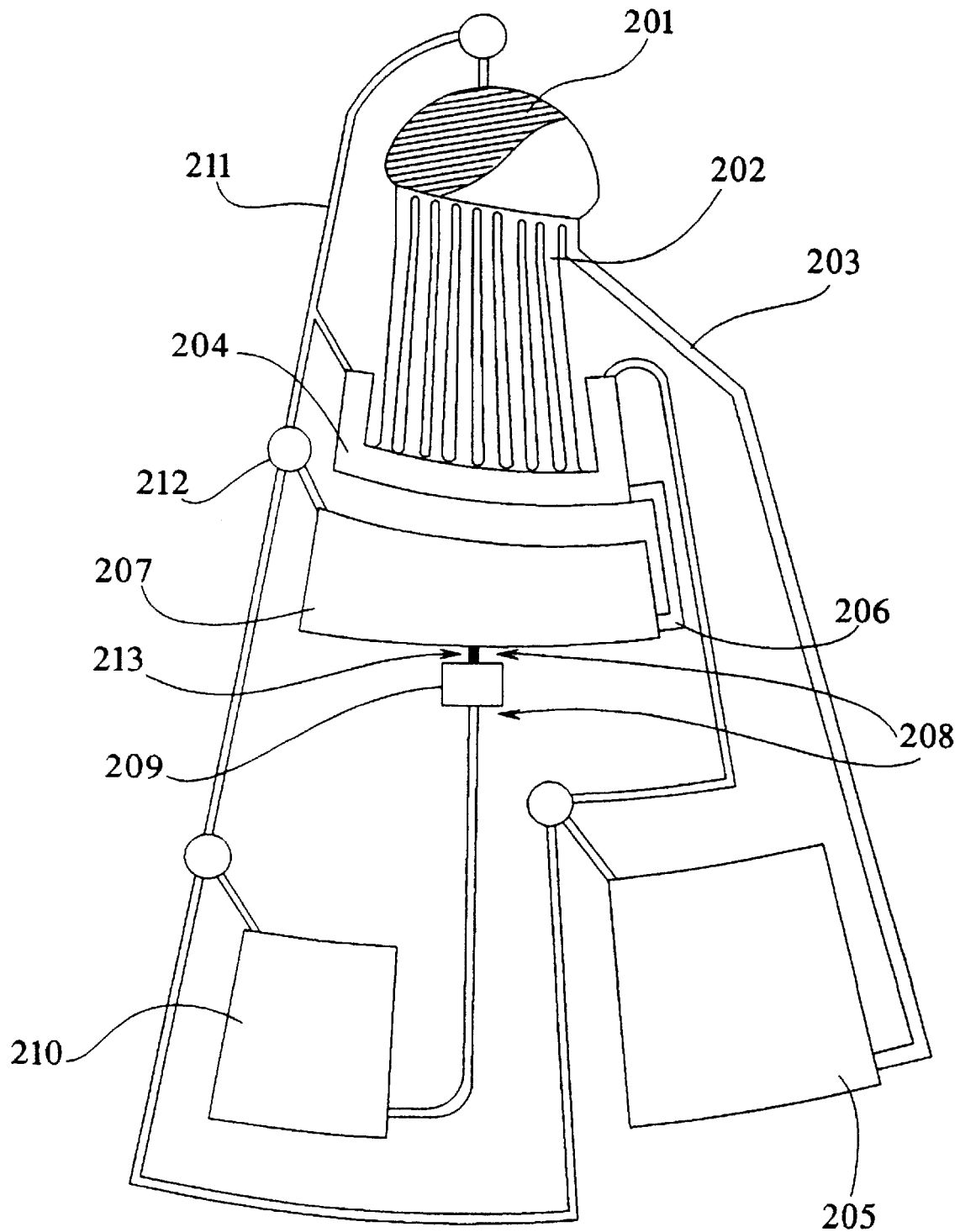
Figure 3B:
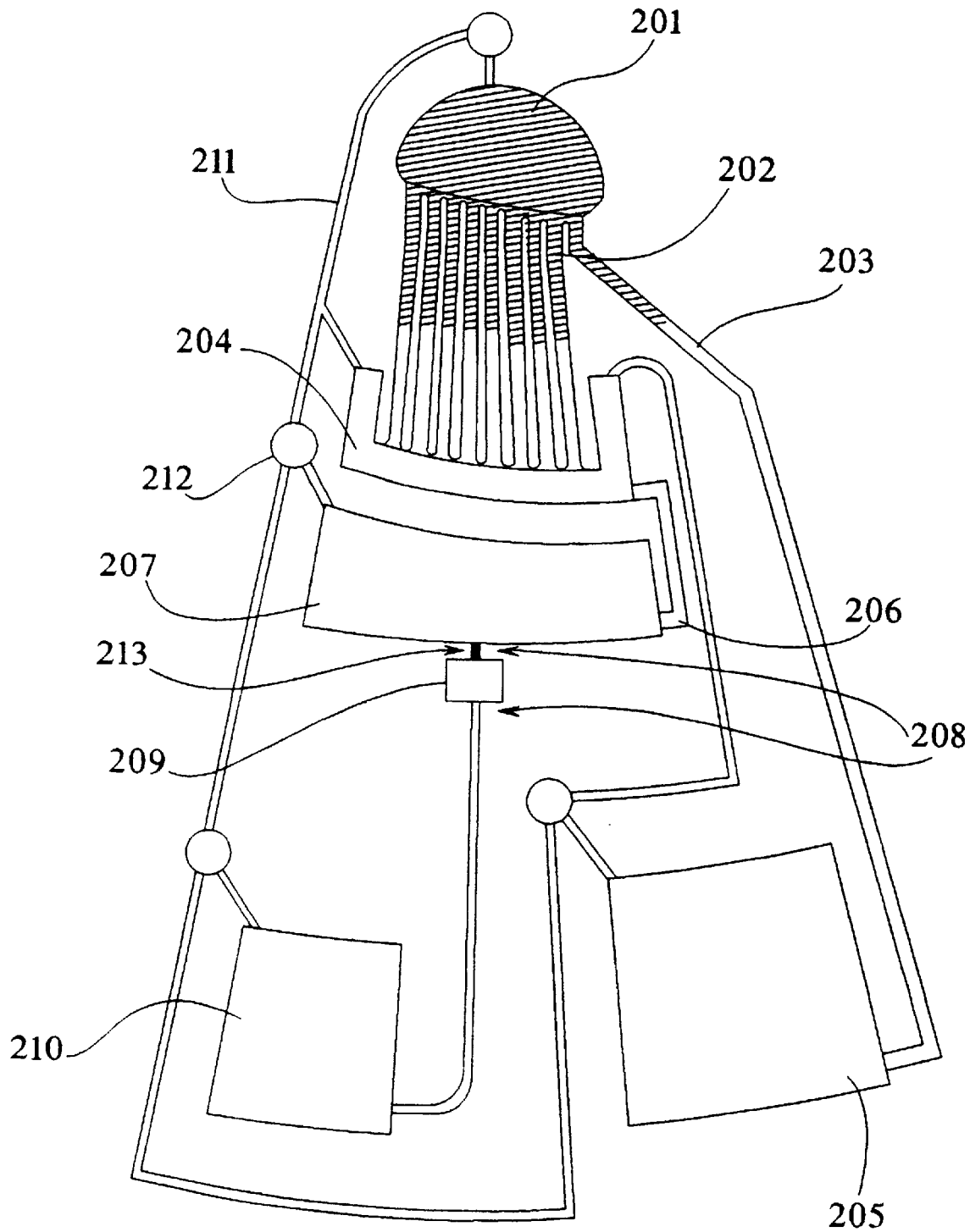
Figure 3C:
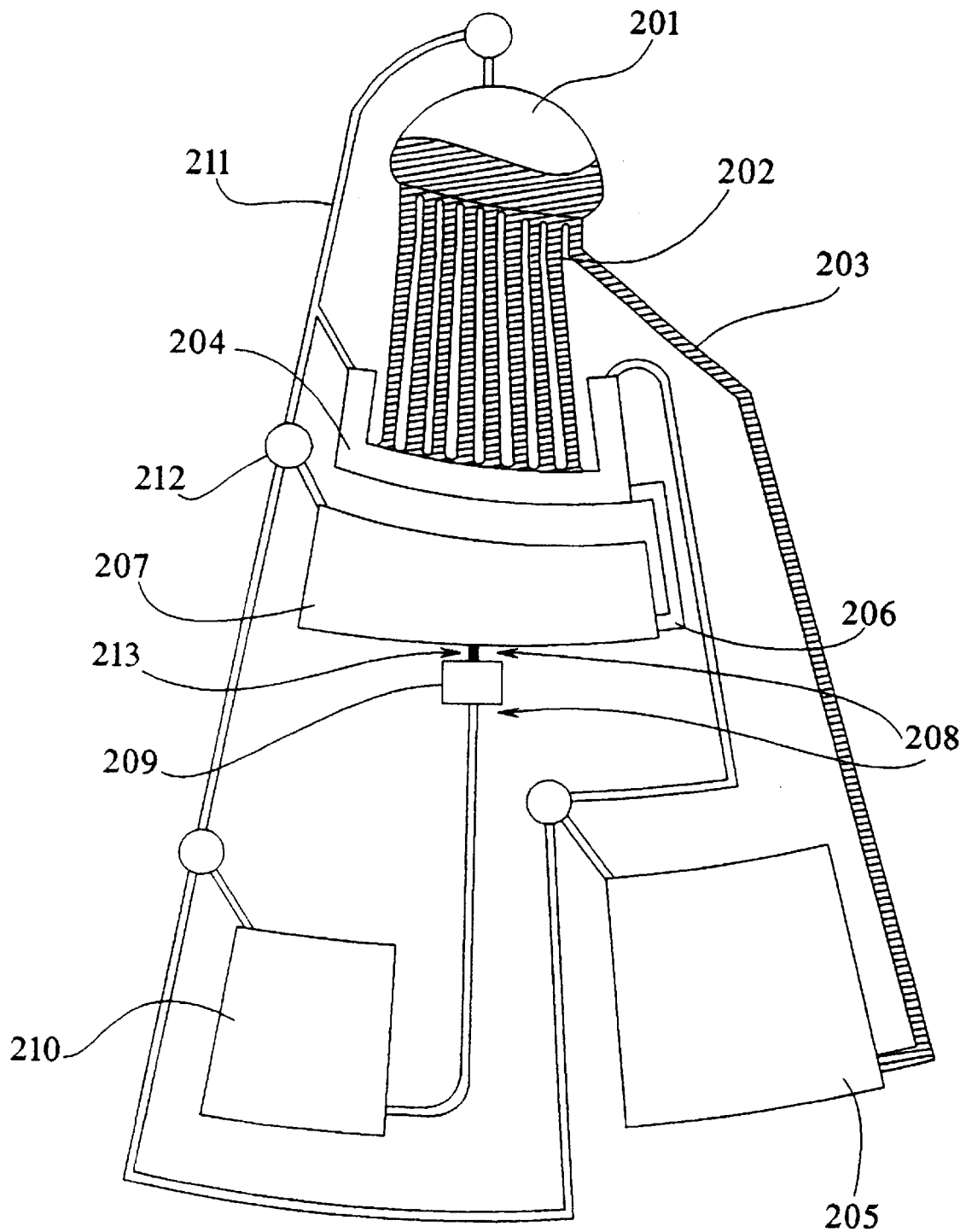

The use of a platform as disclosed in FIGS. 1 and 2 is illustrated in FIGS. 3A through 3J. In the use of this platform an imprecise volume (ranging from 1–150 µL of fluid) of a fluid is applied to the entry port 201 (FIG. 3A). In embodiments of the platform comprising air displacement channels, the fluid will wick into air channel 211 and be stopped by capillary junction 212. Fluid also wicks into metering capillary 202 and overflow capillary 203. Fluid flows through the metering capillary 202 and overflow capillary 203 at zero rotational speed until the fluid reaches capillary junctions at the junction between metering capillary 202 and fluid chamber 204 and overflow capillary 203 and overflow chamber 205 (FIGS. 3B and 3C). Metering capillary 202 is constructed to define a precise volume from about 1–150 µL of fluid between entry port 201 and the capillary junction at fluid chamber 204, which is designed to be at least the amount of the fluid placed by the user in entry port 201.

After sample loading by a user and filling of metering capillary 202 and overflow capillary 203 at zero rotational speed (which can be performed on the disc separately or with then disc engaged with a spindle of a centrifugal device), the platform is spun at a first rotational speed $f_1$, ranging from 100–400 rpm; the exact value is dependent on the position of the capillary junction components on the platform. For example, for an entry port 201 having a depth of 0.6 mm, metering capillary 202 having dimensions of 0.5 mm×0.5 mm in cross-section and a capillary junction between metering capillary 202 and fluid chamber 204 positioned about 2.2–3.8 cm from the center of rotation, and overflow capillary 203 having dimensions of 0.5 mm×0.5 mm in cross-section and a capillary junction between overflow capillary 203 and overflow chamber 205 positioned about 5.4 cm from the center of rotation, this first rotational speed $f_1$ is equal to about 175 rpm for either water or milk.

Figure 3D:
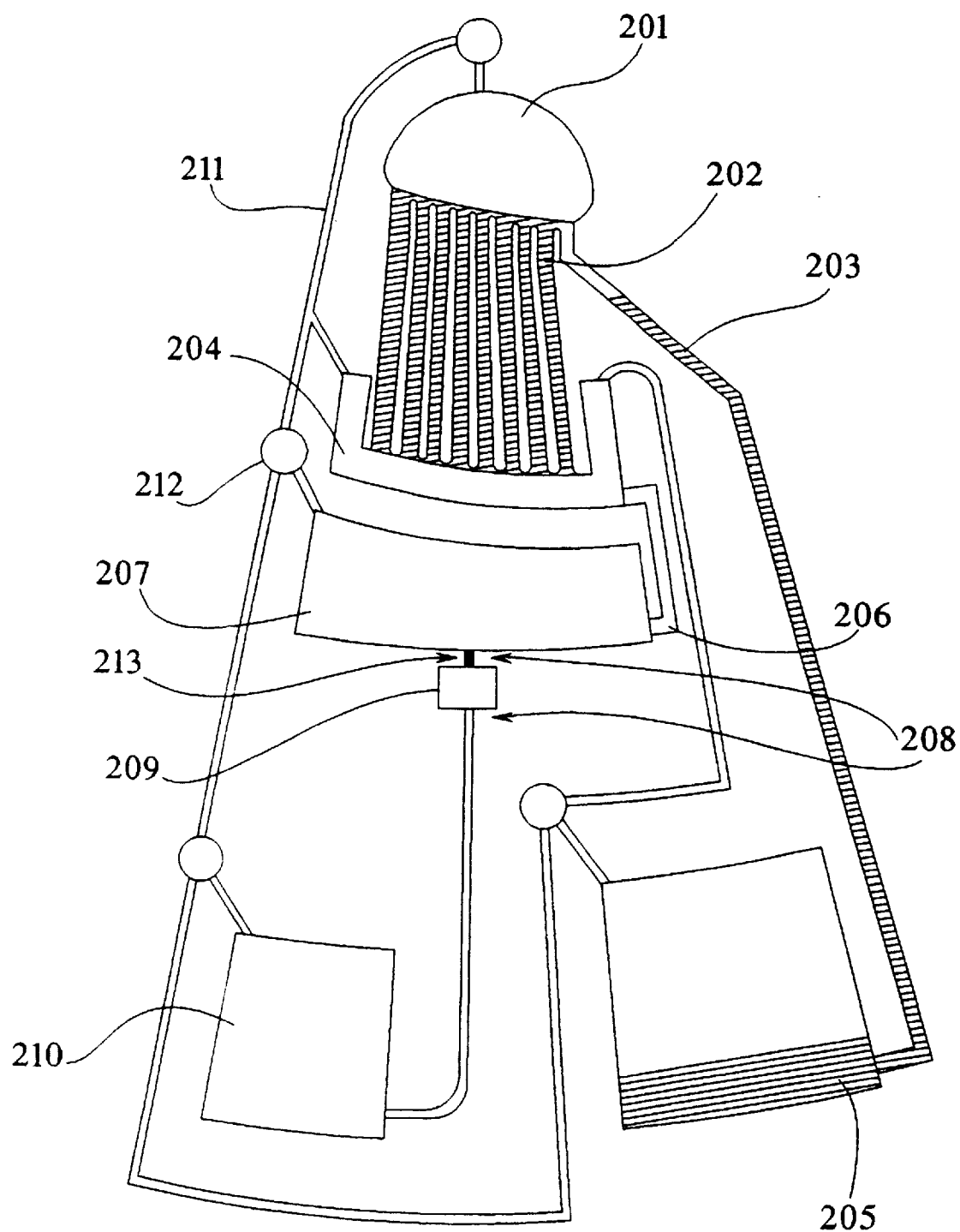
Figure 3E:
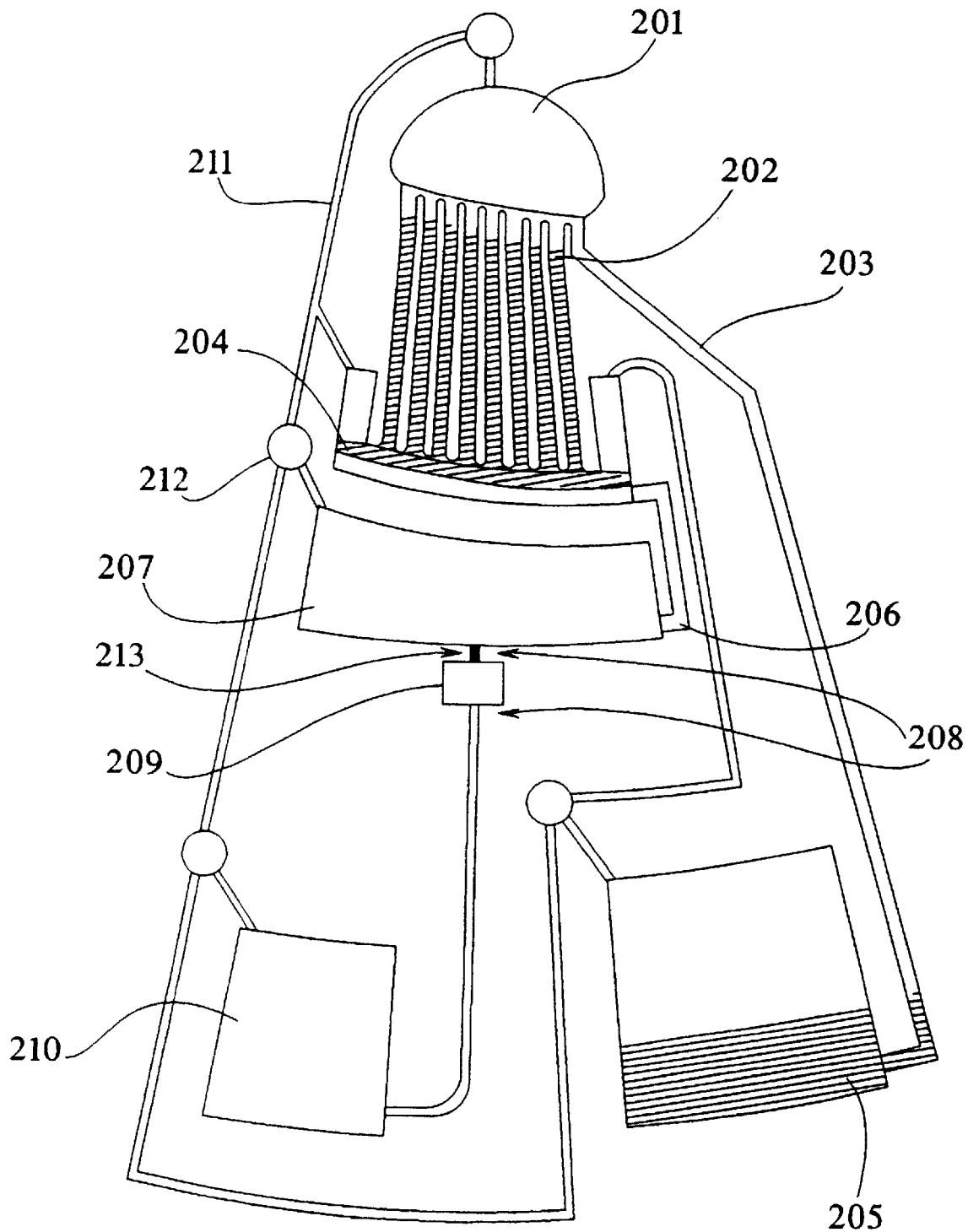
Figure 3F:
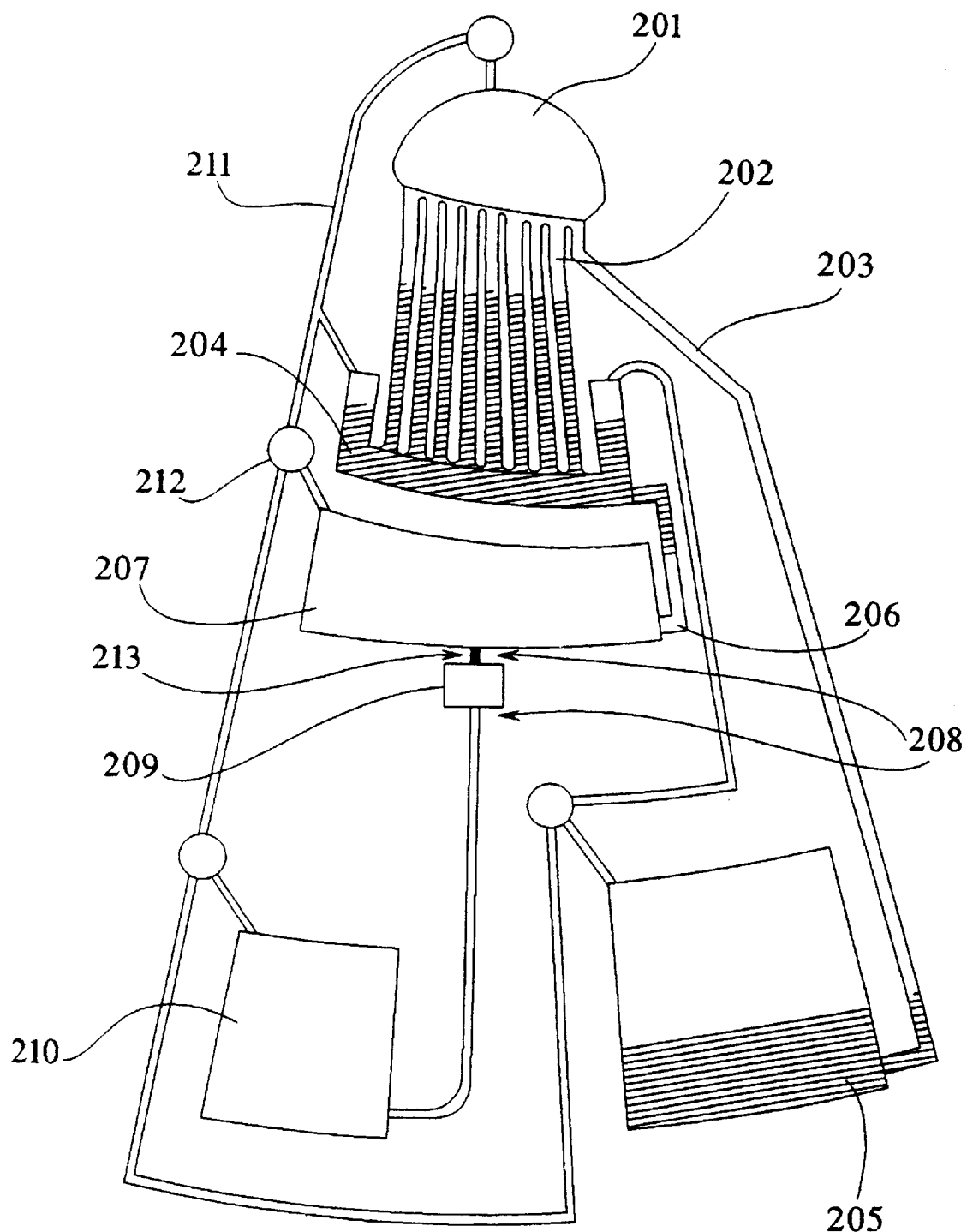
Figure 3G:
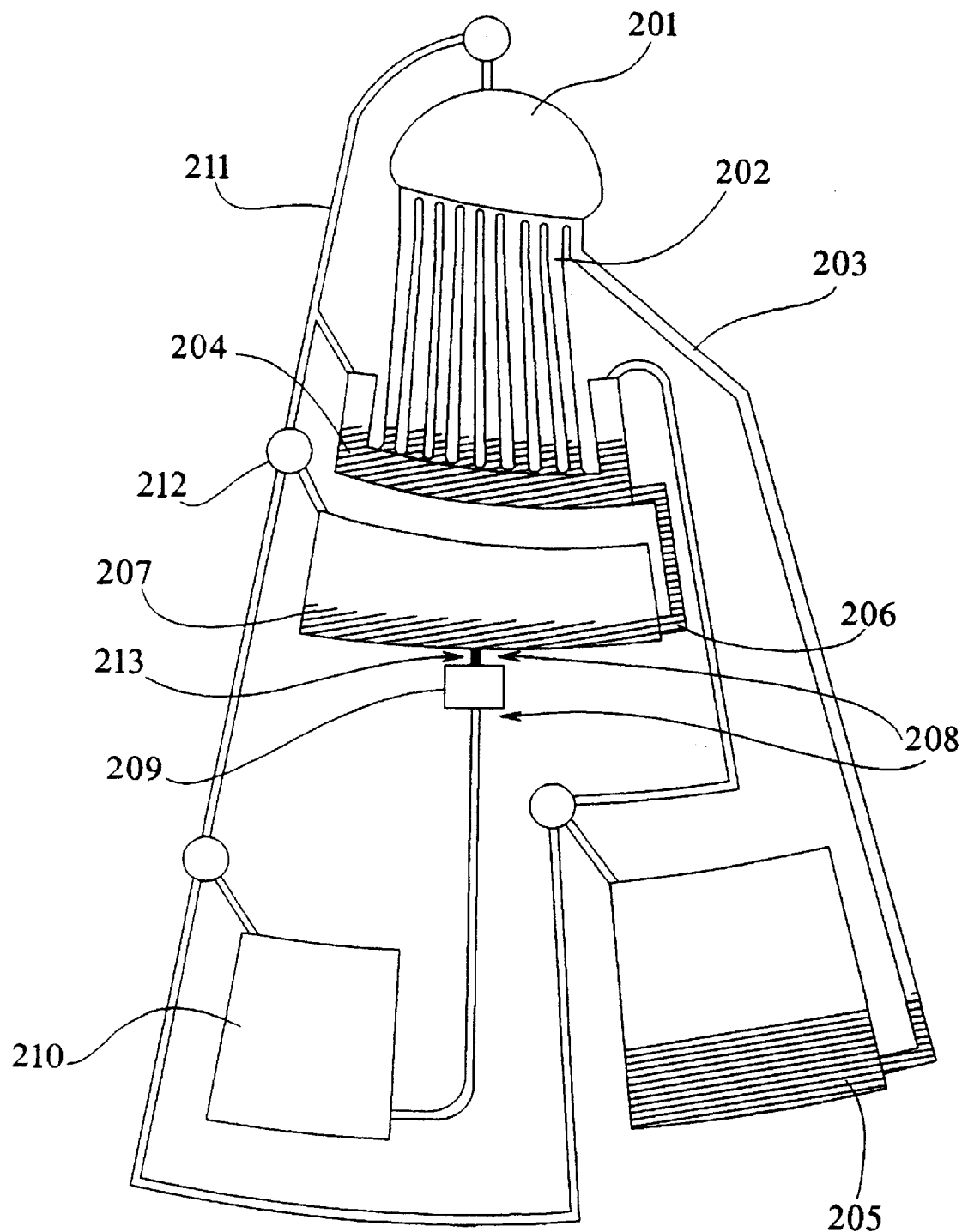
Figure 3H:
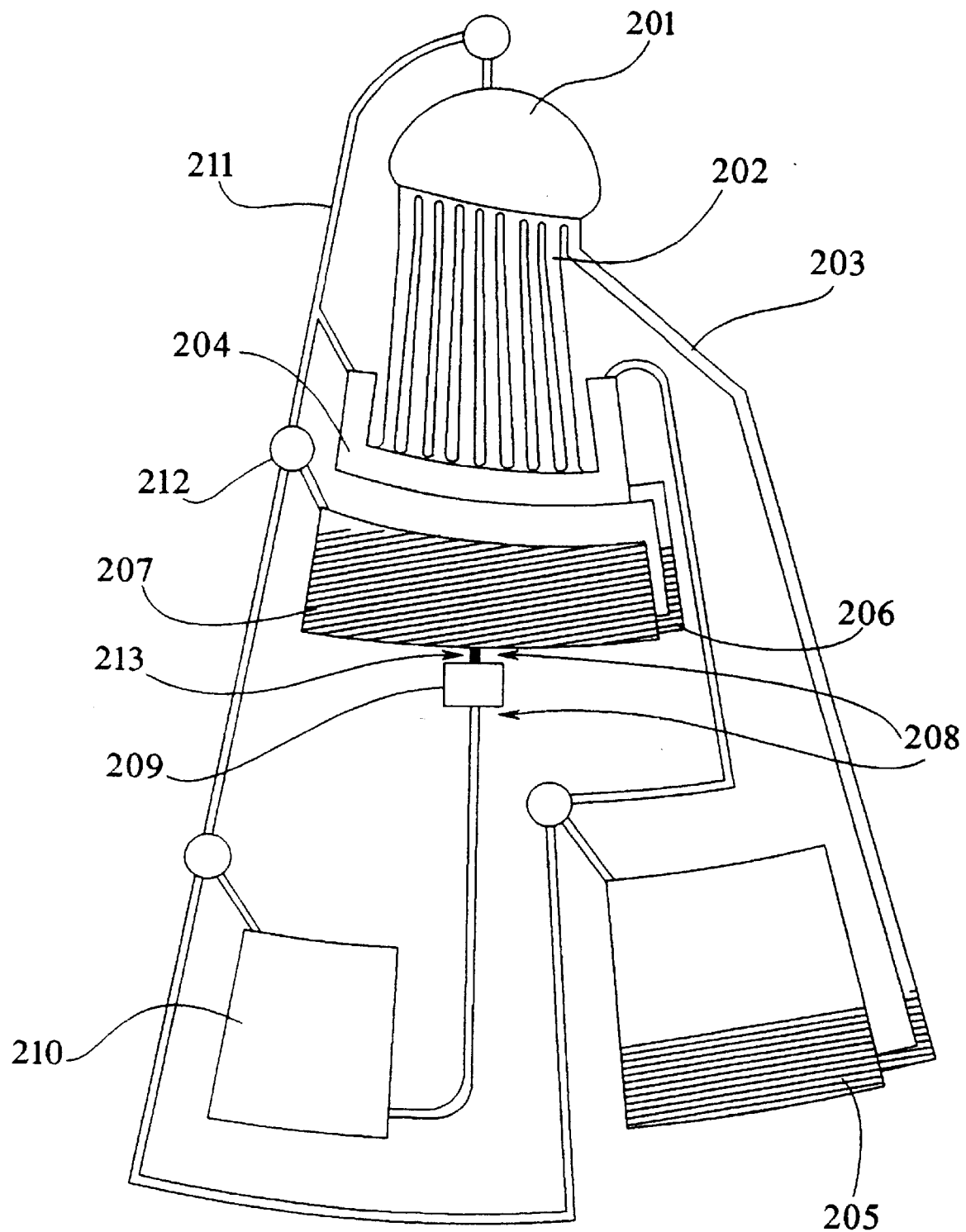

Due to the greater distance of the end of overflow capillary 203 from the center of rotation than the end of metering capillary 202, fluid flows through overflow capillary 203 into overflow chamber 205 and does not flow from metering capillary 202 into fluid chamber 204 at rotational speed $f_1$. The platform is spun until all excess fluid is evacuated from entry port 201 and into overflow chamber 205, except the fluid contained in metering capillary 202 (FIG. 3D).

At a second rotational speed $f_2$, that is greater than the first rotational speed $f_1$, typically in the range of 400–520 rpm, the precise amount of fluid contained in metering capillary 202 is delivered into fluid chamber 204 (FIGS. 3E through 3H) For example, for an entry port 201 having a depth of 0.6 mm, metering capillary 202 having dimensions of 0.5 mm×0.5 mm in cross-section and a capillary junction between metering capillary 202 and fluid chamber 204 positioned about of 2.2–3.8 cm from the center of rotation, this second rotational speed is equal to 400 rpm for either water or milk. Fluid movement into fluid chamber 204 is accompanied by filling of capillary 206 and holding chamber 207.

In embodiments comprising a sacrificial valve 213 in-line with capillary 208 at position 209 shown in FIG. 2, release of the sacrificial valve results in fluid flow into read chamber 210. Sacrificial valves as described above are preferably made of a fungible material that can be removed from the fluid flow path. In preferred embodiments, said sacrificial valves are wax valves and are removed from the fluid flow path by heating, using any of a variety of heating means including infrared illumination and most preferably by activation of heating elements on or embedded in the platform surface as described below. In said embodiments, fluid flow is achieved at rotational speed $f_2$ with removal of the sacrificial valve.

Figure 3I:
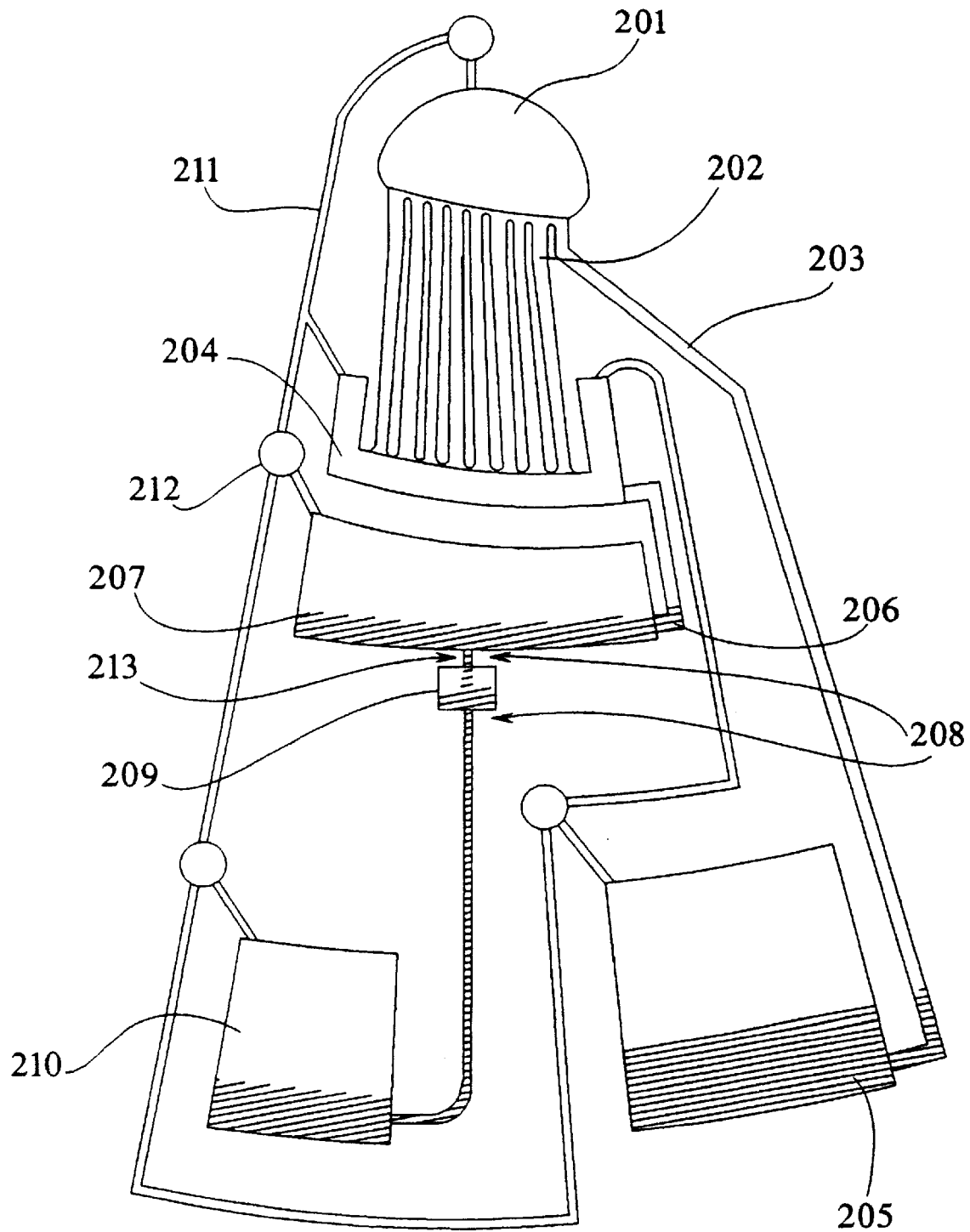
Figure 3J:
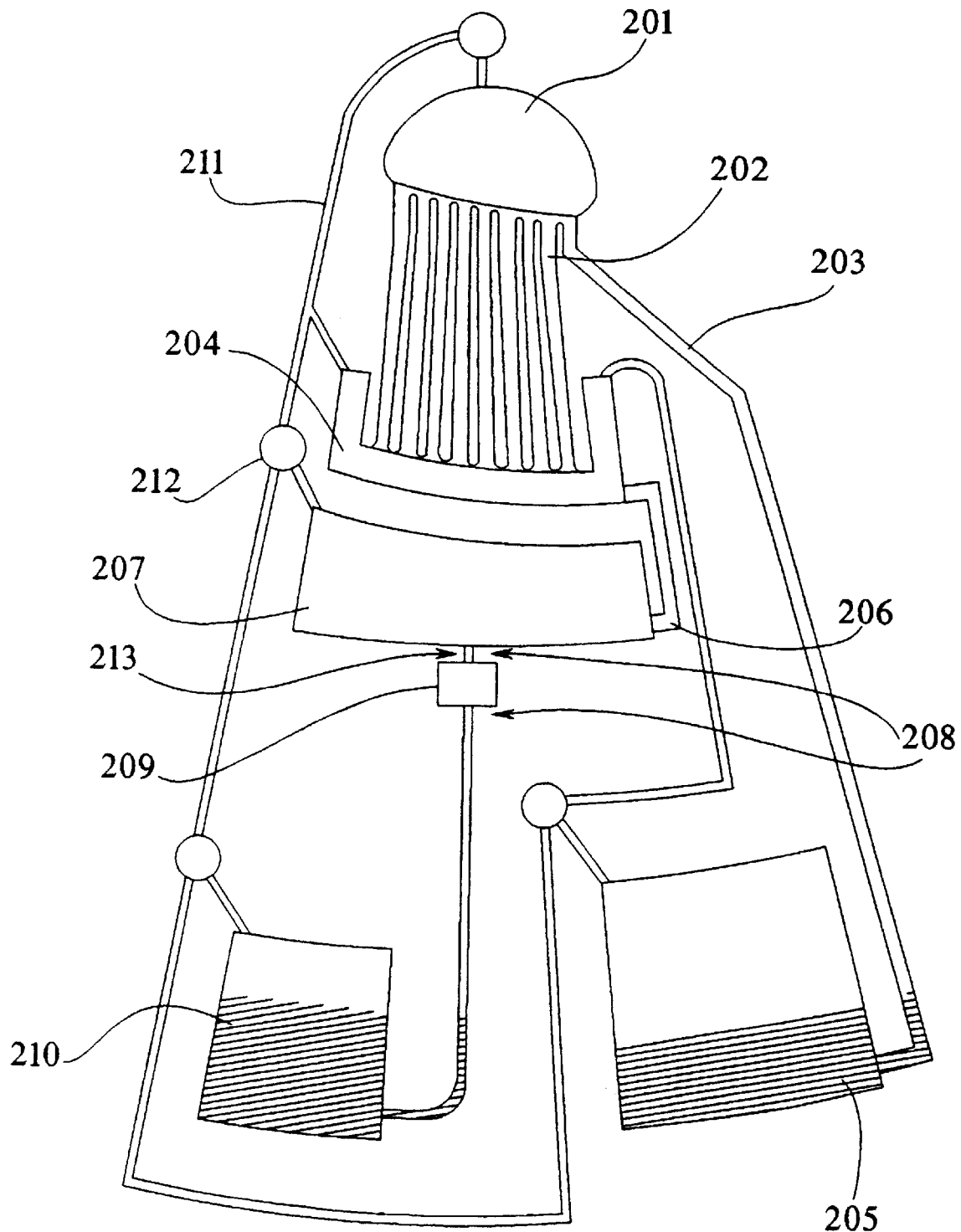
Figure 31:
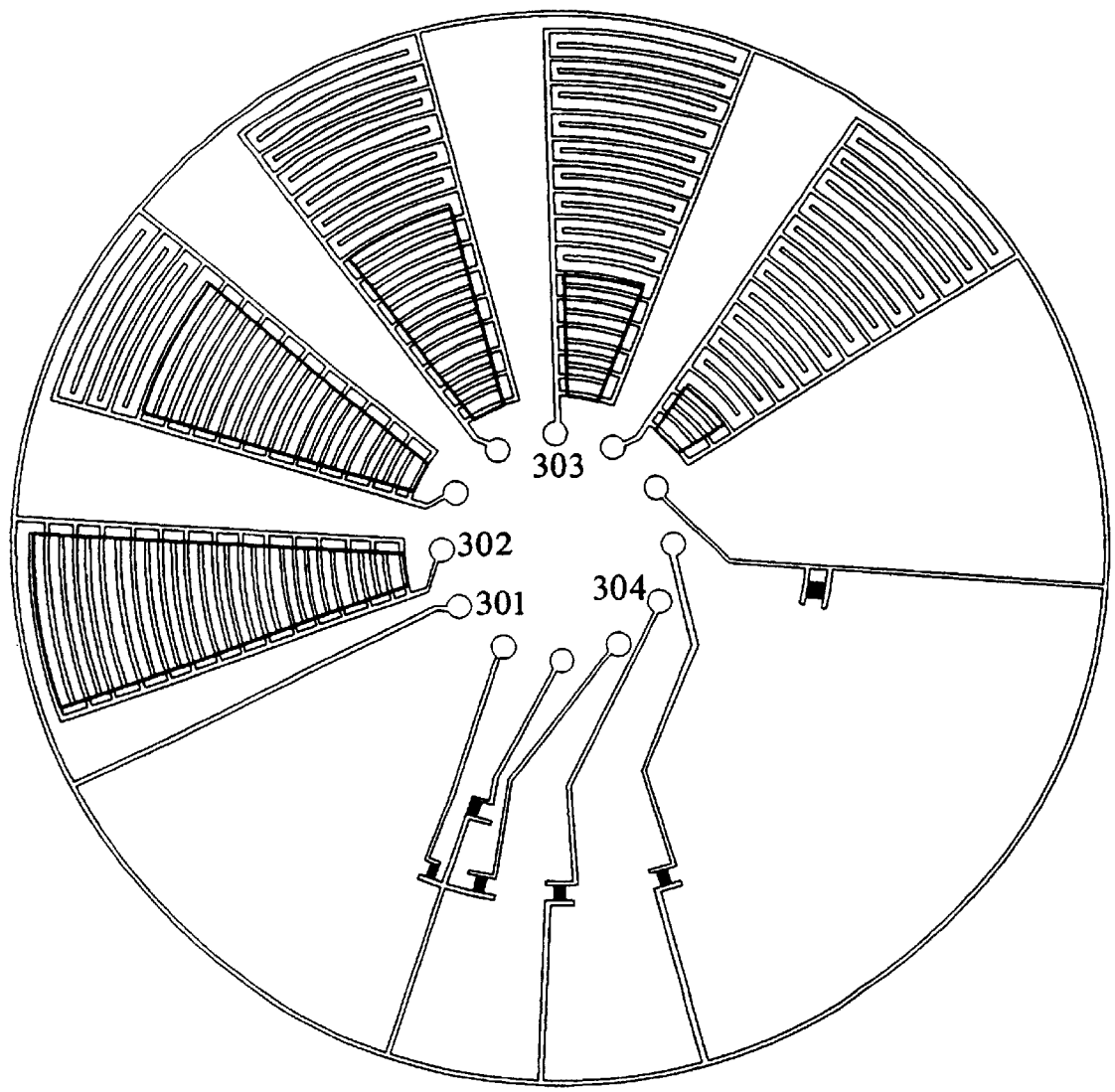
FIG. 31 illustrates screen-printing of a resistive heater element as described in Example 10.

In embodiments of the platforms of the invention comprising antibiotic arrays as described herein and not containing a sacrificial valve at position 209, capillary 208 preferably fills along with filling of holding chamber 207 until the fluid reaches a capillary junction 209 at the junction between capillary 208 and read chamber 210; in such embodiments, the capillary junction has a depth of from about 0.15 mm to about 1 mm. At a third rotational speed $f_3$, that is greater than the second rotational speed $f_2$, typically in the range of >520 rpm, the fluid contained in holding chamber 207 is delivered into read chamber 210 (FIGS. 31 and 3J). For example, for a capillary junction 209 having a depth of 0.75 mm, and capillary 208 having dimensions of 0.25 mm×0.25 mm in cross-section and the capillary junction positioned from about 3.8 cm from the center of rotation, this third rotational speed is equal to 500–800 rpm for either water or milk.

More generally, the third rotational speed is proportional to $1/\sqrt{(R_{outer}-R_{inner})\times\{(R_{outer}\times R_{inner})/2\times\text{the diameter of the capillary}\}}$, where $R_{outer}$ is the dimension of the capillary radius at the outer edge and $R_{inner}$ is the capillary radius at the inner edge, relative to the center of rotation. Thus, for a capillary of square cross-section 0.25 mm and a capillary junction 0.75 mm deep, values of the product $\{(R_{outer}-R_{inner})\times\{(R_{outer}\times R_{inner})/2\times\text{the diameter of the capillary}\}$ ranging from 0.89 to 0.35 yield a third rotational speed of from about 500–800 rpm.

An example of the chemistries of the types of two-step chemical analyses that can be performed using this microfluidics array are illustrated by the antibiotic detection assay. This antibiotic detection assay is performed using the platform design as follows. This chemistry is based on the selective poisoning of an enzyme, carboxypeptidase, by beta lactam antibiotics. Carboxypeptidase is present in a dried form with sugars, buffers or other stabilizers in the holding chamber 207 and a metered amount of milk or other fluid sample solution is introduced into the holding chamber as described above. The milk or other fluid sample solubilizes the enzyme, and the milk/enzyme mixture is incubated at 47° for 3–5 minutes to allow any beta lactam antibiotics present to bind to the carboxypeptidase. The enzyme catalyses cleavage of a D-alanine residue from L-Lysine-D-Ala-D-Ala, and catalysis is inhibited in a concentration-dependent manner by beta-lactam antibiotics present in the sample. In preferred embodiments, this temperature is achieve using a resistive heater element as described below; a description of this resistive heater element is not specifically included in this description of the platform of the invention here in order to focus attention on the disclosed microfluidics structures. It will be understood that any analytic protocol using the microfluidics structures disclosed herein that requires elevated temperatures (i.e., greater than room temperature) advantageously includes resistive heaters as disclosed herein, or other heating elements that are specifically encompassed by the platforms of the invention.

In addition, the holding chamber 207 contains dried reagent comprising a peptide having a D-amino acid at its carboxyl terminus; an example of such a peptide is L-Lysine-D-Ala-D-Ala. Preferably, this peptide is also contained in holding chamber 207 in dried form, and is reconstituted by introduction of milk or other fluid into the chamber as described above. It is an advantage of the microfluidics arrays of the invention that a precisely metered amount of fluid is introduced into holding chamber 207, permitting a standardized amount of carboxypeptidase, peptide substrate and buffers, stabilizers, etc. be contained in the holding chamber.

In the second step of the assay, D-amino acid oxidase (DAAO), flavine adenine dinucleotide (FAD), horse radish peroxidase (HRP), and a chromogen such as syringalazine (4-hydroxy-3,5-dimethoxygenzaldehyde azine) or orthodianisidine (ODA) is contained in dried form in read chamber 210. Displacement of the fluid sample from holding chamber 207 to read chamber 210 results in reconstitution of these reagents, which produce a colored product proportional with the amount of D-amino acid present in the fluid sample after incubation with carboxypeptidase and D-amino acid containing peptide. The D-alanine residue produced by degradation of the peptide substrate by carboxypeptidase in holding chamber 207 is degraded into pyruvate in the presence of DAAO and FAD; the reaction also reduces FAD to $FADH_2$. $FADH_2$ combines with oxygen in the fluid sample to produce hydrogen peroxide and be reoxidized to $FADH_2$ to FAD. The hydrogen peroxide then acts on a chromogen such as syringalazine in the presence of horse radish peroxidase, and the previously transparent chromogen becomes colored. This reaction scheme is illustrated as follows:

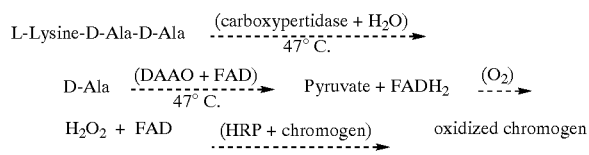

The extent of chromogen production is detected in the read chamber, and related to the presence of antibiotics in the sample by comparison with samples tested in the absence of antibiotic. Most preferably, a standard curve relating the decrease in chromogen production and the amount of antibiotic in the sample is prepared and used to determine the amount of antibiotic in an unknown test sample.

The buffers and reagents used for these chemistries on the platforms of the invention are constituted with appropriate buffers, stabilizers, preservatives, salts, cofactors, adjuvants and other necessary components of the reactions performed on the platform.

An alternative embodiment of the two-step assay microfluidics array is shown in FIGS. 4 through 6, again exemplified for an antibiotic assay disk of the invention. It will be understood that, as in Example 1, in FIG. 4, the arrangement of one assay array 13 on a disk 11 is shown; a multiplicity of such arrays can be advantageously arranged on a microsystems platform, most preferably a disk, of the invention, to provide a multi-use or multi-assay platform.

Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction with reagents was about 25–150 μL.

The components of this antibiotic array are as follows. An entry port 301 having a depth in the platform surface of from about 0.25 mm to about 5 mm and lateral dimensions of from about 0.2 cm to about 2 cm is constructed on the platform, and designed to accommodate a volume of about 1–100 μL. This entry port is fluidly connected with one or a multiplicity of entry capillaries 302 having a square cross-sectional diameter ranging from about 0.02 mm to about 1 mm and having a depth of 0.1 to 1 mm equal to the depth of the entry port, and proximal ends rounded with respect to entry port 301. The length of this metering capillary array was sufficient to contain a total volume of about 20 μL. The entry capillaries 302 are fluidly connected to fluid chamber 303 having a depth in the platform surface of from about 0.02 mm to about 1 mm, wherein the depth is greater than the depth of the entry capillary 302. Each of the fluid chambers of this aspect of the invention is also connected with air ports or air channels, such as 311, that have dimensions ranging from about 0.02 mm to about 5 mm that permit venting of air displaced by fluid movement on the platform. A capillary junction 312 that is about 0.75 mm deep is present in the air channel to prevent fluid flow into the air channel.

The fluid chamber 303 is also constructed to be fluidly connected with an overflow capillary 304 having a cross-sectional diameter of about 0.02 mm to about 0.75 mm and proximal ends rounded with respect to fluid chamber 304. The overflow capillary is fluidly connected with an overflow chamber 306 having a depth in the platform surface of from about 0.02 mm to about 1 mm, greater than the depth of the overflow capillary 304.

Entry port 301 is positioned on the platform from 1 cm to 20 cm from the center of rotation. Entry capillaries 302 extends from entry port 301 from about 0.5 cm to about 10 cm. The position of a first fluid chamber 303 is from about 0.5 cm to about 10 cm from the center of rotation.

The first fluid chamber 303 acts as a capillary barrier that prevents fluid flow from entry capillary 302 at zero rotational speed. Movement of fluid from entry port 301 through entry capillaries 302 and into the first fluid chamber 303 is achieved by rotation at a first, non-zero rotational speed $f_1$. Displacement of fluid into the first fluid chamber 303 is accompanied by fluid filling of channel 305 that is fluidly connected with the first fluid chamber 303 and is positioned at the most radially distal point of the first fluid chamber. Channel 305 is fluidly connected with a second fluid chamber 307 and forms a capillary boundary between channel 305 and chamber 307. This capillary boundary is constructed to be overcome at second rotational speed $f_2$ (where $f_2>f_1$). First fluid chamber 303 is also fluidly connected to overflow capillary 304 that is from about 0.05 mm to about 1 mm deep and has a cross-sectional diameter of from about 0.05 mm to about 1 mm and extends from about 0.2 cm to about 20 cm. Overflow capillary 304 is connected to overflow chamber 306 that has a depth in the platform surface equal to that of overflow capillary 304, so that there is no capillary boundary between overflow capillary 304 and overflow chamber 306. Overflow capillary 304 is positioned in the first fluid chamber 303 at a point radially less distant from entry port 301 than channel 305, thereby defining a volume in the fluid chamber between the position of the overflow capillary 304 and the most radially distant extent of the said first fluid chamber.

Second fluid chamber 307 is further fluidly connected through channel 308 to a small pocket or capillary junction 309, having a depth in the platform surface of from about 0.1 mm to about 5 mm and positioned about 0.2 to 20 cm from the axis of rotation. Channel 308 has a cross-sectional diameter ranging from about 0.02 mm to about 1 mm and extends from about 0.2 cm to about 10 cm, and further extends to a third fluid chamber 310. Third fluid chamber 310 has a depth in the platform surface of from about 0.1 mm to about 5 mm, that is greater than the depth of capillary 308. Air recirculation channels 311 that have dimensions of from about 0.02 mm to about 1 mm provide pathways for air displaced by fluid movement, while capillary junctions 312 that are about 0.75 mm deep prevent fluid from entering the air channels. In some embodiments of the device a sacrificial valve 313 is placed as shown in the channel 309. In certain embodiments, a valve 314 is placed in channel 305 to control fluid movement from the first fluid chamber 303 to the second fluid chamber 307.

Figure 6A:
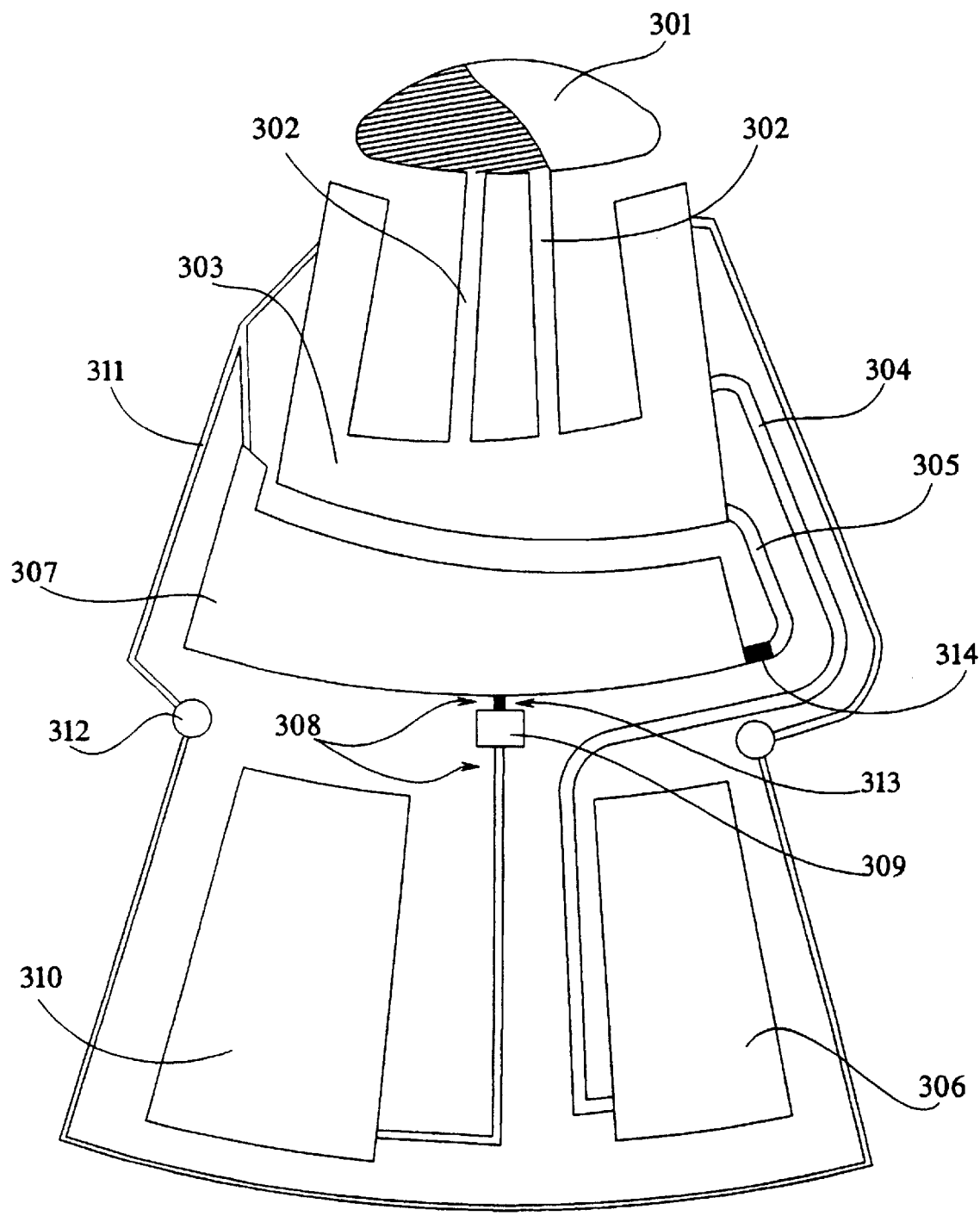
Figure 6B:
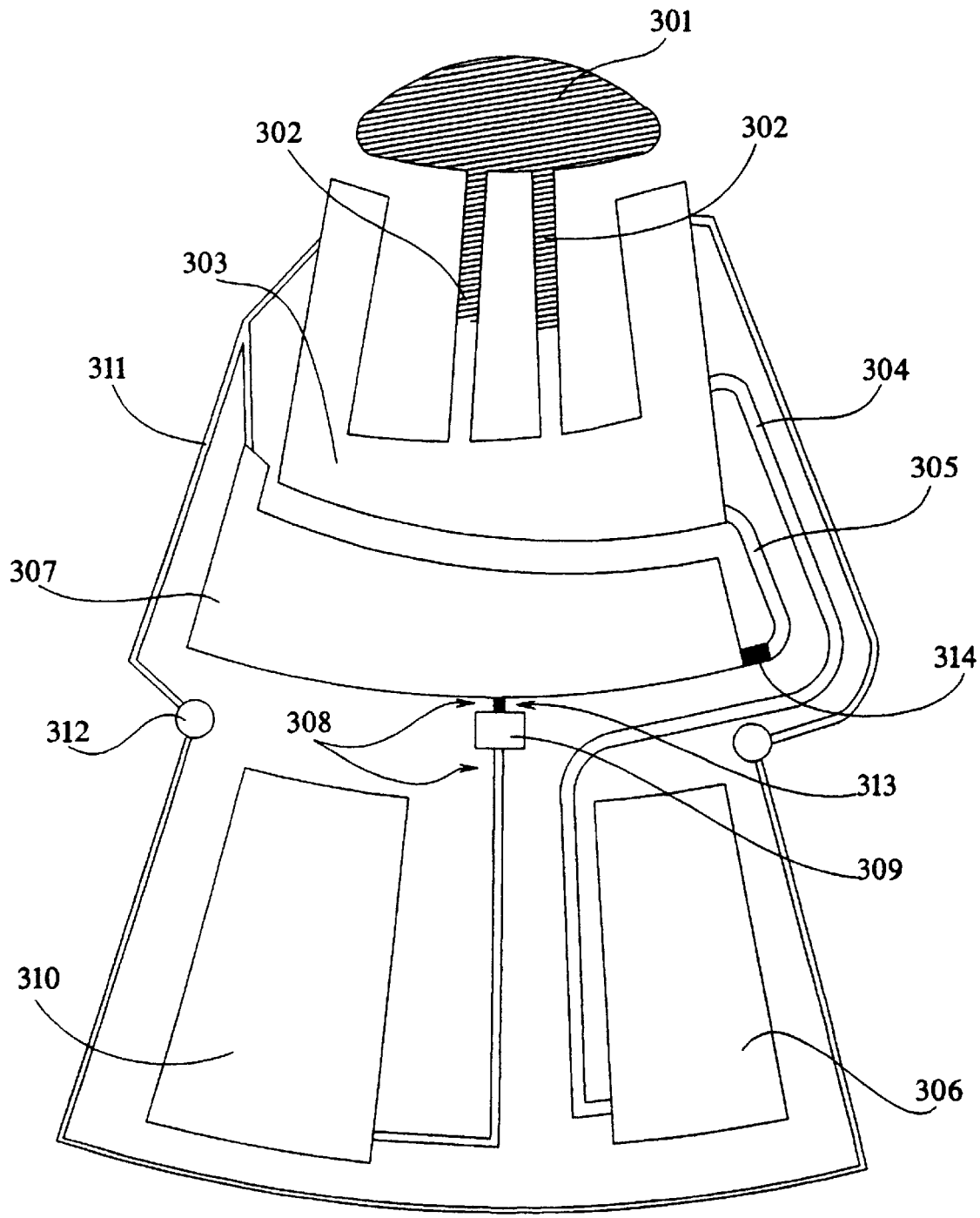
Figure 6C:
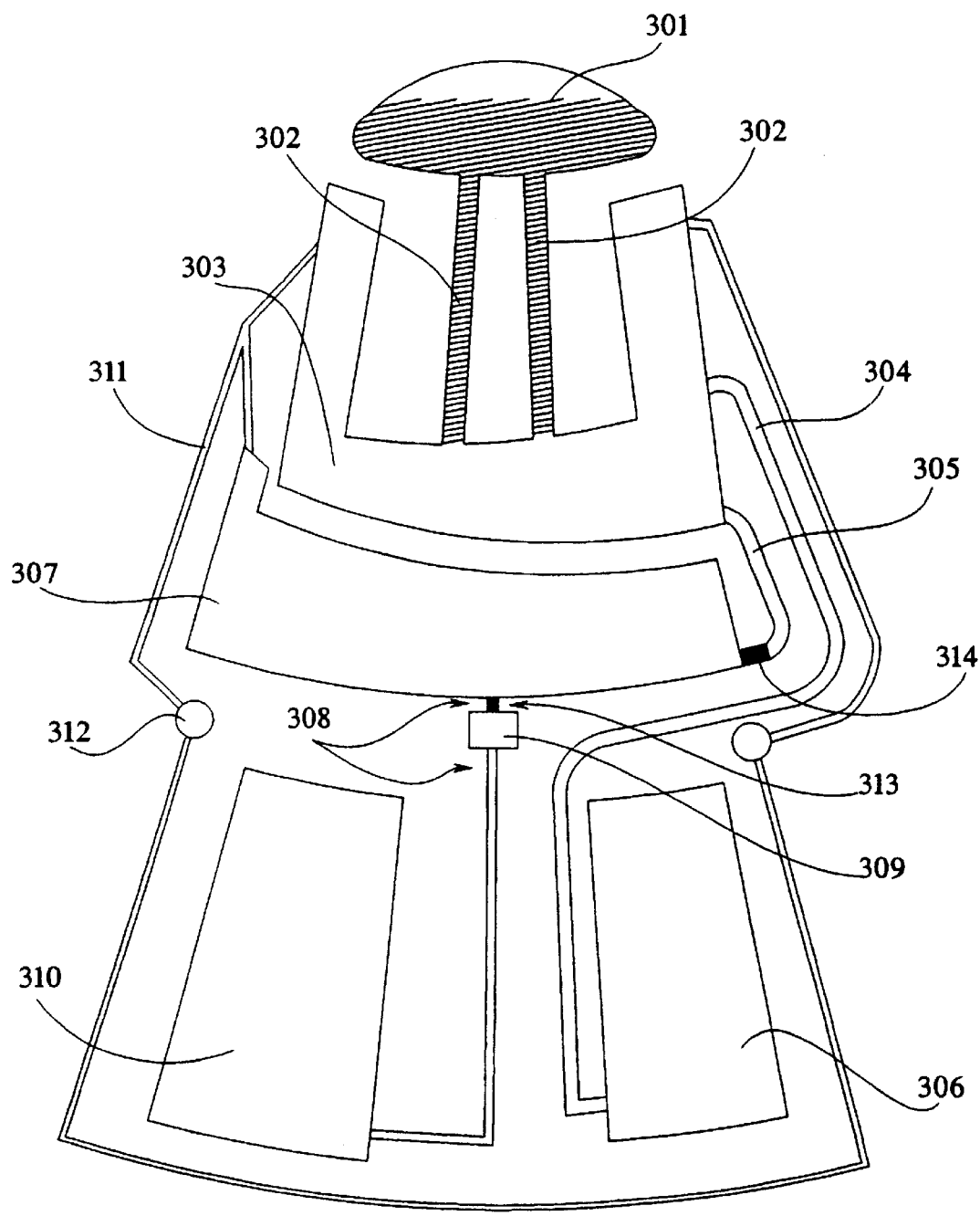
Figure 6D:
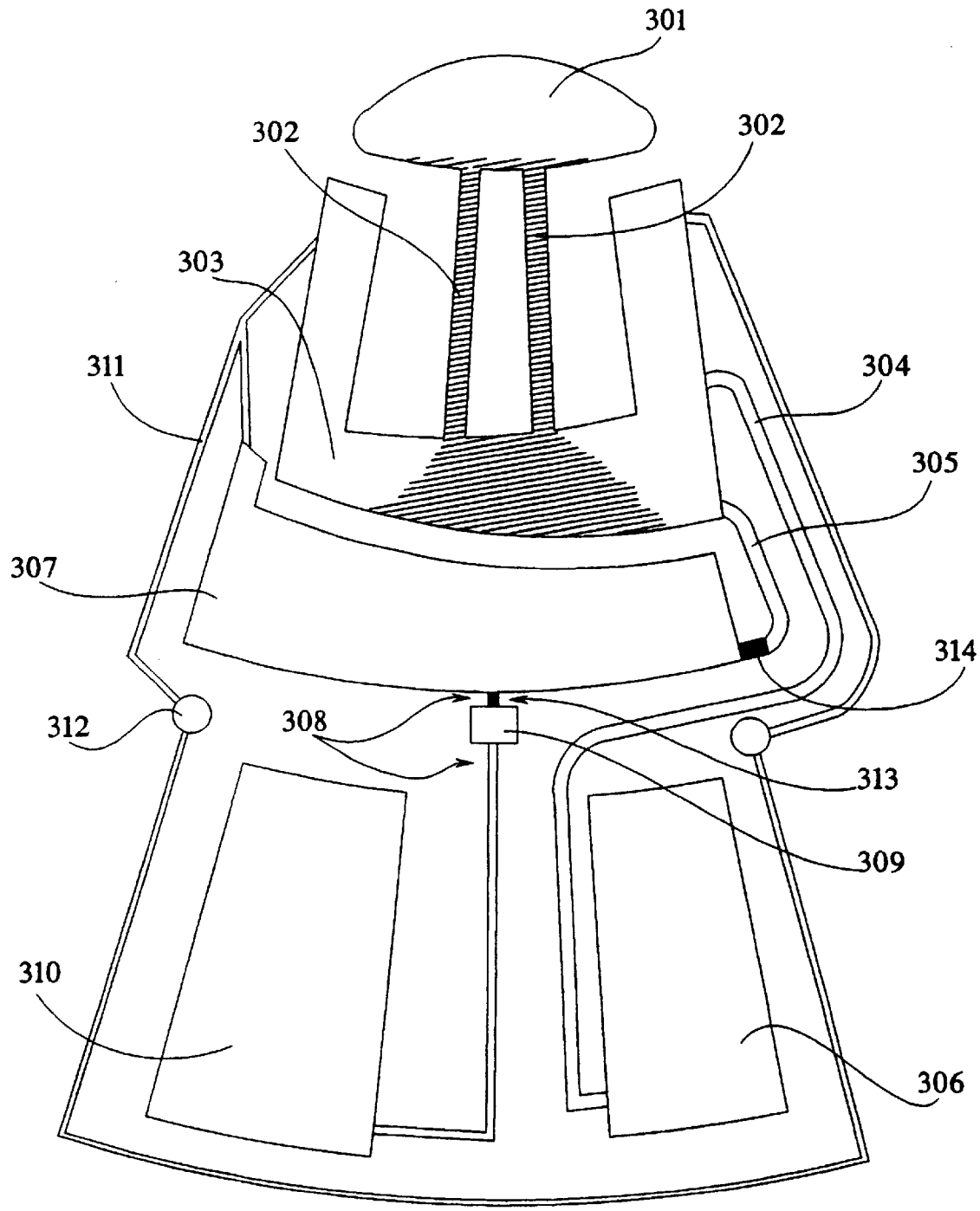
Figure 6E:
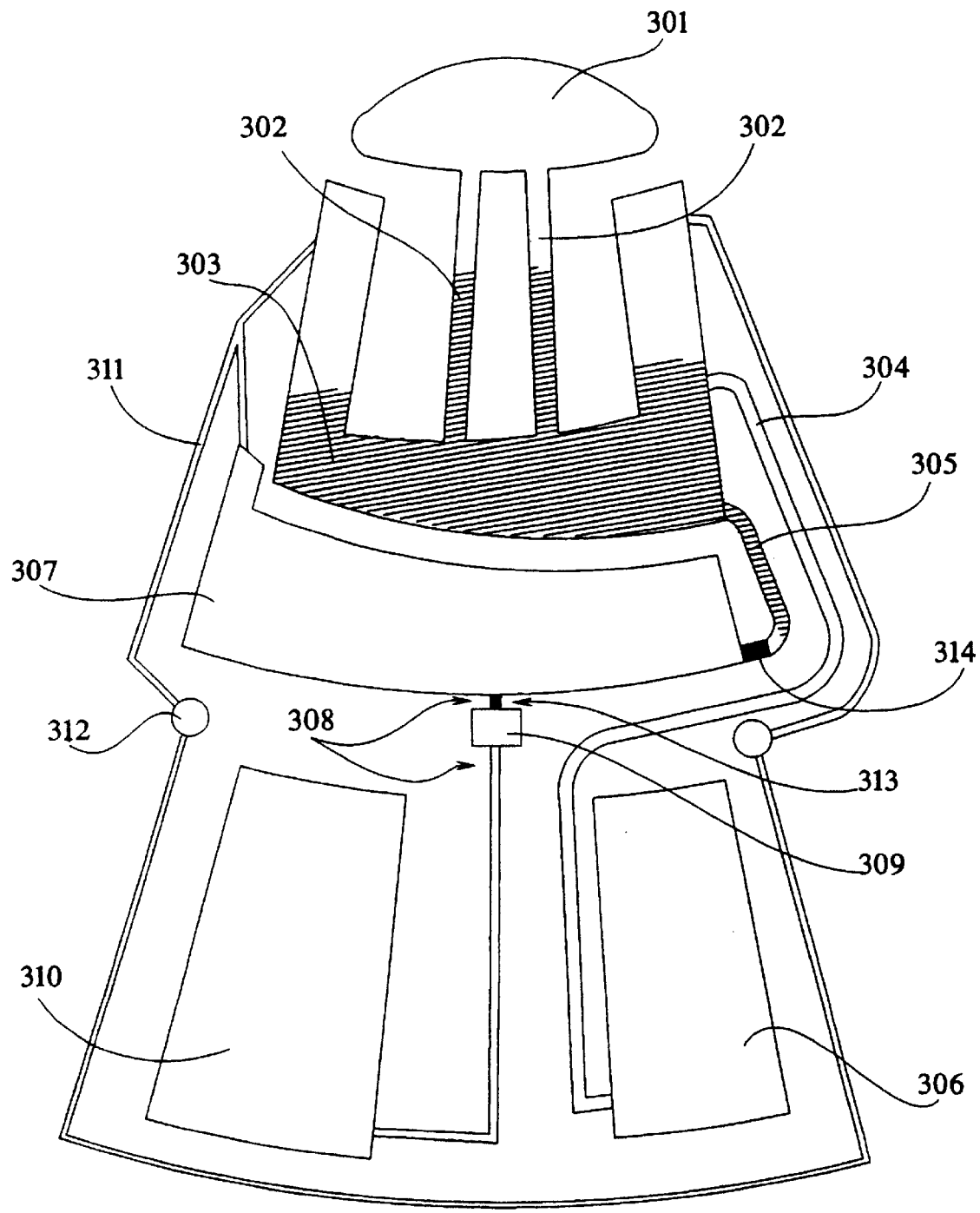
Figure 6F:
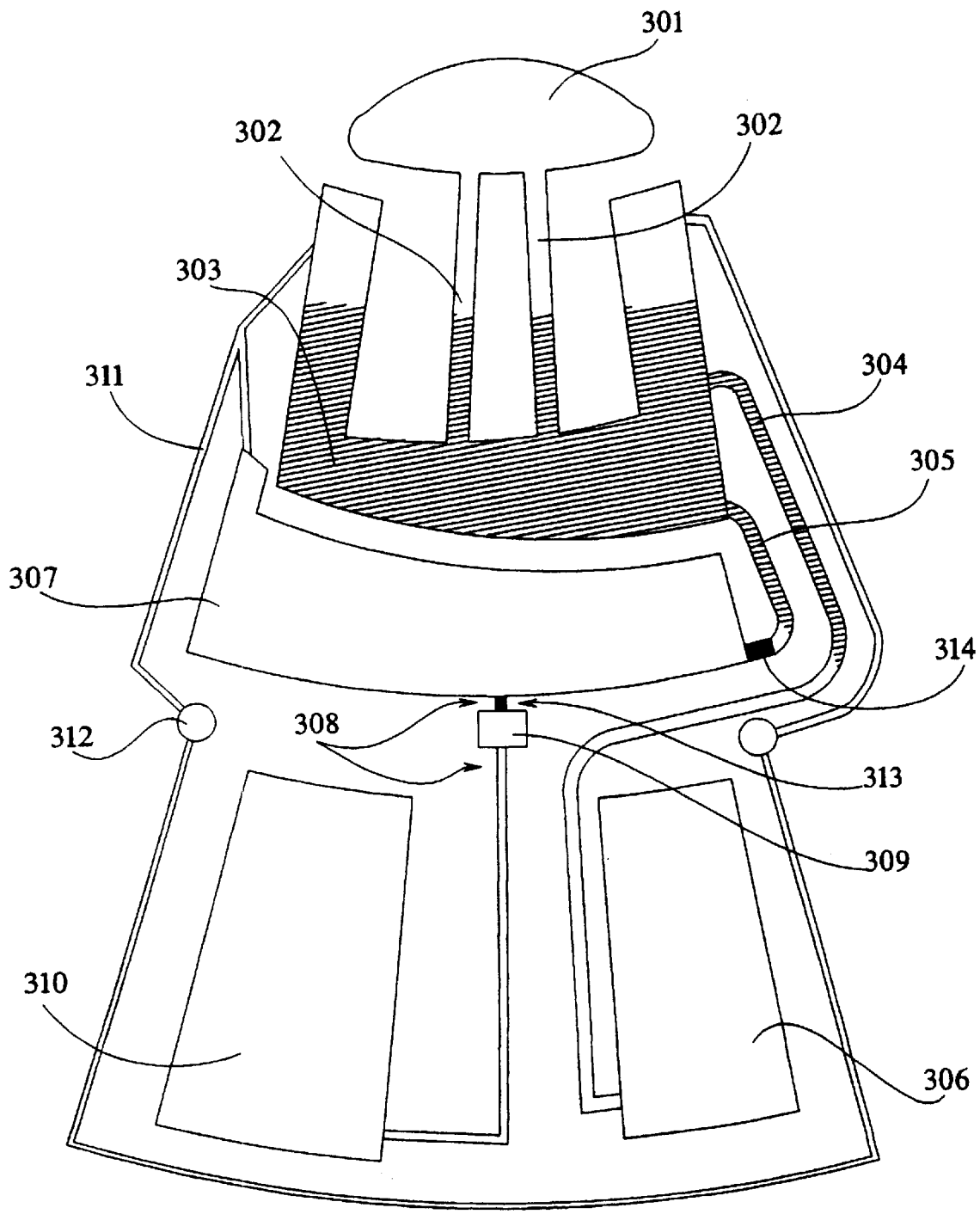
Figure 6G:
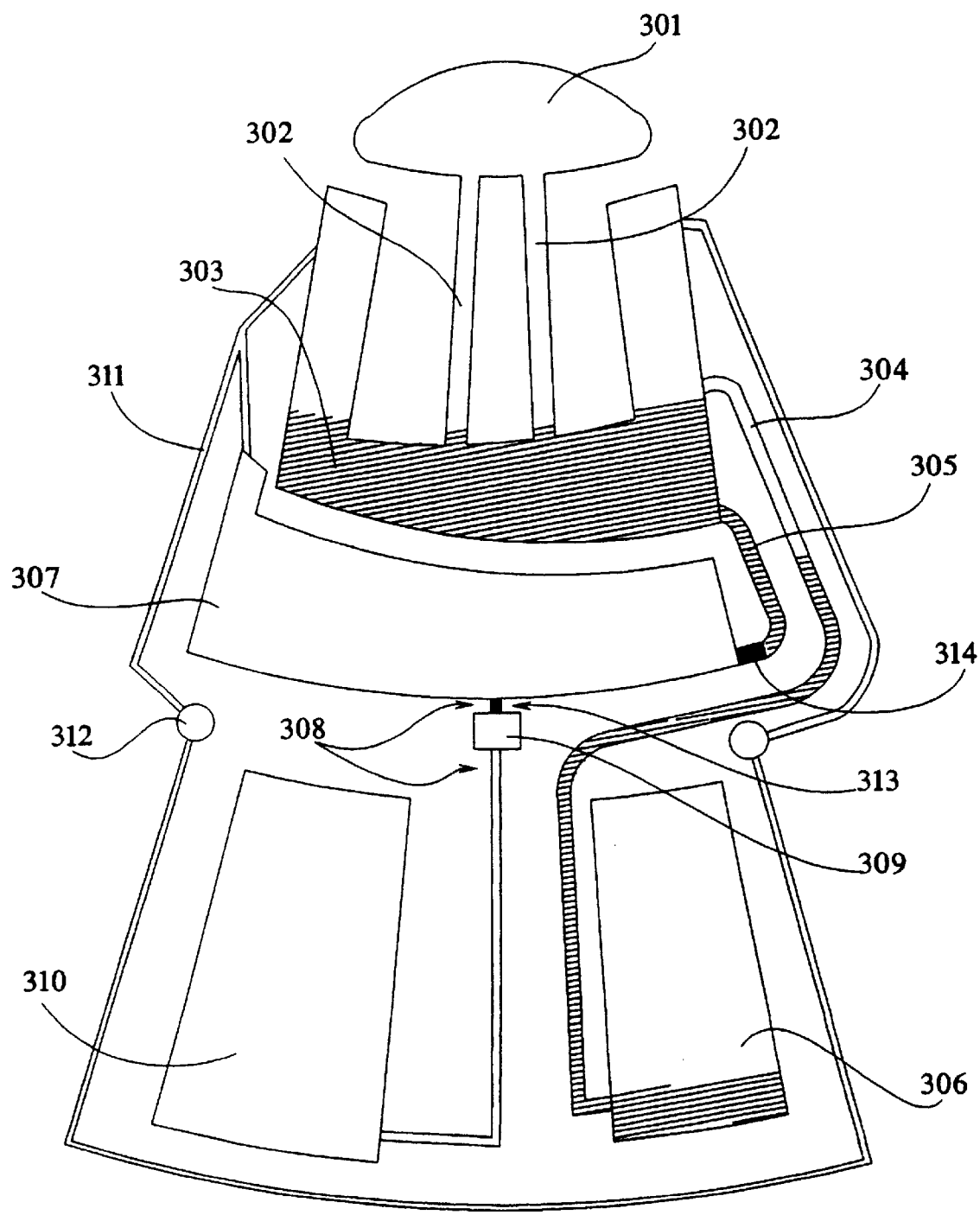

The use of this platform is illustrated in FIGS. 6A through 6J. An imprecise volume (ranging from 1–150 μL of fluid) of a fluid is applied to the entry port 301 (FIG. 6A). Fluid wicks into entry capillary 302 and stops at the capillary junction between entry capillary 302 and the first fluid chamber 303 (FIGS. 6B and 6C). Fluid flows through the entry capillary B and into the first fluid chamber 303 at a first rotational speed $f_1$, ranging from 100–500 rpm; the exact value is dependent on the position of the components on the platform (FIGS. 6D and 6E). For example, for an entry port 301 having a depth of 0.75 mm, entry capillary 302 having dimensions of 0.25 mm×0.5 mm in cross-section and a length of 0.5–1 cm from the center of rotation, this first rotational speed $f_1$ is equal to about 250 rpm for either water or milk. The fluid further enters capillary channel 305, stopping at the capillary junction with the second fluid chamber 307. As rotation continues, the fluid continues to fill the first fluid chamber 303, overflow capillary 304 fills (FIG. 6F), and excess fluid fills overflow chamber 306 until the level of fluid in the first fluid chamber 303 falls below the position of overflow capillary 304 (FIG. 6G).

Figure 6H:
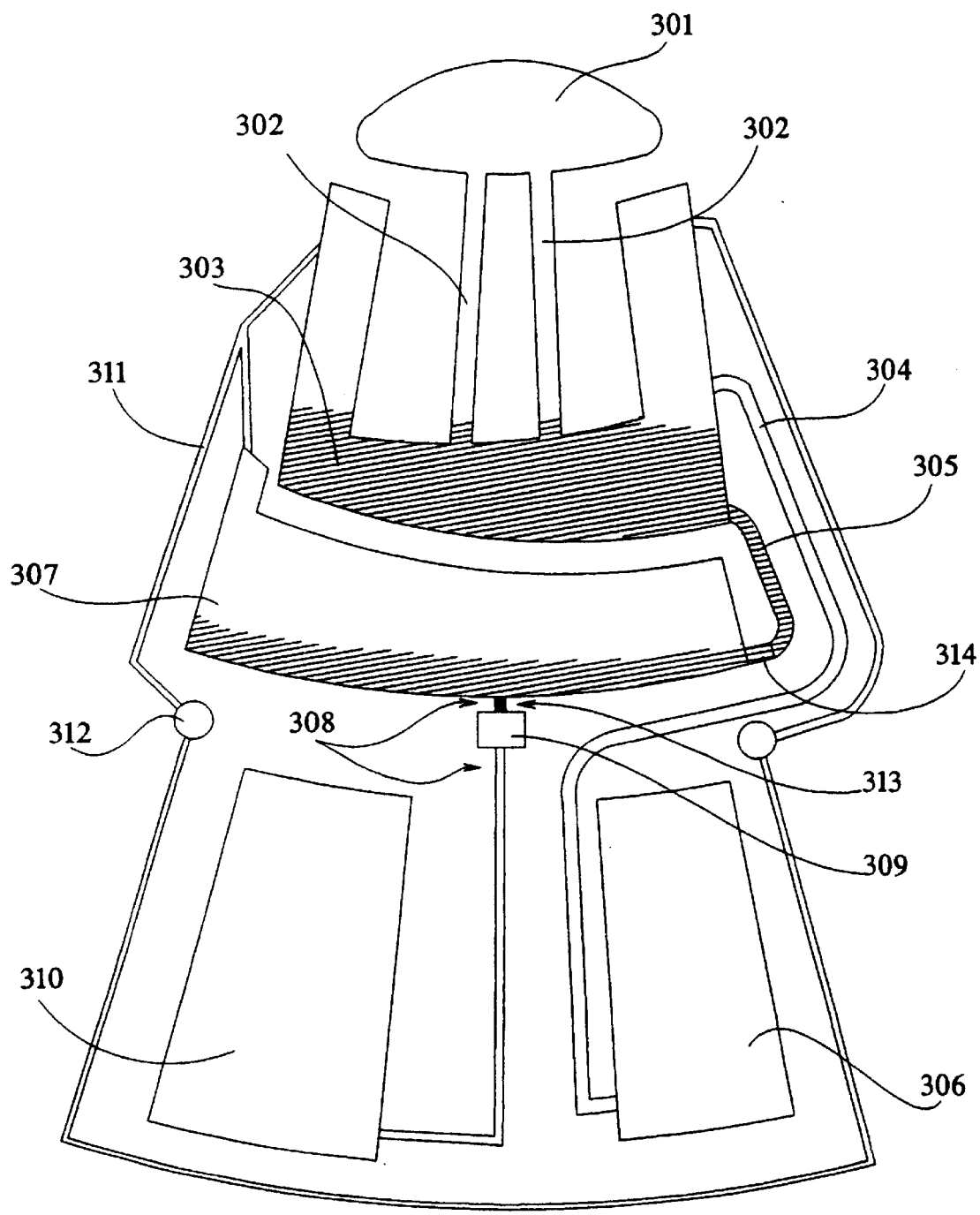
Figure 6I:
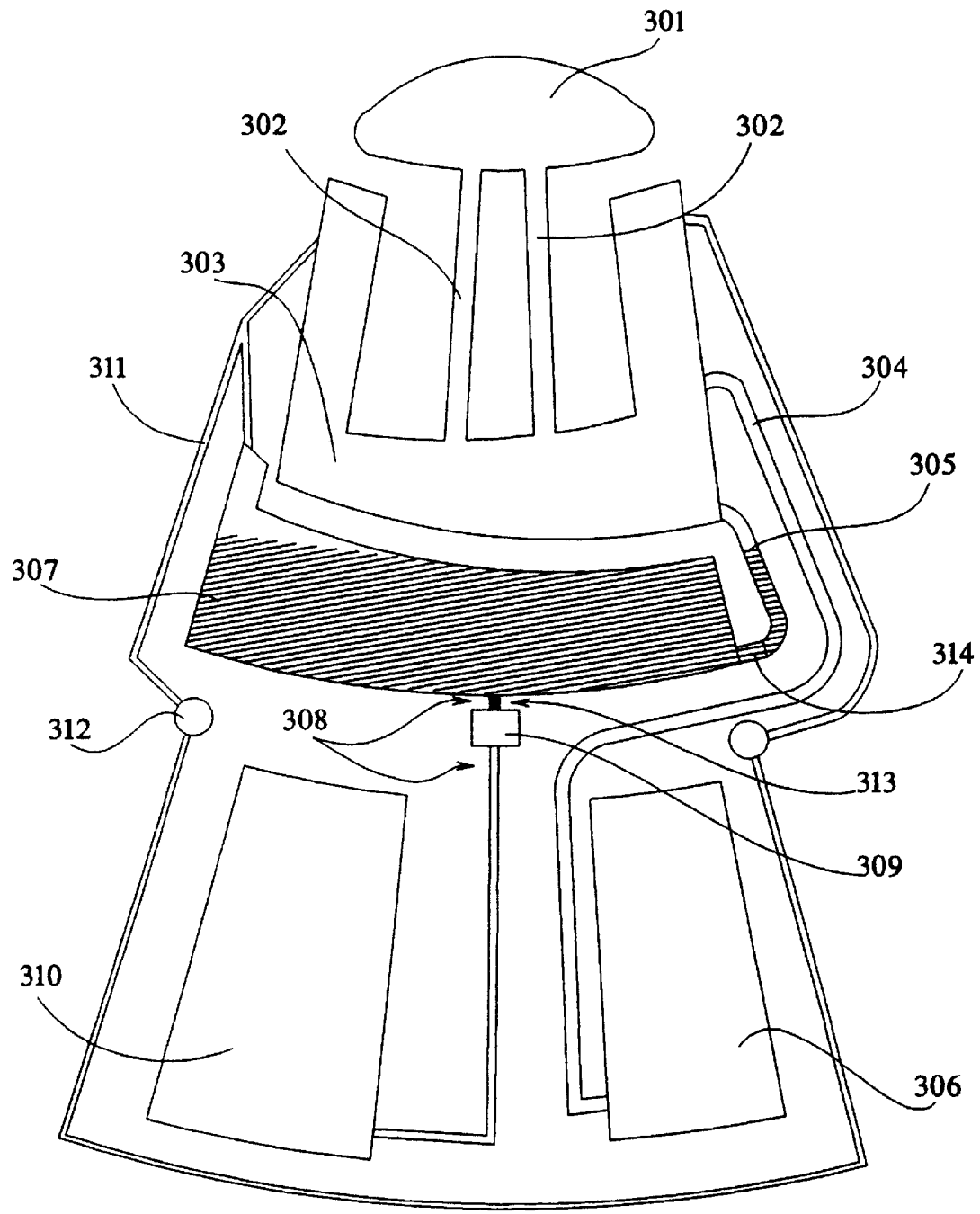
Figure 6J:
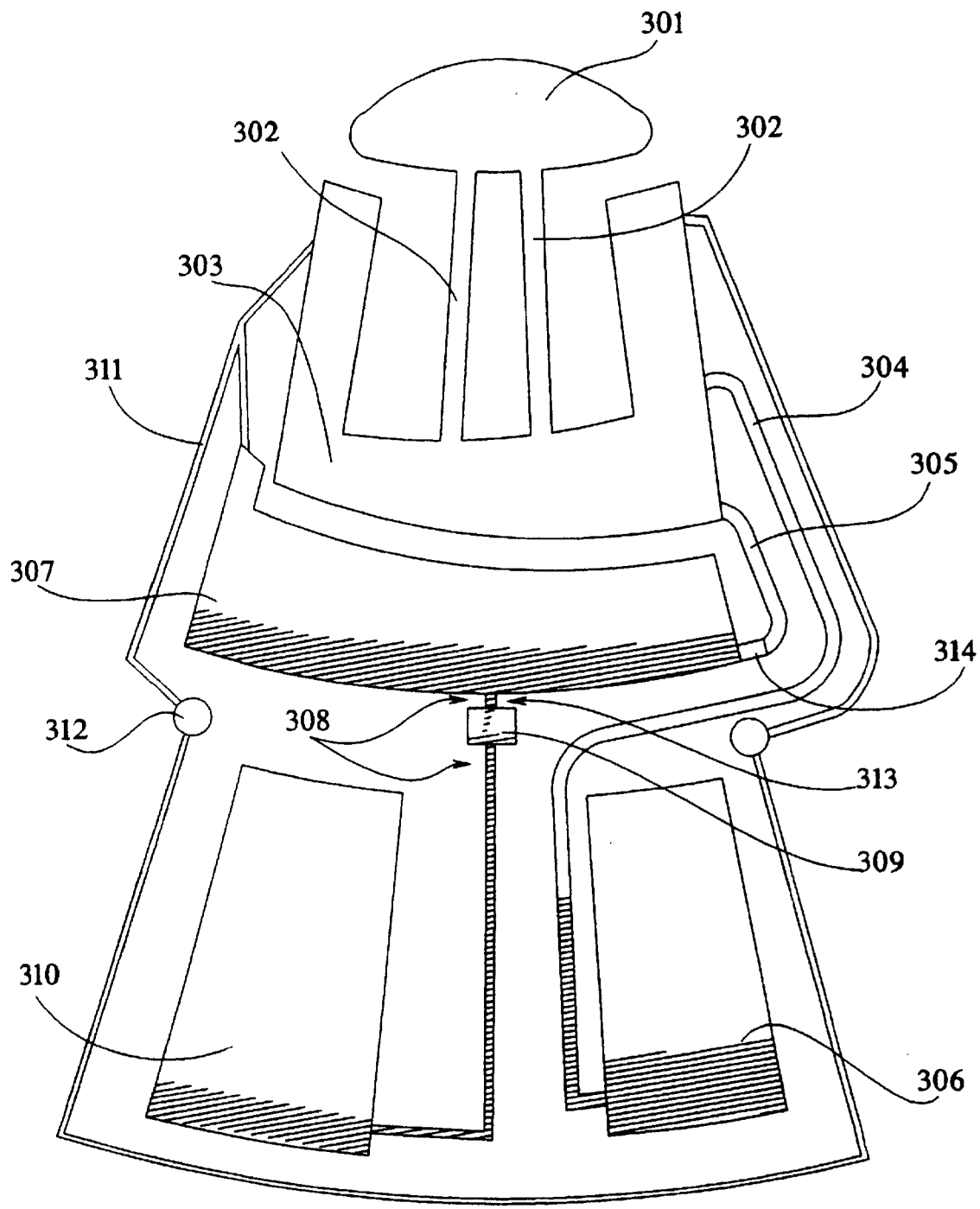
Figure 6K:
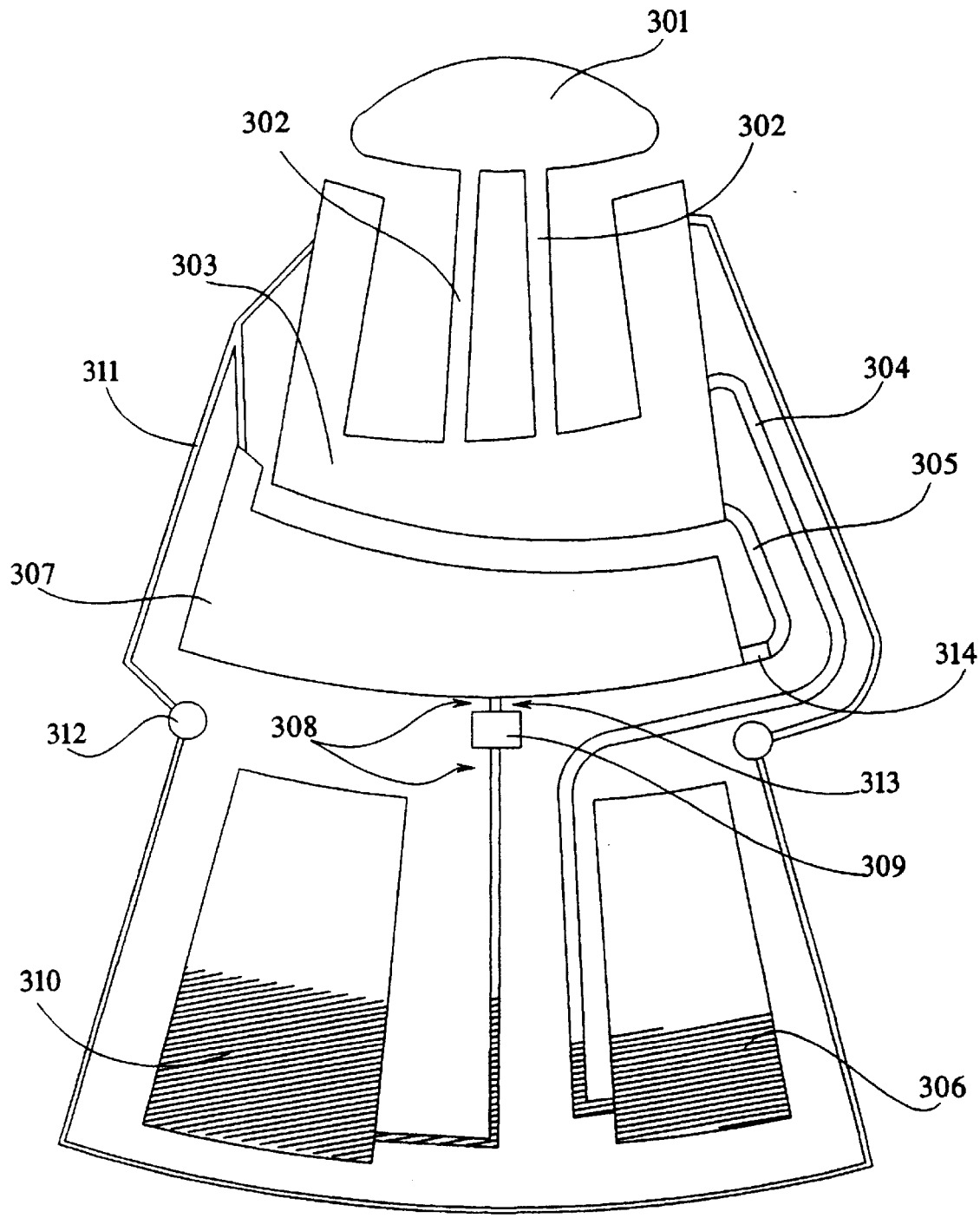

At a second rotational speed $f_2$, that is greater than the first rotational speed $f_1$, typically in the range of 100–1000 rpm, the capillary junction between channel 305 and the second fluid chamber 307 is overcome, and fluid remaining in the first fluid chamber 303 is delivered into the second fluid chamber 307 (FIGS. 6H and 6I). For example, for channel 305 having dimensions of 0.25 mm×0.5 mm in cross-section and a length of 2.5–3.3 cm from the center of rotation, this second rotational speed is equal to 280 rpm for either water or milk.

In an alternative embodiment, a sacrificial valve 314 is placed at the junction of channel 305 and the second fluid chamber 308, which sacrificial valve is released to permit fluid flow through channel 305 and into the second fluid chamber 308. In such embodiments, fluid flow can be achieved at either $f_1$ or $f_2$ rotational velocity.

Figure 5:
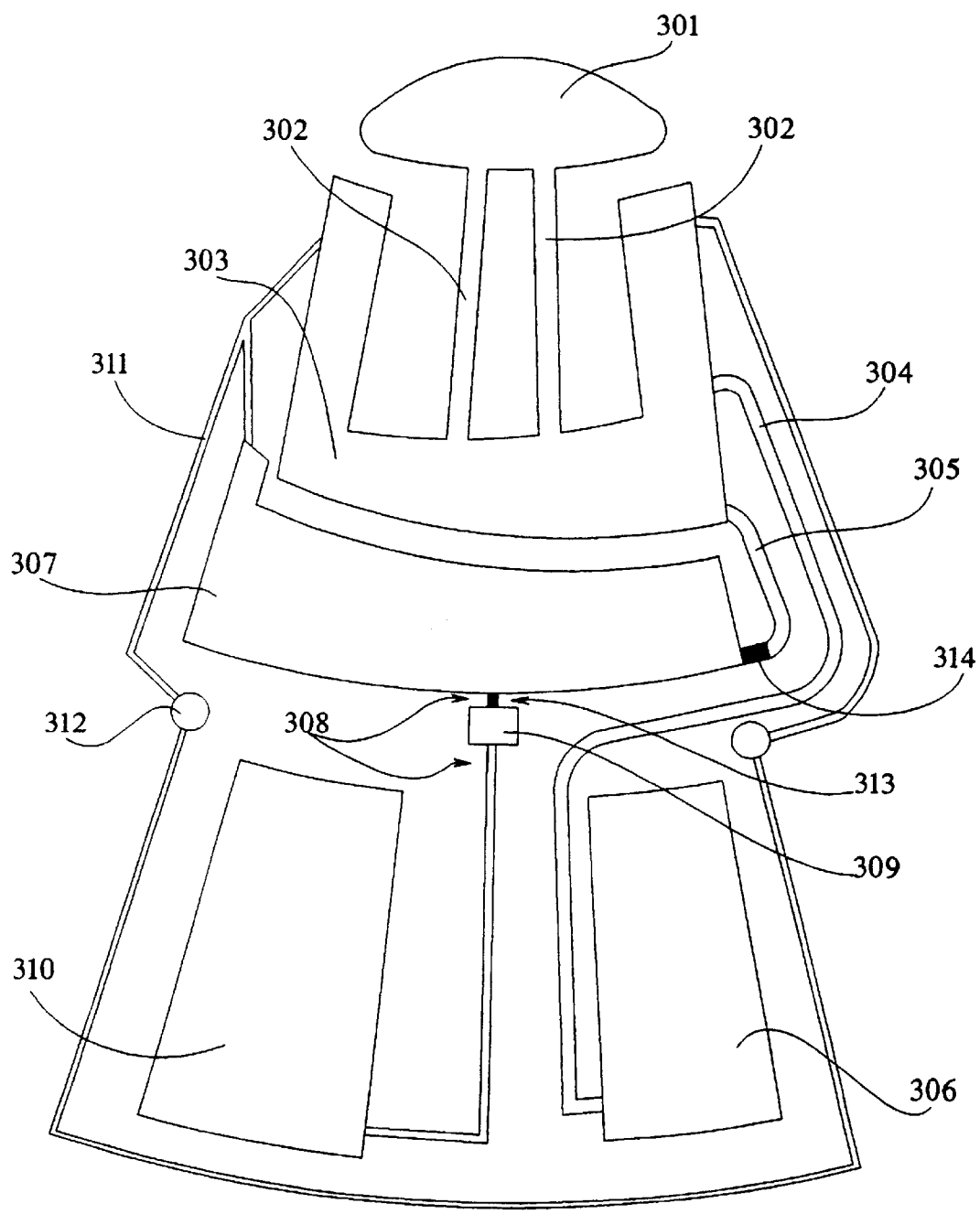

In embodiments comprising a sacrificial valve 313 in-line with capillary 308 at position 309 shown in FIG. 5, release of the sacrificial valve results in fluid flow into the third fluid chamber 310. Sacrificial valves are as described above are preferably made of a fungible material that can be removed from the fluid flow path. In preferred embodiments, said sacrificial valves are wax valves and are removed from the fluid flow path by heating, using any of a variety of heating means including infrared illumination and most preferably by activation of heating elements on or embedded in the platform surface as described below. In said embodiments, fluid flow is achieved at rotational speed $f_2$ with removal of the sacrificial valve.

In embodiments of the platforms of the invention comprising antibiotic arrays as described herein and not containing a sacrificial valve at position 310, capillary 309 preferably fills along with filling of the second chamber 308 until the fluid reaches a capillary junction 309 at the junction between capillary 308 and the third fluid chamber 310; in such embodiments, the capillary junction has a depth of about 0.75 mm (ranging from about 0.25 mm to about 1 mm). At a third rotational speed $f_3$, that is greater than the second rotational speed $f_2$, typically in the range of >500 rpm, the fluid contained in the second chamber 308 is delivered into the third fluid chamber 310 (FIGS. 6H through 6K). For example, capillary 309 having dimensions of 0.25 mm×0.25 mm in cross-section and a length of 3.36–3.7 cm from the center of rotation, this third rotational speed is equal to 400 rpm for either water or milk.

This embodiment of the platforms of the invention can be used for any two-step analytical assay. Using the antibiotic assay described above as an example, the second fluid chamber 308 contains a reagent, such as carboxypeptidase, and its substrate, for example L-lysine-D-alanine-D-alanine, and incubation is performed therein to produce D-Ala. The remaining reagents are placed in the third fluid chamber 310, and the reaction including color development advantageously proceeds in situ whereby chamber 310 is a read chamber. The extent of chromogen production is detected in the read chamber, and related to the presence of antibiotics in the sample by comparison with samples tested in the absence of antibiotic. Most preferably, a standard curve relating the decrease in chromogen production and the amount of antibiotic in the sample is prepared and used to determine the amount of antibiotic in an unknown test sample.

The invention also provides microfluidics arrays for separating the fluid component from a particulate suspension. An example of such a particulate suspension is blood, where red and white blood cells are suspended in plasma. Thus, this aspect of the microfluidics embodiments of the invention is illustrated using separation of blood plasma from whole blood.

Figure 7:
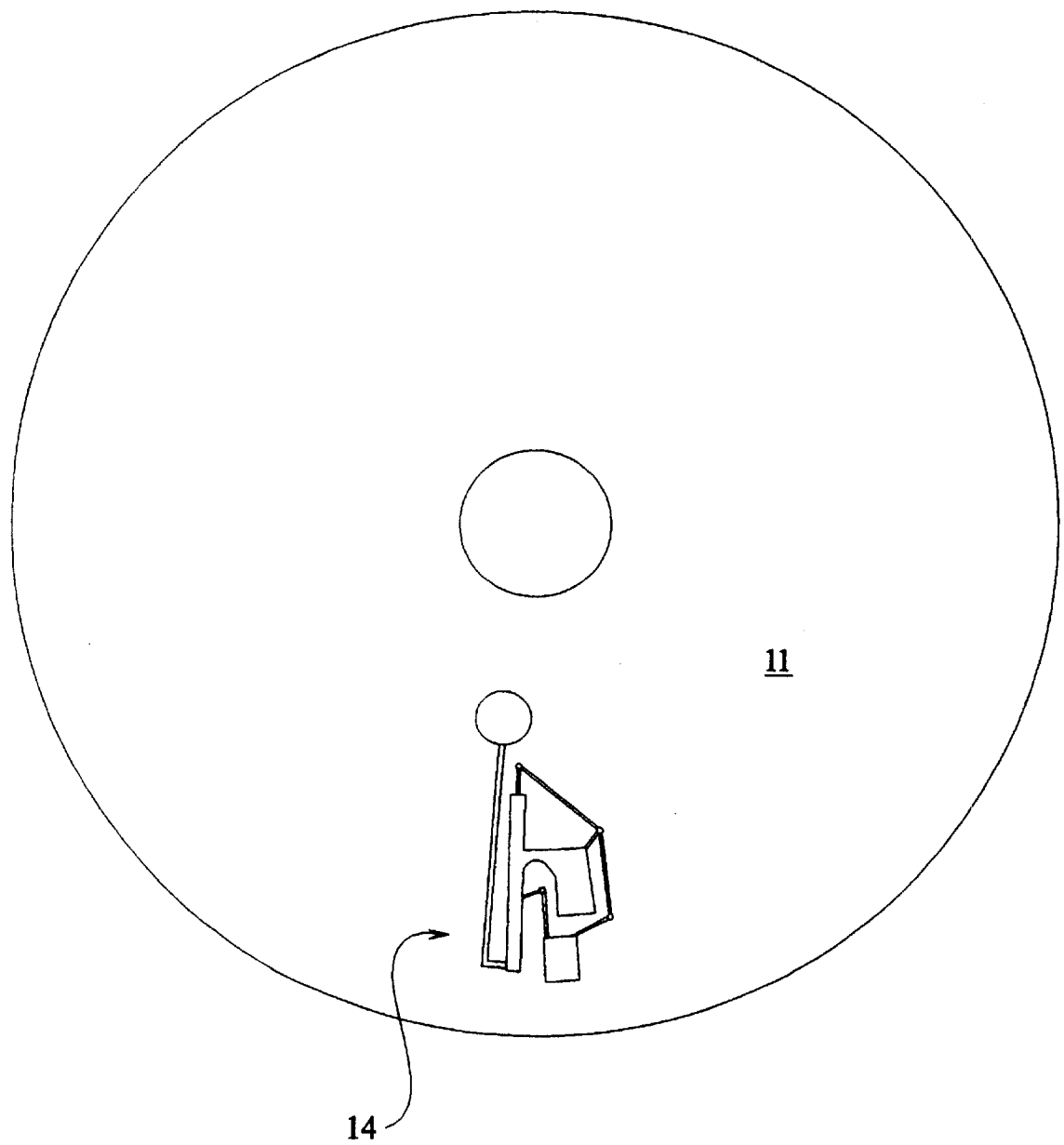
FIGS. 7 through 9 illustrate the microfluidics array of the microsystem platform described in Example 3.
Figure 8:
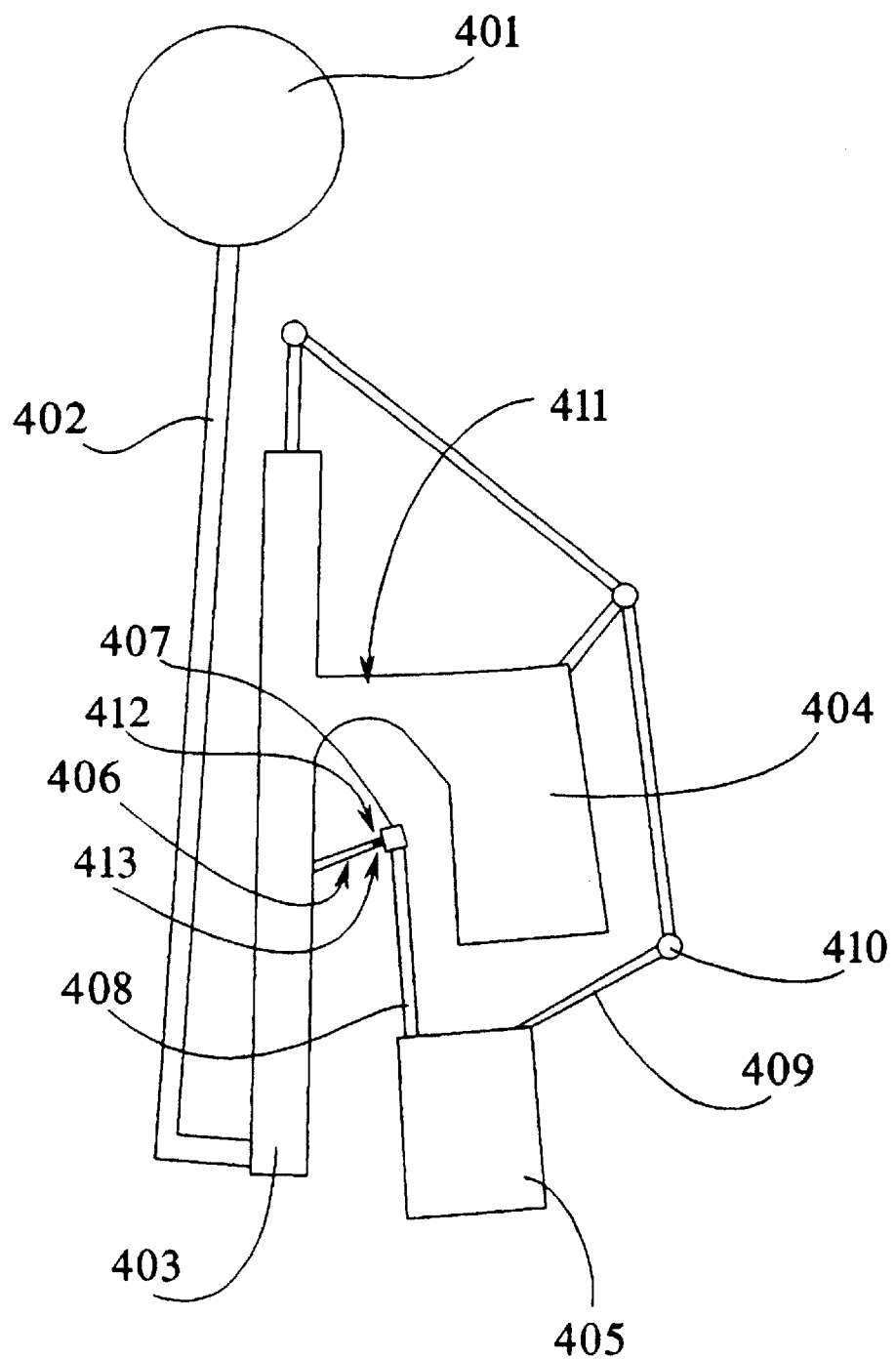

A microsystems platform provided by the invention and specifically designed for separating vertebrate blood cells and components is illustrated in FIGS. 7 through 9. In FIG. 7, the arrangement of one assay array 14 on a disk 11 is shown; a multiplicity of such arrays can be advantageously arranged on a microsystems platform, most preferably a disk, of the invention, to provide a multi-use or multi-assay platform.

The components of the blood separation array are shown in greater detail in FIG. 8. It will be understood by a comparison of FIGS. 7 and 8 that the center of the platform 11 is at the top of FIG. 8, and the edge or lateral extent of the platform is at the bottom of FIG. 8, illustrated by a curved line. Rotation of the blood separation array on platform disks of the invention can be in either direction, although rotation in a consistent, particular direction is preferred. Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume was about 1–50 μL.

The components of the blood separation array are as follows. An entry port 401 having a depth in the platform surface ranging from about 0.1 mm to about 5 mm and lateral dimensions of about 0.1 to about 2 cm is constructed on the platform, and designed to accommodate a volume of about 5 to about 50 μL. This entry port is fluidly connected to an entry capillary 402, having a cross-sectional diameter of from about 0.02 mm to about 1 mm and a depth of about 0.5 to 1 mm. The length of this entry capillary was sufficient to contain a total volume of from about 1 to about 15 μL. Entry capillary 402 is further fluidly connected to a separation column 403 having a cross-sectional diameter of from about 0.1 mm to about 2 mm, a depth of from about 0.25 mm to about 1 mm, and a length sufficient to contain a total volume of 10 to about 20 μL. This separation column is also fluidly connected with a passage 411 to overflow chamber 404. Passage 411 has a cross-sectional diameter ranging from about 0.5 mm to about 2 mm, a depth of about 0.25 mm to about 1 mm, and a length of 0.5 mm to about 5 mm). Overflow chamber 404 has a depth of from about 0.25–1 mm.

A small capillary exit 406 is also fluidly connected with separation chamber 403, having a cross-sectional diameter of from about 0.05 mm to about0.25 mm, a depth of about 0.025 mm to about 0.125 mm, and a length about 0.25 mm to about 5 mm. This capillary is arranged to traverse a direction radially more proximal to the axis of rotation than the insertion point with separation column 403. This small capillary 406 terminates in a capillary junction 407 that is fluidly connected with capillary 408, extending in a radial direction to decant chamber 405. A sacrificial valve 413 is positioned in small capillary 406 at the juncture with the capillary junction. Capillary 408 has a cross-sectional diameter ranging from about 0.05 mm to about 1 mm, a depth of about 0.05 mm to about 1 mm, and a length of from about 1 mm to about 100 mm. This capillary is arranged in a radially outward direction between capillary junction 407 and decant chamber 405. Passage 411 is positioned on separation column 403 to be significantly more proximal to the axis of rotation than the insertion point of small capillary 406.

Air displacement channels 409 that have dimensions of from about 0.02 mm to about 1 mm permit venting of air displaced by fluid movement on the platform. Capillary junctions 410 that are about 0.75 mm deep are present in the air channels to prevent fluid flow into the air channels.

Figure 9A:
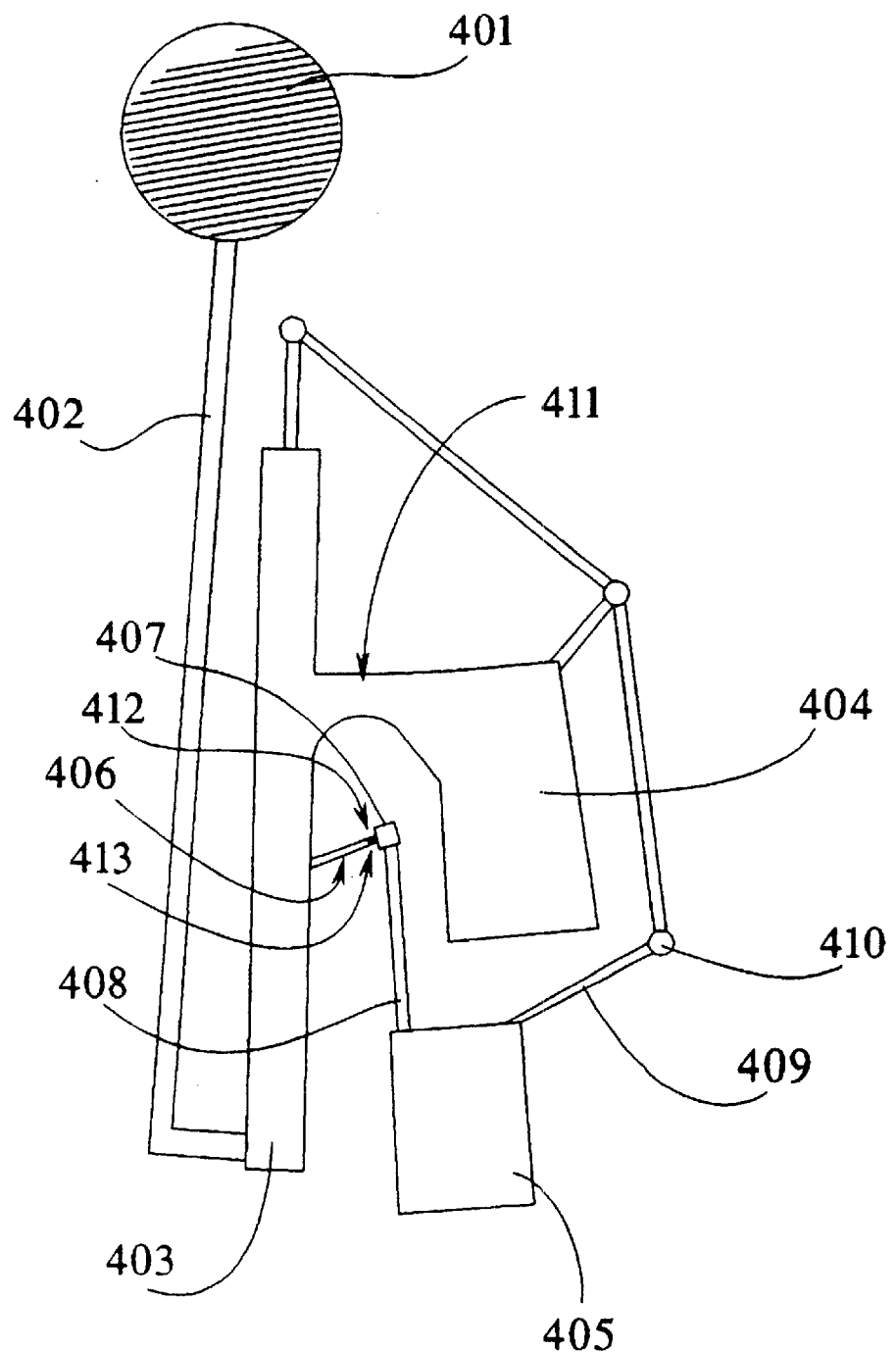
Figure 9B:
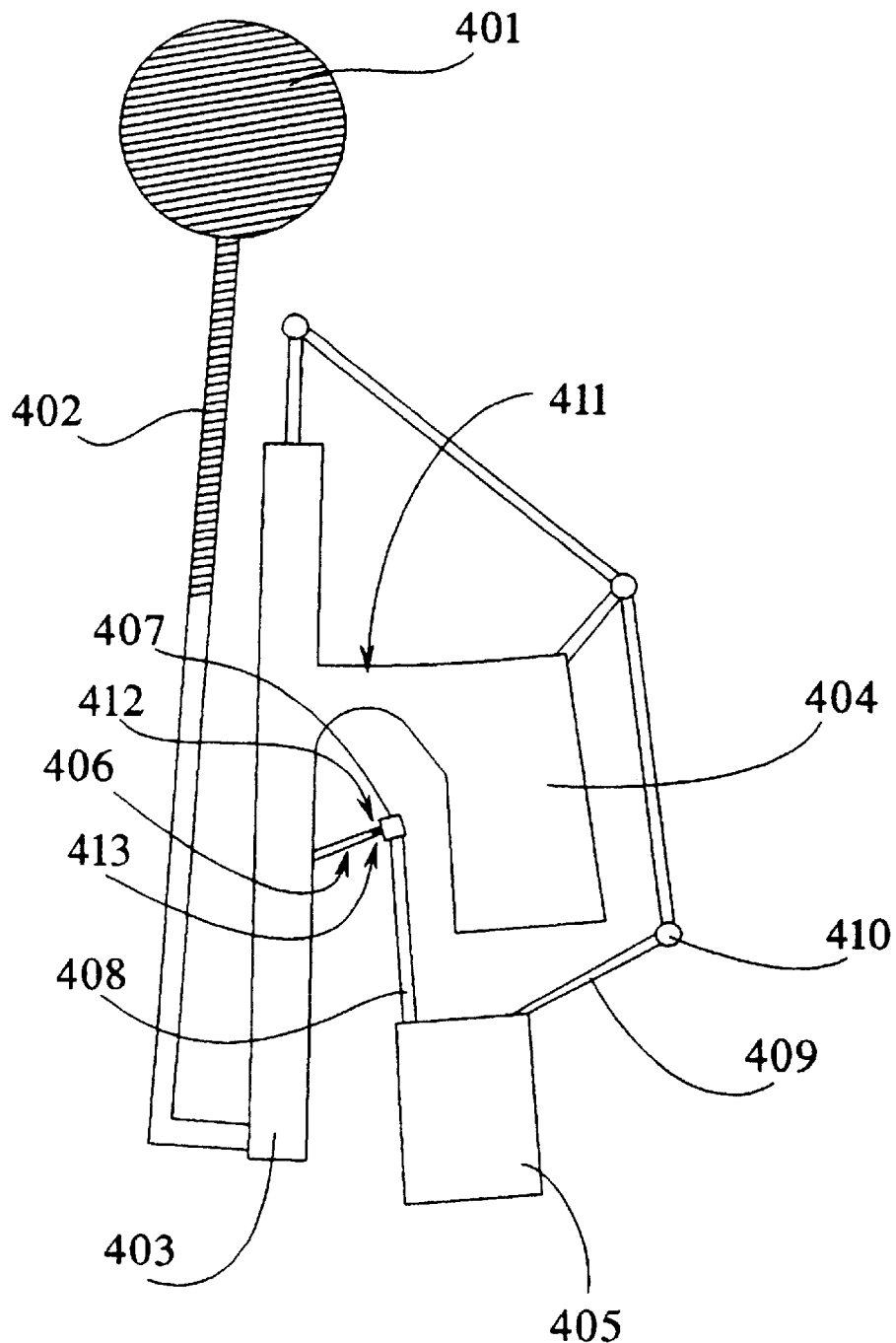
Figure 9C:
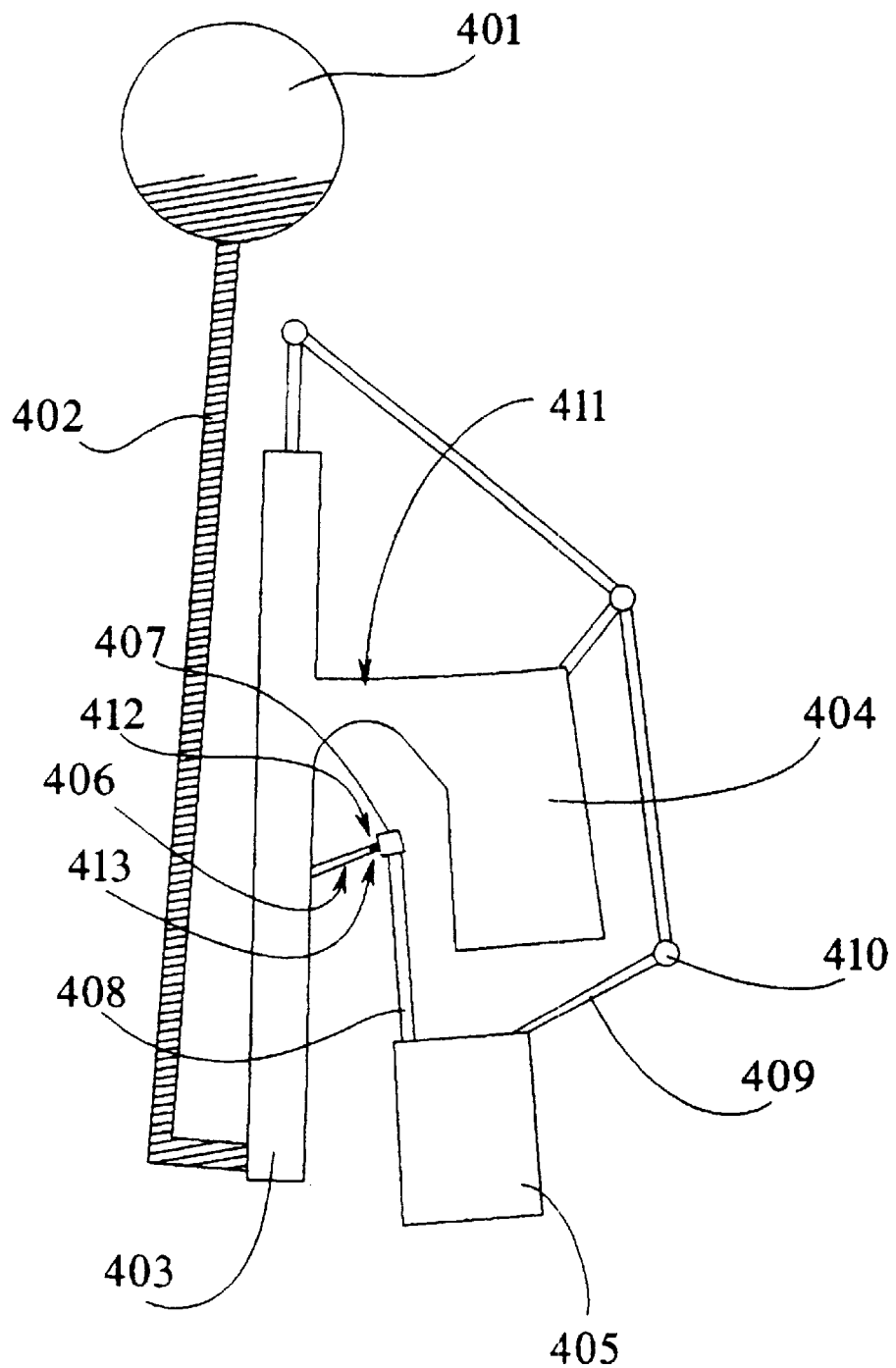

The use of this platform is illustrated in FIGS. 9A through 9H for separating plasma from whole blood. An imprecise volume (ranging from 1–150 μL of fluid) of blood is applied to the entry port 401 (FIG. 9A). Blood enters the entry capillary 402 by capillary action, and stops at the capillary junction between entry capillary 402 and the separation chamber 403 (FIGS. 9B and 9C).

Figure 9D:
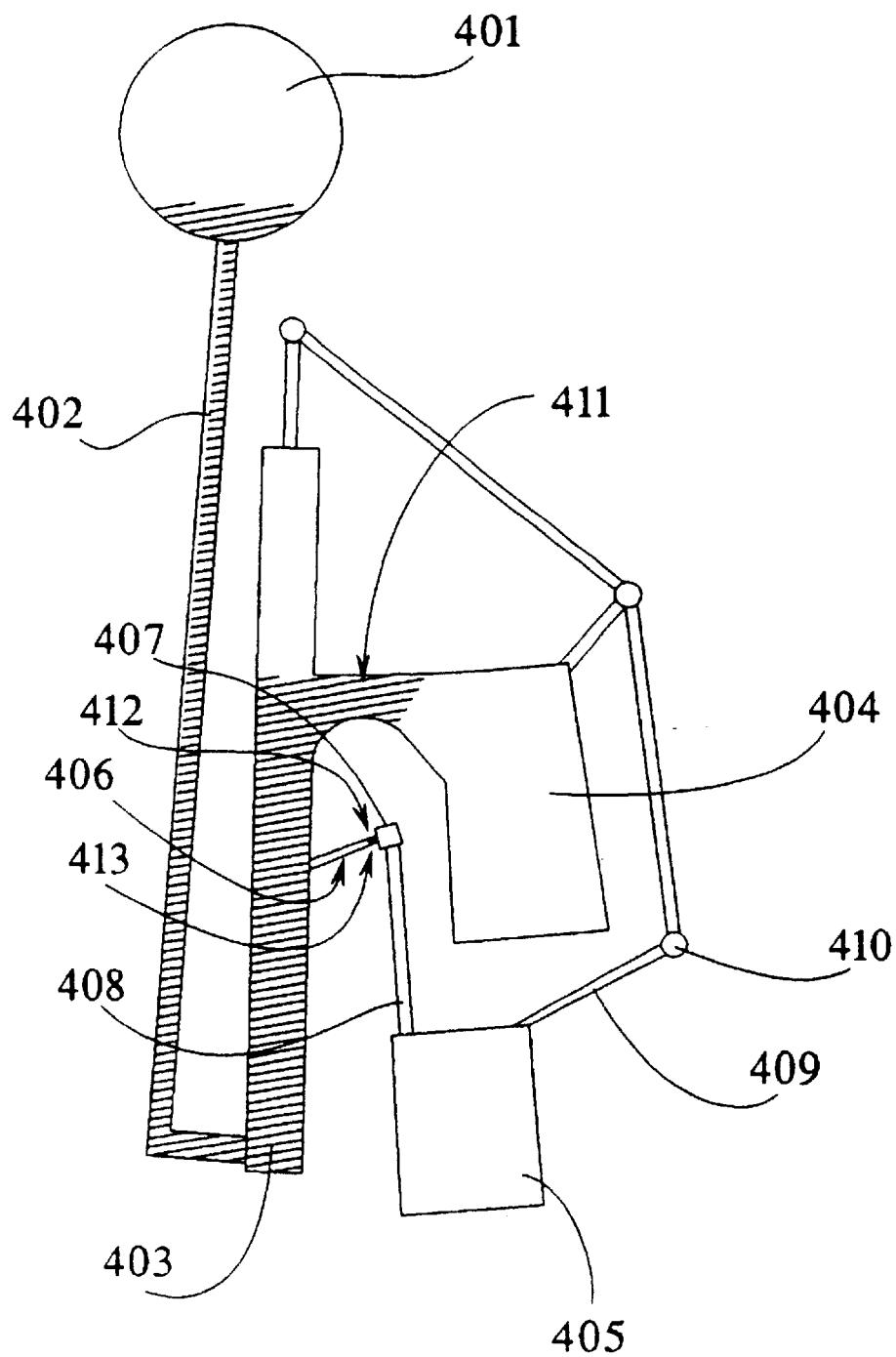
Figure 9E:
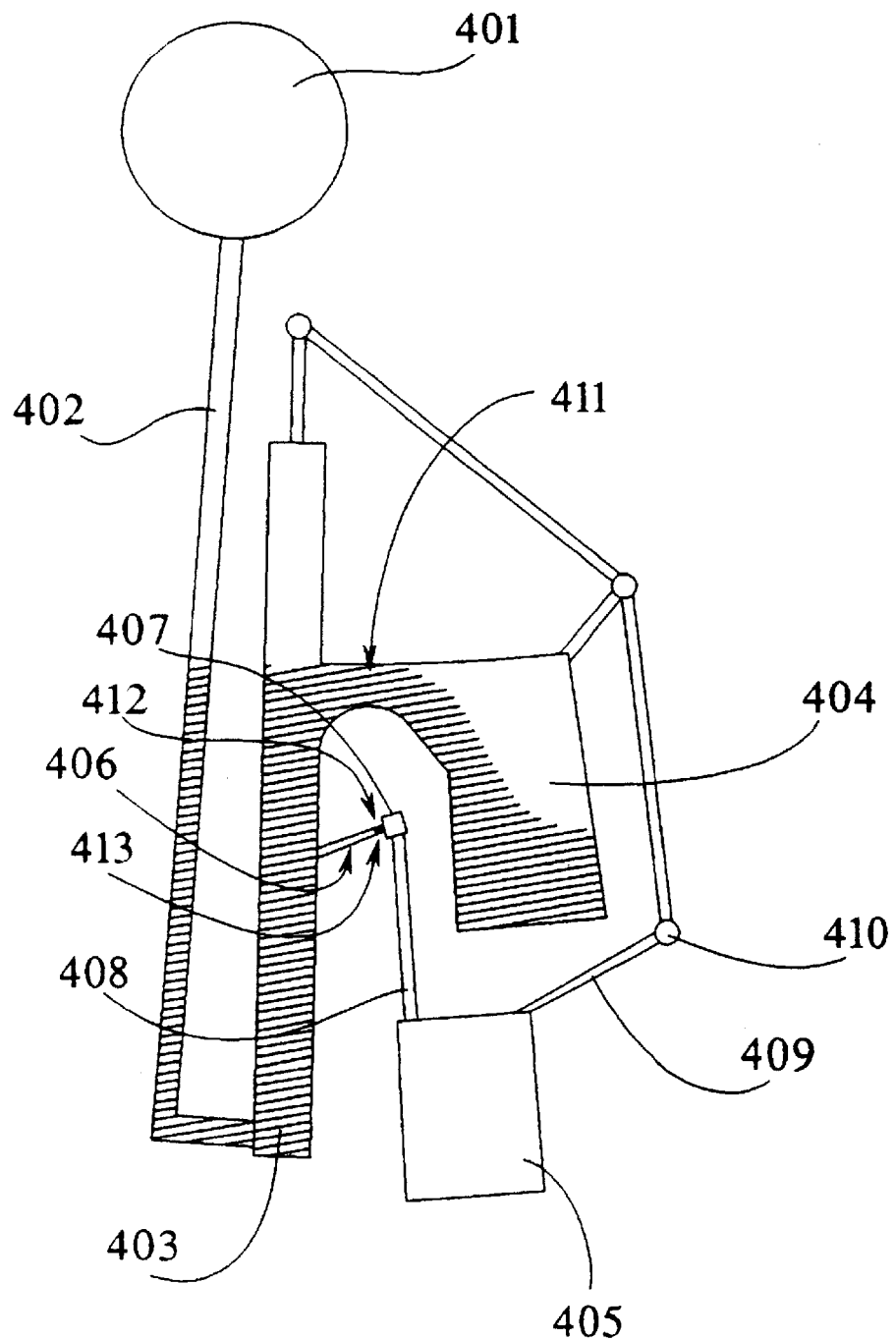

At a first rotational speed $f_1$, ranging from 100–300 rpm (the exact value is dependent on the position of the components on the platform), blood flows from the entry capillary 402 into separation chamber 403 (FIG. 9D). Blood continues to fill separation column 403 until blood reaches the position of passage 411, whereupon excess blood flows through passage 411 and into overflow chamber 404 (FIGS. 4E and 4F). Advantageously, small channel 406 has dimensions that prevent wicking of blood into the channel as blood flows past the insertion point of small channel 406 into separation column 403.

Figure 9F:
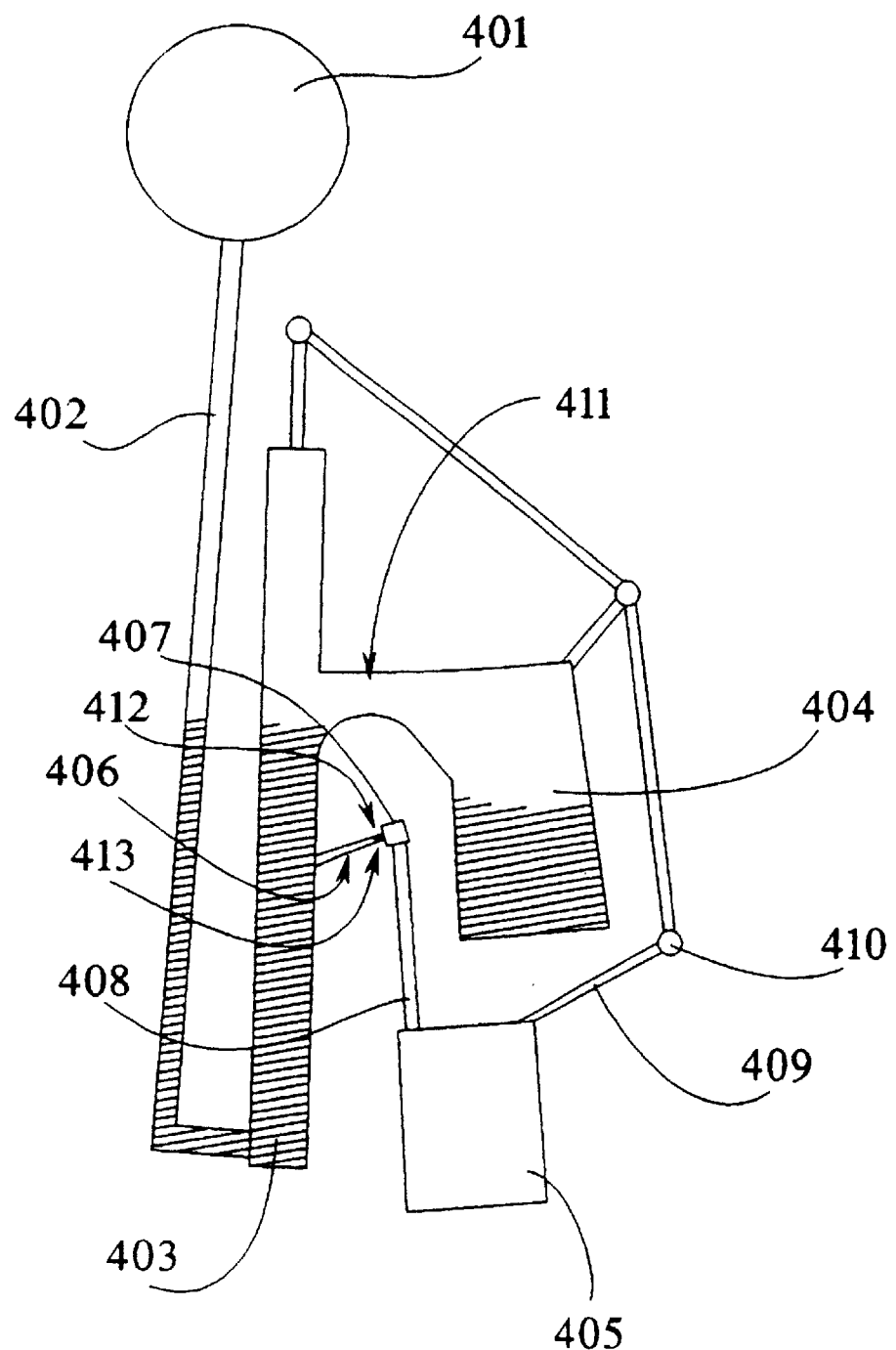
Figure 9G:
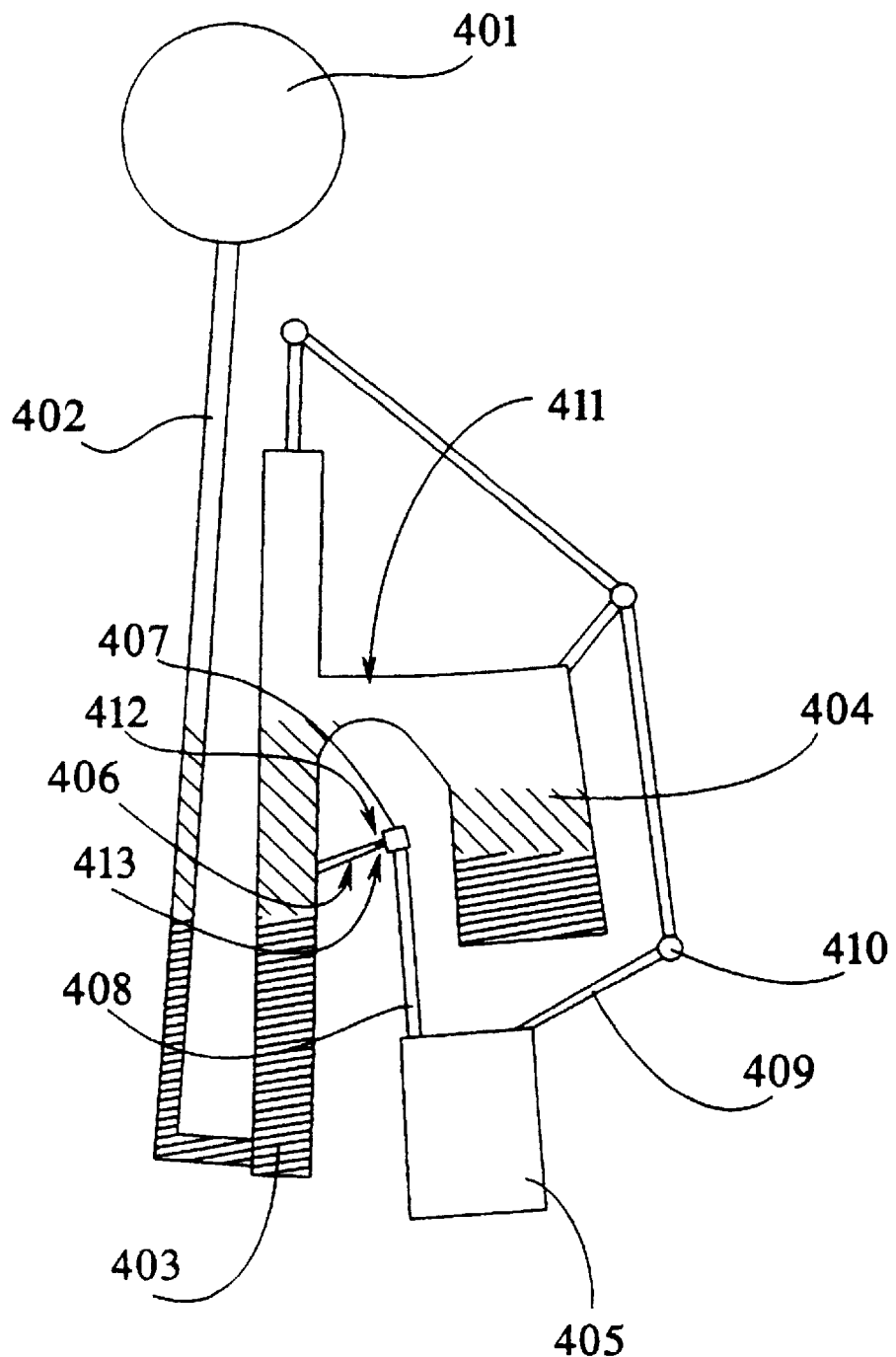
Figure 9H:
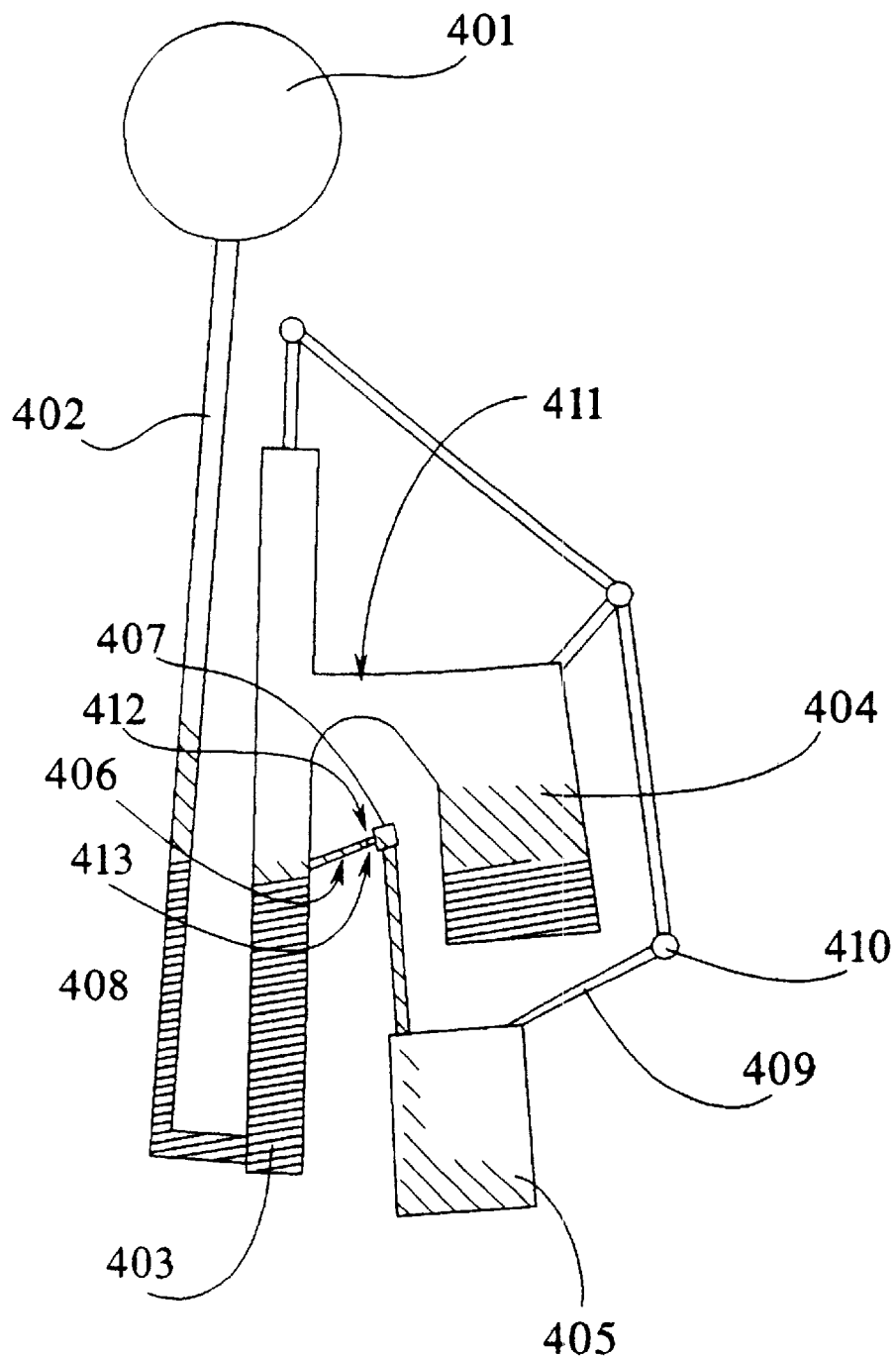

As shown in FIG. 9F, after sufficient time of rotation at the first non-zero rotational speed $f_1$, the excess blood has been transferred into overflow chamber 404 and the separation column 403 is filled with blood to the position of passage 411. Rotation at a second rotational speed $f_2$, that is greater than the first rotational speed $f_1$, typically in the range of 1000–5000 rpm, blood components are separated into red blood cell, white blood cell (i.e., "buffy coat"), and plasma fractions (FIG. 9G). Advantageous dimensions of small capillary 406 permit fluid flow of the plasma fraction through capillary 406 that is stopped at capillary junction 407. Fluid flow of plasma into decant chamber 405 results from fluid flow overcoming the capillary barrier 407 by rotation at a third rotational speed $f_3$, that is greater than the second rotational speed $f_2$, typically in the range of >1000–5000 rpm (FIG. 9H).

Figure 10:
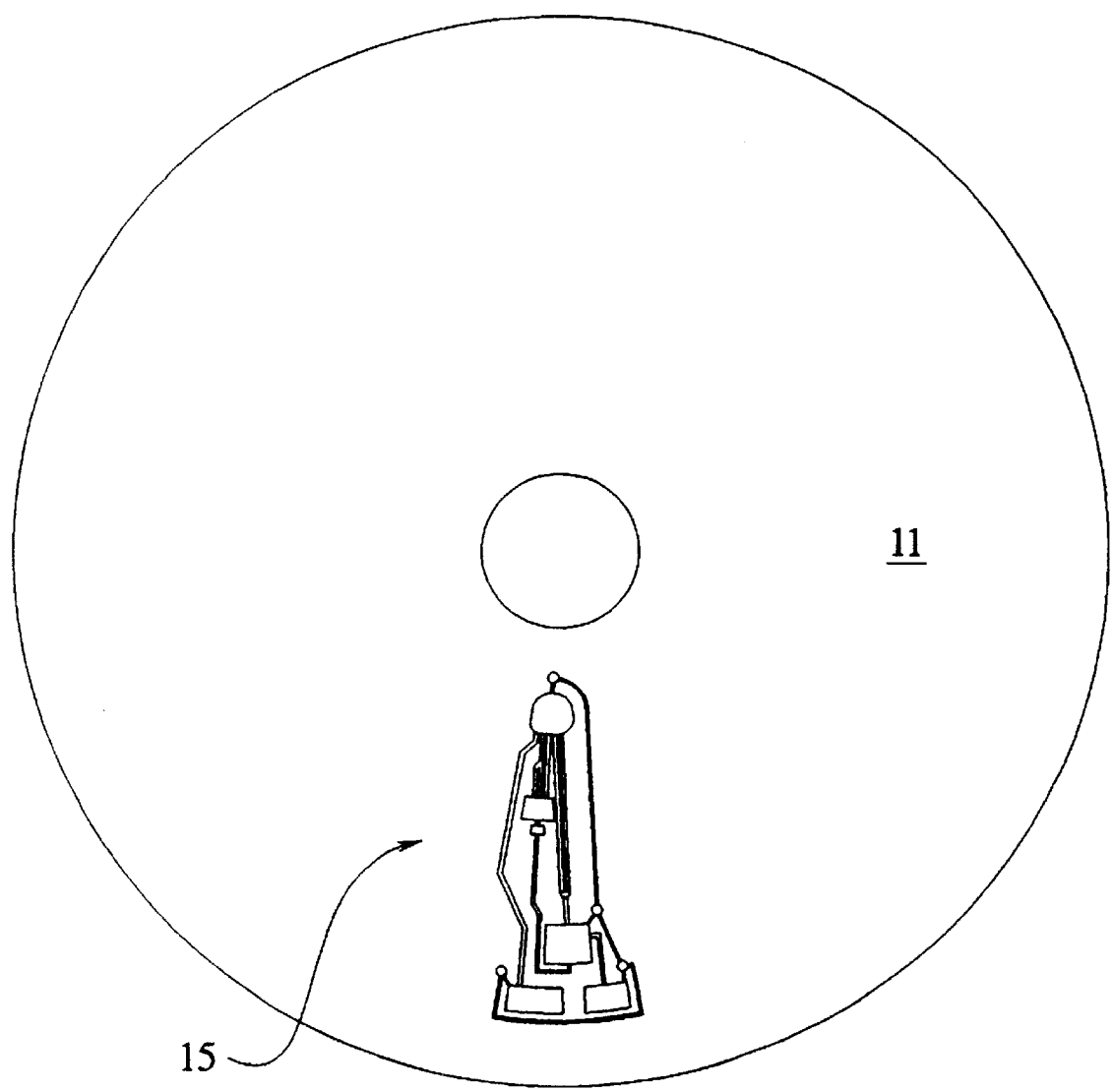
FIGS. 10 through 12 illustrate the microfluidics array of the microsystem platform described in Example 4.
Figure 11:
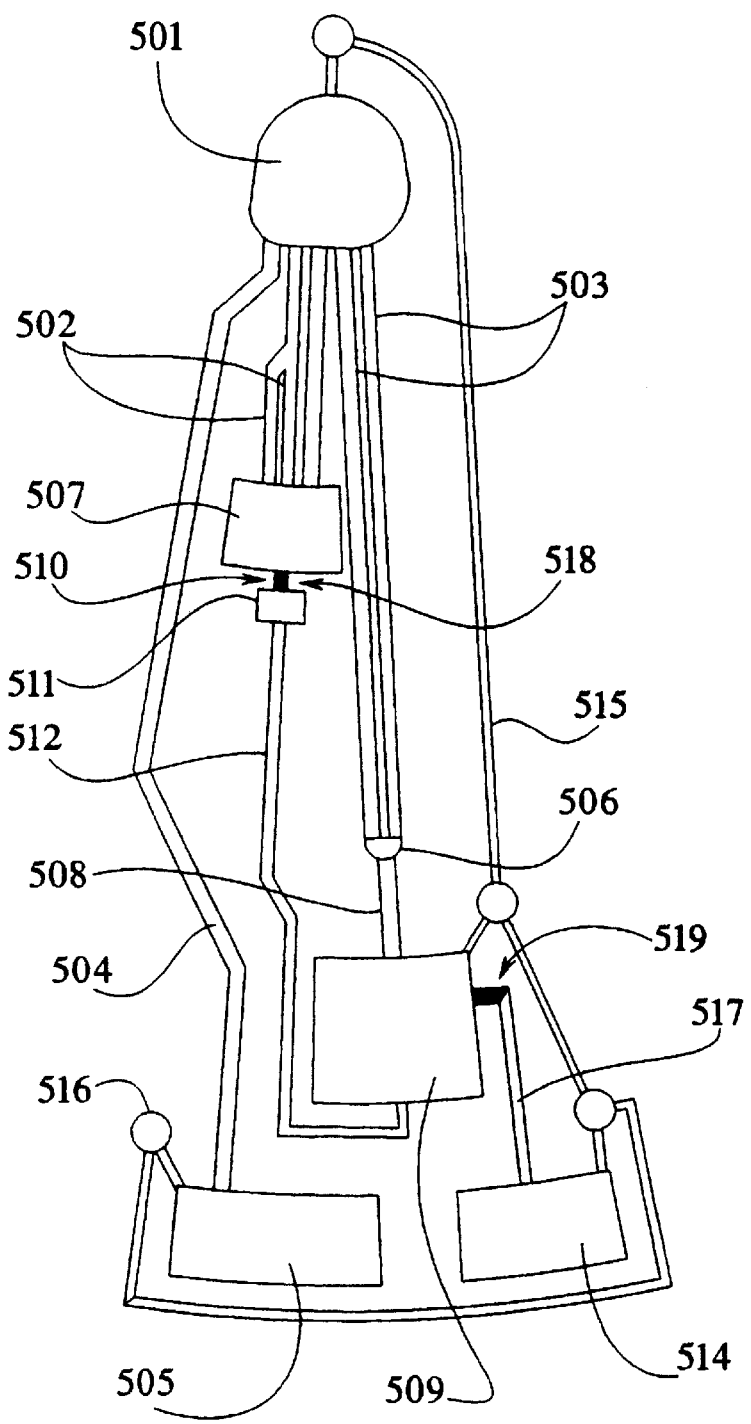

An alternative embodiment of the fluid separation platform is also provided by the invention, again illustrated by the separation of plasma from whole blood. This embodiment of the blood separation microfluidics array is shown in FIGS. 10 through 12. It will be understood that, as above, in FIG. 10, the arrangement of one separation array 15 on a disk 11 is shown; a multiplicity of such arrays can be advantageously arranged on a microsystems platform, most preferably a disk, of the invention, to provide a multi-use or multi-assay platform. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume was about 5–50 $\mu$L.

The components of this separation array are as follows. An entry port 501 having a depth in the platform surface of about 0.1 mm to about 1 mm and lateral dimensions of about 0.1 cm to about 2 cm is constructed on the platform, and designed to accommodate a volume of about 5 to about 50 $\mu$L. This entry port is fluidly connected with a first array of metering capillaries 502 and a second array of metering capillaries 503, wherein each of the capillaries has a cross-sectional diameter of from about 0.02 mm to about 1 mm. The length of the second metering capillary array 503 is longer than that of the first metering capillary array 502. The first metering capillary array 502 is fluidly connected with a ballast chamber 507, having a depth in the platform surface ranging radially from about 0.1 mm to about 5 mm and greater than the depth of the first metering capillary array 502, wherein the first metering capillary array 502 forms a capillary junction between the array and the ballast chamber. The second capillary array 503 is fluidly connected with capillary junction 506.

The entry port is also constructed to be fluidly connected with an overflow capillary 504 having a cross-sectional diameter of about 0.02 mm to about 1 mm and proximal ends rounded with respect to entry port 501. The overflow capillary is fluidly connected with an overflow chamber 505 having a depth in the platform surface of from about 0.1 mm to about 5 mm, greater than the depth of the overflow capillary 504. Each of the overflow and fluid chambers is also connected with air ports or air channels, such as 514, that have dimensions ranging from about 0.1 mm to about 1 mm and that permit venting of air displaced by fluid movement on the platform. Capillary junctions 516 that are about 0.75 mm deep are present in the air channels to prevent fluid flow into the air channels.

Entry port 501 is positioned on the platform from 0.5 cm to 20 cm from the center of rotation. Metering capillary array 502 extends from about 0.6 cm to about 10 cm from entry port 501. Metering capillary array 503 extends about 0.5 cm to about 10 cm from entry port 501. The length of metering capillary array 503 is about at least about 20% longer than metering capillary array 502, and the extent of the length of overflow capillary 504 is at least about 20% greater than the extent of the length of either the first metering capillary array 502 or the second metering capillary array 503. The position of ballast chamber 507 is about 1 cm to about 10 cm from the center of rotation, the position of capillary junction 506 is about 1.5 to 15 cm from the center of rotation, and the position of overflow chamber 505 is thus about 2.5 to about 20 cm from the axis of rotation.

The ballast chamber 507 acts as a capillary barrier that prevents fluid flow from the first metering capillary array 502 at a first, non-zero rotational speed $f_1$ sufficient to permit fluid flow comprising excess blood overflow from the entry port 501 through overflow capillary 504 and into overflow chamber 505. Capillary junction 506 is a capillary barrier that prevents fluid flow from the second metering capillary array 503 at said first, non-zero rotational speed $f_1$ sufficient to permit fluid flow comprising excess blood overflow from the entry port 501 through overflow capillary 504 and into overflow chamber 505. These capillary boundaries are constructed to be overcome at a second rotational speed $f_2$ (where $f_2 > f_1$).

Ballast chamber 508 is fluidly connected to capillary 510 that is from about 0.02 mm to about 1 mm deep and has a cross-sectional diameter of about 0.02 mm to about 1 mm and that extends from about 0.1 cm to about 5 cm. Capillary 510 is connected to capillary junction 511. Alternatively, capillary 510 is fluidly connected with a sacrificial valve 515. Sacrificial valves as described below are preferably made of a fungible material that can be removed from the fluid flow path. In preferred embodiments, said sacrificial valves are wax valves and are removed from the fluid flow path by heating, using any of a variety of heating means including infrared illumination and most preferably by activation of heating elements on or embedded in the platform surface. In said embodiments, fluid flow is achieved at rotational speed $f_2$ with removal of the sacrificial valve. Sacrificial valve 515 or capillary junction 511 are further fluidly connected with channel 512 which is from about 0.1 mm to about 1 mm deep and has a cross-sectional diameter of about 0.1 mm to about 1 mm. Channel 512 extends about 0.1 cm to about 20 cm and is fluidly connected with separation chamber 509 at a point most distal from the axis of rotation.

Second metering capillary array 503 is fluidly connected with capillary junction 506, which is overcome at a rotational speed $f_2 > f_1$. Capillary junction 506 is further fluidly connected to channel 508, which is further fluidly connected to separation chamber 509. Channel 508 is from about 0.02 mm to about 1 mm deep and has a cross-sectional diameter of from about 0.02 mm to about 1 mm. Channel 508 extends from about 0.2 cm to about 10 cm. Separation chamber 509 is from about 0.2 mm to about 5 mm deep and has a cross-sectional dimension ranging from about 1 mm to about 20 mm, and is positioned from about 10 mm to about 100 mm from the center of rotation.

Separation chamber 509 is fluidly connected with decant channel 517 at a point close to the chamber's most axis-proximal extent. Decant channel 517 is about 0.02 mm to about 1 mm deep and has a cross-sectional diameter ranging from about 0.02 mm to about 1 mm. Decant channel 517 extends from about 4.3 cm to about 5 cm and is fluidly connected with decant chamber 514. Decant chamber 514 is from about 0.2 mm to about 2 mm deep and has a cross-sectional diameter of from about 1 mm to about 10 mm. Decant chamber 514 is positioned about 5.2 cm from the center of rotation.

Figure 12A:
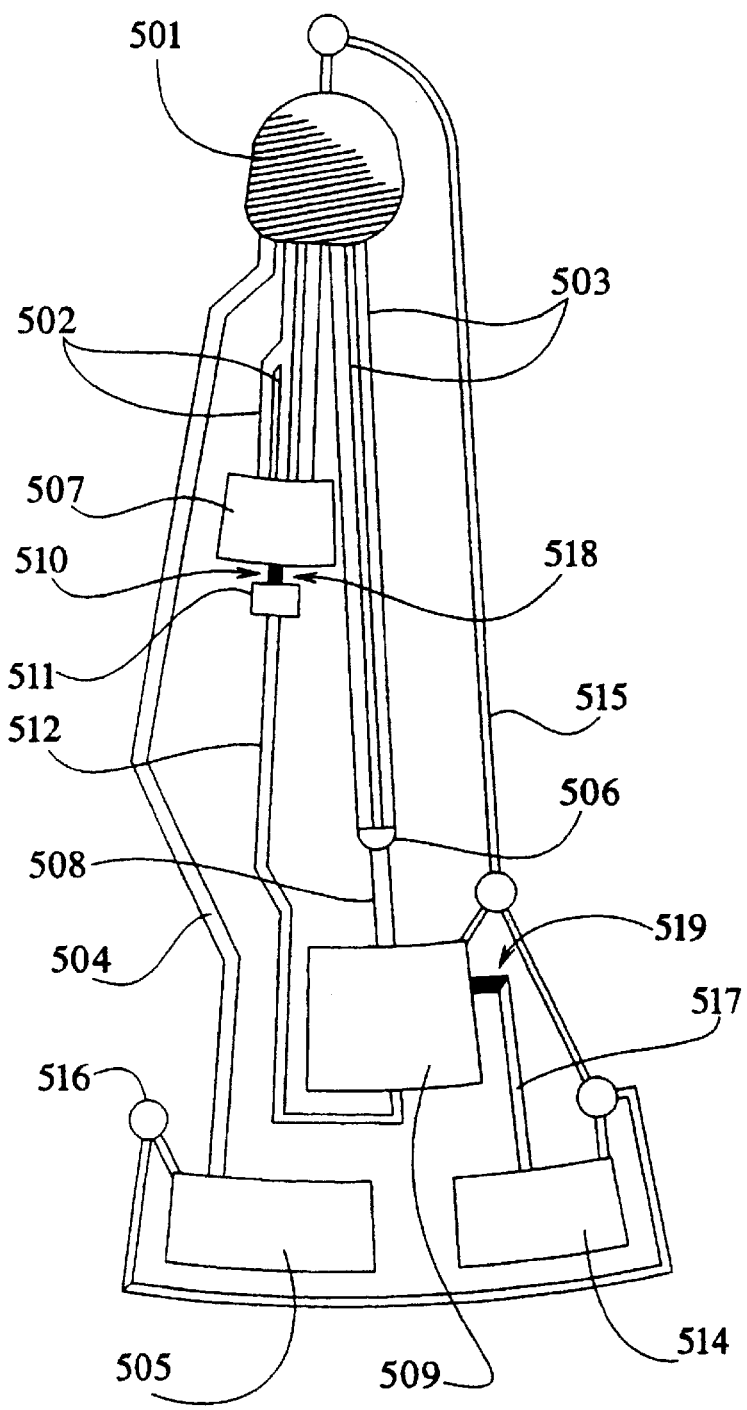
Figure 12B:
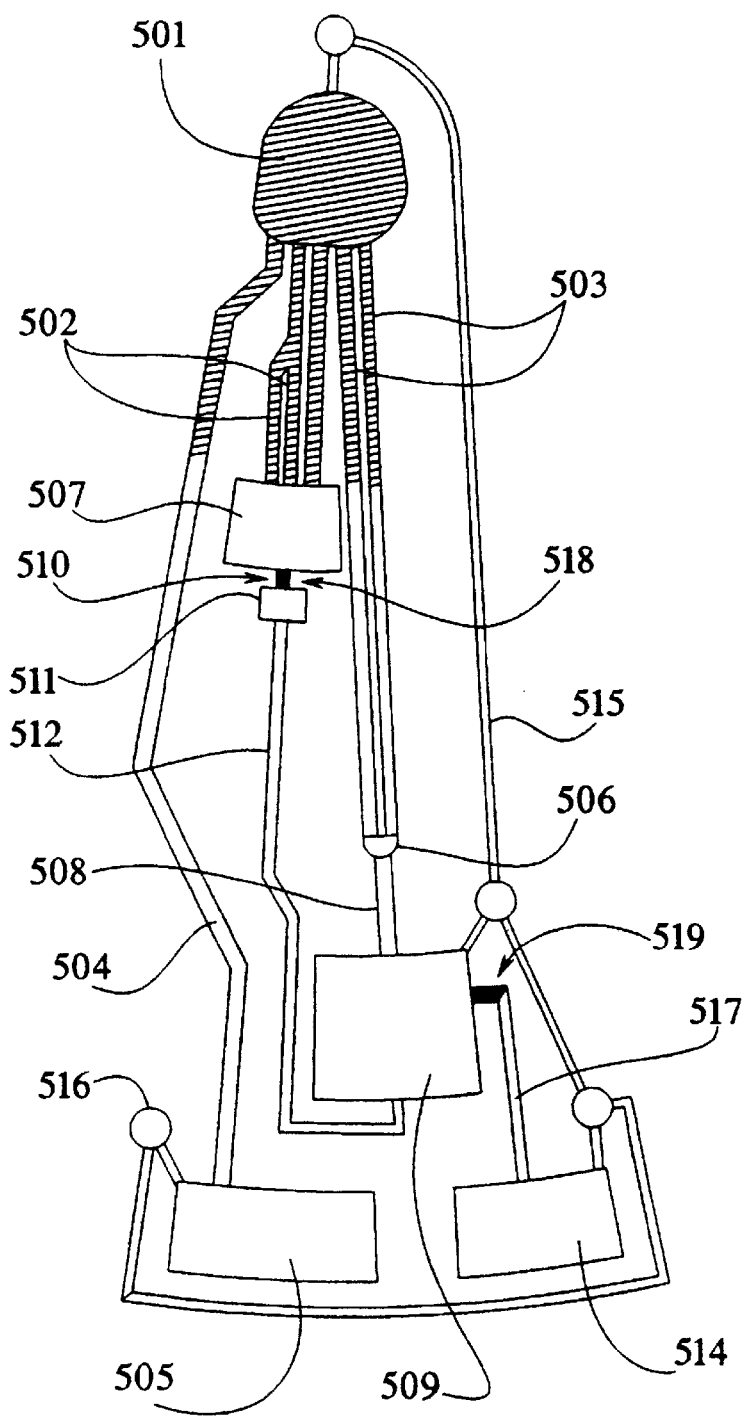
Figure 12C:
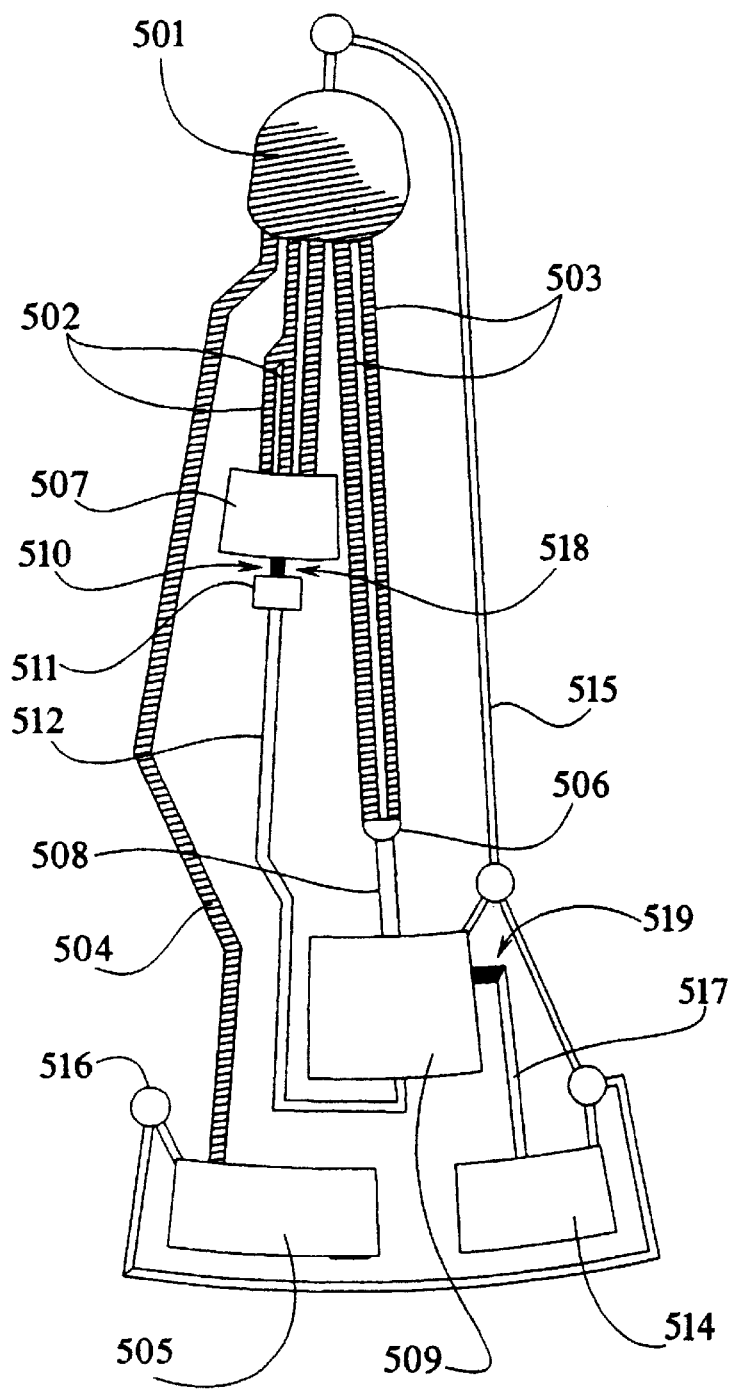

The use of this embodiment of the microfluidics separation arrays of the invention is illustrated in FIGS. 12A through 12J. An imprecise volume (ranging from 1–150 $\mu$L of fluid) of blood is applied to the entry port 501 (FIG. 12A). Blood enters the each of the metering capillary arrays 502 and 503 and stops at the capillary junction between metering capillary array 502 and ballast chamber 507 and between metering capillary 503 and capillary junction 506 (FIGS. 12B and 12C). Blood also enters and fills overflow capillary 504, stopping at the capillary junction with overflow chamber 505.

Figure 12D:
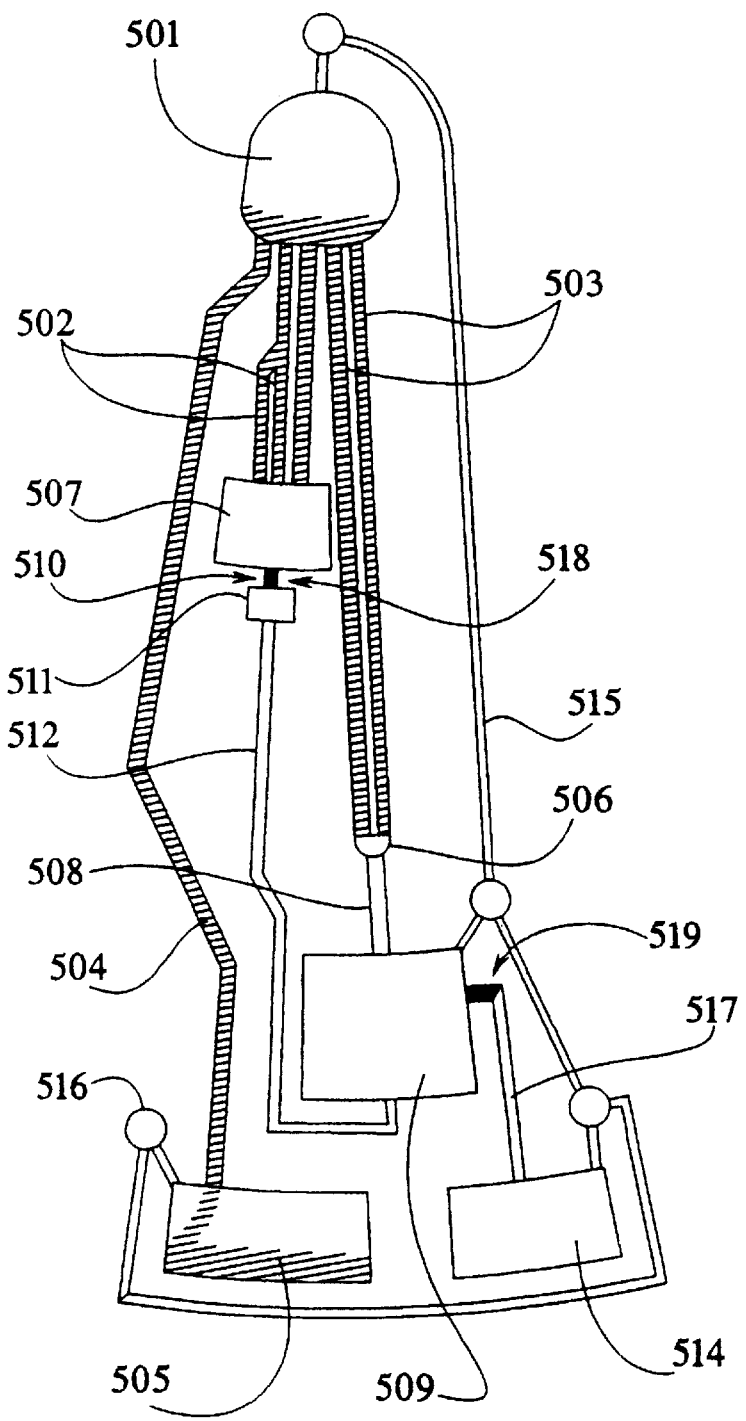
Figure 12E:
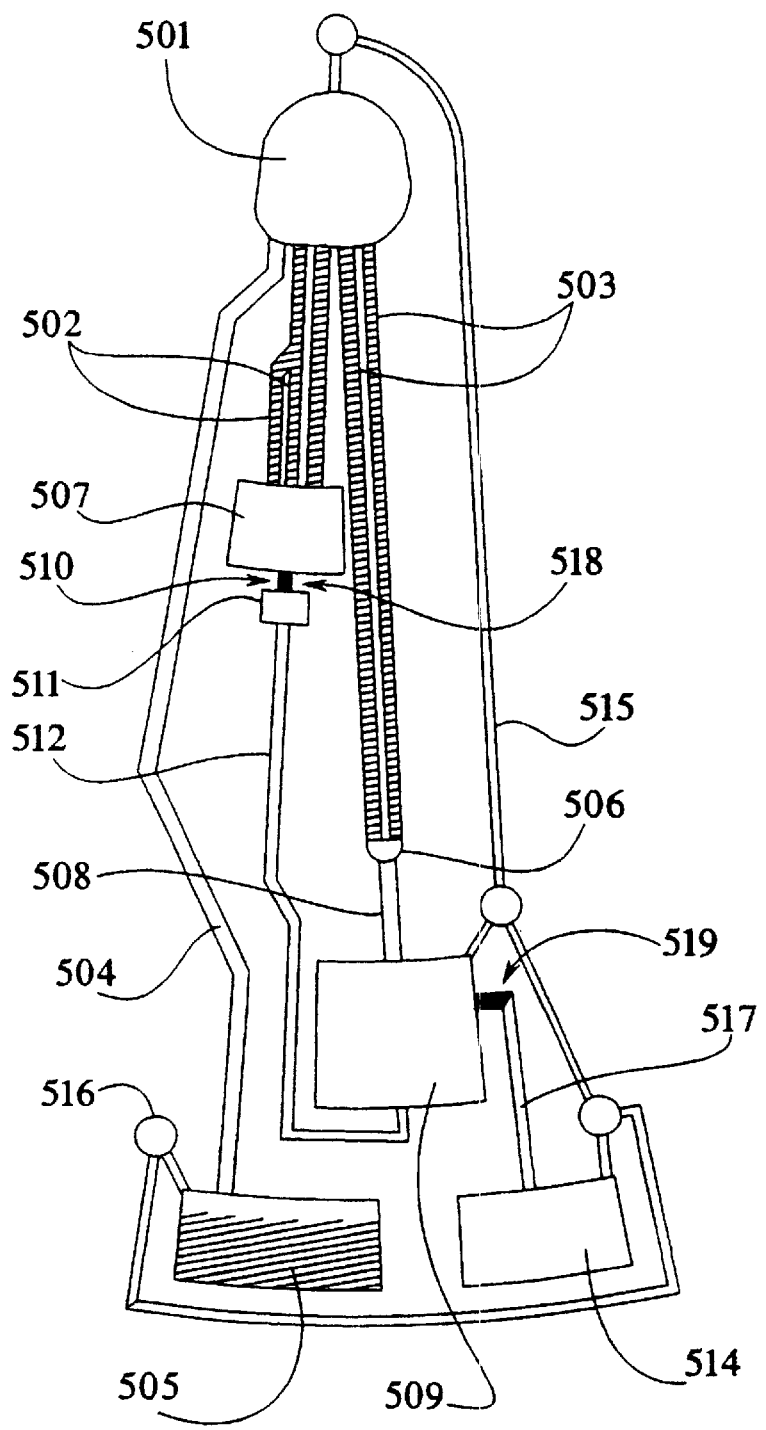
Figure 12F:
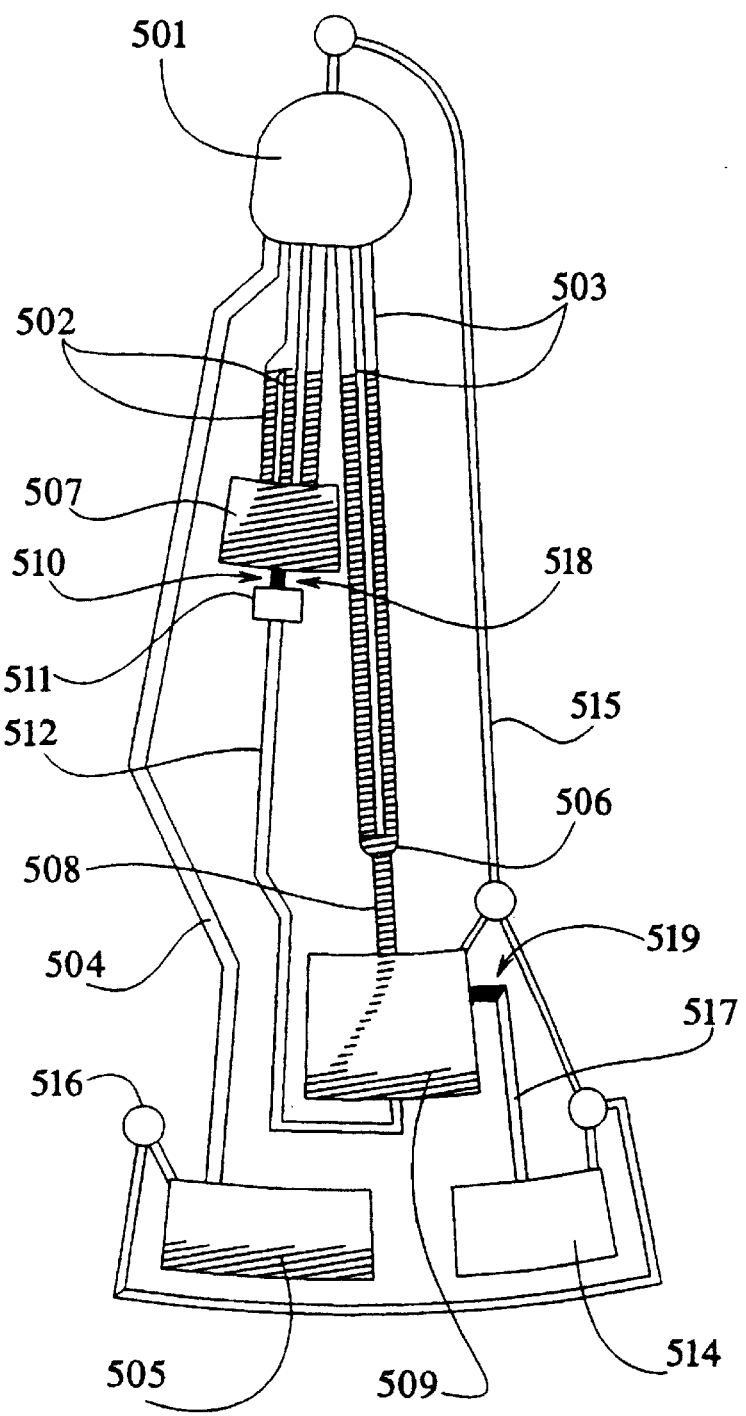

At a first rotational speed $f_1$, ranging from 100–500 rpm (the exact value is dependent on the position of the components on the platform), blood flows from the entry port 501 through overflow capillary 504 and into overflow chamber 505 (FIGS. 12D and 12E). At a second rotational speed $f_2$, that is greater than the first rotational speed $f_1$, typically in the range of 300–800 rpm, the capillary junction between the first metering capillary array 502 and ballast chamber 508 is overcome, and blood from the first metering capillary array fills ballast chamber 508 (FIG. 12F). Similarly, at second rotational speed $f_2$, capillary junction 506 is overcome, and blood from second metering capillary array 503 enters separation chamber 509 (FIG. 12F). Advantageously, the volume of blood in second metering capillary array 503 is insufficient to fill separation chamber 509 to the level of insertion of decant channel 517.

Figure 12G:
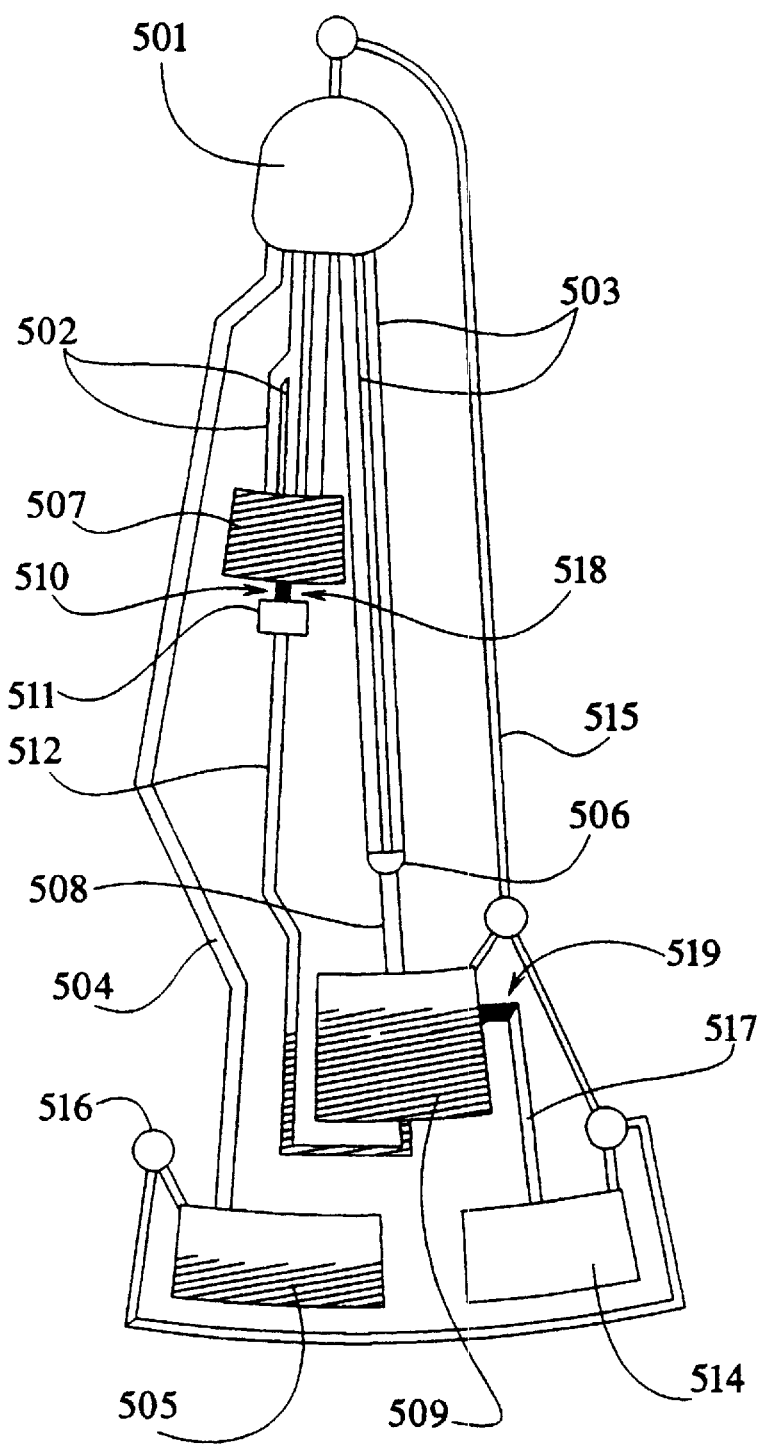
Figure 12H:
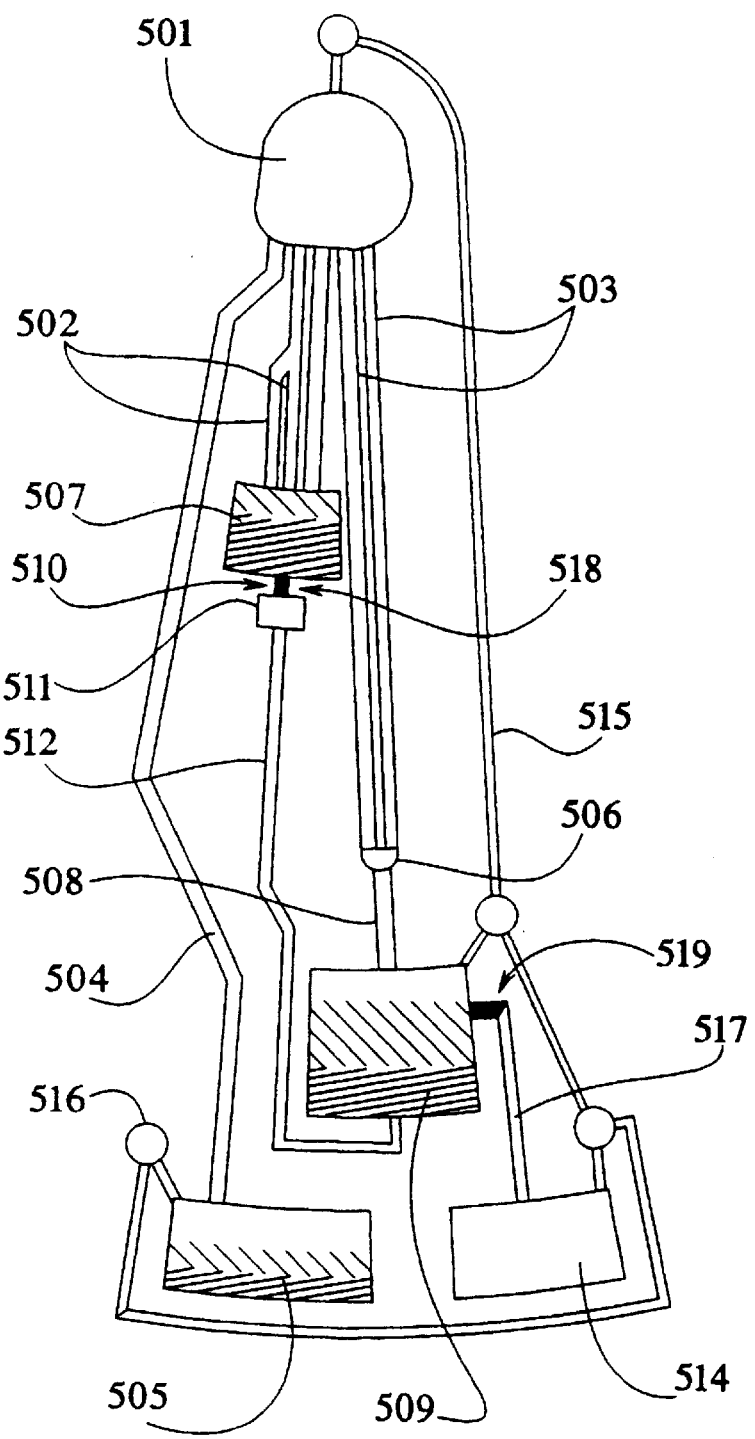

By rotation at a third rotational speed $f_3$, that is greater than the second rotational speed $f_2$, typically in the range of 1000–5000 rpm, blood components in separation chamber 509 are separated into red blood cell, white blood cell (i.e., "buffy coat"), and plasma fractions (FIGS. 12G and 12H). Separation of blood components is not achieved in ballast chamber 507, due to its position on the platform, and the capillary junction 511 or sacrificial valve 515 are not overcome at third rotational speed $f_3$. Advantageously, the separated plasma does not extend to decant capillary 517.

Figure 12I:
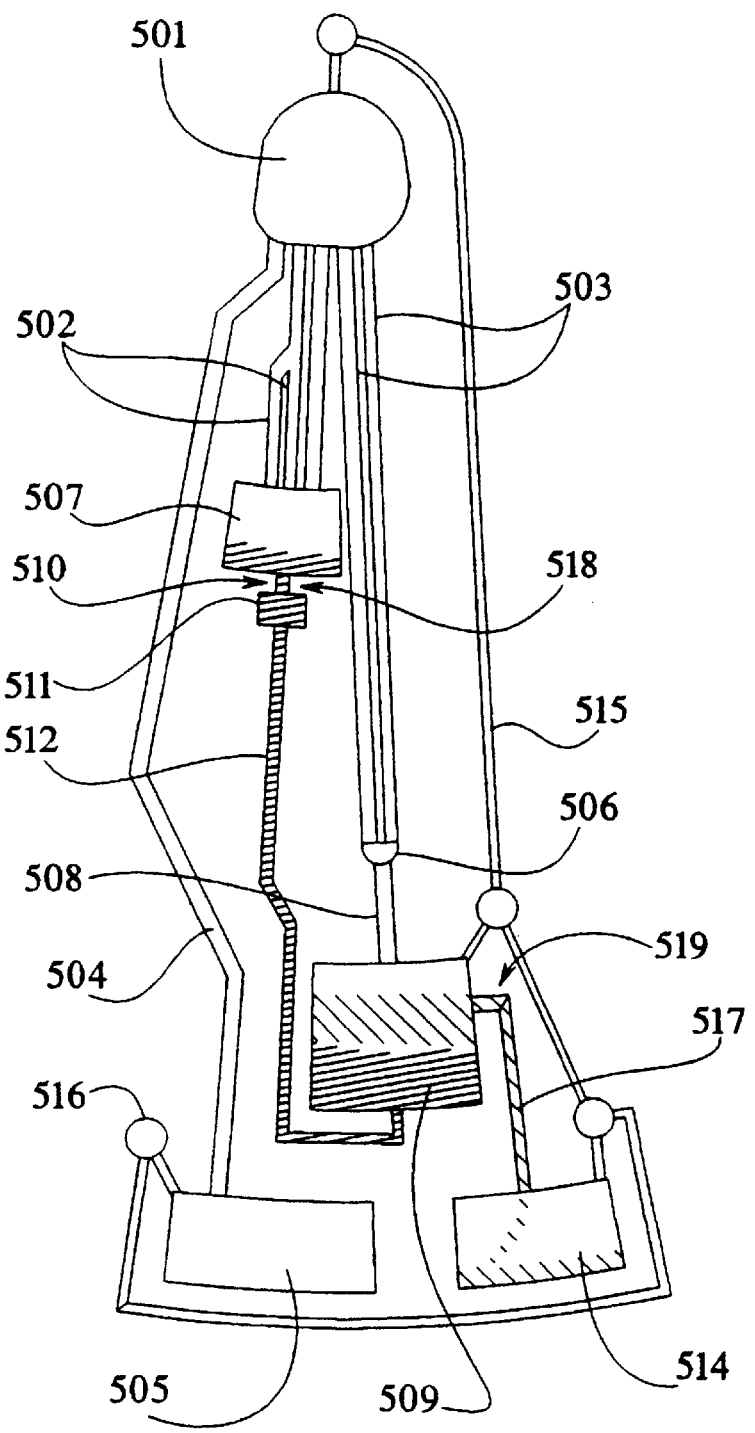
Figure 12J:
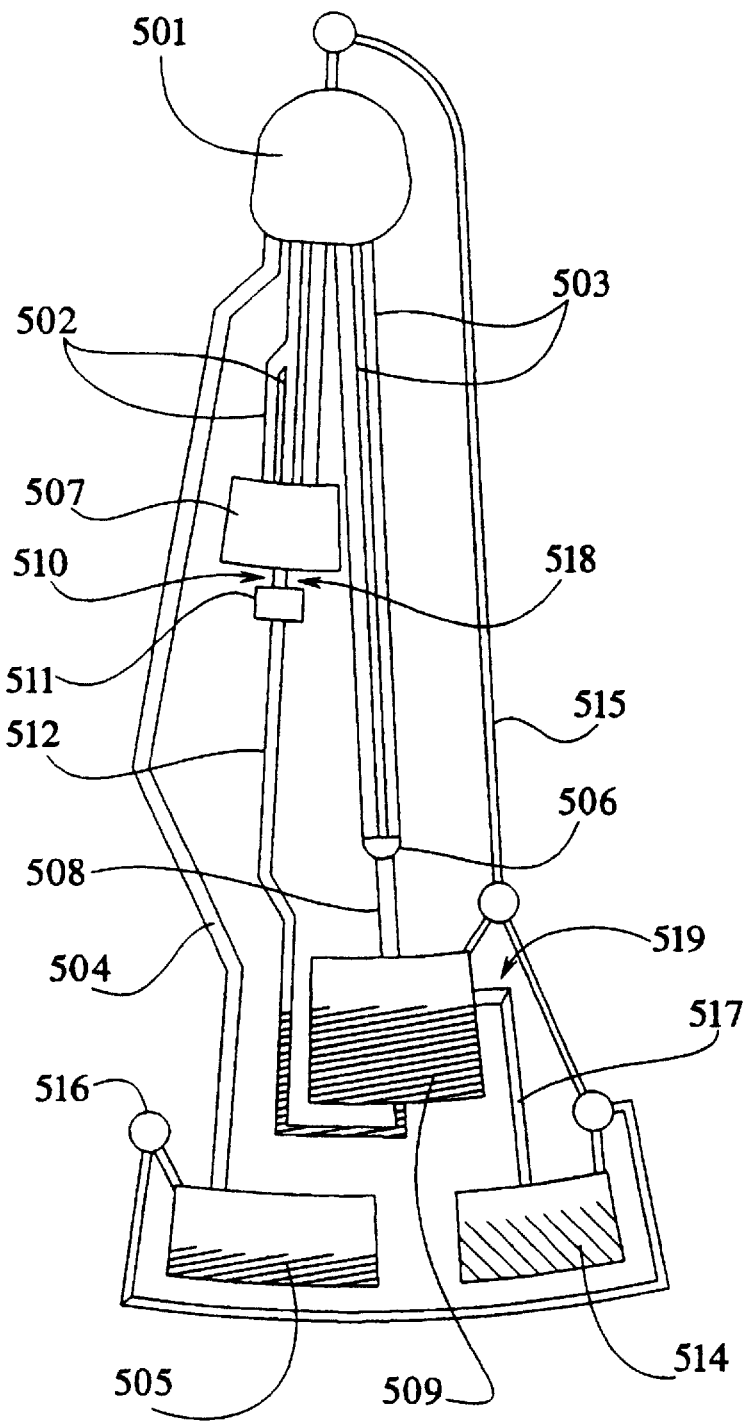

Release of sacrificial valve 517, or rotation at a fourth rotational speed $f_4$, that is greater than the third rotational speed $f_3$, and typically in the range of 1000–5000 rpm, result in flow of blood from ballast chamber 508 through channel 512 and into separation chamber 509 at the "bottom" or most axis-distal extent of the separation chamber (FIG. 12I). This results in filling of the separation chamber to a position equal to the insertion point of decant channel 517 (FIG. 12J). Plasma flow through decant channel 517 and into decant chamber 514 in an amount equal to the amount of blood contained in ballast chamber 508. Decant channel 517 is advantageously provided with dimensions that retard passage of unfractionated blood, or plasma contaminated with greater than 0.1–1% of blood cells found in whole blood.

Figure 13:
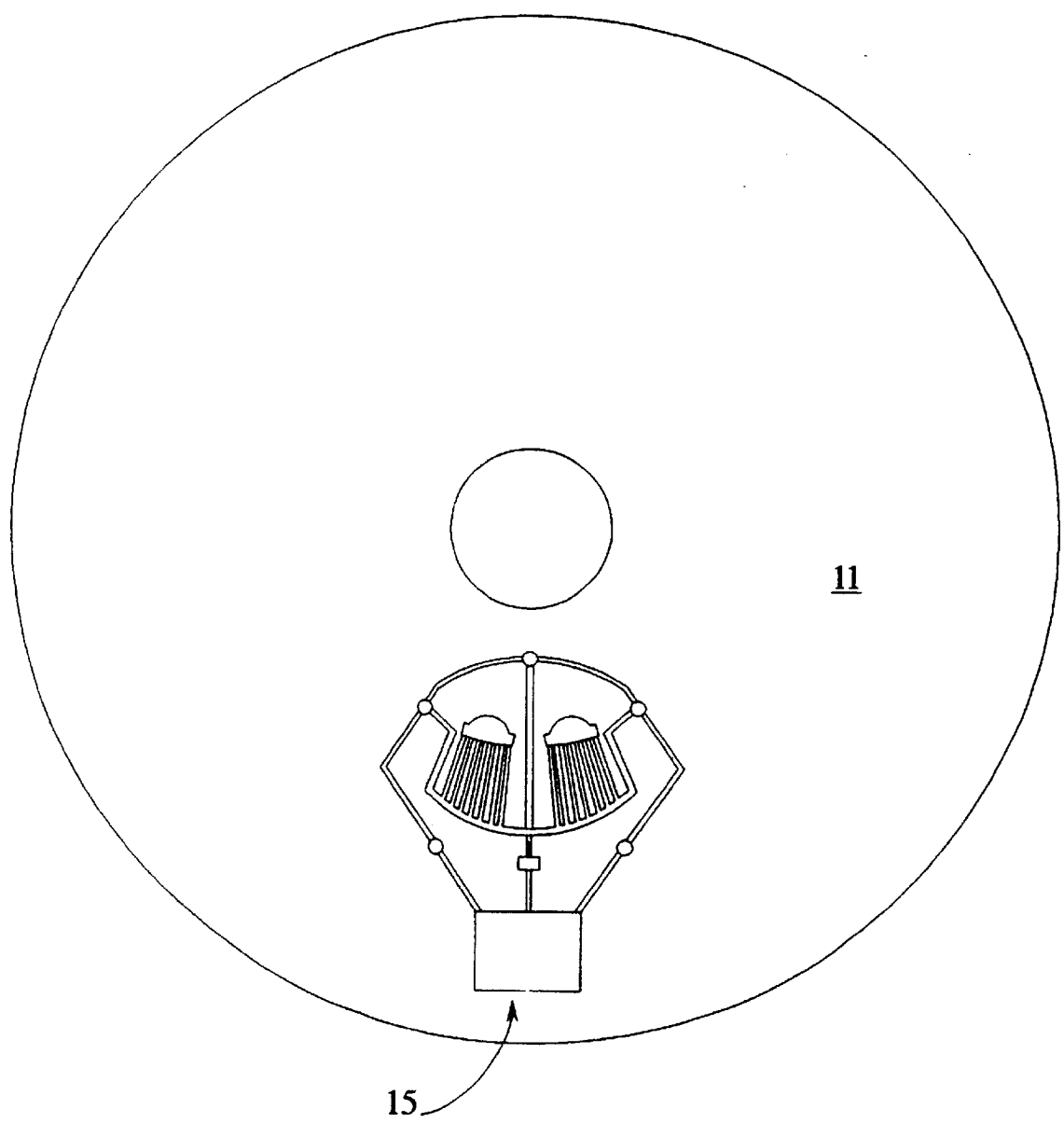
FIGS. 13 through 15 illustrate the microfluidics array of the microsystem platform described in Example 5.
Figure 14:
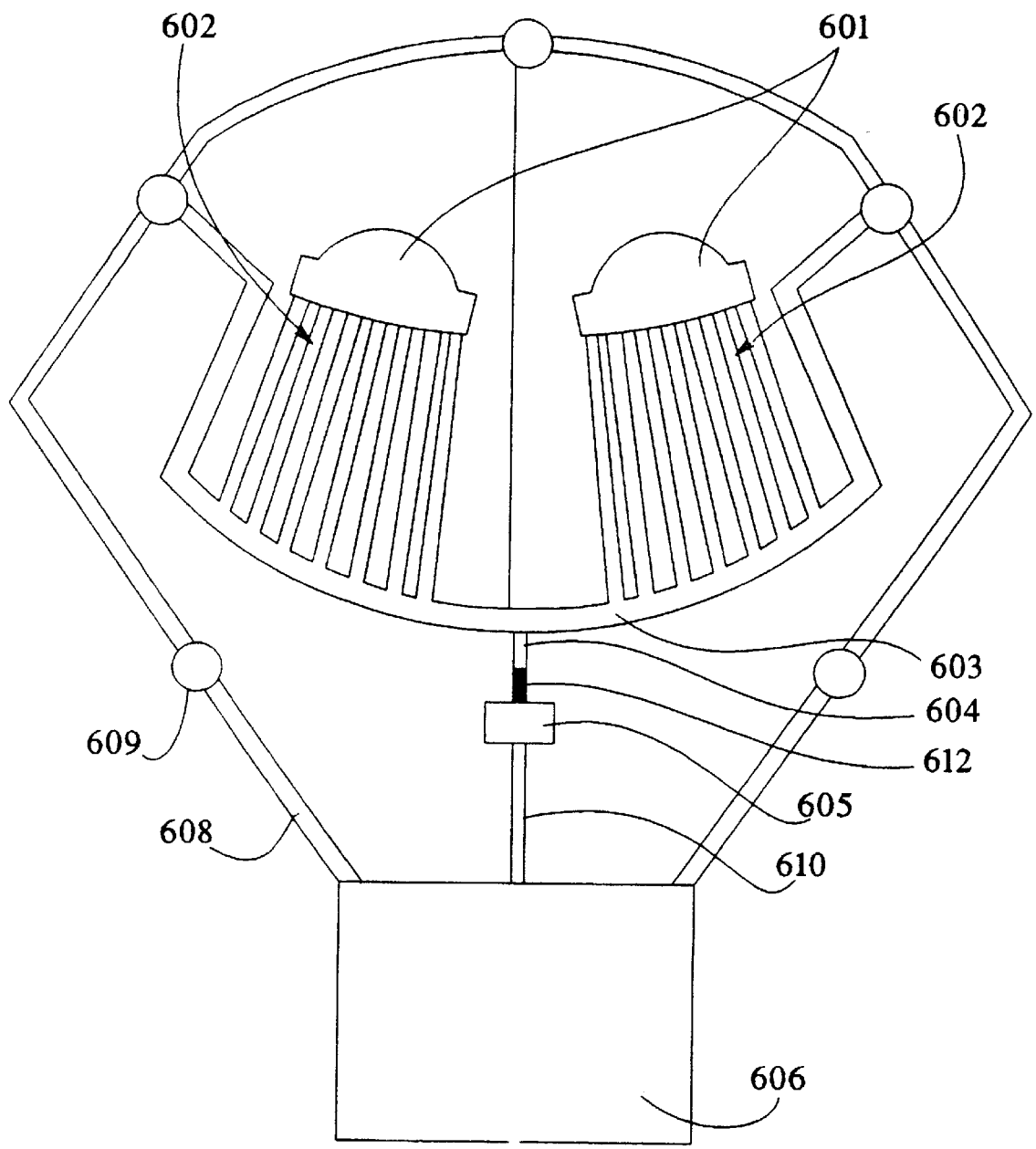

The invention also provides mixing chambers and arrays of mixing chambers for mixing two or more fluids that differ in viscosity, solute concentration or concentration of suspended particulates. A first embodiment of microfluidics platform comprising the mixing chambers and arrays of the invention is shown in FIGS. 13–15 for mixing equal volumes of different liquids. In FIG. 13, the arrangement of one assay array 15 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 14. It will be understood by a comparison of FIGS. 13 and 14 that the center of the platform 11 is at the top of FIG. 14, and the edge or lateral extent of the platform is at the bottom of FIG. 14, illustrated by a curved line. Rotation of the mixing array on platform disks of the invention can be in either direction, although rotation in a consistent, particular direction is preferred. Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume was about 50 $\mu$L.

The components of the mixing array are as follows. Entry ports 601 having a depth in the platform surface ranging from about 0.1 mm to about 1 mm and lateral dimensions of from about 1 cm to about 5 cm are constructed on the platform, and designed to accommodate a volume of about 5–50 $\mu$L. Each entry port is fluidly connected with one of a paired array of metering capillaries 602 having a square cross-sectional diameter of from about 0.1 mm to about 0.5 mm and proximal ends rounded with respect to entry ports 601; the length of each metering capillary array was sufficient to contain a total volume of about 25 $\mu$L. Metering capillaries 602 are fluidly connected to a curved capillary barrier 603 having a depth in the platform surface of about 0.25 mm to about 1 mm that is greater than the depth of metering capillaries 602. The capillary barrier 603 and other fluid components of the mixing array are also connected with air channels 608, that have dimensions ranging from about 0.25 mm to about 1 mm and that permit venting of air displaced by fluid movement on the platform. In addition, capillary junctions 609 that are about 0.75 mm deep are present in the air channels to prevent fluid backflow into the air channel.

Capillary barrier 603 is fluidly connected by a narrow capillary channel 604 to mixing chamber 605, which is fluidly connected with channel 610, which is further connected with mixed fluid receiving chamber 606. Alternatively, capillary 604 comprises a sacrificial valve 612. Sacrificial valves used in this embodiment of the invention are as described below. Capillary channel 604 ranges from about 0.1 mm to about 1 mm in depth and has a cross-sectional diameter of from about 0.1 mm to about 1 mm). Capillary channel 604 extends from about 0.1 to about 10 cm. Mixing chamber 605 is about 0.1 mm to about 1 mm deep and has a cross-sectional diameter of from about 0.5 mm to about 5 mm), is positioned about 1 cm to about 30 cm from the center of rotation. Capillary channel 610 ranges from about 0.1 mm to about 1 mm deep and has a cross-sectional diameter of from about 0.1 mm to about 1 mm). Capillary channel 610 extends from about 0.2 cm to about 30 cm. In an advantageous embodiment, mixing chamber 605 is constructed such that the insertion point of capillary channel 604 and the insertion point of capillary channel 610 are offset at opposite ends of the mixing chamber. As a consequence, fluid flowing through capillary channel 604 is forced to encounter the opposite wall of mixing chamber 605 before fluid flow can proceed through capillary channel 610. This results in the creation of turbulence in the mixed laminar fluid stream in capillary channel 604 caused by the conjoint flow of fluid from the first and second metering channels without appreciable mixing. The turbulence created by the structure of mixing chamber 605 is sufficient to disrupt laminar flow and cause fluid mixing in the chamber prior to continued fluid flow through capillary channel 610 and into mixed fluid receiving chamber 606. Alternatively, the positions of the capillaries 604 and 610 can be at any convenient position in mixing chamber 605, wherein the Coriolis forces of fluid flow are sufficient to disrupt laminar flow and provide turbulence that results in efficient mixing.

Mixed fluid receiving chamber 606 is about 0.1 mm to about 5 mm deep, has a cross-sectional diameter of from about 1 mm to about 20 mm, and is positioned from about 1 cm to about 30 cm from the center of rotation.

Figure 15A:
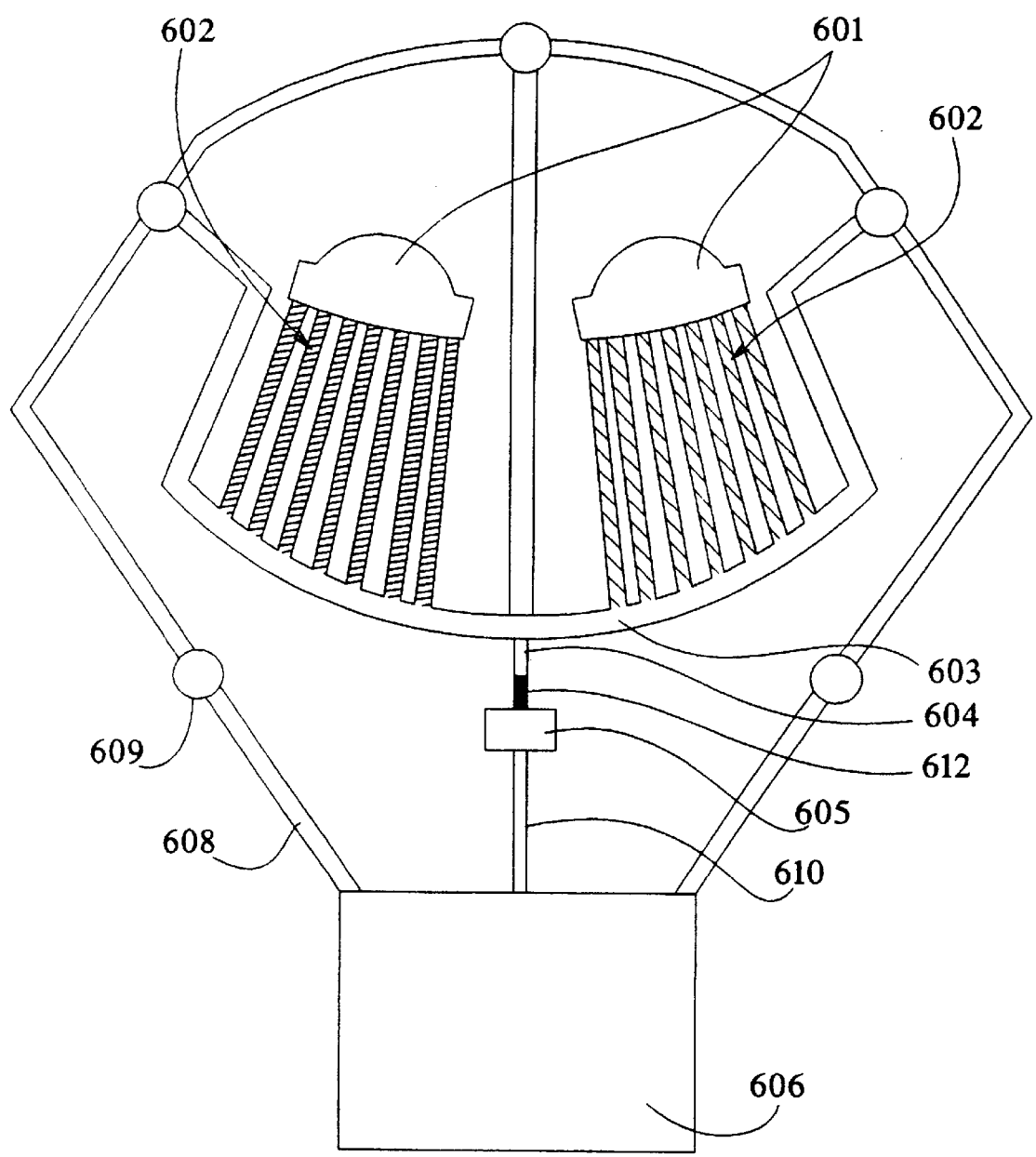

The use of this embodiment of the invention for mixing equal volumes of fluid (ranging from 1–150 $\mu$L is illustrated in FIGS. 15A through 15D. Equal volumes of each fluid to be mixed is applied to the entry ports 601 (FIG. 15A). Fluid enters the each of the metering capillary arrays 602 and stops at capillary barrier 603.

Figure 15B:
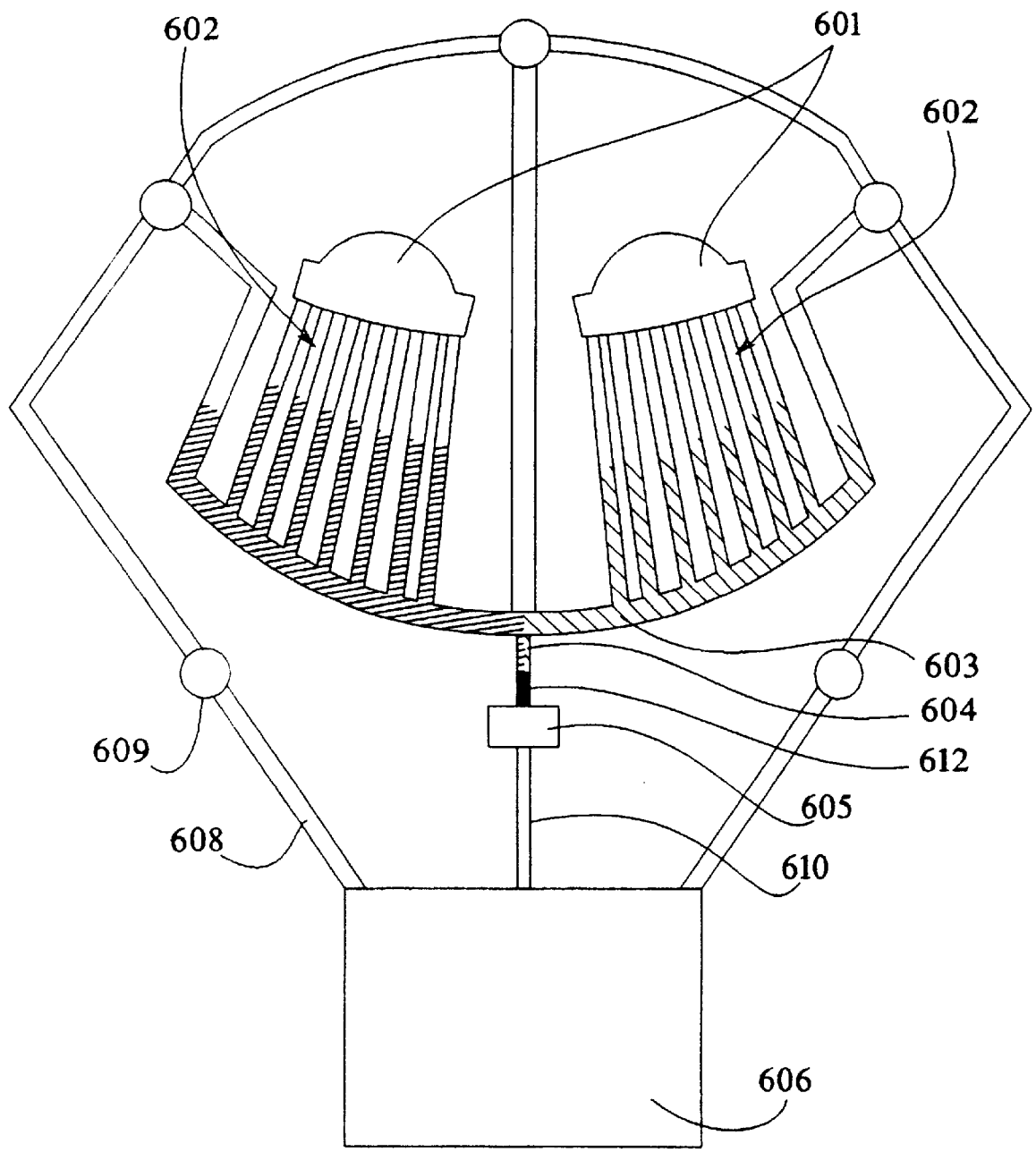
Figure 15C:
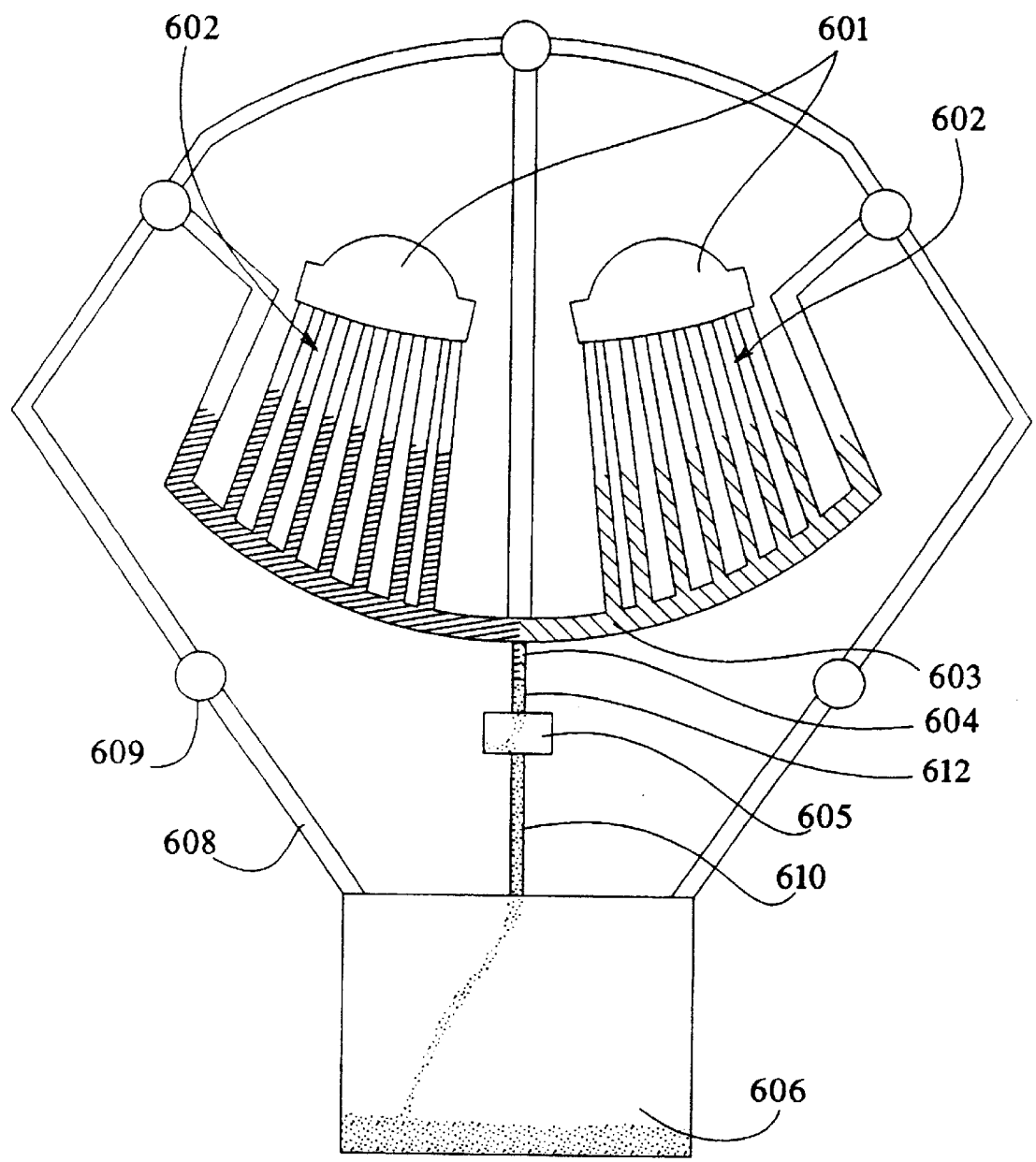
Figure 15D:
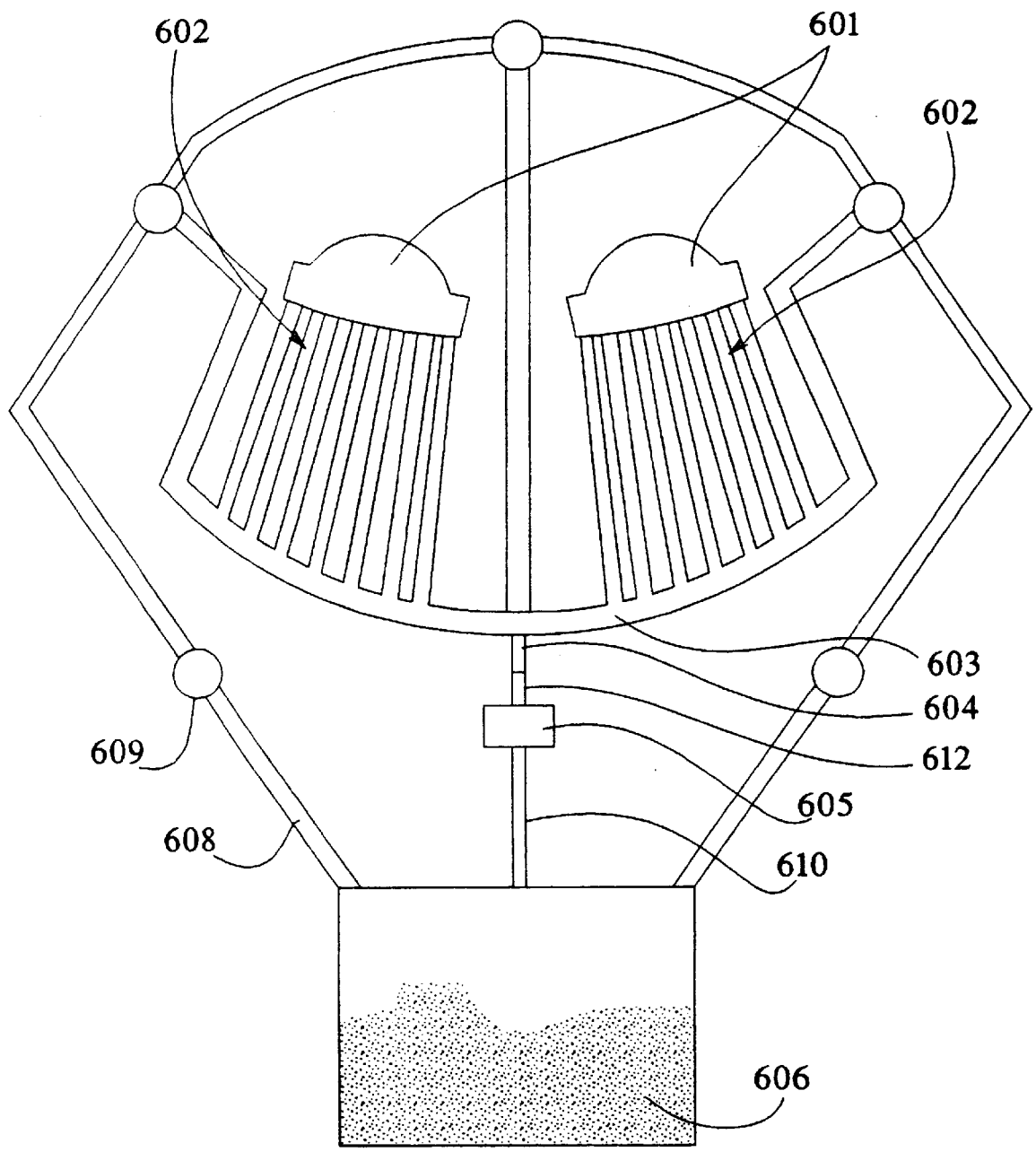
Figure 16:
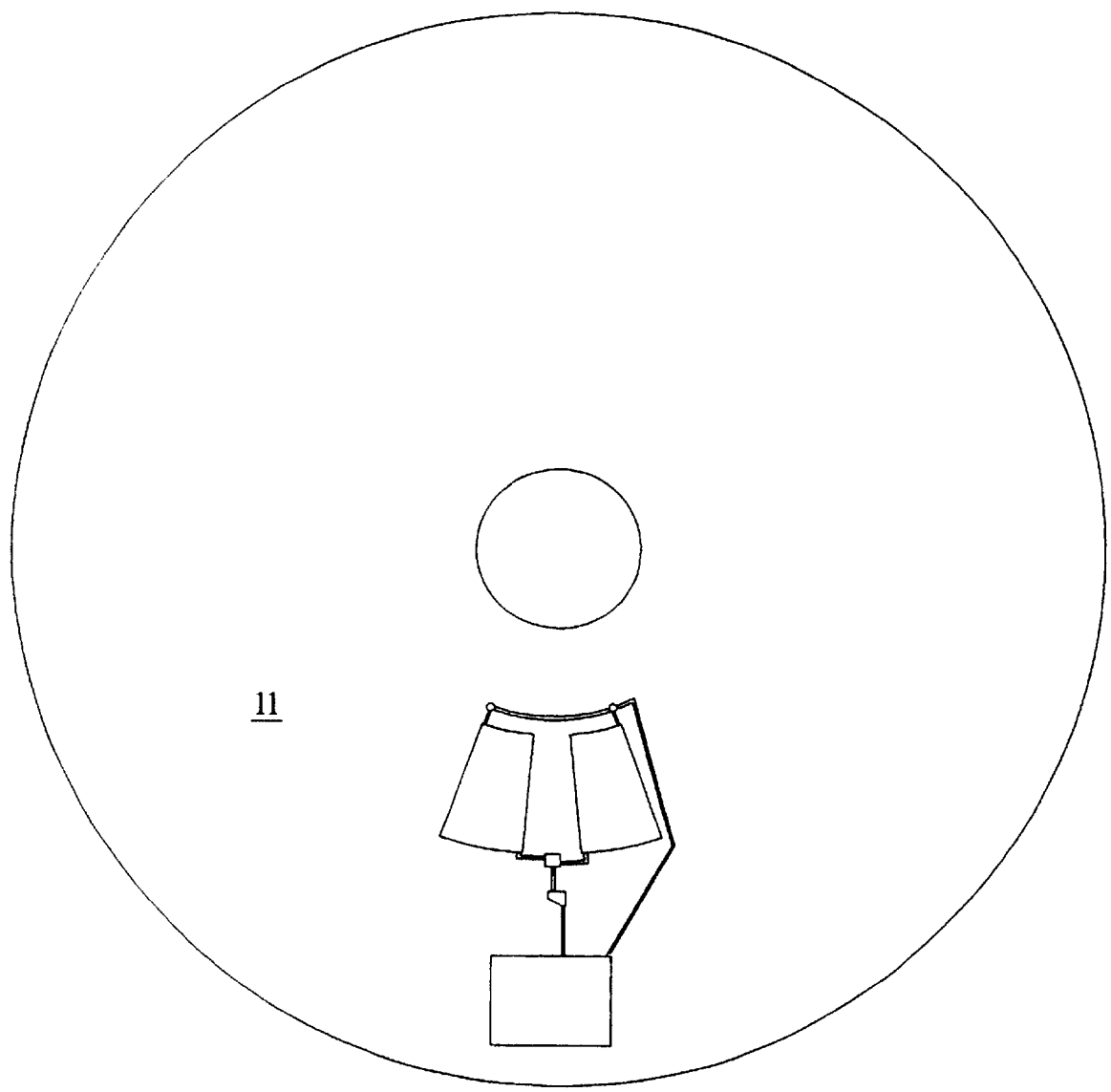
FIGS. 16 through 18 illustrate the microfluidics array of the microsystem platform described in Example 6.

At a first rotational speed $f_1$, ranging from 50–500 rpm (the exact value is dependent on the position of the components on the platform), the fluids from each capillary array flows into and fills the capillary barrier 603 (FIG. 15B). In embodiments comprising a sacrificial valve 612, the valve prevents fluid flow into channel 604; otherwise, fluid flow proceeds into channel 604 at rotational speed $f_1$. Upon release of sacrificial valve 612, fluid flow proceeds from capillary junction 603 through channel 604 and into mixing chamber 605 (FIG. 15C). Fluid flow within mixing chamber 605 is turbulent, in contrast to fluid flow through capillary barrier 603 or channel 604, which is primarily laminar, so that mixing occurs predominantly in mixing chamber 605. Fluid flow proceeds through channel 610 and the mixed fluid solution is displaced into mixed fluid receiving chamber 606 (FIG. 15D).

Figure 19:
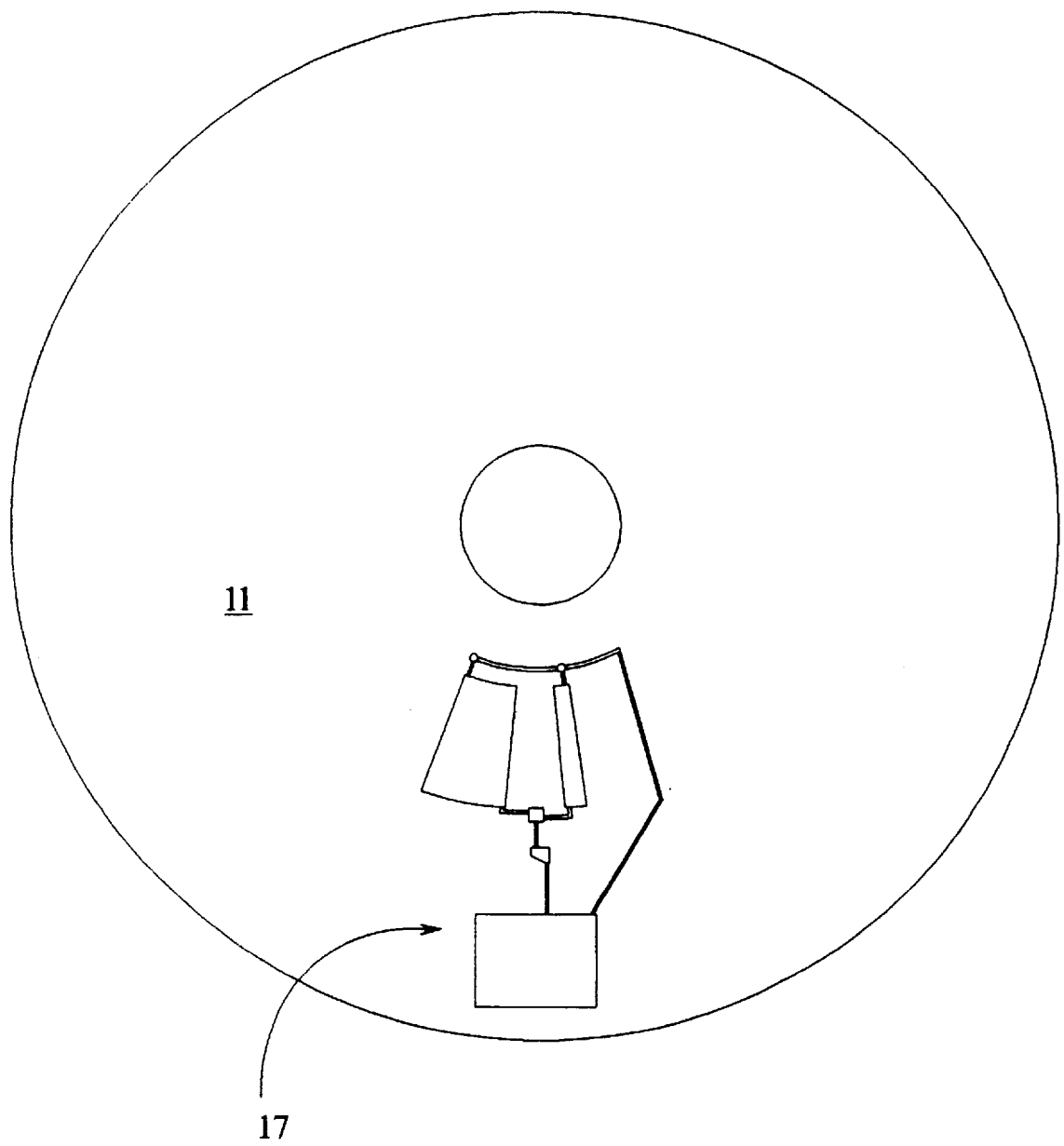
FIGS. 19 through 21 illustrate the microfluidics array of the microsystem platform described in Example 7.
Figure 20:
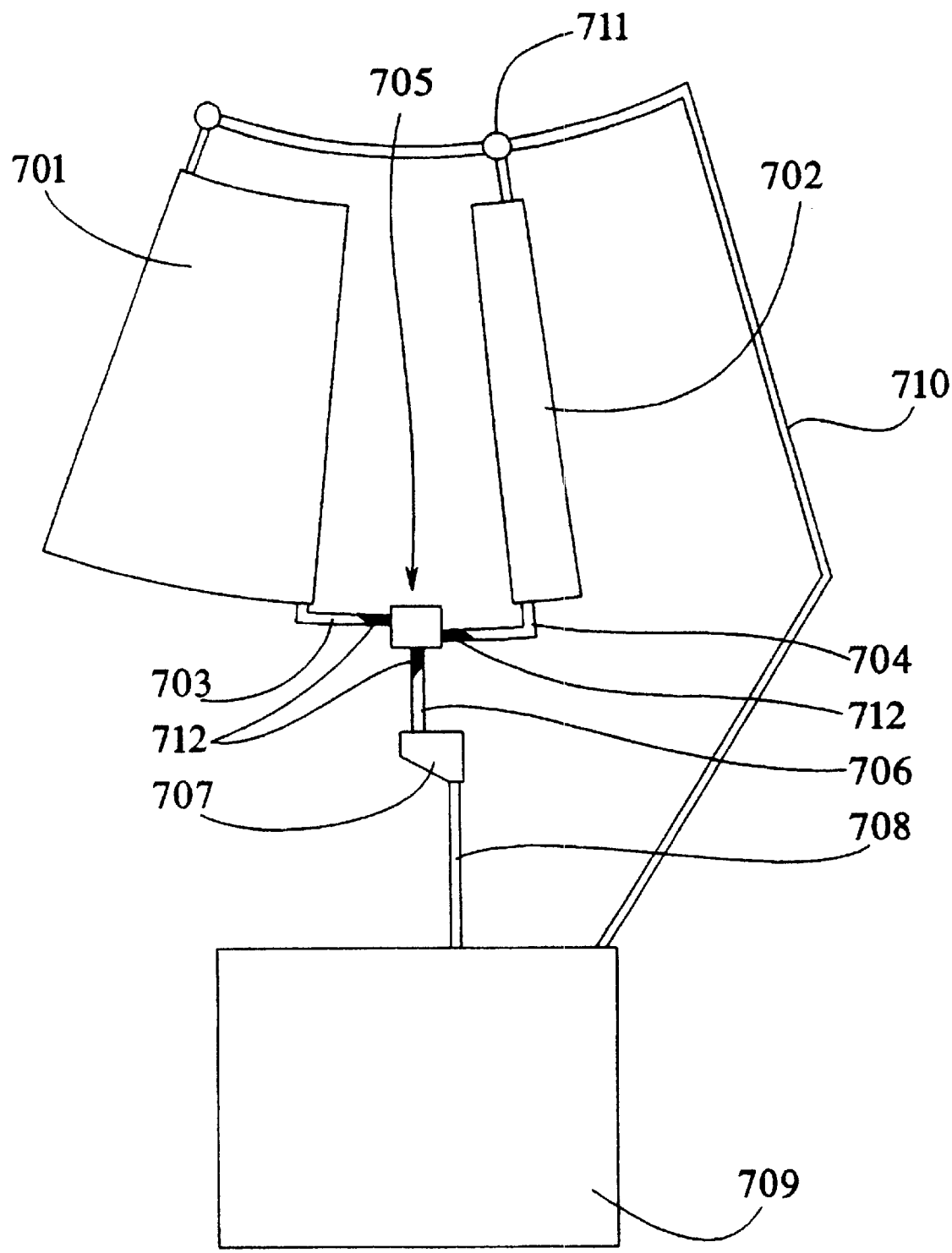

The invention also provides mixing arrays for mixing unequal volumes of fluid. One example of such an additional embodiment of the microsystems platform provided by the invention and specifically designed for performing mixing of unequal volumes of different liquid samples is illustrated in FIGS. 19 through 21. In FIG. 19, the arrangement of one assay array 17 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 20. It will be understood by a comparison of FIGS. 19 and 20 that the center of the platform 11 is at the top of FIG. 20, and the edge or lateral extent of the platform is at the bottom of FIG. 20, illustrated by a curved line. Rotation of the mixing array on platform disks of the invention can be in either direction, although rotation in a consistent, particular direction is preferred. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume is about 2–200 $\mu$L.

The components of this mixing array are as follows. Fluid reservoirs 701 and 702, each containing one of a pair of liquids to be mixed, are constructed on the platform, having a depth in the platform surface ranging from about 0.1 mm to about 5 mm and lateral dimensions of from about 0.2 cm to about 10 cm). In this embodiment, fluid reservoir 701 is designed to accommodate a volume of about 1 to about 500 $\mu$L, and fluid reservoir 702 is designed to accommodate a volume of about ranging from about 1 to about 500 $\mu$L, wherein the volume of fluid reservoir 702 is less than the volume of fluid reservoir 701. In particular and in addition, the viscosity of the fluid in the fluid reservoirs may differ, so that mixing produces a mixed fluid of intermediate viscosity. Also, in this embodiment the concentration of solute of suspended particulate may differ between the fluids. Each fluid reservoir is fluidly connected with a capillary channel 703 or 704 to capillary junction 705. Each capillary channel is from about 0.0.2 mm to about 1 mm deep, has a cross-sectional diameter ranging from about 0.1 mm to about 1 mm, and extends about 2 cm to about 100 cm. Capillary junction 705 has a depth in the platform surface ranging from about 0.02 mm to about 1 mm that is greater than the depth of capillaries 703 to 704. Alternatively, capillaries 703 or 704 comprise a sacrificial valve 712. Sacrificial valves used in this embodiment of the invention are as described below. Use of said sacrificial valves can be used in addition to or in place of capillary junction 705.

The fluid components of the mixing array are also connected with air channels 710, that have dimensions ranging from about 0.1 mm to about 1 mm and permit venting of air displaced by fluid movement on the platform. In addition, capillary junctions 711 that are about 0.75 mm deep are present in the air channels to prevent fluid backflow into the air channel.

Capillary junction 705 is fluidly connected by a narrow capillary channel 706 to mixing chamber 707, which is fluidly connected with channel 708, which is further connected with mixed fluid receiving chamber 709. Alternatively, capillary 706 comprises a sacrificial valve 712, as described below. Capillary, channel 706 ranges from about 0.1 mm to about 1 mm, has a cross-sectional diameter of from about 0.1 mm to about 1 mm and extends from about 0.2 cm to about 30 cm. Mixing chamber 707 is from about 0.1 mm to about 1 mm deep, has a cross-sectional diameter ranging from about 0.1 mm to about 1 mm, and is positioned from about 0.2 cm to about 30 cm from the center of rotation. Capillary channel 708 ranges from about 0.1 mm to about 1 mm, has a cross-sectional diameter ranging from about 1 mm to about 20 mm and extends from about 0.2 cm to about 30 cm. Capillary channel 706 and capillary channel 708 are advantageously offset in their connection with the mixing chamber as described above, or are positioned at any convenient position in the mixing chamber for those embodiments relying on Coriolis forces to create mixing.

Capillary 708 is fluidly connected with mixed fluid receiving chamber 709. Mixed fluid receiving chamber 709 is about 0.1 mm to about 1 mm, has a cross-sectional diameter of about 1 mm to about 20 mm, and is positioned from about 1 cm to about 30 cm from the center of rotation.

Figure 21A:
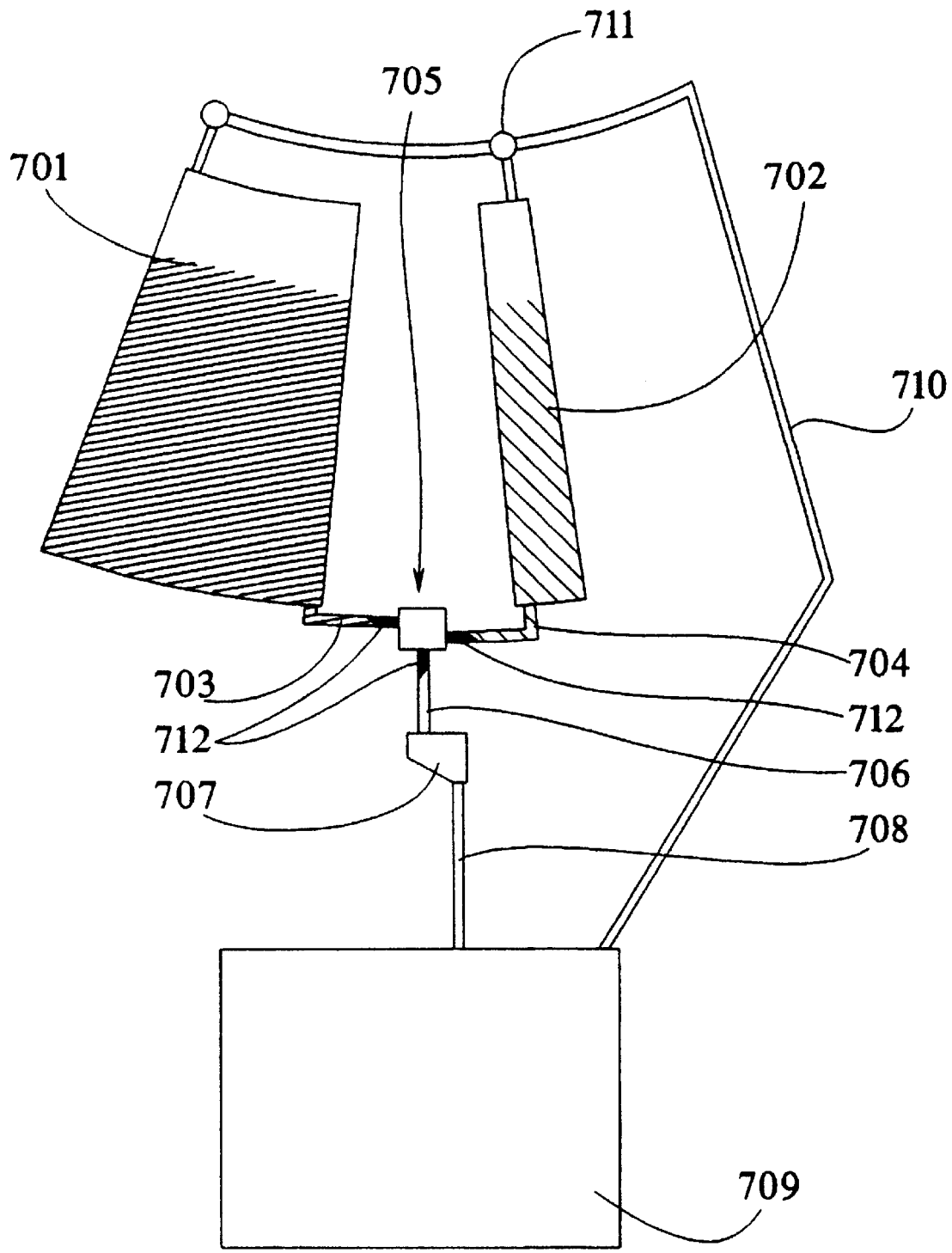

The use of this embodiment of the microfluidics components of the invention is illustrated in FIGS. 21A through 21E. A volume (ranging from 1–150 $\mu$L of fluid) of each of the fluids to be mixed is applied to the fluid reservoirs 701 and 702 (FIG. 21A). Fluid enters the each of the capillaries 703 and 704 and stops at capillary junction 705. Alternatively, the platforms of the invention are provided containing the fluids to be mixed already in fluid reservoirs 701 and 702. In these embodiments, it is preferred that sacrificial valves 712 be provided in capillaries 703 and 704, to prevent evaporation, wetting or leakage of fluid from the reservoirs prior to use.

Figure 21B:
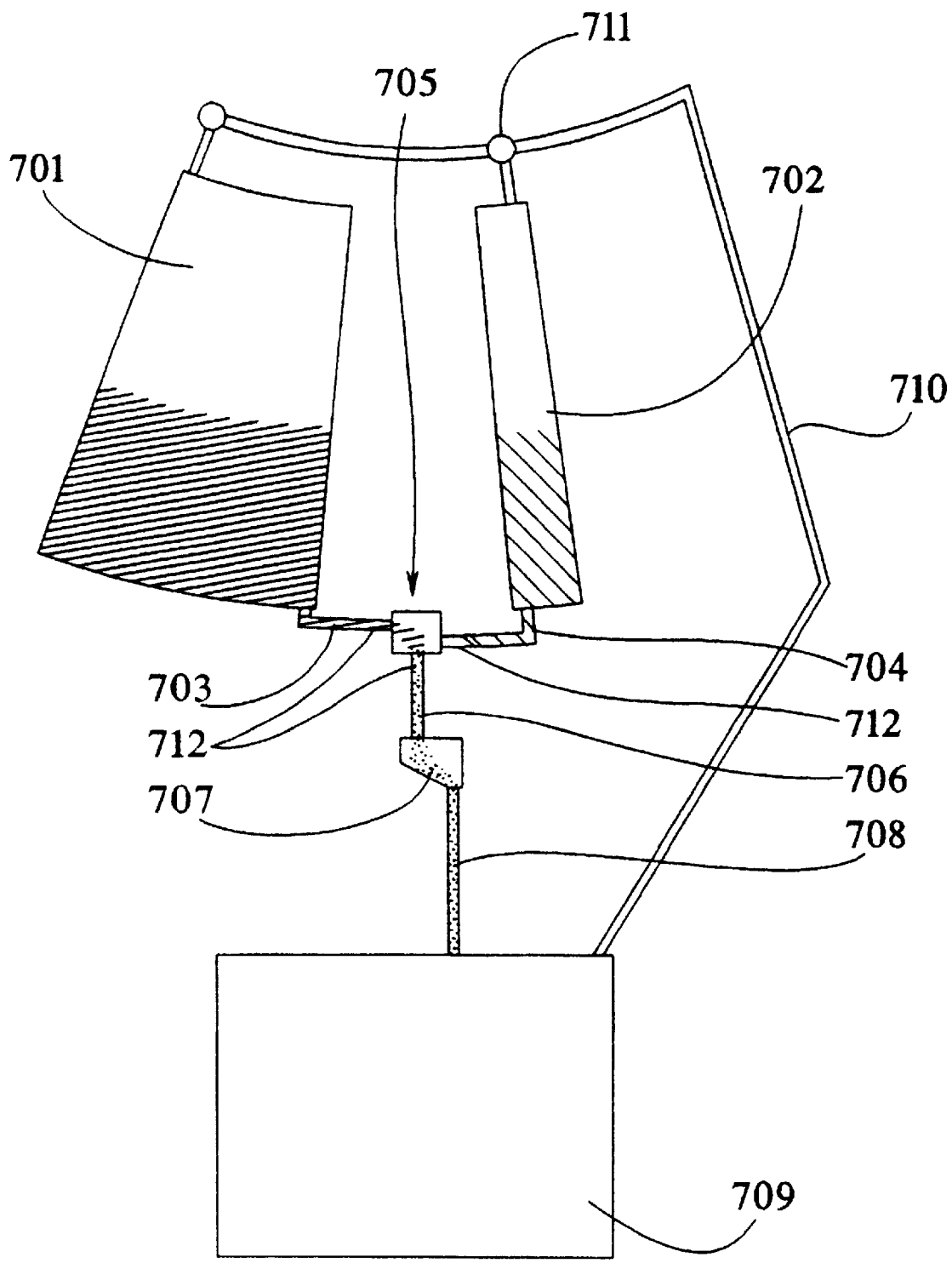
Figure 21C:
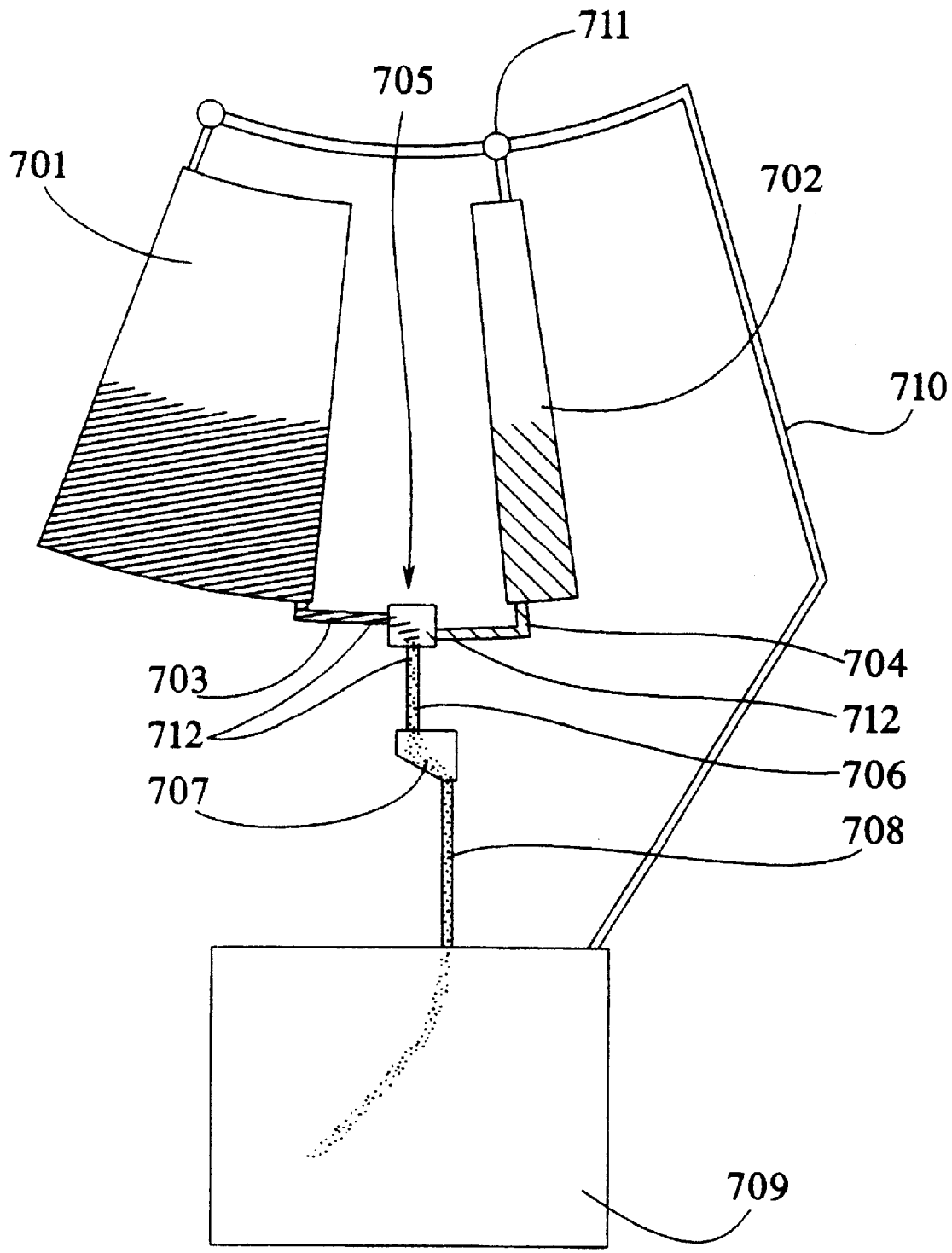
Figure 21D:
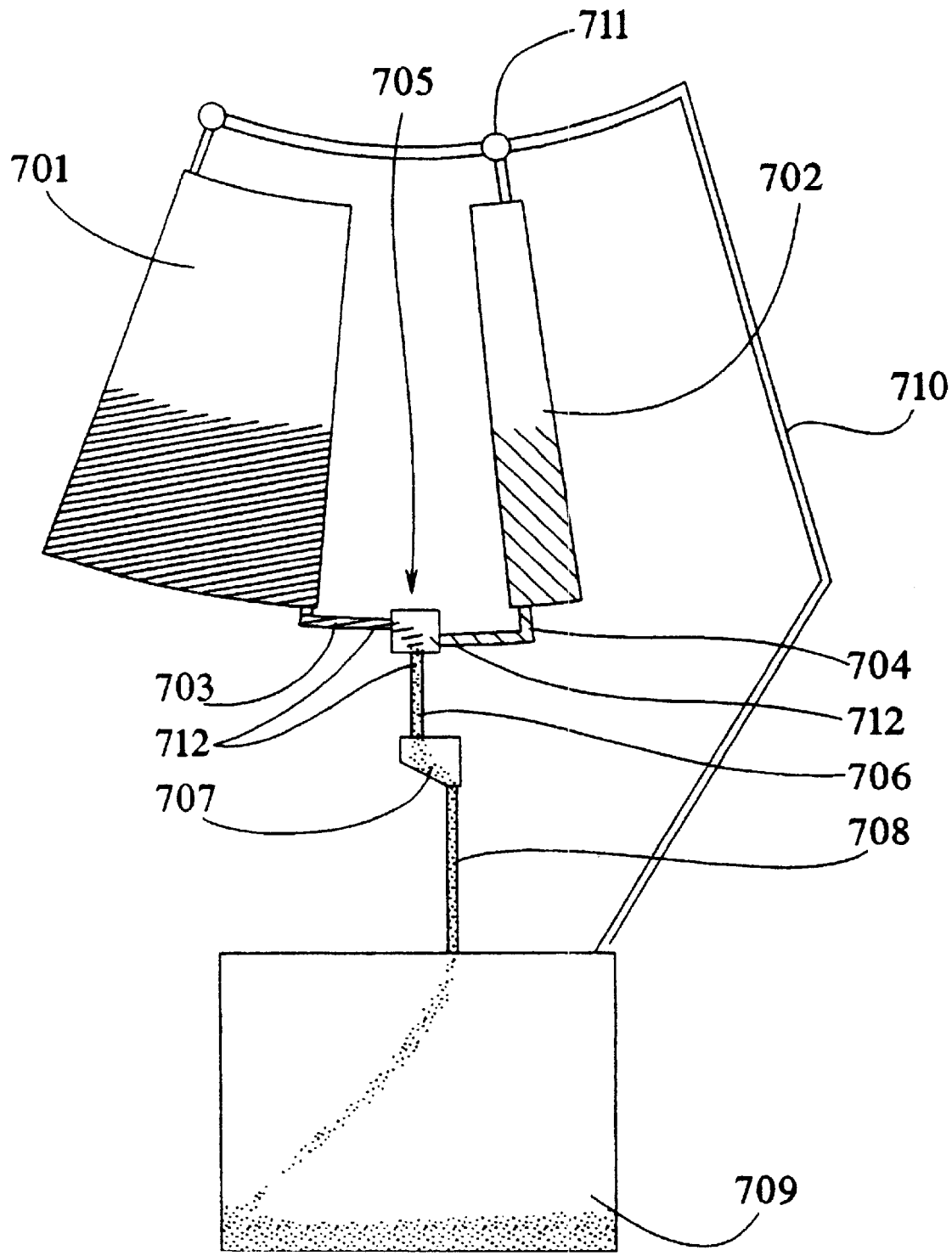
Figure 21E:
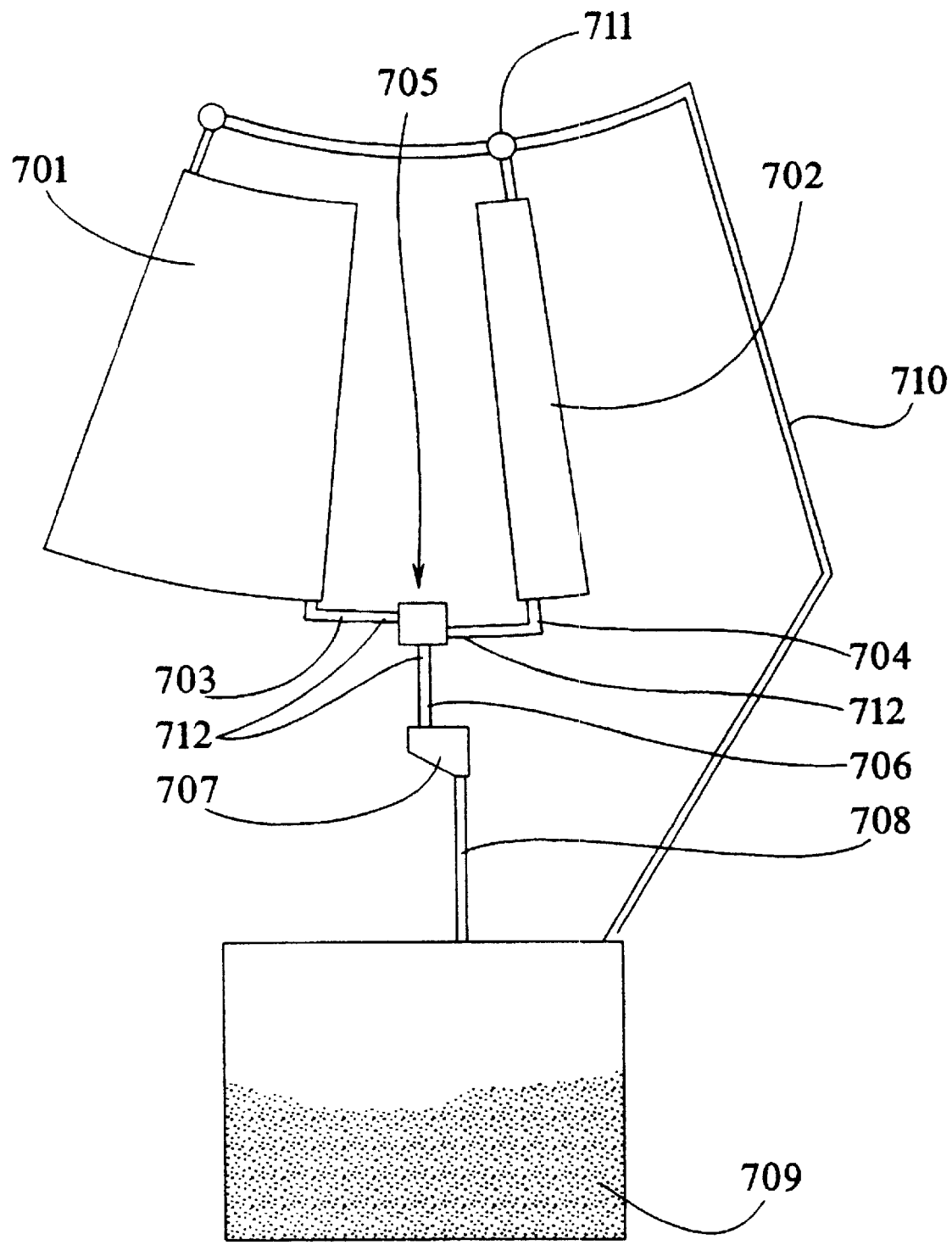

At a first rotational speed $f_1$, ranging from 100–1000 rpm (the exact value is dependent on the position of the components on the platform), the fluids from each capillary flows past capillary junction 605 and through mixing chamber 707 (FIGS. 21B and 21C). In embodiments comprising a sacrificial valve 712, the valve prevents fluid flow into channels 703 and 704. Upon release of sacrificial valve 712, fluid flow proceeds from capillary junction 705 through channel 706 and into mixing chamber 707 (FIG. 21C). Fluid flow within mixing chamber 707 is turbulent, in contrast to fluid flow through capillary barrier 705 or channel 706, which is primarily laminar, so that mixing occurs predominantly in mixing chamber 707. Fluid flow proceed through channel 708 and the mixed fluid solution is displaced into mixed fluid receiving chamber 709 (FIGS. 21D and 21E).

Figure 22:
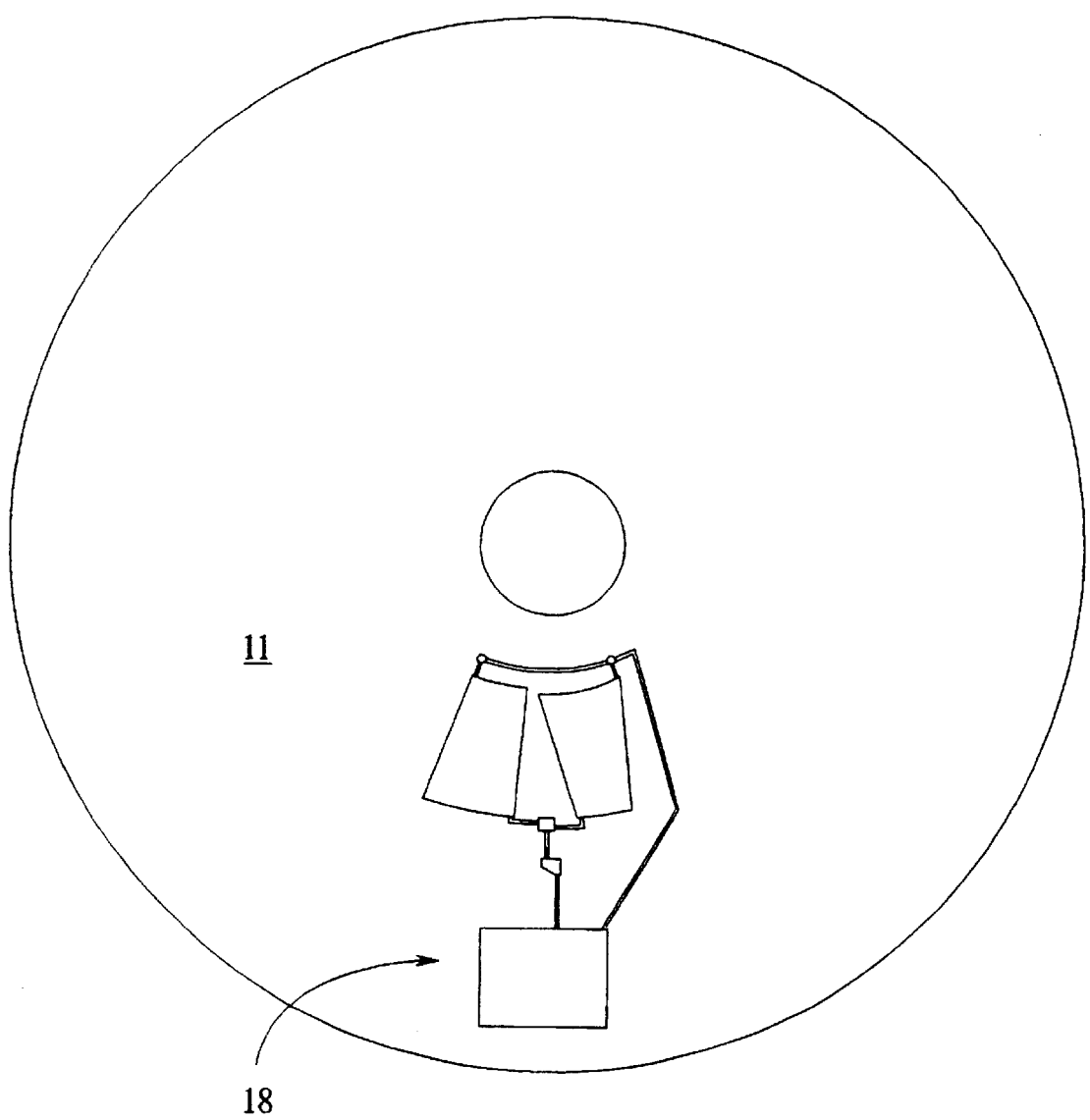
FIGS. 22 through 24 illustrate the microfluidics array of the microsystem platform described in Example 8.
Figure 23:
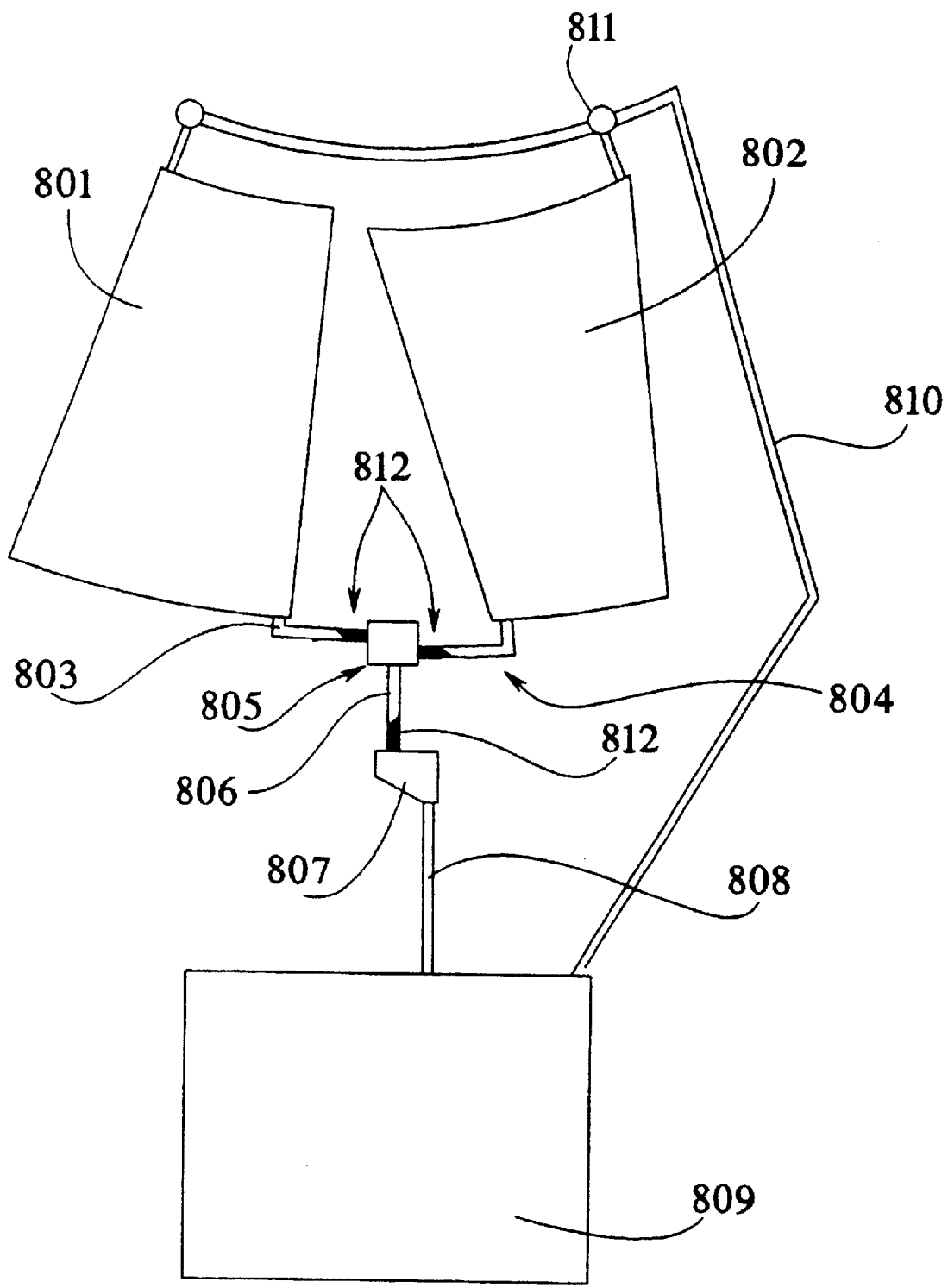

In another embodiment of the mixing chamber arrays of the invention are provided platforms capable of forming a gradient of two or more liquids that differ in viscosity, solute concentration or concentration of suspended particulates. Such an additional embodiment of the microsystems platform provided by the invention and specifically designed for performing mixing of different volumes of liquid samples to form a gradient in the concentration of a species in which the two fluids differ is illustrated in FIGS. 22–24. In FIG. 22, the arrangement of one assay array 18 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 23. It will be understood by a comparison of FIGS. 22 and 23 that the center of the platform 11 is at the top of FIG. 23, and the edge or lateral extent of the platform is at the bottom of FIG. 23, illustrated by a curved line. Rotation of the mixing array on platform disks of the invention can be in either direction, although rotation in a consistent, particular direction is preferred. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume is about 40 $\mu L$.

The components of the mixing array are as follows. Fluid reservoirs 801 and 802, each containing one of a pair of liquids to be mixed, are constructed on the platform, having a depth in the platform surface from about 0.1 mm to about 5 mm and lateral dimensions ranging from about 1 cm to about 10 cm. Fluid reservoir 801 is designed to accommodate a volume of from about 1 to about 500 $\mu L$, and fluid reservoir 802 is designed to accommodate a volume of about 1 to about 500 $\mu L$, wherein the shape of fluid reservoir 802 is different than the shape of fluid reservoir 801. In particular and in addition, fluid reservoirs 801 and 802 are shaped so that the rate of fluid output in the two reservoirs differs between the reservoirs at a particular rotational speed, due to a change in the pressure "head" (related to the cross-sectional area of the fluid at each point in the reservoir), so that the proportion of fluid in the mixture from one of the reservoirs is at a maximum at the beginning of rotation and is at a minimum when the fluids from the reservoirs are completely mixed at the end of rotation, thus forming a gradient. Gradients produced according to this aspect of the invention can consist of salt gradients, including sodium chloride and cesium chloride or sulfate gradients, gradients of low molecular weight species such as sucrose, synthetic polymer gradients such as Ficoll or Hypaque, or gradients of a drug, toxin, enzyme substrate or other small molecule of interest.

Each fluid reservoir is fluidly connected with a capillary channel 803 or 804 to capillary junction 805. Each capillary channel ranges from about 0.1 mm to about 1 mm deep, has a cross-sectional diameter of from about 0.1 mm to about 1 mm and extends about 2 cm to about 100 cm. Capillary junction 805 has a depth in the platform surface of from about 0.1 mm to about 1 mm that is greater than the depth of capillaries 803 to 804. Alternatively, capillaries 803 or 804 comprise a sacrificial valve 812, as described below. Use of said sacrificial valves can be used in addition to or in place of capillary junction 805.

The fluid components of the mixing array are also connected with air channels 810, that have dimensions of from about 0.1 mm to about 1 mm and permit venting of air displaced by fluid movement on the platform. In addition, capillary junctions 811 that are about 0.75 mm deep are present in the air channels to prevent fluid backflow into the air channel.

Capillary junction 805 is fluidly connected by a narrow capillary channel 806 to mixing chamber 807, which is fluidly connected with channel 808, which is further connected with mixed fluid receiving chamber 809. Alternatively, capillary 806 comprises a sacrificial valve 812. Capillary channel 806 is from about 0.1 mm to about 1 mm, has a cross-sectional diameter of from about 0.1 mm to about 1 mm and extends from about 0.2 cm to about 30 cm. Mixing chamber 807 is from about 0.1 mm to about 1 mm, has a cross-sectional diameter of from about 0.1 mm to about 1 mm, and is positioned from about 0.2 cm to about 30 cm from the center of rotation. Capillary channel 808 is from about 0.1 mm to about 1 mm, has a cross-sectional diameter of about 1 mm to about 20 mm and extends from about 0.2 cm to about 30 cm. Capillary channel 806 and capillary channel 808 are advantageously offset in their connection with the mixing chamber as described above, or are positioned at any convenient position in the mixing chamber for those embodiments relying on Coriolis forces to create mixing.

Capillary 808 is fluidly connected with mixed fluid receiving chamber 809. Mixed fluid receiving chamber 809 is about 0.75 mm deep (ranging from about 0.1 mm to about 1 mm) and having a cross-sectional diameter of about 5 mm (ranging from about 1 mm to about 20 mm) from about, and is positioned from about 1 cm to about 30 cm from the center of rotation.

Figure 24A:
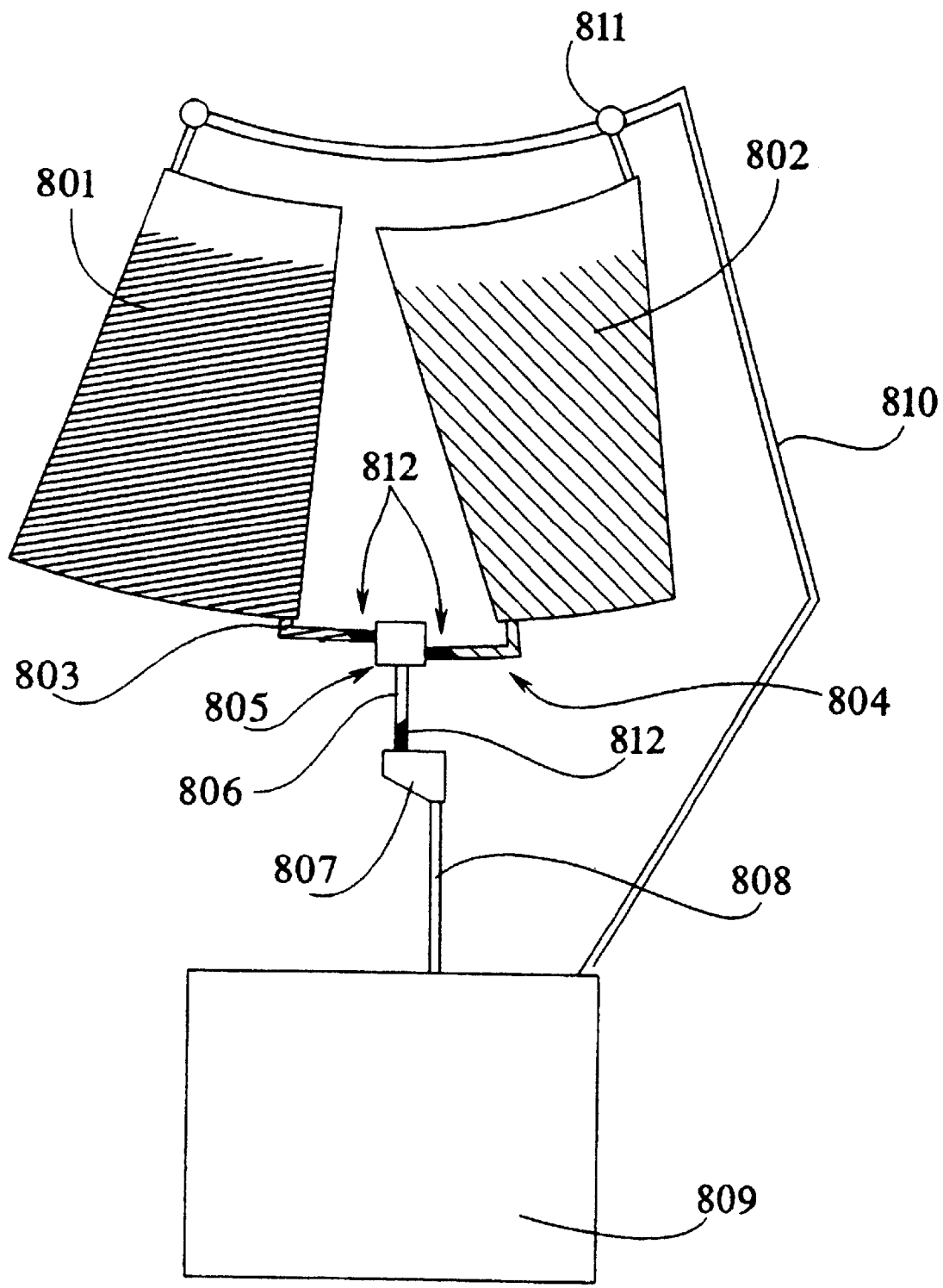

Use of this microfluidics platform to produce a gradient as described herein is illustrated in FIGS. 24A through 24E. A volume (ranging from 1–150 $\mu L$ of fluid) of each of the fluids to be mixed is applied to the fluid reservoirs 801 and 802 (FIG. 24A). Fluid enters the each of the capillaries 803 and 804 and stops at capillary junction 805. Alternatively, the platforms of the invention are provided containing the fluids to be mixed already in fluid reservoirs 801 and 802. In these embodiments, it is preferred that sacrificial valves 812 be provided in capillaries 803 and 804, to prevent evaporation, wetting or leakage of fluid from the reservoirs prior to use.

Figure 24B:
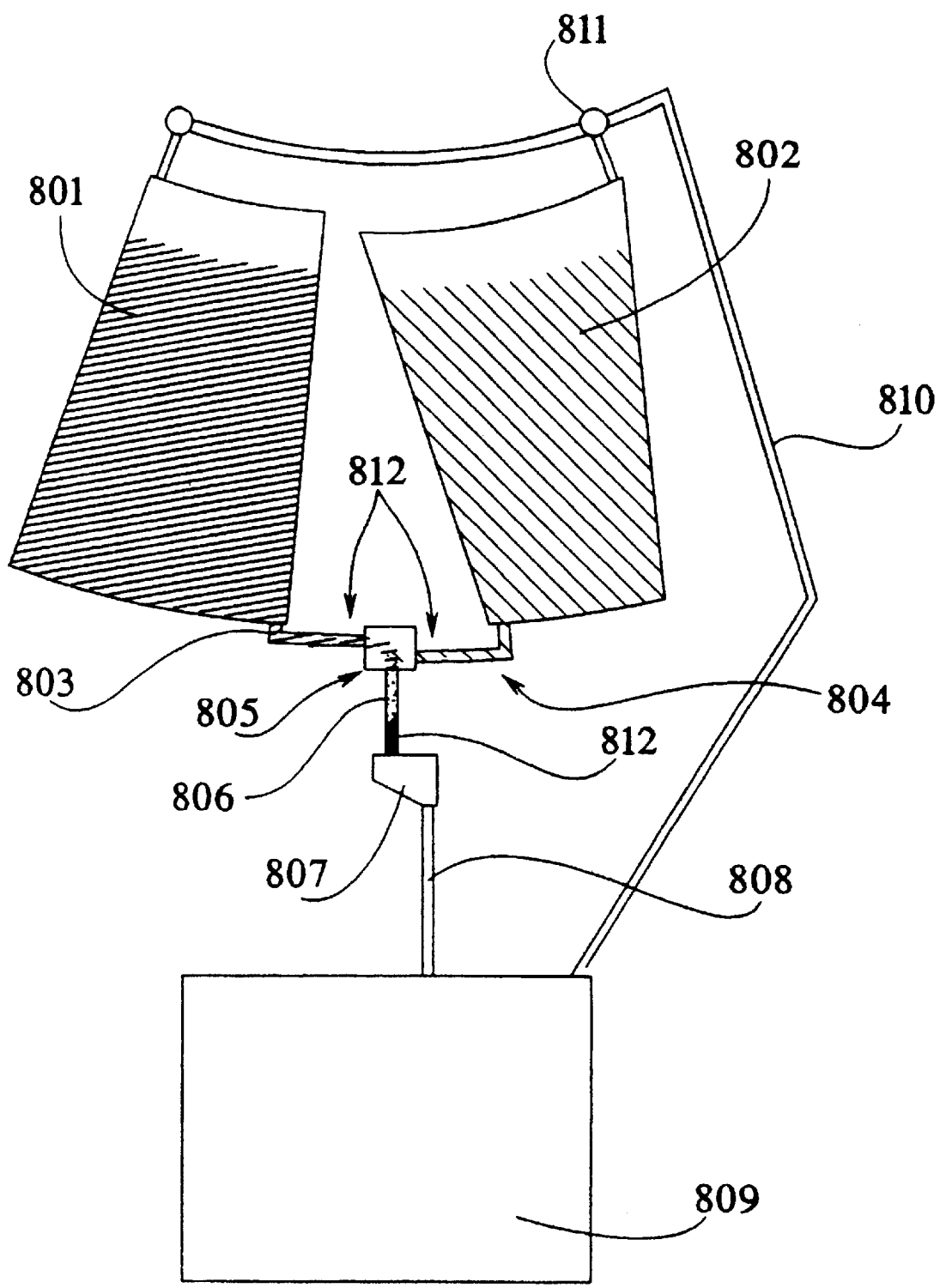
Figure 24C:
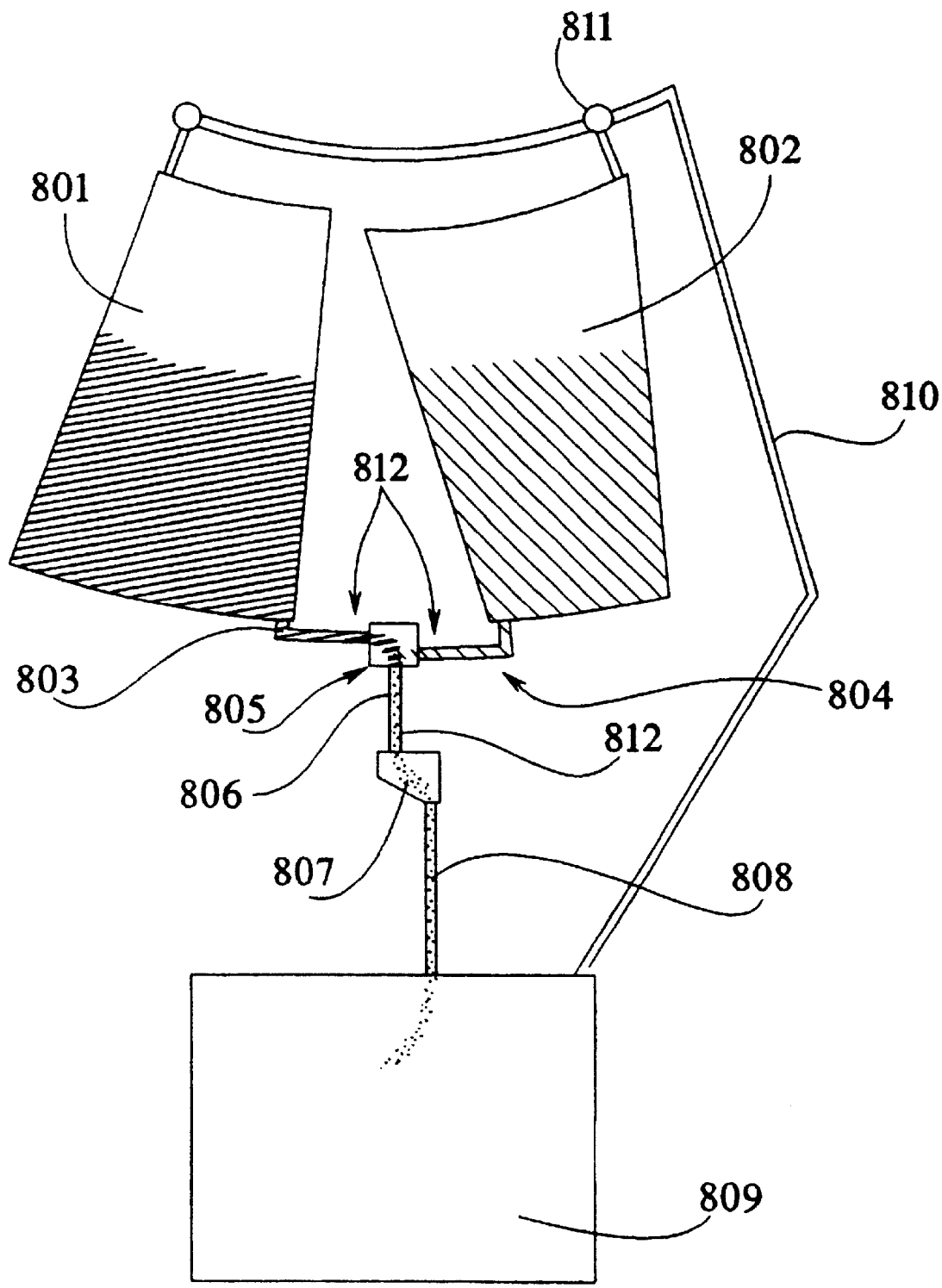
Figure 24D:
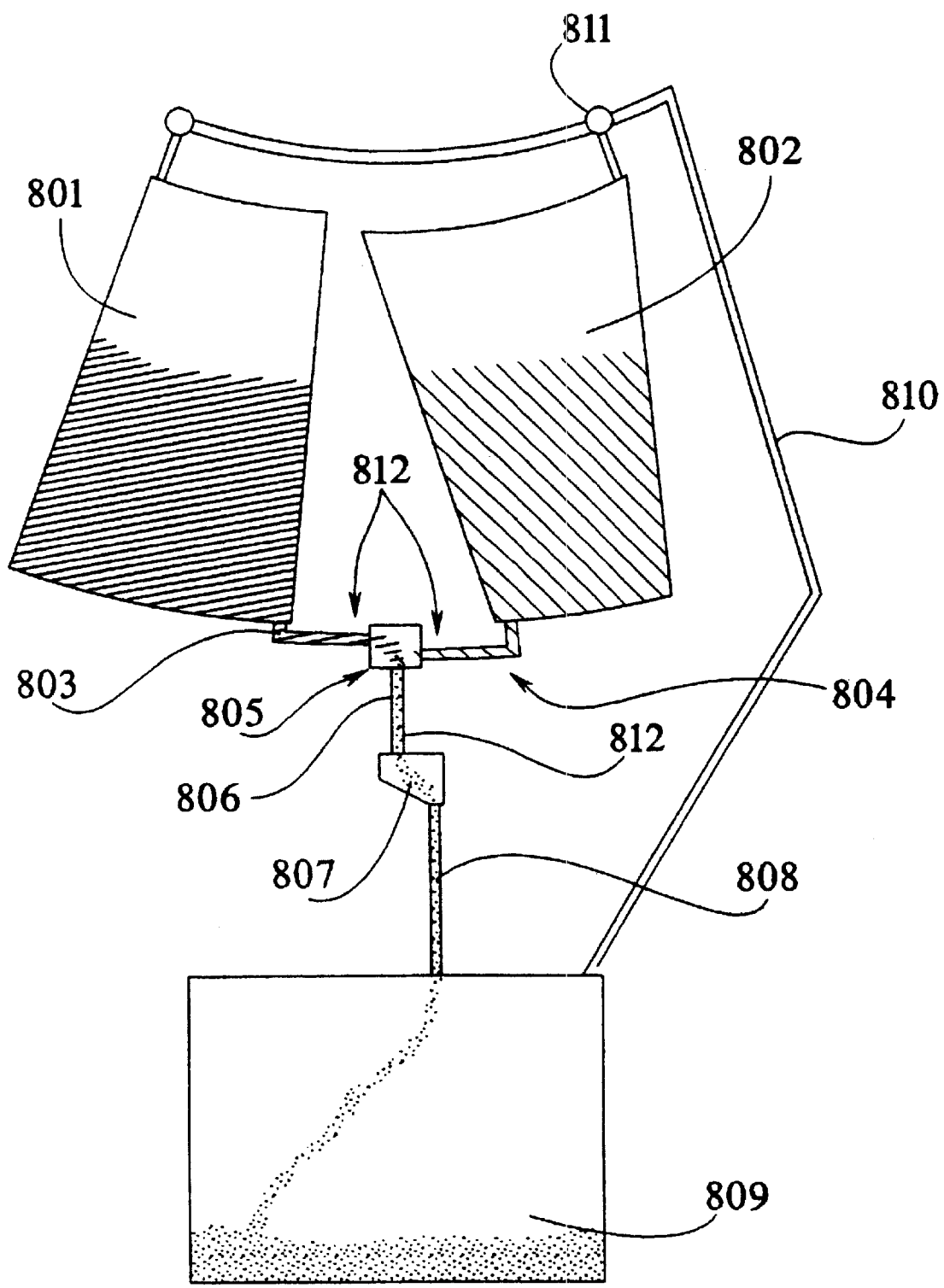
Figure 24E:
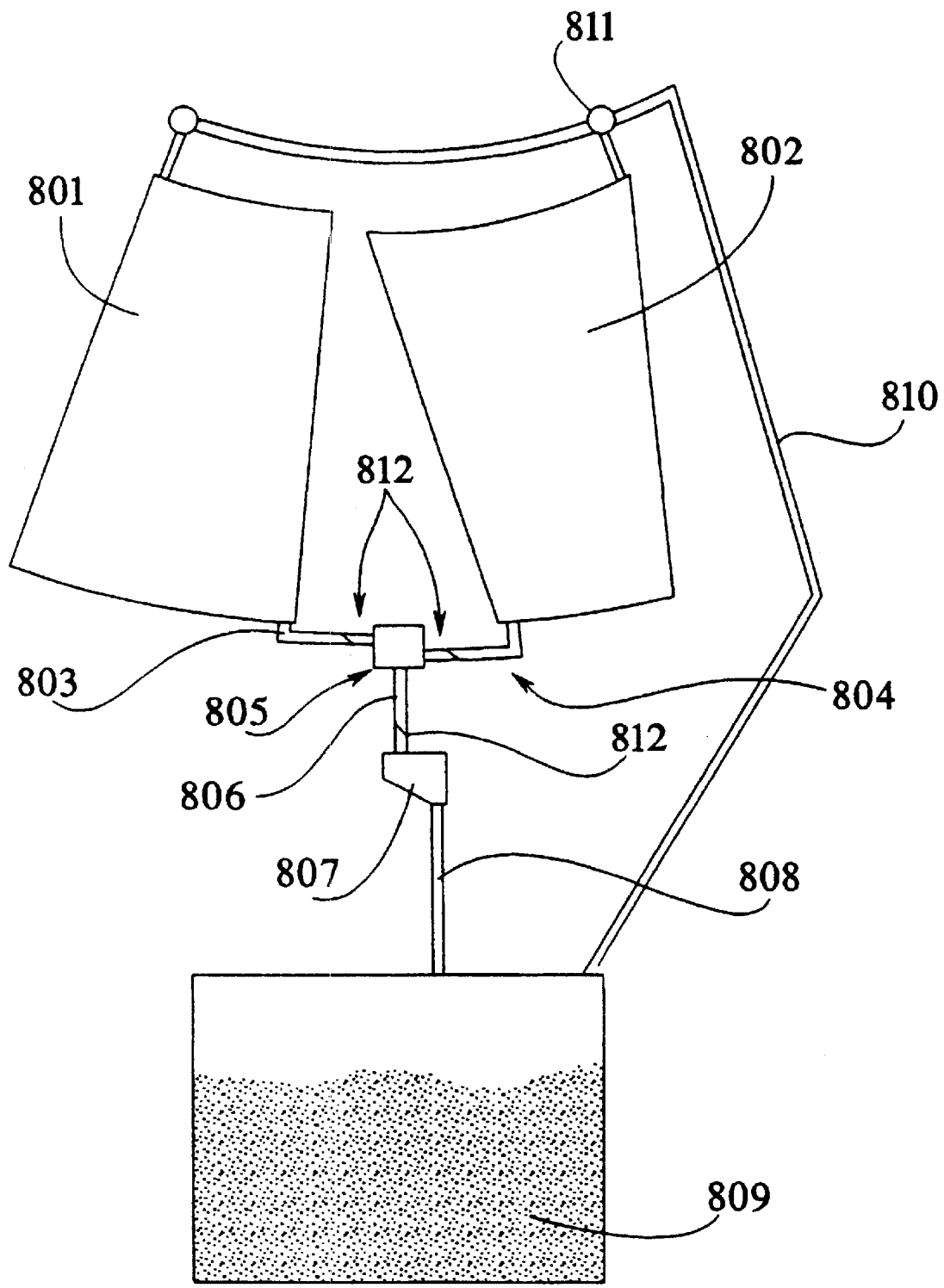

At a first rotational speed $f_1$, ranging from 100–1000 rpm (the exact value is dependent on the position of the components on the platform), the fluids from each capillary flows past capillary junction 805 and through mixing chamber 807 (FIGS. 24B and 24C). In embodiments comprising a sacrificial valve 812, the valve prevents fluid flow into channels 803 and 804. Upon release of sacrificial valve 812, fluid flow proceeds from capillary junction 805 through channel 806 and into mixing chamber 807 (FIG. 24D). Fluid flow within mixing chamber 807 is turbulent, in contrast to fluid flow through capillary barrier 805 or channel 806, which is primarily laminar, so that mixing occurs predominantly in mixing chamber 807. Fluid flow proceed through channel 808 and the mixed fluid solution is displaced into mixed fluid receiving chamber 809 (FIGS. 24D and 24E).

Figure 28:
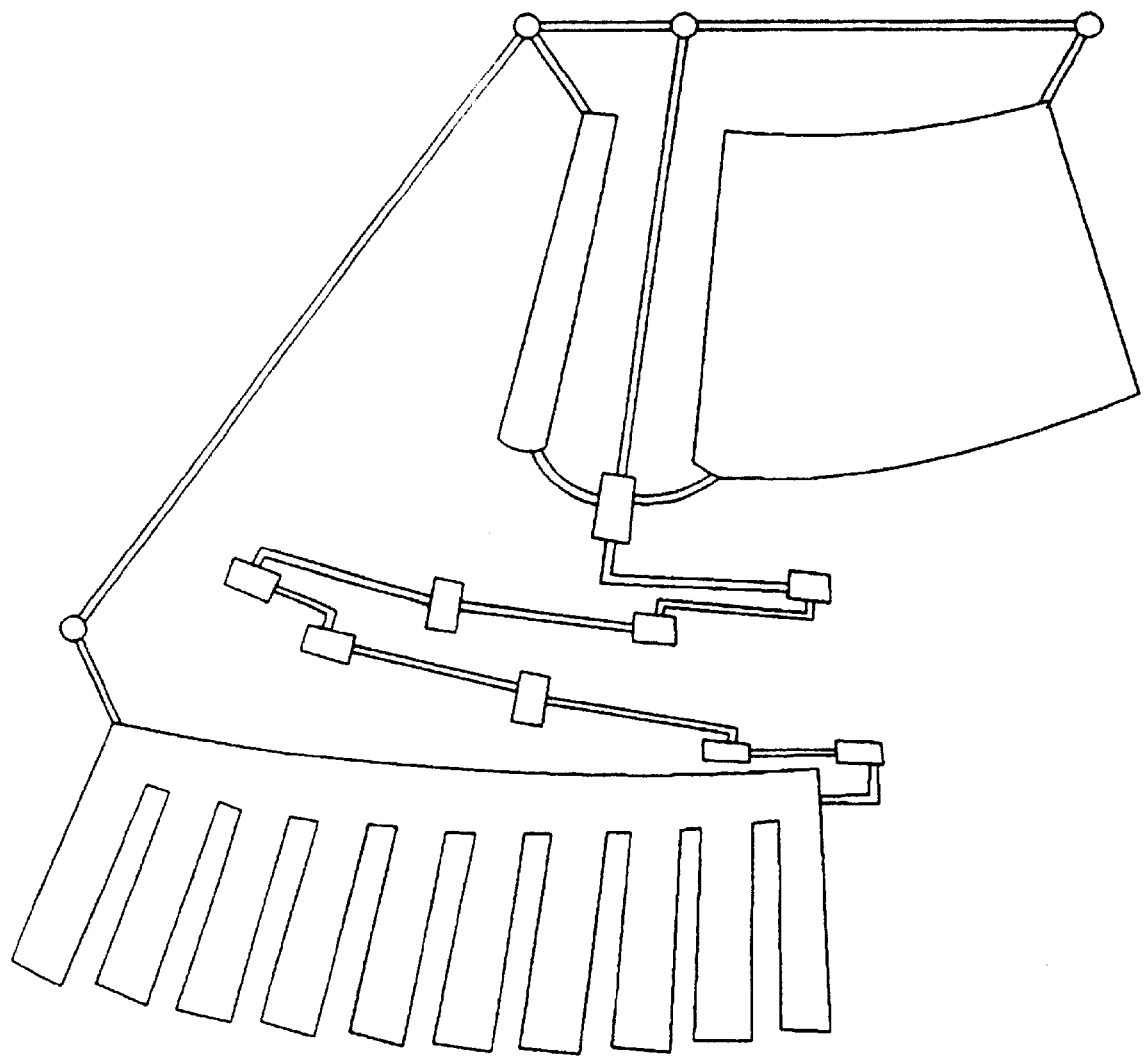
FIG. 28 illustrates a microfluidics array of a multiplicity of mixing chambers of the microsystem platform described in Example 8.

In addition to the embodiments described herein, the invention provides microfluidics arrays comprising a multiplicity of mixing chambers fluidly connected in series to one another. Such an arrangement is illustrated in FIG. 28. In particular, mixing cascades as shown in FIG. 28 are useful for mixing liquids of dramatically different volumes or viscosities, such as mixing a low volume, high viscosity liquid with a high volume, low viscosity liquid. In these embodiments, the mixing array comprises a multiplicity of mixing chambers arrayed radially across the platform surface, each mixing chamber having an inlet capillary extending radially from a position more proximal to the center of rotation than the mixing chamber, and an outlet capillary extending radially to a position more distal to the center of rotation than the mixing chamber. In an advantageous embodiment of this array, the capillaries are connected with the mixing chamber so that their positions in the mixing chamber are offset from one another, wherein fluid flow from the inlet capillary impinges on a wall of the mixing chamber at a position other than the position occupied by the outlet capillary, thereby producing turbulent flow within the mixing chamber that mixes the fluids. Alternatively, the capillaries can be positioned in the mixing chamber at any convenient position, and Coriolis forces have be relied upon to facilitate mixing. In either type of array, the inlet capillary of the first mixing chamber is fluidly connected with the fluid reservoirs (either directly or through a capillary junction), and the inlet capillary of the other mixing chamber in the array is the outlet channel of the mixing chamber immediately more proximal to the center of rotation; similarly, the outlet capillary of each mixing chamber is the inlet capillary of the mixing chamber immediately more distal to the center of rotation, and wherein the outlet capillary of the mixing chamber positioned the most distal from the center of rotation is fluidly connected with a mixed fluid receiving chamber. Thus, the fluid is repetitively mixed in a multiplicity of mixing chambers arrayed more and more distally from the center of rotation, ending with a reservoir or chamber sufficient in volume to accommodate the volume of the mixed fluid. The dimensions of the capillaries, fluid reservoirs, mixing chambers and mixed fluid receiving chamber in these arrays are as described above.

FIG. 28 also illustrates another embodiment of the mixing arrays of the invention. In this embodiment, used in conjunction with the gradient-forming embodiment described above, a specialized mixed fluid receiving chamber, termed a gradient chamber, is provided; one embodiment of this receiving chamber is shown in FIG. 28. This chamber permits the gradient fluid stream to be aliquotted into the individual compartments of the chamber, wherein the concentration of the gradient decreases with increasing distance from the gradient chamber inlet capillary. With gradients constituting decreasing concentrations of an analyte, drug, toxin or other species to be tested, the chamber can be modified to contain a detection means in each compartment, so that the concentration effect of the changing component of the gradient can be determined.

Figure 25:
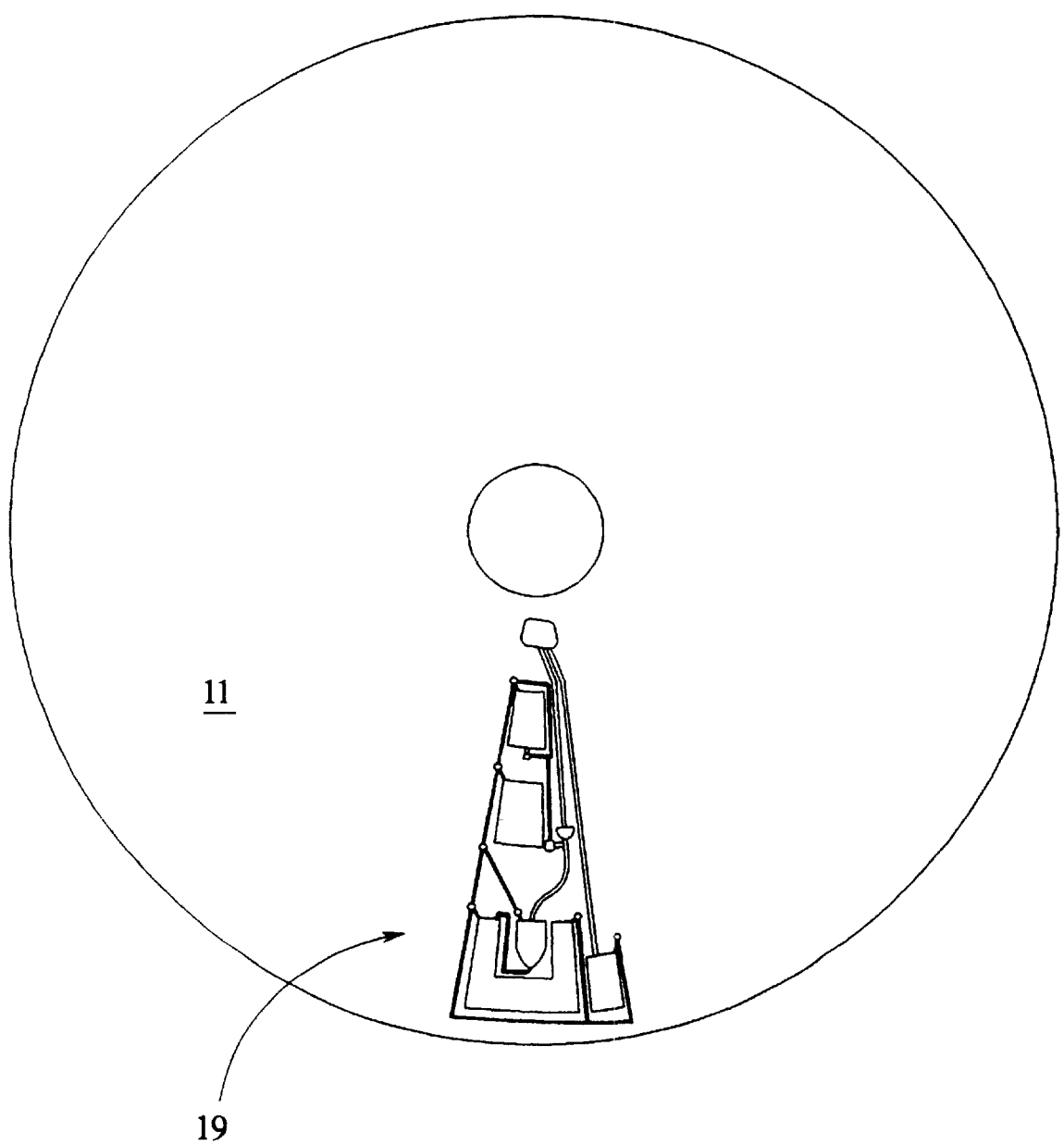
FIGS. 25 through 27 illustrate the microfluidics array of the microsystem platform described in Example 9.
Figure 26:
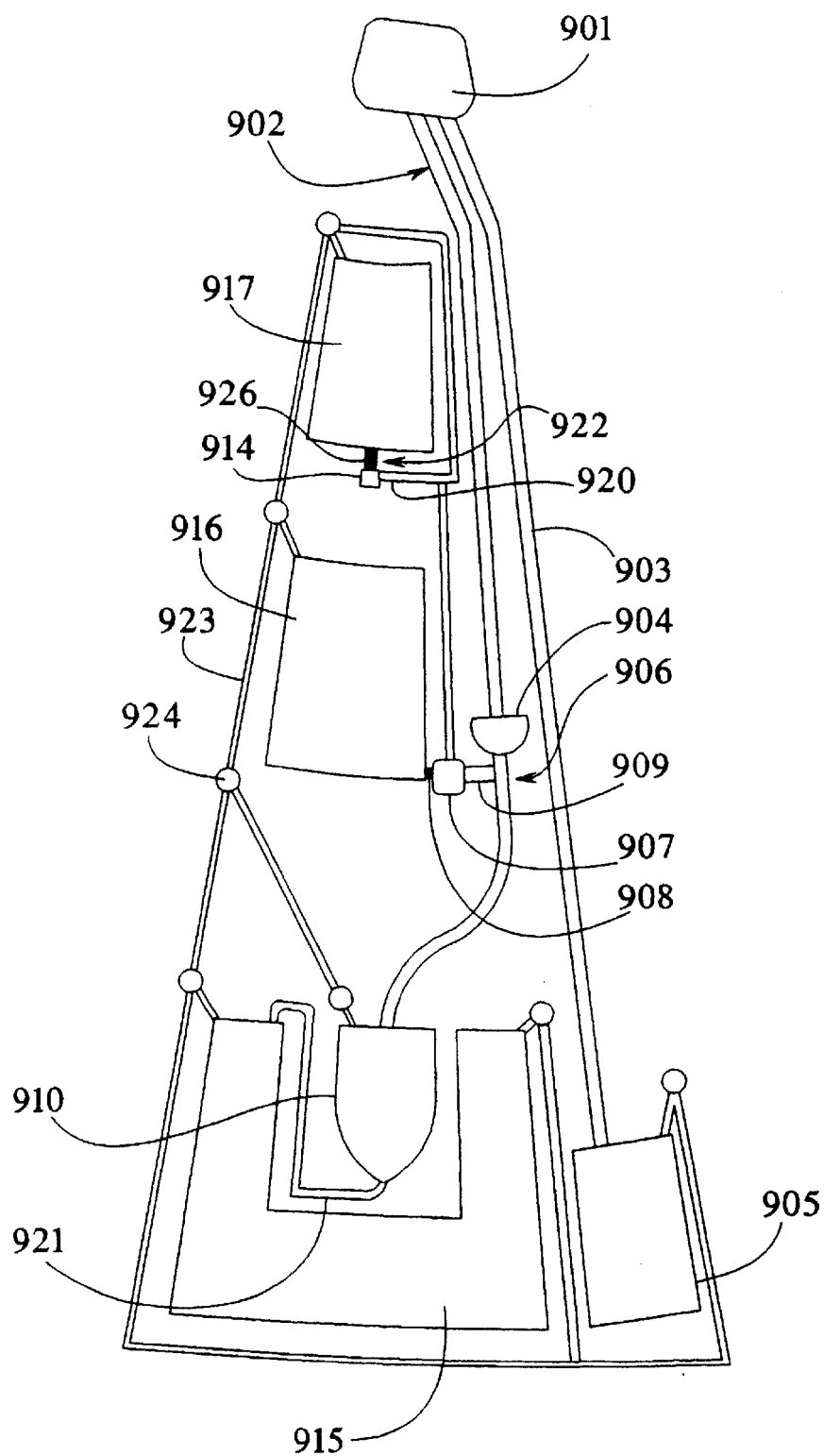

In yet another embodiment of the microfluidics platforms of this invention are provided a microsystems platform specifically designed for performing a specific binding assay. These embodiments are exemplified using an immunoassay as illustrated in FIGS. 25 through 27. In FIG. 25, the arrangement of one assay array 19 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 26. It will be understood by a comparison of FIGS. 25 and 26 that the center of the platform 11 is at the top of FIG. 26, and the edge or lateral extent of the platform is at the bottom of FIG. 26, illustrated by a curved line. Rotation of the mixing array on platform disks of the invention can be in either direction, although rotation in a consistent, particular direction is preferred. Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction was about 10–100 µL.

In this aspect of the platforms of the invention there is provided an incubation chamber that comprises a specific binding reagent. For the purposes of this invention, the term "specific binding reagent" is intended to encompass biomolecules having a specific binding affinity between pairs thereof providing a specific molecular binding interaction with a binding affinity constant of between about $10^{-4}$ and 10–15 M. Examples of such pairs of specific binding reagents include but are not limited to antigen and antibody, including antisera, polyclonal antibodies and most preferably monoclonal antibodies; receptor and ligands, including cell-surface receptors; integrins and adhesion proteins, including ICAM-I and ICAM-II; and carbohydrates and lectins, including phytohemagglutinin. As provided by the invention, specific binding reagents comprising a first member of a specific binding pair is provided in an incubation chamber as a coating on the surface of the chamber, as a dried or lyophilized reagent contained in the chamber and reconstituted upon addition of a fluid or fluid sample to the chamber; contained on a support media, such as latex or other beads, or in a gel or other support media. Said first member of a specific binding pair is designed or intended to detect the presence of an analyte, for example, a cell expressing a cognate antigen, receptor or adhesion protein or having a carbohydrate moiety at the cell surface specific for a particular lectin. Said specific binding reagent is applied to the incubation chamber of the platform by depositing the reagent on the surface using any appropriate means, including inkjet printing, computer-positioned syringes, microetching and microlithographic methods, including photolithography, screen and airbrush printing methods, solution coating, dipping, and conventional microtitre-well techniques. In applying said specific binding reagent, the surface or detection chamber can be treated to provide a two-dimensional array or pattern, wherein certain areas on the surface or detection chamber are treated with said specific binding reagent and others are not in a recognizable manner.

The components of the specific binding assay array are as follows. An entry port 901 having a depth in the platform surface ranging from about 0.1 mm to about 1 mm deep and lateral dimensions of about 0.1 cm to about 2 cm is constructed on the platform, and designed to accommodate a volume of about from 2 µL to 100 µL. This entry port is fluidly connected with a metering capillary 902 having cross-sectional diameter of from about 0.1 mm to about 1 mm, and having a depth of about 0.25 mm to 1 mm; the length of this metering capillary was sufficient to contain a total volume of about 2 to about 100 µL. The metering capillary 902 is fluidly connected to capillary junction 904.

The entry port is also constructed to be fluidly connected with an overflow capillary 903 having a cross-sectional diameter of about 0.1 mm to about 1 mm and proximal ends rounded with respect to entry port 901. The overflow capillary is fluidly connected with an overflow chamber 905 having a depth in the platform surface of about 0.1 mm to about 1 mm, greater than the depth of the overflow capillary 903. Each of the overflow and fluid chambers is also connected with air ports or air channels, such as 523, that have dimensions of about 0.1 mm to about 1 mm and that permit venting of air displaced by fluid movement on the platform. Capillary junctions 524 that are about 0.75 mm deep are present in the air channels to prevent fluid flow into the air channels.

Entry-port 901 is positioned on the platform from 1 cm to 20 cm from the center of rotation. Metering capillary 902 extends from entry port 901 from about 0.5 cm to about 5 cm. Overflow capillary 902 extends from entry port 901 from about 1 cm to about 20 cm. The extent of the length of overflow capillary 903 is 20% longer than metering capillary 902. The position of overflow chamber 905 is from about 1 cm to about 20 cm from the center of rotation, and the position of capillary junction 904 is from about 1 cm to about 20 cm from the center of rotation.

Capillary junction 904 is fluidly connected with capillary channel 906, which in turn is fluidly connected with incubation chamber 910. Capillary channel 906 has a cross-sectional diameter of about 0.1 mm to about 1 mm and extends from about 0.2 cm to about 10 cm from the capillary junction. Incubation chamber 910 has a depth in the platform surface ranging from about 0.1 mm to about 1 mm, that is greater than the depth of capillary channel 906. Capillary channel 906 is also fluidly connected with channel 909 through capillary junction 907. Capillary junction 907 is constructed to prevent fluid flow backwards through the junction. Channel 909 has a cross-sectional diameter of about 0.1 mm to about 1 mm and extends from about 0.2 cm to about 5 cm from the capillary junction. Capillary junction 907 has a depth in the platform surface of about 0.1 mm to about 1 mm, greater than the depth of the channel 909 or capillary channel 906. Incubation chamber 910 also contains a specific binding species, most preferably an antibody, specific for a component of the sample. This species is advantageously contained within incubation chamber 910 as a coating on the surface of the chamber, or attached to beads or other carrier within the chamber, or to a fuctionalized inner surface of the chamber or otherwise as described above.

Capillary junction 907 is further fluidly connected with wash buffer reservoir 516, having a depth in the platform surface of from about 0.1 mm to about 1 mm and positioned at a distance from about 10 mm to about 200 mm from the axis of rotation.

Capillary junction 907 is further fluidly connected with reagent capillary 920, which is further fluidly connected with capillary junction 914, which is further fluidly connected with channel 926, and which is fluidly connected with reagent reservoir 917. Reagent capillary 920 has a cross-sectional diameter of about 0.1 mm to about 1 mm and extends from about 0.2 cm to about 20 cm reagent reservoir 917. Capillary junction 914 has a depth in the platform surface ranging from about 0.1 mm to about 1 mm and is positioned at a distance from about 10 mm to about 200 mm from the axis of rotation. Reagent capillary 926 has a cross-sectional diameter of from about 0.1 mm to about 1 mm and extends from about 0.2 cm to about 20 cm from the capillary junction. Reagent reservoir 917 has a depth in the platform surface of about 0.1 mm to about 1 mm, and is positioned at a distance from about 10 mm to about 200 mm from the axis of rotation.

Incubation chamber 910 is fluidly connected at a point most distal to the axis of rotation to U-shaped capillary 921. U-shaped capillary 921 has a cross-sectional diameter of about 0.1 mm to about 1 mm and extends from about 0.2 cm to about 20 cm between incubation chamber 910 and waste reservoir 915. This capillary extends in a U-shape to a point that is at least as proximal to the axis of rotation than the most axis-proximal extent of incubation chamber 910. This positioning of the U-shaped channel relative to incubation chamber 910 ensures that additional fluids flowing into incubation chamber 910 and displacing fluid therefrom will displace said fluid homogeneously, i.e., the first fluid in the chamber will be pushed out of the chamber whilst being replaced by the second fluid.

This U-shaped capillary is also fluidly connected with waste reservoir 915. Waste reservoir 915 has a depth in the platform surface of about 0.1 mm to about 5 mm and is positioned at a distance from about 10 mm to about 200 mm from the axis of rotation; as shown in FIG. 26, the waste reservoir is typically positioned at the farthest distance from the axis of rotation of any of the components of the array.

In certain embodiments of the invention, sacrificial valves 922 can be positioned at the junction of capillary junction 904 and capillary channel 906, at the junction of capillary junction 907 and wash buffer capillary 908, or at the junction of reagent reservoir 918 and capillary junction 919.

Figure 27A:
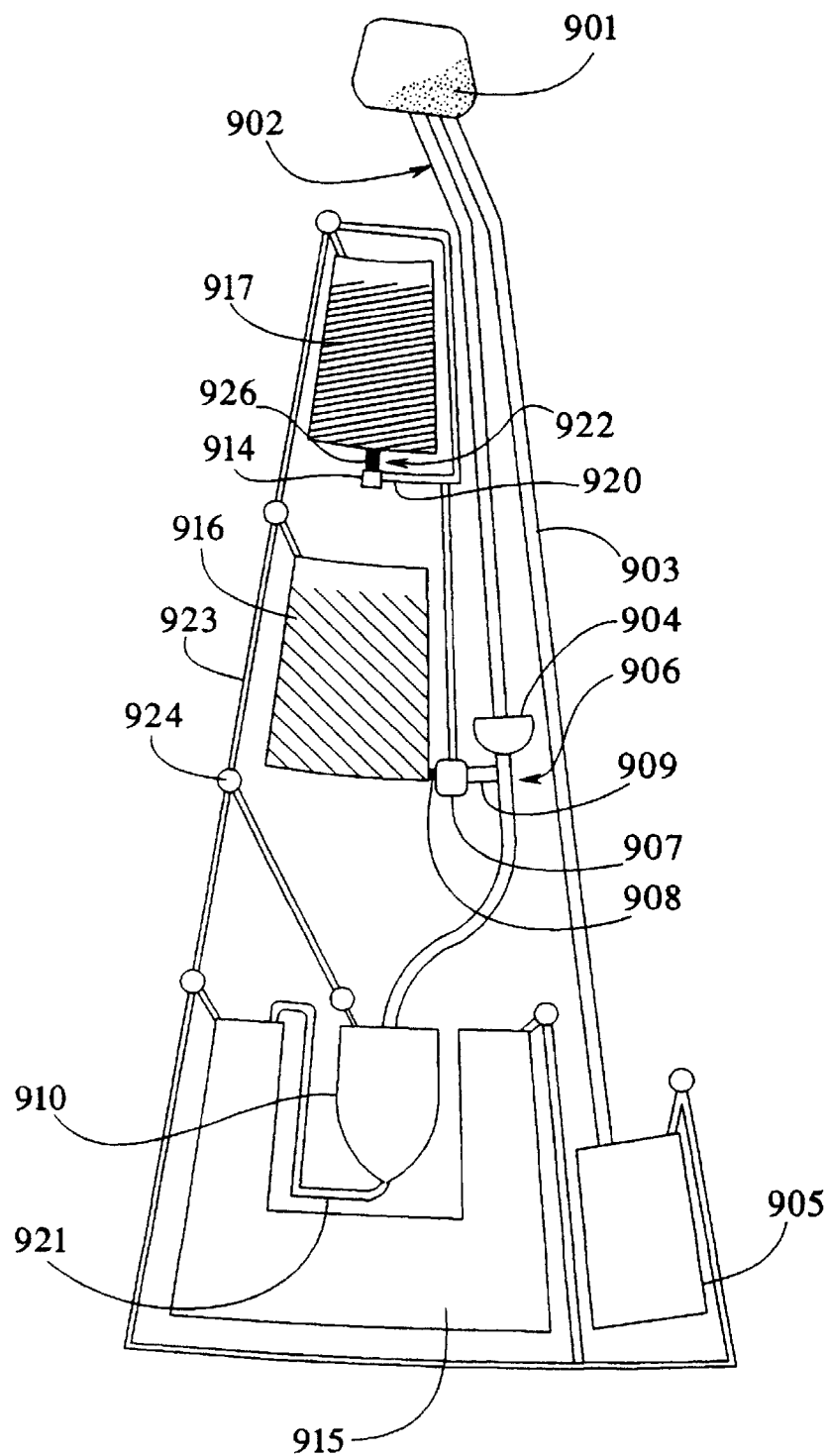
Figure 27B:
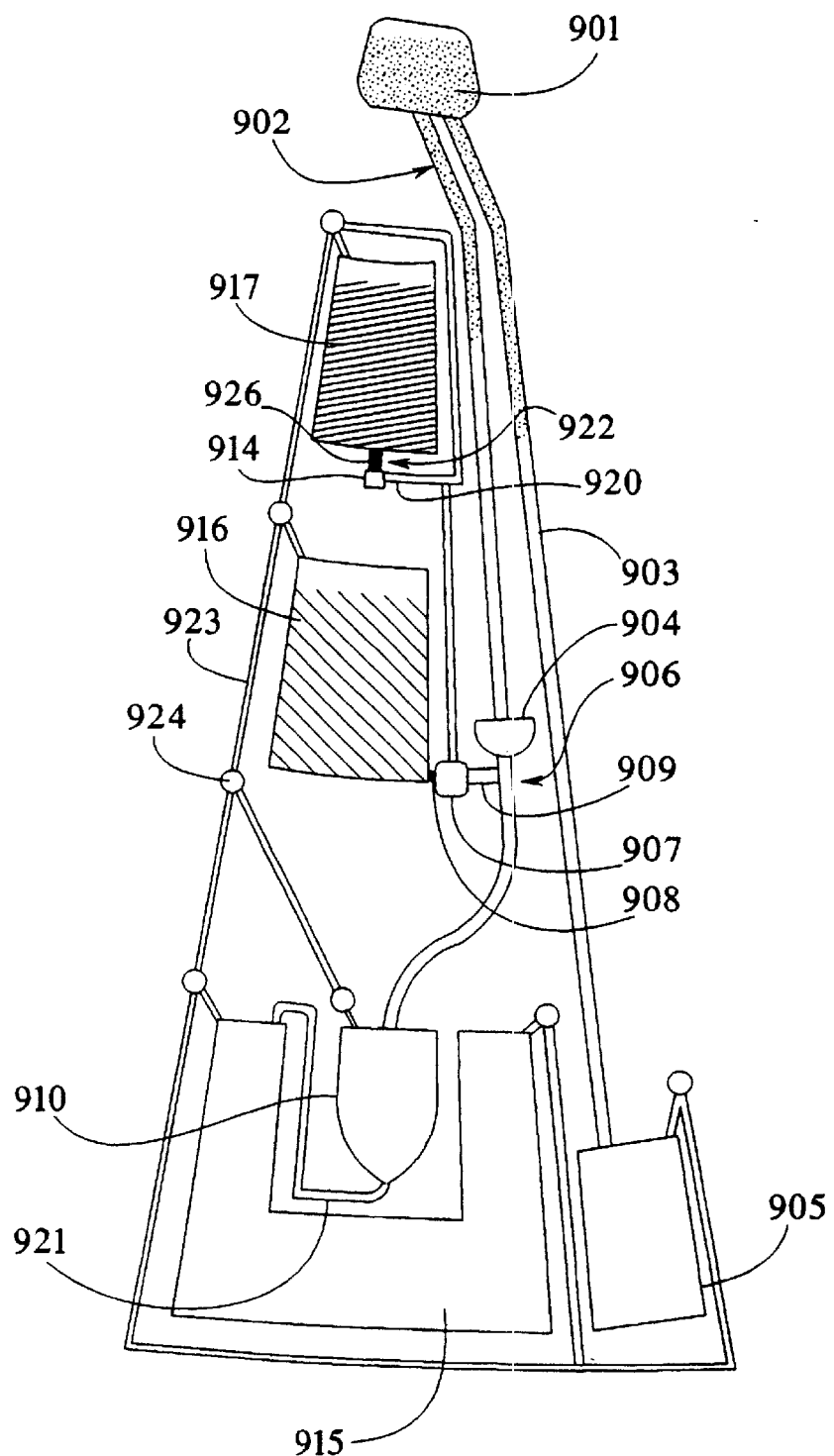
Figure 27C:
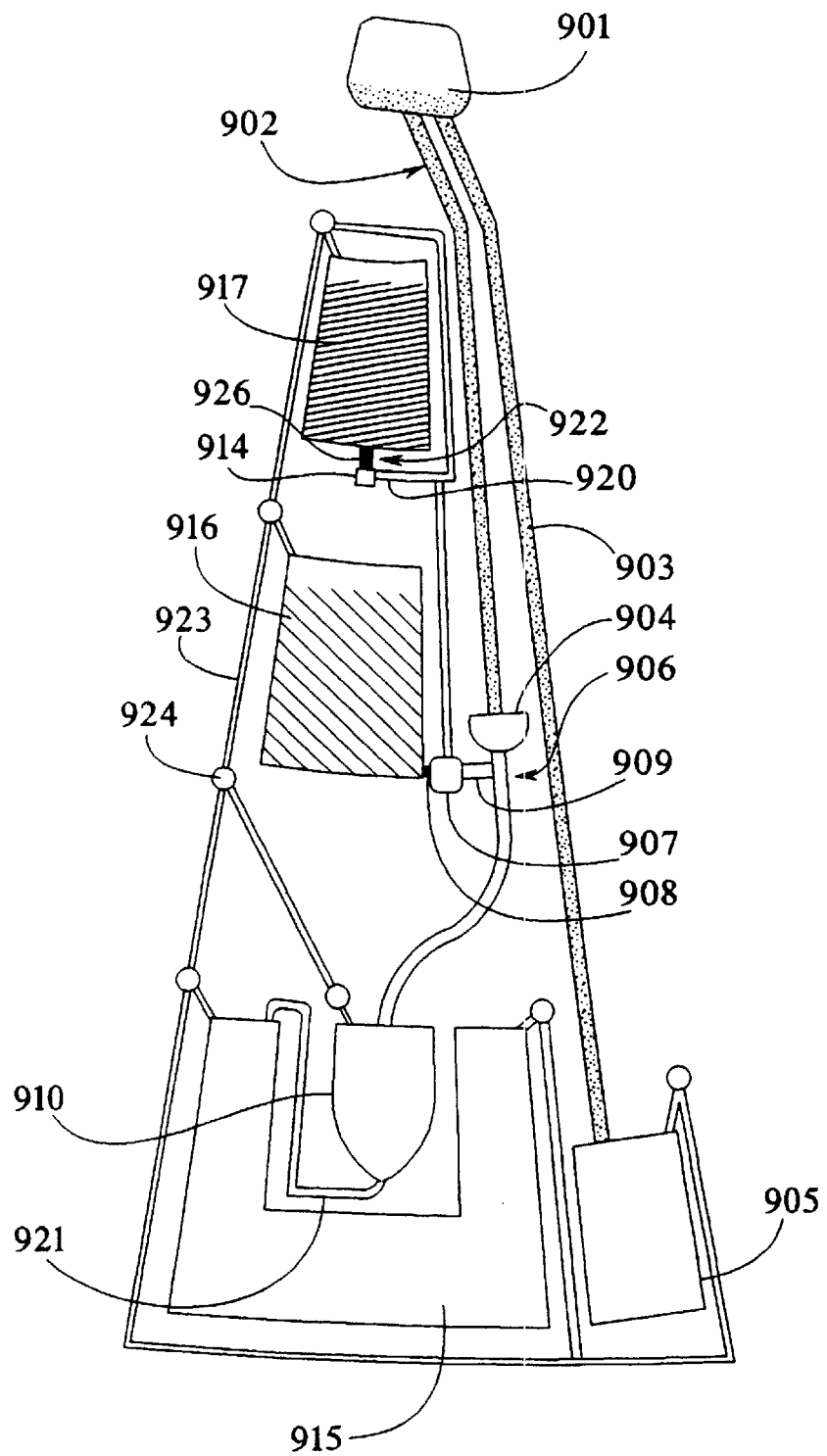

The use of this platform for performing an immunoassay is illustrated in FIGS. 27A through 27L. In the use of this platform reagent reservoir 916 and wash reservoir 915 are pre-loaded on the disk, and most preferably the disk contains sacrificial valves 922 at the junction of capillary junction 907 and wash buffer capillary 908, and at the junction of reagent reservoir 918 and capillary junction 919. An imprecise volume (ranging from 1–150 $\mu$L of fluid) of a fluid is applied to the entry port 901 (FIG. 27A). Fluid wicks into metering capillary 902 and stops at the capillary junction between metering capillary 902 and capillary junction 904 (FIGS. 27B and 27C). After sample loading by a user and filling of metering capillary 902 and overflow capillary 903 at no rotational speed, the platform is spun at a first rotational speed $f_1$, ranging from 100–500 rpm; the exact value is dependent on the position of the components on the platform.

Figure 27D:
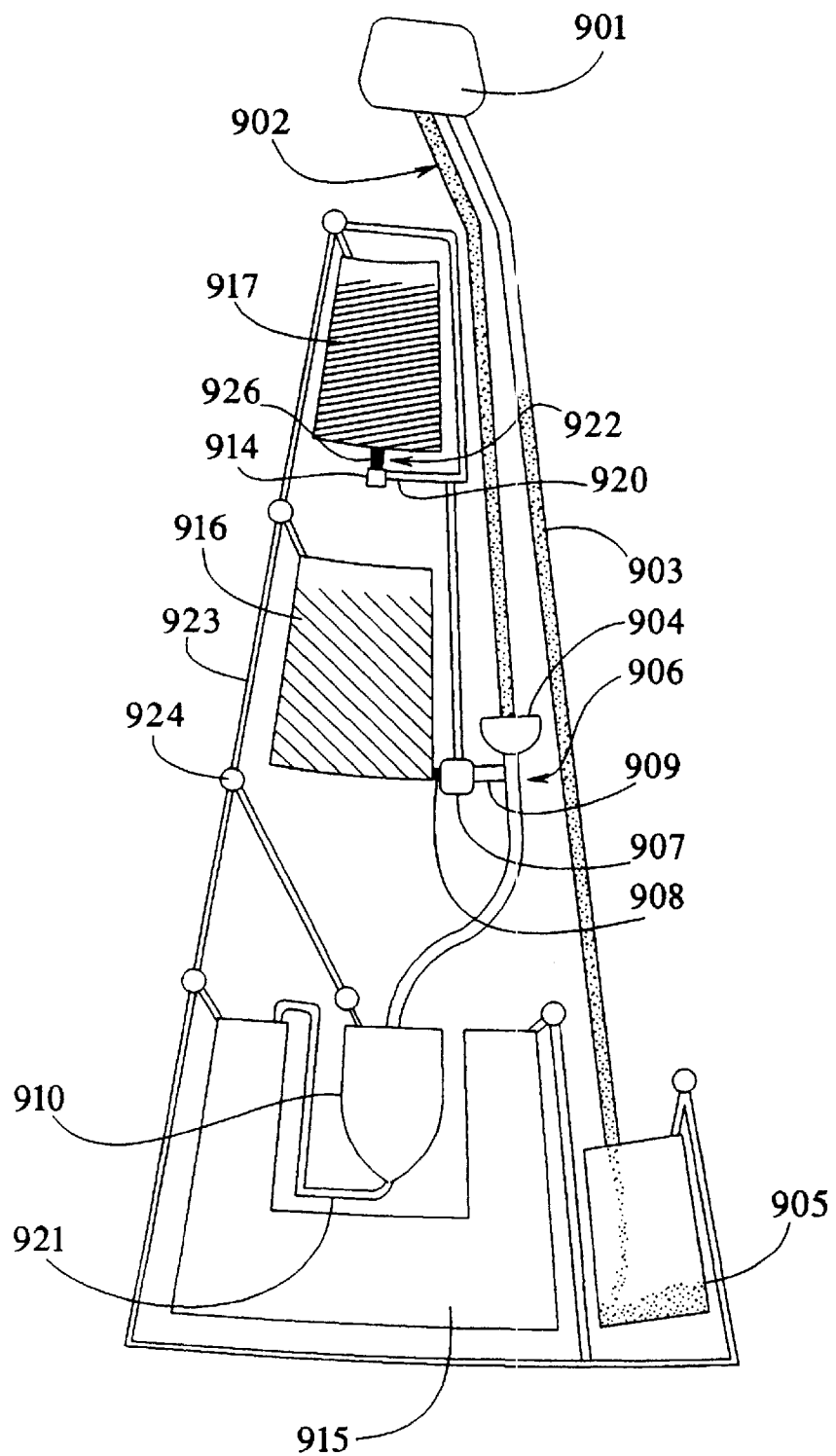
Figure 27E:
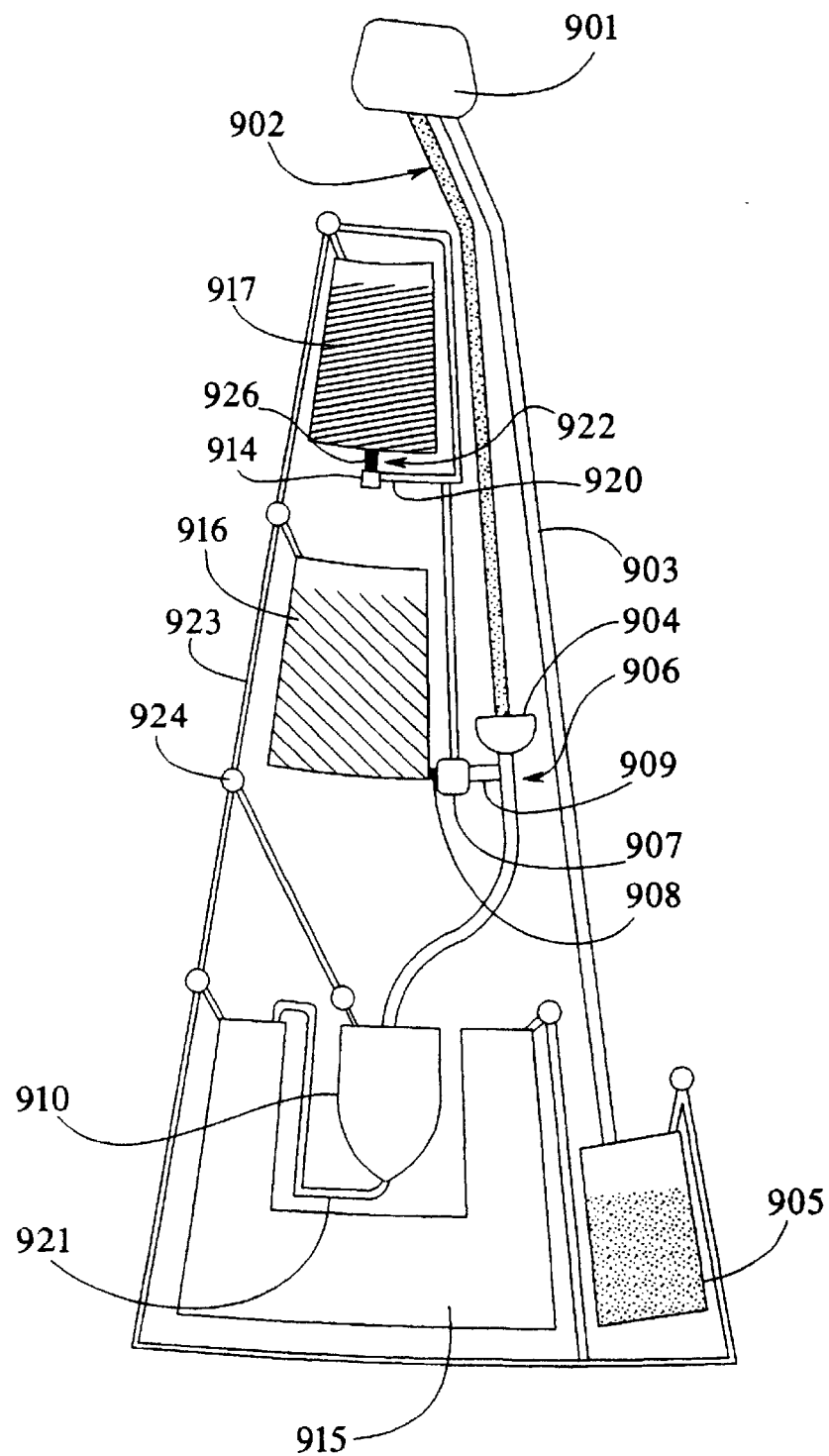

Due to the greater distance of the end of overflow capillary 903 from the center of rotation than the end of metering capillary 902, fluid flows through overflow capillary 903 into overflow chamber 905 (FIG. 27D). The platform is spun until all excess fluid is evacuated from entry port 901 and into overflow chamber 905, except the fluid contained in metering capillary 902 (FIG. 27E).

Figure 27F:
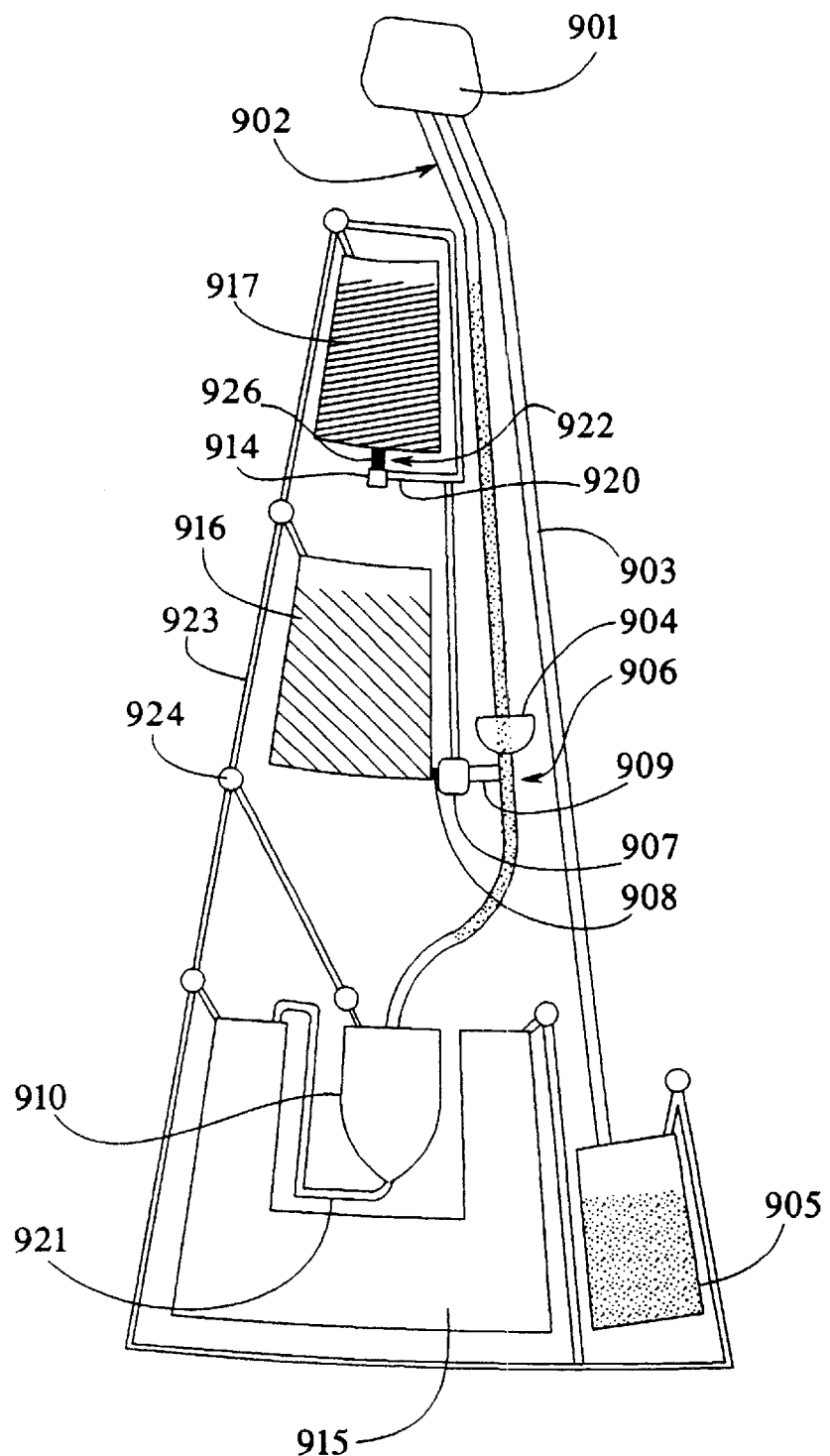
Figure 27G:
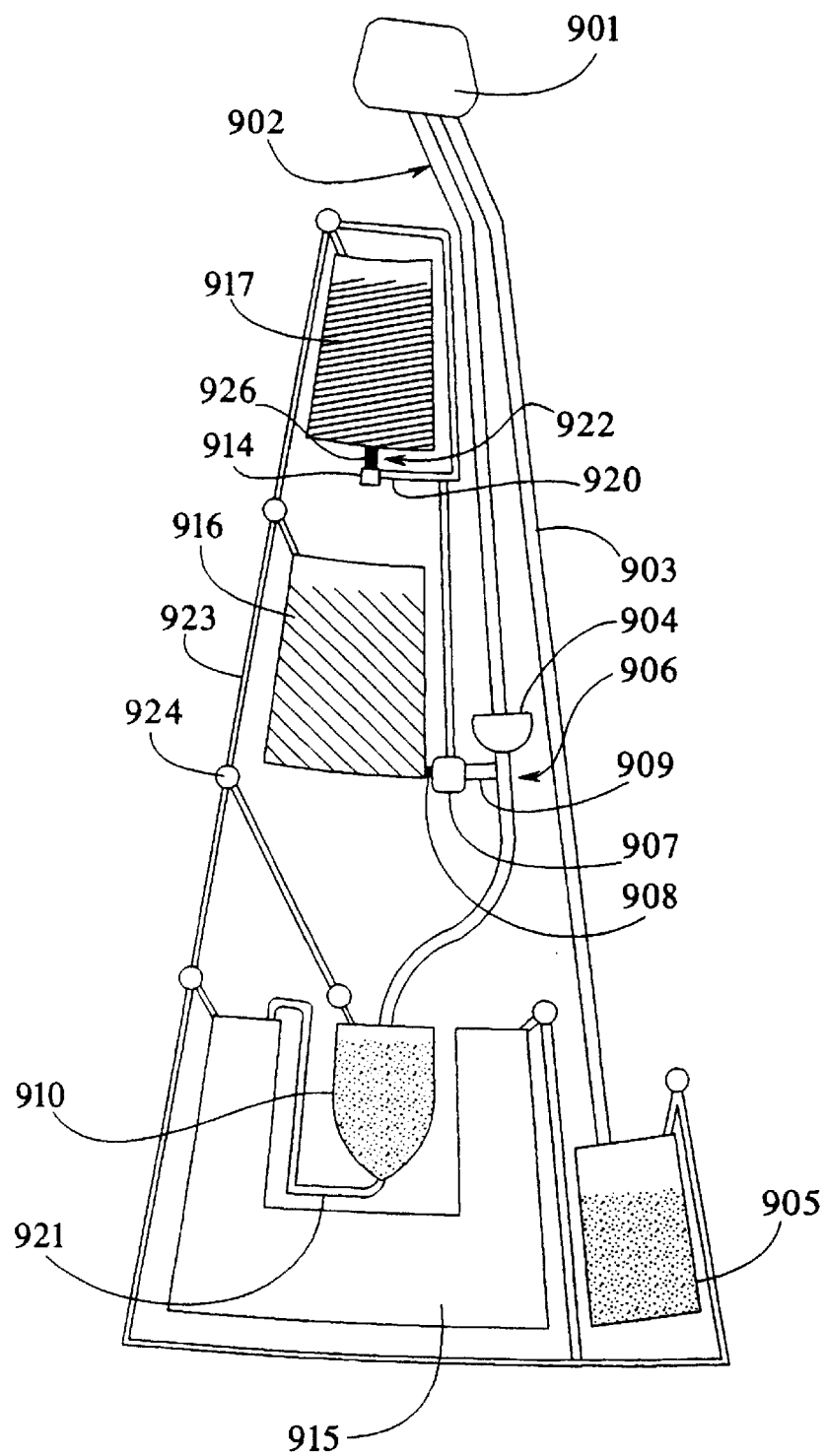

At a second rotational speed $f_2$, that is greater than the first rotational speed $f_1$, typically in the range of 100–1000 rpm, the capillary junction 904 at the distal end of the metering capillary 902 is overcome, and sample from metering capillary 902 fills incubation chamber 910 (FIGS. 27F and 27G). A portion of the sample wicks into U-shaped capillary 914 to the level of the sample in incubation chamber 910 (FIG. 27G). The sample is incubated for a time sufficient for maximum saturation binding of the component in the sample that specifically bind to the specific binding species.

Figure 27H:
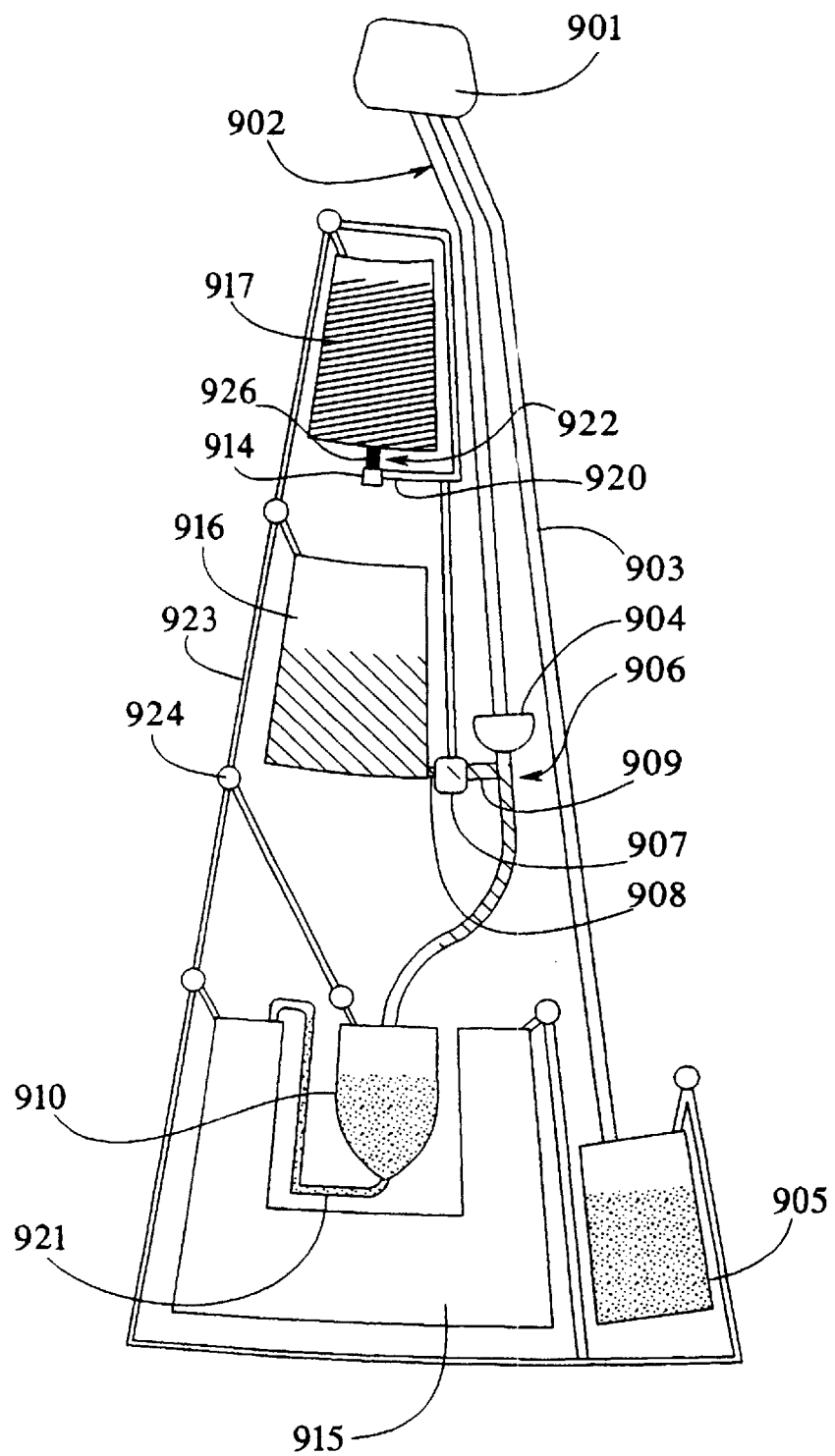
Figure 27I:
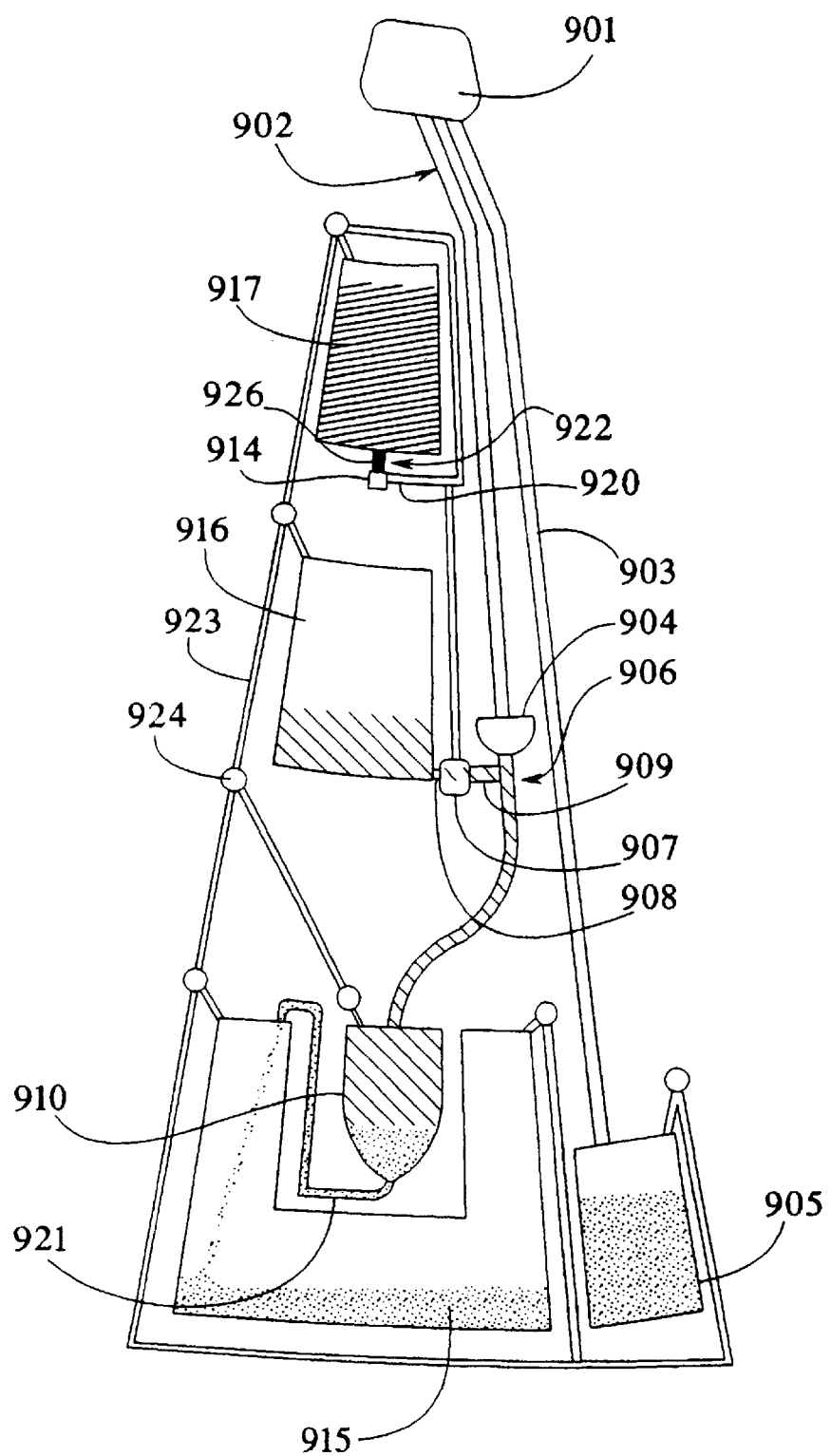
Figure 27J:
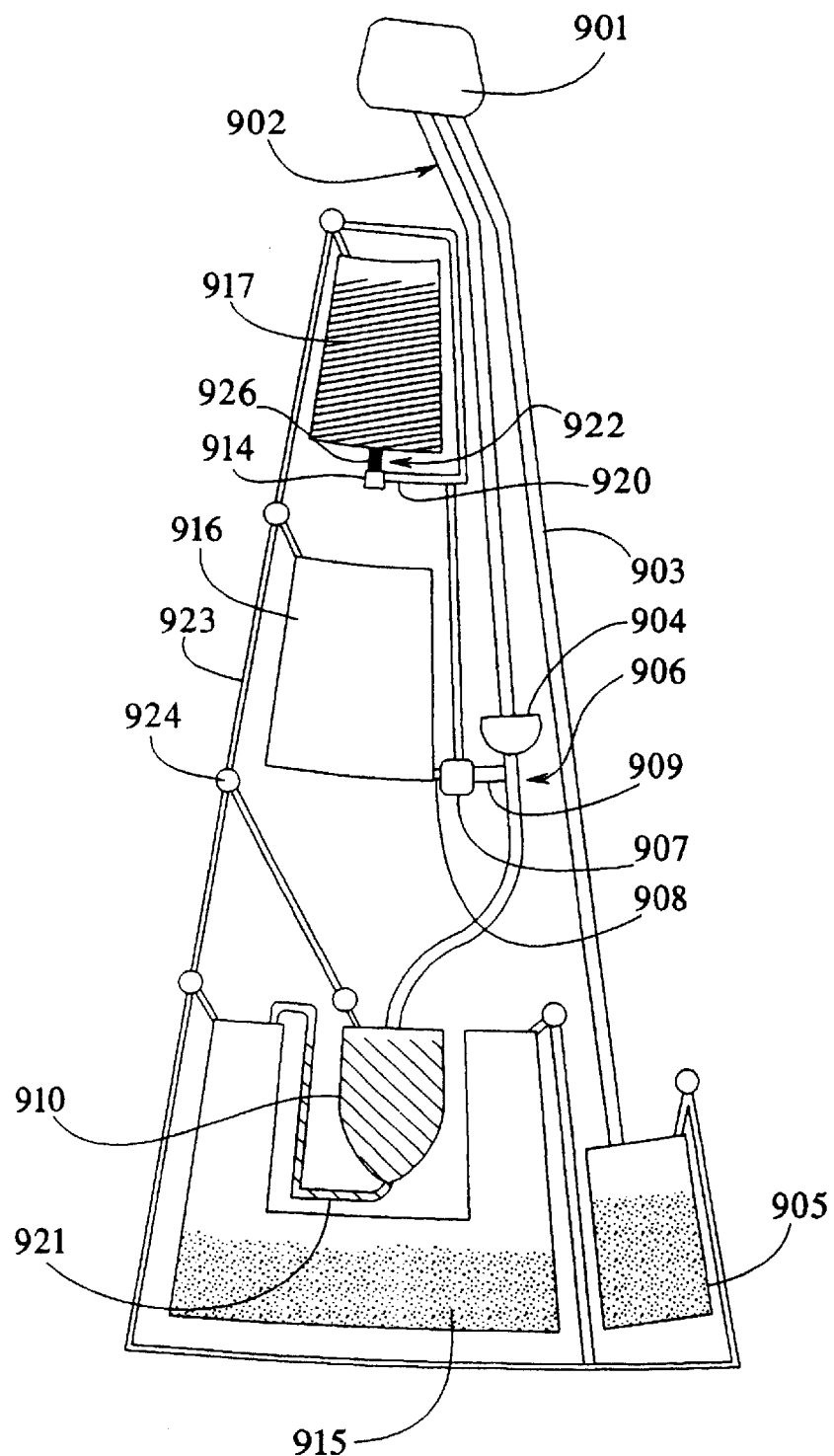

At a third rotational speed $f_3$, that is greater than the second rotational speed $f_2$, typically in the range of 100–1500 rpm, the capillary junction 908 is overcome, and wash buffer from reservoir 916 flows through capillary 909, capillary 906, and into incubation chamber 910. Wash buffer fluid flow forces the sample through U-shaped capillary 914 and into waste reservoir 915 (FIGS. 27H through 27J). Preferably, sacrificial valves 922 are released to permit wash buffer fluid flow.

At a fourth rotational speed $f_4$, that is greater than the third rotational speed $f_3$, typically in the range of 100–2000 rpm, the capillary junction 919 is overcome, and reagent buffer from reservoir 917 flows through capillary 918, capillary 920, capillary junction 908, capillary 906, and into incubation chamber 910. Reagent buffer fluid flow forces the wash buffer through U-shaped capillary 914 and into waste reservoir 515 (FIGS. 27H through 27J). Preferably, sacrificial valves 922 are released to permit reagent buffer fluid flow.

The reagent buffer contains a chromogen or other developing agent for detection of specific binding in incubation chamber 910.

2. Resistive Heater and Temperature Sensing Components

Temperature control elements are provided to control the temperature of the platform. The invention provides heating elements, specifically resistive heating elements, and elements for detecting temperature at specific positions on the platform. Heating devices are preferably arrayed to control the temperature of the platform over a particular and defined area, and are provided having a steep temperature gradient with distance on the platform from the heater.

Certain resistors, including commercially-available resistive inks (available from Dupont) exhibit a positive temperature coefficient (PTC), i.e., an increase in resistance with increasing temperature. Applying a fixed voltage across a PTC resistor screen-printed on a plastic substrate results in rapid heating, followed by self-regulation at an elevated temperature defined by the circuit design heat sink and ambient temperature. In such screen-printed resistors, connection to a power source is made by first printing parallel silver conductors followed by printing the PTC ink between the conductors as shown in FIG. 29.

Figure 29A:
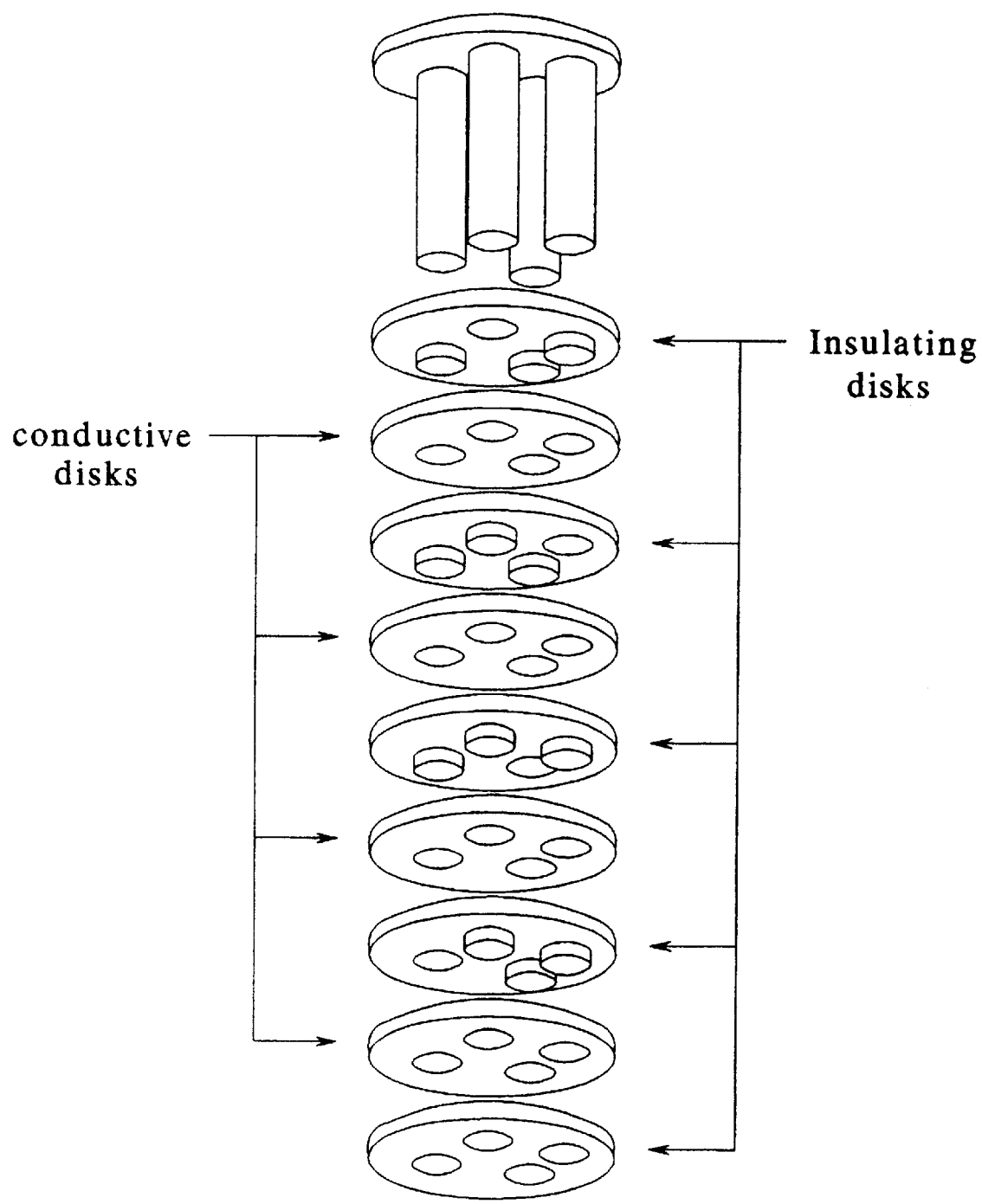
FIG. 29 illustrates the electronic spindle of the invention.
Figure 29B:
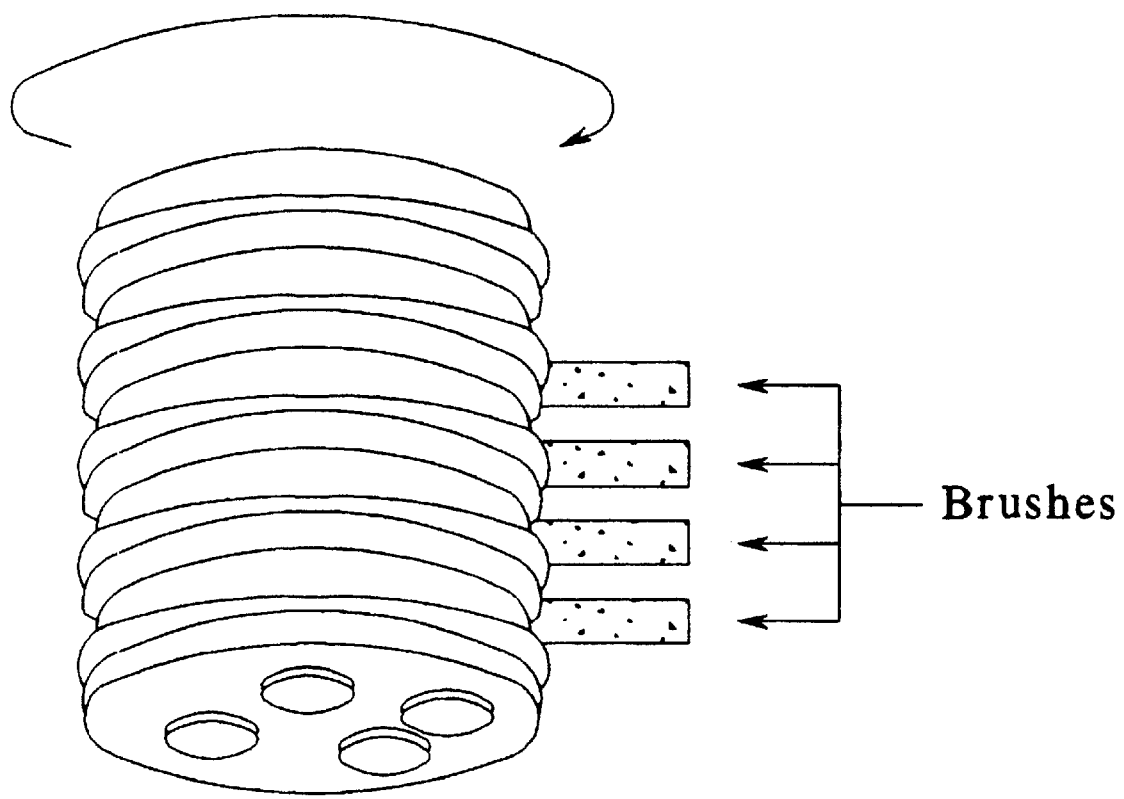
Figure 29C:
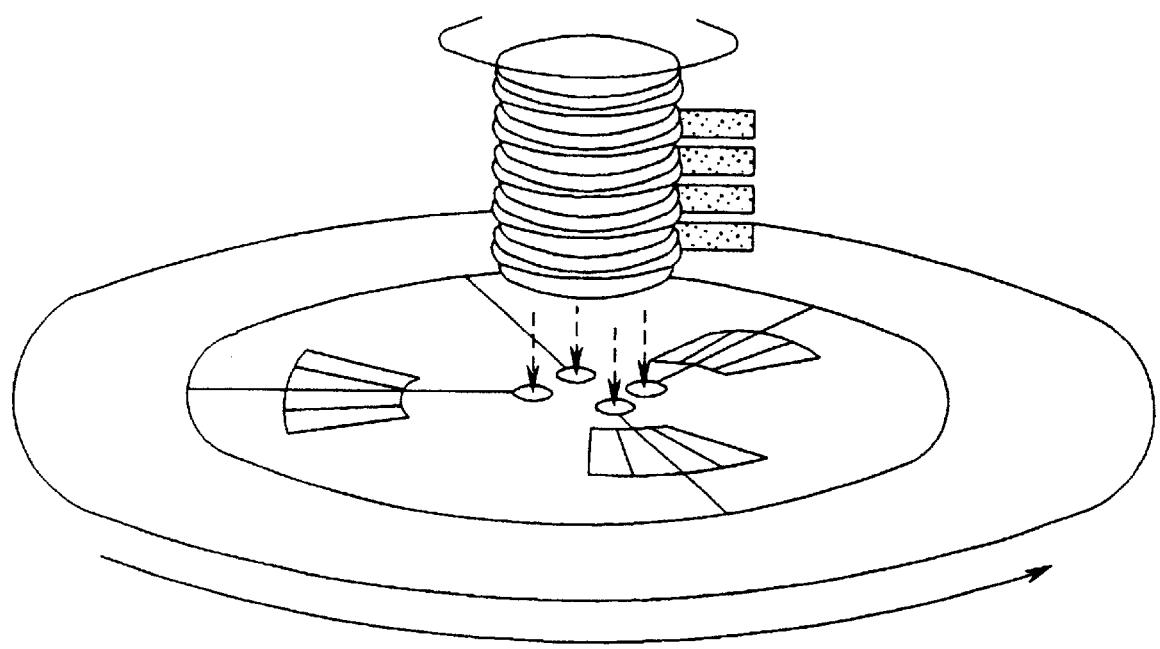

As shown in FIG. 29, a resistive heating element comprises a conductive ink connected with electrical contacts for activation of the heater, and resistive inks applied between the conductive ink and in electrical contact therewith, wherein application of a voltage (direct or alternating current) between the conductive inks results in current flow through the resistive inks and production of heat. There are two important types of resistive inks used in the resistive heating elements of this invention The first is a standard polymer thick film ink, such as Dupont 7082 or Dupont 7102 ink. These inks produce a surface temperature that is not self-limiting, and the temperature resulting from the use of these inks is dependent primarily on the magnitude of the applied voltage. In contrast, the positive temperature coefficient (PTC) inks show increase resistivity with increasing voltage, so that surface temperature is self-limiting because the amount of heat-producing current goes down as the applied voltage goes up. PTC inks are characterized as having a particular temperature where this self-limiting property is first exhibited; at voltages that produce temperatures less than the critical temperature, the amount of heat is dependent on the magnitude of the applied voltage.

Resistive inks useful according to the invention include Dupont 7082, 7102, 7271, 7278 and 7285, and other equivalent commercially available polymer thick film ink and PTC inks.

Conductive inks useful according to the invention include Dupont 5028, 5025, Acheson 423SS, 426SS and SS24890, and other equivalent commercially available conductive inks.

Additional components of the dielectric layer that serves to insulate the electrical circuit. Dielectric layers advantageously comprise dielectric inks such as Dupont 5018A. Insulation can also be achieved using pressure sensitive transfer adhesive such as 7952MP (3M Co.), or a pressure sensitive transfer adhesive deposited onto a polyester carrier layer such as 7953MP (3M Co.) or thermoplastic bonding films such as 3M 406, 560 or 615.

Resistive heaters of the invention are advantageously used to incubate fluids at a stable temperature and for melting sacrificial valves as described below, and also for thermal cyclic.

Figure 30A:
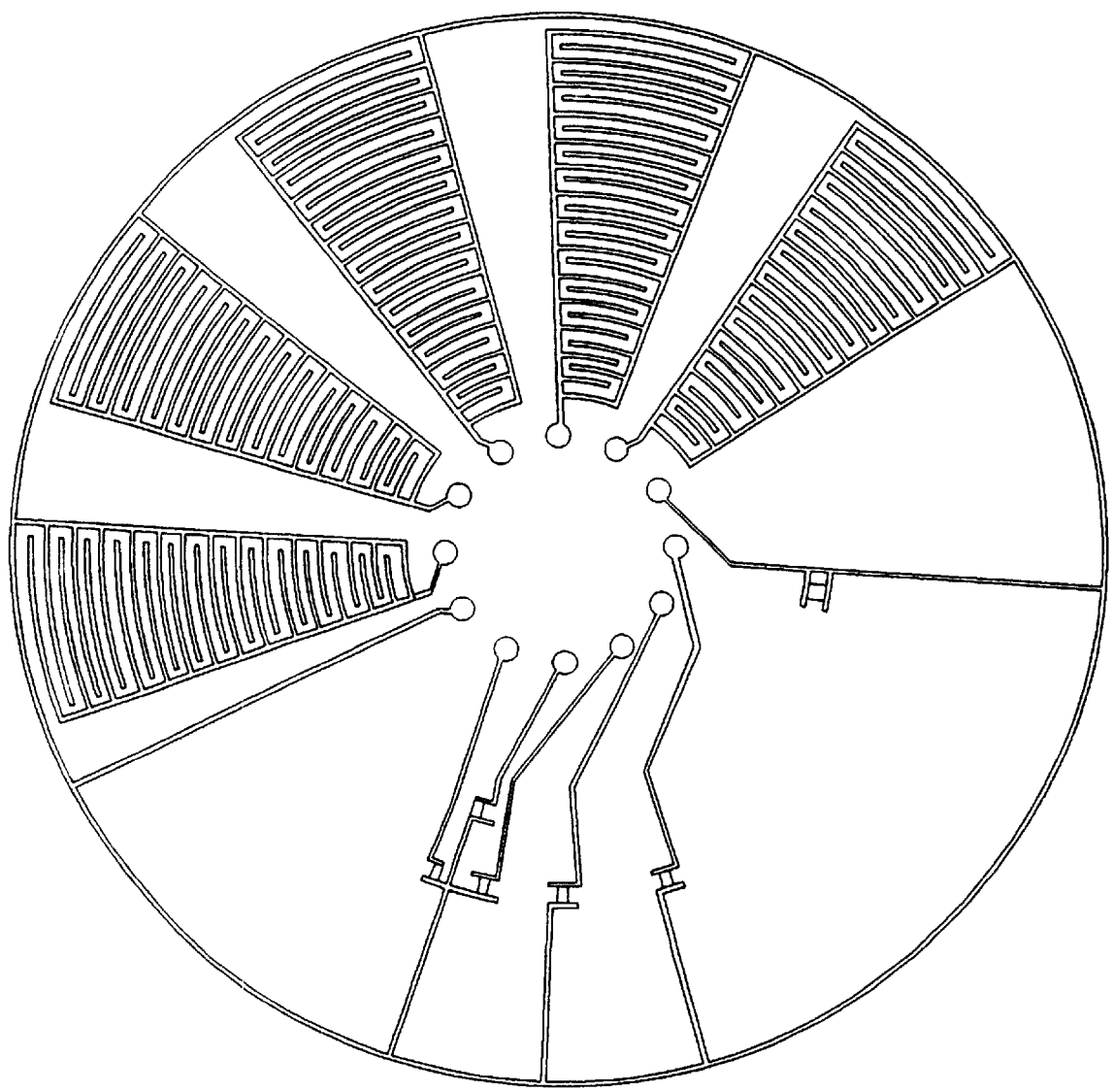
FIG. 30 illustrates screen-printing of a resistive heater element as described in Example 10.
Figure 30B:
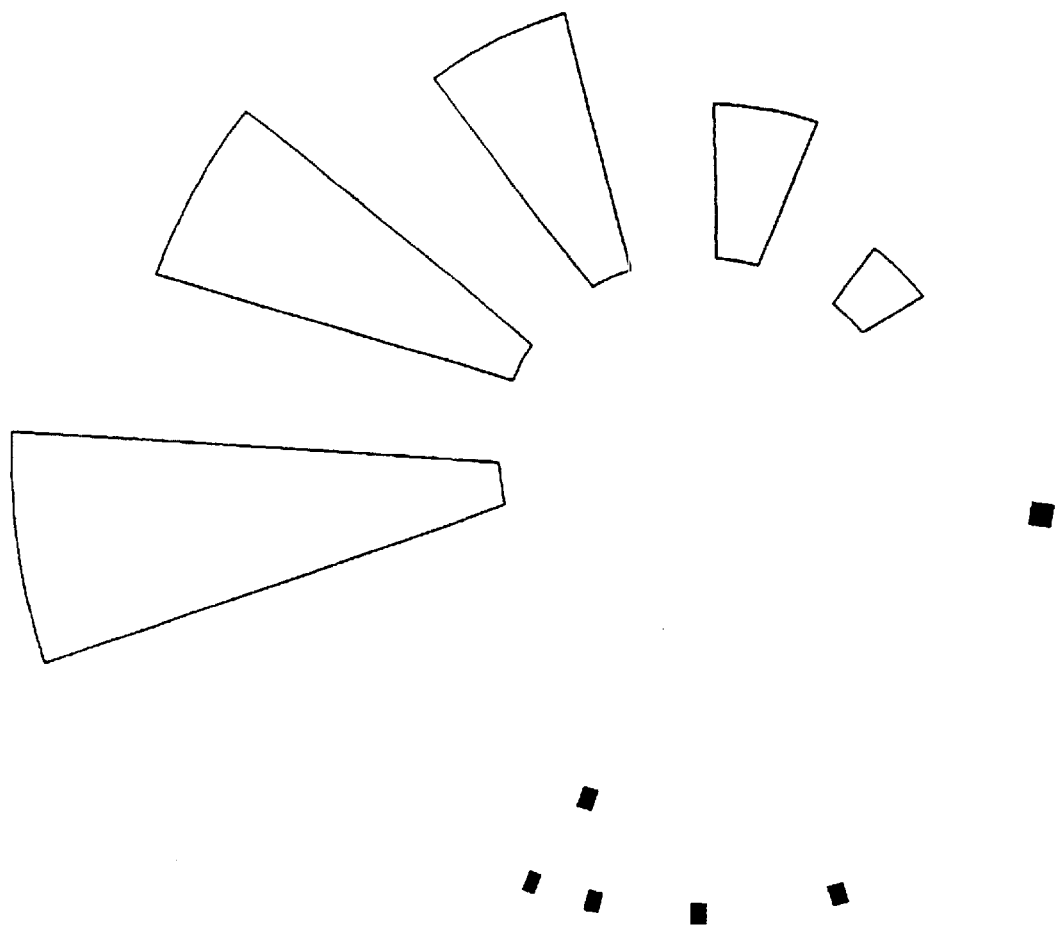
Figure 30C:
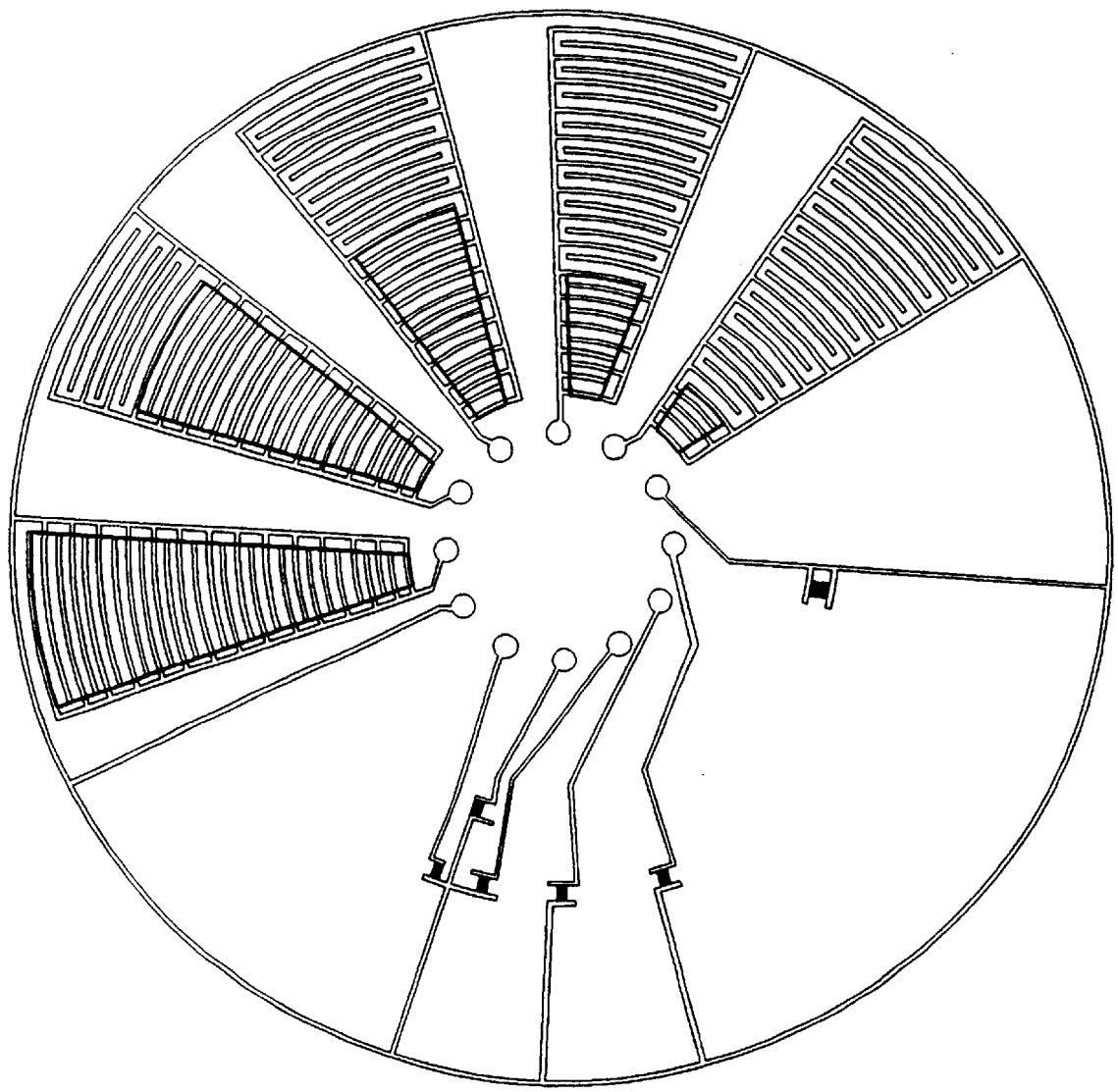

Resistive and conductive inks are preferably screen-printed using methods and techniques well known in the art. See Gilleo, 1995, *Polymer Thick Film* (Van Nostrand Reinhold). Inks are typically screen printed to a thickness of about 10 microns; however, repetitive screen printing of resistive inks can be used to deposit thicker layers having reduced resistances. Both conductive and resistive inks are heat cured, typically at between 110° C. and 120° C. for about 10 minutes. The outline of this printing process is shown in FIG. 30. Importantly, each of the layers must be correctly registered with one another for resistive heating to be provided. Heaters can be screen printed to any required size; a minimum area for a screen-printed heater has been determined to be about 0.25 mm$^2$ (0.5 mm×0.5 mm).

The ability to tailor the resistance (and hence the temperature profile) of the resistive heaters using choice of ink formulation and reprinting of heater circuits provides control of the final electrical and thermal properties of the resistive heating elements of the invention. The resistance can also be controlled through connection of series and parallel configurations of resistive elements. For example, the particular circuits shown in FIG. 31 allow for many parallel resistive elements per unit area; other configurations can be chosen for other applications.

3. Sacrificial Valves

The ability to specifically generate heat at a particular location on a microsystems platform of the invention also enables the use of sacrificial valves that can be released or dissolved using heat. For the purposes of this invention, the term "sacrificial valve" is intended to encompass materials comprising waxes, plastics, and other material that can form a solid or semi-solid fluid-tight obstruction in a microchannel, capillary, chamber, reservoir or other microfluidics component of the platforms of the invention, and that can be melted or deformed to remove the obstruction with the application of heat. Sacrificial valves are preferably made of a fungible material that can be removed from the fluid flow path. In preferred embodiments, said sacrificial valves are wax valves and are removed from the fluid flow path by heating, using any of a variety of heating means including infrared illumination and most preferably by activation of resistive heating elements on or embedded in the platform surface as described herein. For the purposes of this invention, the term "wax" is intended to encompass any solid, semi-solid or viscous liquid hydrocarbon, or a plastic. Examples include mondisperse hydrocarbons such as eicosane, tetracosane and octasone, and polydisperse hydrocarbons such as paraffin. In the use of wax sacrificial valves, application of a temperature higher than the melting temperature of the wax melts the valve and removes the occlusion from the microchannel, capillary or other fluidic component of the microsystems platforms of the invention. Particularly when the sacrificial valve is melted on a rotating microsystems platform of the invention, the melted wax to flow through the microchannel, capillary or other fluidic component of the microsystems platforms of the invention and away from the original site of the valve.

One drawback, however, is the possibility that the wax will recrystallize as it flows away from the original valve site, and concomitantly, away from the localized heat source. Recrystallization results in re-occlusion of the microchannel, capillary or other fluidic component of the microsystems platforms of the invention, potentially and most likely at a site other than the site of a localized heat source, and therefore likely to foul fluid movement on the disc. One solution for this problem is the inclusion in the sacrificial wax valves of the invention of a wax recrystallization chamber positioned "downstream" from the position of the wax valve. Preferably, the wax recrystallization chamber is fluidly connected with the microchannel, capillary or other fluidic component of the microsystems platforms of the invention that was occluded by the wax sacrificial valve. Typically, the wax recrystallization chamber is a widening of the microchannel, capillary or other fluidic component of the microsystems platforms of the invention so that recrystallized wax can harden on the walls of the microchannel, capillary or other fluidic component of the microsystems platforms of the invention with enough distance between said walls that the recrystallized wax does not re-occlude the microchannel, capillary or other fluidic component of the microsystems platforms of the invention. Preferably, the heating element, most preferably the resistive heating element of the invention, extends past the site of the wax valve and overlaps at least a portion of the wax recrystallization chamber, thereby retarding the propensity of the wax valve to recrystallize.

It is also recognized that this propensity of wax valves to recrystallize can be exploited to create a wax valve at a particular location in a microchannel, capillary or other fluidic component of the microsystems platforms of the invention. In this embodiment, a particular location can be kept below a threshold temperature by failing to apply heat at that location, and a wax valve material can be mobilized from a storage area on a platform by heating and them allowed to flow under centripetal acceleration to a particularly "cold" site where a wax valve is desired. An advantage of wax valves in this regard is that the proper positioning an activation of resistive heater elements enables flexibility in choosing when and whether a particular microchannel, capillary or other fluidic component of the microsystems platforms of the invention is to be occluded by a wax sacrificial valve.

In particularly preferred embodiments, the sacrificial valves of the invention comprise a cross-linked polymer that displays thermal recover, most preferably a cross-linked, prestressed, semicrystalline polymer; an example of a commercially available embodiment of such a polymer is heat recoverable tubing (#FP301H, 3M Co., Minneapolis, Minn.). Using these materials, at a temperature less than the "melting" temperature ($T_m$), the polymer occludes a microchannel, capillary or other fluidic component of the microsystems platforms of the invention. At a temperature greater than $T_m$, however, the polymer reverts to its prestressed dimensions by shrinking. Such shrinking is accompanied by release of the occlusion from the microchannel, capillary or other fluidic component of the microsystems platforms of the invention. Such embodiments are particular preferred because the polymer remains in situ and does not recrystallize or otherwise re-occlude the microchannel, capillary or other fluidic component of the microsystems platforms of the invention. Also, such embodiments do not require the more extensive manipulation in preparing the platforms of the invention that wax valves require.

In another embodiment, the sacrificial valves of the invention comprise a thin polymeric layer or barrier dividing two liquid-containing microchannel, capillary or other fluidic component of the microsystems platforms of the invention, that can burst when sufficient temperature and/or pressure is applied.

Another embodiment of the sacrificial valves of the invention are provided wherein a screen-printed resistive heater element is itself a valve. In this embodiment, the resistive heater element is screen-printed on a substrate such as polyester that divides two liquid-containing microchannel, capillary or other fluidic component of the microsystems platforms of the invention. In these embodiments, localized application of heat using a resistive heating element is used to melt the substrate dividing the liquid-containing microchannel, capillary or other fluidic component of the microsystems platforms of the invention. Preferably, in this embodiment the two liquid-containing microchannel, capillary or other fluidic component of the microsystems platforms of the invention are positioned in adjacent layers through the vertical thickness of the platform.

As described above, the screen-printed resistive heater elements of this invention provide localized application of heat to a microsystems platform. The degree of localization achieved using these resistive heating elements is sufficient to provide for the placement of two adjacent sacrificial valves separated by a distance of 0.15 cm.

4. Electrical Connection Through a Slip Ring Rotor

The invention also provides a specialized rotor spindle for making electrical connection through a spindle to a rotating structure. An example of the specialized spindle structure of the invention is shown in FIG. 1. The spindle is provided with a series of electrically conductive rings, each of which are electrically isolated from the others. Each conductive ring is led to contacts that impinge upon circuits resident on the rotating structure. Electrical power or data signals are delivered to and from the apparatus by means of conductive brushes that contact the conductive rings. Signals may be conducted while the apparatus is rotating or when stationary.

Rotating structures such as centrifugal rotors and the microsystems platforms of this invention containing internal channels and reservoirs are used to control fluid movement. Such disks and rotors are known in the art as centrifugal analyzers and have been used to separation chemical and biochemical species as well as enabling the synthesis of chemical and biochemicals.

However, a limitation of conventional centrifugal analyzers is that those analytical or synthetic procedures that required electrical input on the rotating structure itself were not enabled. Instead, mechanical and non-mechanical processes were used to regulate fluid movement in centrifuge rotors and other centripetally-motivated devices. Mechanical processes included valve actuation and pumping liquid toward the center of rotation; non-mechanical processes included heating, cooling, electrophoresis, and sensing through combinations of optical, electrical, chemical and biological means. The mechanical and non-mechanical processes known in the prior art were not capable of precisely regulating fluid movement when compared with equivalent, non-rotating devices that used electrical power.

Rotating structures permit precise control of fluid movement. Conventional centrifugal fluid control is restricted to outward flow in a radial direction that is primarily regulated through liquid placement (such as volume, positional radius, and liquid height), channel geometry (including considerations of channel radius) and rotational rate.

Temperature control is achieved over the entire rotor, by refrigerating the centrifugal compartment, for example. However, many chemical and biological processes require precisely controlled elevated temperature for optimal performance; for example, enzymatic reactions such as those used in immunoassays often have temperature optima of about 37° C. In vitro amplification reactions (such as polymerase chain reaction) require even more elevated temperatures, such as cycling between 70° C. and 95° C.

A rotating structure presents unique difficulties in terms of thermal control, particularly heating. Conventional options included placement of the centrifuge rotor inside of an oven, subjecting one area to infrared radiation, and clamping the device between thermally controlled platens. Each of these approaches present difficulties. Ovens have unpredictable thermal gradients that prevent tight control of temperature in the interior of a rotating structure. Infrared presents similar difficulties, while clamping precludes spinning while heating unless the entire heating apparatus is also spun. All of these approaches suffer from an inability to directly measure the temperature inside the rotating structure. These reasons and other have prevented full integration of centripetally-motivated separation with analytical procedures in a single centrifugal rotor; typically, separations and analysis are performed separately in the prior art.

This invention provides a solution to this problem, specifically by enabling the transmission of electrical signals between a rotating structure such as a centrifuge rotor or microsystem platform of this invention and a fixed position electrical source. Electrical devices that can be advantageously controlled on a spinning rotor include temperature regulation devices, sensors, electrophoretic devices, integrated circuits and mechanical valves. These structures in turn permits a wider array of chemical processes to be performed on a disk than those permitted with current technology.

The invention provides a specialized rotor spindle for transmitting electrical signals between a rotating centrifuge rotor and a stationary electrical source as follows; the structure of the spindle will be best appreciated with reference to FIG. 1. Into an electrically non-conductive plate is embedded a plurality of electrically conductive posts. The non-conductive plate is made of any insulating, electrically non-conductive material, including most preferably hardened plastics, rubber, WHAT ELSE??, and other electrical insulators and non-conductors. The electrically conductive posts are made from any electrically conducting metal, including copper, aluminum, WHAT ELSE???, and are preferably spring-loaded from the bottom of the non-conductive plate. A mechanical spindle is positioned on the side of the non-conductive plate opposite to the side of the plate containing the conductive posts. This plate is referred to as a spindle plate. A number of conductive disks equal to the number of conductive posts are layered on the spindle plate. The electrical contacts in the conductive plate are arranged so that each conducive plate is in electrical contact with a single conductive post. For the purposes of this invention, the term "in electrical contact" is intended to mean that an electric current can be produced through the electrical contacts at voltages (direct or alternative current) that may be effectively achieved in a centrifugal apparatus as described. Each conductive disk is similarly electrically isolated from other disks with interspersed sheets or disks of nonconducting material, preferably the same non-conductive material used to make the non-conductive plate. The last layer positioned farthest way from the spindle plate is a nonconductive layer and is arranged so that the tips of the conductive posts are at the surface or emerge from this plate. This final plate containing the ends of the conductive posts is referred to as the contact plate. An assembled unit, consisting of baseplate, posts, conductive element within the stack, is referred to as a signal channel. Typically one channel will be reserved as a common or ground channel.

The contact stack is held within a chassis that permits a series of electrically conductive brushes to impinge upon each of the conductive disks of the contact stack. These brushes are arranged such that an electric signal can be propagated from one brush to one contact on the contact plate independently of electrical signals conducted from any other brush. The spindle is held in a spring-loaded bearing assembly such that the contact stack can rotate freely and present resistive pressure when pressed from below. The assembled unit is referred to as an electronic spindle.

In the use of the electronic rotor of the invention, a centrifugal rotor or microsystems platform disk of this invention containing electrical contacts is aligned with the contacts on the contact plate of the electronic spindle in such a fashion that the electrical contact on the rotor are in electrical contact with the conductive posts on the contact plate of the electronic spindle. An electric signal can be propagated from the brushes of the electronic spindle to the contacts on the disk using the electronic spindle, most importantly when the rotor is spinning. Contact between the contact plate and the rotor is maintained by positive pressure provided by the spring-loaded bearing assembly and conductive posts. Electrical devices resident on the disk can then be monitored or controlled by signals through the electronic rotor. In a preferred embodiment, the rotor and the spindle contain complementary mechanical components that precisely align the rotor on the spindle to ensure proper electrical contact between the contacts on the rotor and the conductive posts on the spindle.

In a preferred embodiment thermal control structures resident on a rotating disk may be controlled through the electronic spindle. A resistive heating element prepared in a rotor as described herein is prepared having electrical contact leads positioned to be brought into electrical contact with one signal channel and the common channel of the electronic spindle. A thermistor element as described herein is placed on the disk in close proximity to the resistive heating element to enable thermistor response to be proportional to the temperature of the resistive heating element. The temperature of the heating element will be a function of the voltage and current applied to the disk through the electronic rotor and the speed at which the disk is being rotated (which will promote convective cooling). A thermal profile may be accurately monitored through the thermistor response and temperature controlled through adjustment of heating voltage and disk speed using the electronic spindle of the invention.

In another preferred embodiment, the polymerase chain reaction ("PCR") can be carried out on a rotating disk through thermal control using the electronic spindle. In this embodiment, a reaction chamber on a rotating disk is provided with the reagents necessary for PCR to provide a reaction mixture (see Saiki et al., 1985, *Science*_:_-_). This reaction chamber is in close proximity to a heater and thermistor as described herein to enable thermistor output to be proportional to the temperature of the reaction mixture. The reaction chamber is subjected to a cycling temperature profile sufficient to permit amplification of the template. Since the rate and precision at which a temperature change can be accomplished is a determining factor in the success of PCR amplification, control of voltage and speed of rotation as enabled using the electronic spindle of the invention permits PCR to be performed on a rotating platform.

In yet another preferred embodiment, other enzyme-requiring assays (such as enzyme linked immunosorbant assay ("ELISA")) can be performed and optimized on a rotating platform through thermal control using the electronic spindle of the invention. As those skilled in the art perform it, ELISA assays consist of antibody/antigen binding interactions followed by the conversion of a calorimetric or radioactive substrate into a detectable product. Detection is carried out through electrochemical or optical processes, depending the nature of the detectable product. Both antibody/antigen binding and enzymatic reactions have optimal temperatures (typically 37° C.) that can be achieved on a rotating platform using the resistive heater/thermistor pair described above using the electronic spindle.

Electromechanical valves known in the prior art can also be incorporated in a rotating platform of centrifuge rotor using the electronic spindle of the invention. Mechanical, electrolytic or thermal valves on a rotating disk have been described (for example, in co-owned and co-pending U.S. Ser. No. 08/761,063). By judicious activation of such valves the fractionation of complex mixtures can be carried out on a rotating platform. In preferred embodiments, complex biological mixtures such as milk or blood are subjected to centrifugal force to effect separation of constituent parts. Electromechanical, electrolytic or thermal valves can be opened, for example, to withdraw a fractionated supernatant away from a sedimented layer and into an adjacent chamber. Sample fractionation can be accomplished using repetitive sedimentation at different rotational rates, with appropriate valve activation used to partition portions of the fractionated to separate reservoirs or other compartments on the rotor. Upon fractionation the constituents may then be subjected to other processes such as PCR, immunoassay or electrophoresis.

Another application of the electronic spindle of the invention is to activate sensors on the rotating platform. In a preferred embodiment, sensors for detecting pH, are controlled and monitored through the electronic spindle.

The following Examples are intended to further illustrate certain preferred embodiments of the invention and are not limiting in nature.

EXAMPLE 1

Antibiotic Assay Disk

A microsystems platform provided by the invention and specifically designed for performing antibiotic assays is illustrated in FIGS. 1 and 2. Disk embodiments of the platforms of the invention were fashioned from machined acrylic and injection-molded polycarbonate. The overall disc dimensions include an outer radius of about 6 cm and an inner radius of about 0.75 cm, wherein the disk was mounted on the spindle of a rotary device. The thickness of the disc ranged from about 0.9 mm to about 1.5 mm.

The components of the antibiotic array were prepared as follows. An entry port 201 having a depth in the platform surface from about 0.75 mm and lateral dimensions of from about 0.2 cm to about 2 cm were constructed on the platform, and designed to accommodate a volume of about 60 μL. This entry port was fluidly connected with an array of eight metering capillaries 202 having a square cross-sectional diameter of about 0.5 mm and proximal ends rounded with respect to entry port 201; the length of this metering capillary array was sufficient to contain a total volume of about 20 μL. The entry port was also constructed to be fluidly connected with an overflow capillary 203 having a cross-sectional diameter of from about 0.02 mm to about 0.75 mm and proximal ends rounded with respect to entry port 201. The overflow capillary was fluidly connected with an overflow chamber 205 having a depth in the platform surface of about 0.75 mm, greater than the depth of the overflow capillary 203. Metering capillary 202 was fluidly connected to fluid chamber 204 having a depth in the platform surface of about 0.63 mm and greater than the depth of the metering capillary 202. Each of the overflow and fluid chambers was also connected with air ports or air channels, such as 211, that have dimensions of about 0.25 mm deep and permitted venting of air displaced by fluid movement on the platform. A capillary junction 212 that is about 0.75 mm deep is present in the air channel to prevent fluid flow into the air channel.

Entry port 201 was positioned on the platform from about 2 cm from the center of rotation. Metering capillary 202 extended about 1 cm from entry port 201. The extent of the length of overflow capillary 203 was at least about 20% greater than the extent of the length of metering capillary 202. The position of fluid chamber 204 was from about 3.2 cm from the center of rotation, and the position of overflow chamber 205 was thus from about 5 cm from the axis of rotation.

The fluid chamber 204 acted as a capillary barrier that prevents fluid flow from metering capillary 202 at a first, non-zero rotational speed $f_1$ sufficient to permit fluid flow comprising overflow from the entry port 201 through overflow capillary 203 and into overflow chamber 205. This capillary boundary was constructed to be overcome at a second rotational speed $f_2$ (where $f_2 > f_1$). Fluid chamber 204 was fluidly connected to capillary 206 that was 0.25 mm deep and had a cross-sectional diameter of about 0.5 mm and was connected to holding chamber 207. Holding chamber 207 had a depth in the platform surface of 0.75 mm, greater than the depth of capillary 206. Filling of fluid chamber 204 is accompanied by fluid flow through capillary 206 into holding chamber 207. Holding chamber 207 was fluidly connected by way of capillary 208, having a square cross-sectional diameter of about 0.25 mm and was connected with read chamber 210, having a depth in the platform surface of about 0.75 mm, greater than the depth of capillary 208. In certain embodiments, a sacrificial valve 213 was placed as shown in the channel 209.

As illustrated in FIGS. 3A through 3J, in the use of this platform an imprecise volume (ranging from 20–60 μL of fluid) of a fluid was applied to the entry port 201 (FIG. 3A). In embodiments of the platform comprising air displacement channels, the fluid wicked into air channel 211 and was stopped by capillary junction 212. Fluid also wicked into metering capillary 202 and overflow capillary 203. Fluid flowed through the metering capillary 202 and overflow capillary 203 at no rotational speed until the fluid reached capillary junctions at the junction between metering capillary 202 and fluid chamber 204 and overflow capillary 203 and overflow chamber 205 (FIGS. 3B and 3C). Metering capillary 202 was constructed to define a precise volume from about 20–60 μL of fluid between entry port 201 and the capillary junction at fluid chamber 204, which was designed to be at least the amount of the fluid placed by the user in entry port 201.

After sample loading by a user and filling of metering capillary 202 and overflow capillary 203 at no rotational speed, the platform was spun at a first rotational speed $f_1$, ranging from of 175 rpm, which was sufficient for this microfluidics array having an entry port 201 with a depth of 0.6 mm, metering capillary 202 with dimensions of 0.5 mm×0.5 mm in cross-section and a length of 2.2–3.8 cm from the center of rotation and an overflow capillary 203 with dimensions of 0.5 mm×0.5 mm in cross-section and a length of 5.4 cm from the center of.

Due to the greater distance of the end of overflow capillary 203 from the center of rotation than the end of metering capillary 202, fluid flowed through overflow capillary 203 into overflow chamber 205. The platform was spun until all excess fluid is evacuated from entry port 201 and into overflow chamber 205, except the fluid contained in metering capillary 202 (FIG. 3D).

At a second rotational speed $f_2$ of 360 rpm, the precise amount of fluid contained in metering capillary 202 was delivered into fluid chamber 204 (FIGS. 3E through 3H)

Fluid movement into fluid chamber 204 was accompanied by filling of capillary 206 and holding chamber 207.

In embodiments comprising a sacrificial valve 213 in-line with capillary 208 at position 209 shown in FIG. 2, release of the sacrificial valve resulted in fluid flow into read chamber 210. In said embodiments, fluid flow is achieved at rotational speed $f_2$ with removal of the sacrificial valve.

In embodiments of the platforms of the invention comprising antibiotic arrays as described herein and not containing a sacrificial valve at position 209, capillary 208 preferably filled along with filling of holding chamber 207 until the fluid reached capillary junction 209 at the junction between capillary 208 and read chamber 210; in such embodiments, the capillary junction had a depth of about 0.75 mm. At a third rotational speed $f_3$ of about 520 rpm, the fluid contained in holding chamber 207 was delivered into read chamber 210 (FIGS. 3I and 3J).

This embodiment of the microfluidics platforms of the invention was designed to use the carboxypeptidase inhibition assay described above for detecting beta-lactam antibiotics. The extent of chromogen production was detected in the read chamber, and related to the presence of antibiotics in the sample by comparison with samples tested in the absence of antibiotic. The amount of antibiotic in a test sample was determined using this platform of the invention.

EXAMPLE 2

Two-Step Assay Disk: Alternative Embodiment

Figure 4:
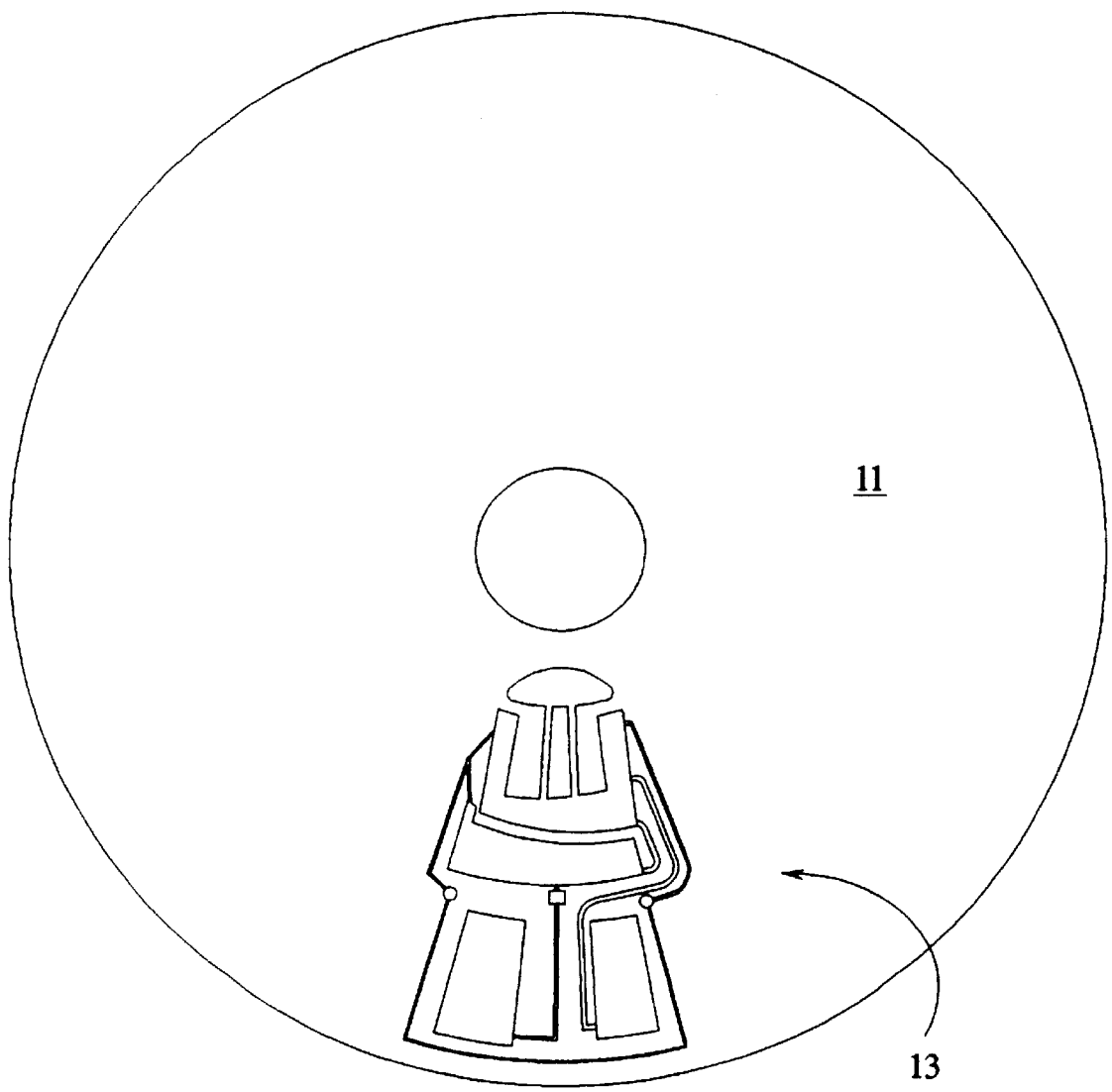
FIGS. 4 through 6 illustrate the microfluidics array of the microsystem platform described in Example 2.

In an alternative embodiment, a two-step assay disk of the invention was provided as shown in FIGS. 4 and 5. Disk embodiments of the platforms of the invention were fashioned from machined acrylic. The overall disc dimensions included an outer radius of about 6 cm and an inner radius of about 0.75 cm, wherein the disk was mounted on the spindle of a rotary device. The thickness of the disc ranged from about 0.9 mm to about 1.5 mm. The working fluid volume for reaction with reagents was about 20 μL.

The components of this two-step assay array were prepared as follows. An entry port 301 having a depth in the platform surface of about 0.75 mm and lateral dimensions of from about 0.2 cm to about 2 cm was constructed on the platform, and designed to accommodate a volume of about 60 μL. This entry port was fluidly connected with a multiplicity of entry capillaries 302 having a square cross-sectional diameter of about 0.5 mm, having a depth of 0.5 mm and proximal ends rounded with respect to entry port 301; the length of this entry capillary array was sufficient to contain a total volume of about 20 μL. The entry capillaries 302 were fluidly connected to fluid chamber 303 having a depth in the platform surface of about 0.6 mm, wherein the depth was greater than the depth of the entry capillary 302. Each of the fluid chambers of this aspect of the invention was also connected with air ports or air channels, such as 311, that have dimensions of about 0.25 mm deep and permitted venting of air displaced by fluid movement on the platform. A capillary junction 312 that was about 0.75 mm deep was present in the air channel to prevent fluid flow into the air channel.

The fluid chamber 303 was also constructed to be fluidly connected with an overflow capillary 304 having a cross-sectional diameter of from about 0.02 mm to about 0.75 mm and proximal ends rounded with respect to fluid chamber 304. The overflow capillary was fluidly connected with an overflow chamber 306 having a depth in the platform surface of about 0.75 mm, greater than the depth of the overflow capillary 304.

Entry port 301 was positioned on the platform about 1 cm from the center of rotation. Entry capillaries 302 extends about 2 cm from entry port 301. The position of a first fluid chamber 303 was from about 3 cm from the center of rotation.

The first fluid chamber 303 acted as a capillary barrier that prevented fluid flow from entry capillary 302 at zero rotational speed. Movement of fluid from entry port 301 through entry capillaries 302 and into the first fluid chamber 303 was achieved by rotation at a first, non-zero rotational speed $f_1$. Displacement of fluid into the first fluid chamber 303 was accompanied by fluid filling of channel 305 that was fluidly connected with the first fluid chamber 303 and was positioned at the most radially distal point of the first fluid chamber. Channel 305 was fluidly connected with a second fluid chamber 307 and formed a capillary boundary between channel 305 and chamber 307. This capillary boundary was constructed to be overcome at second rotational speed $f_2$ (where $f_2 > f_1$). First fluid chamber 303 was also fluidly connected to overflow capillary 304 that was 0.25 mm deep and had a cross-sectional diameter of about 0.5 mm and that extended from about 1 cm to about 5 cm and was connected to overflow chamber 306. Overflow chamber 306 had a depth in the platform surface equal to that of overflow capillary 304, so that there was no capillary boundary between overflow capillary 304 and overflow chamber 306. Overflow capillary 304 was positioned in the first fluid chamber 303 at a point radially less distant from entry port 301 than channel 305, thereby defining a volume in the fluid chamber between the position of the overflow capillary 304 and the most radially distant extent of the said first fluid chamber.

Second fluid chamber 307 was further fluidly connected through channel 308 to a small pocket or capillary junction 309. Channel 308, having a cross-sectional diameter of about 0.25 mm and that extended from about 0.2 cm to about 20 cm, was fluidly connected to a third fluid chamber 310, having a depth in the platform surface of about 0.75 mm, that was greater than the depth of capillary 308. Air recirculation channels 311 that had dimensions of about 0.25 mm deep provided pathways for air displaced by fluid movement, while capillary junctions 312 that were about 0.75 mm deep prevent fluid from entering the air channels. In some embodiments of the device a sacrificial valve 313 was placed as shown in FIG. 5 in the channel 309. In certain embodiments, a valve 314 was placed in channel 305 to control fluid movement from the first fluid chamber 303 to the second fluid chamber 307.

As illustrated in FIGS. 6A through 6J, in the use of this platform an imprecise volume (ranging from 1–150 μL of fluid) of a fluid was applied to the entry port 301 (FIG. 6A). Fluid wicked into entry capillary 302 and stopped at the capillary junction between entry capillary 302 and the first fluid chamber 303 (FIGS. 6B and 6C). Fluid flowed through the entry capillary B and into the first fluid chamber 303 at a first rotational speed $f_1$ of 40 rpm (FIGS. 6D and 6E). The fluid further entered capillary channel 305, stopping at the capillary junction with the second fluid chamber 307. As rotation continued, the fluid continued to fill the first fluid chamber 303, overflow capillary 304 fills (FIG. 6F), and excess fluid filled overflow chamber 306 until the level of fluid in the first fluid chamber 303 fell below the position of overflow capillary 304 (FIG. 6G).

At a second rotational speed $f_2$ of 280 rpm, the capillary junction between channel 305 and the second fluid chamber 307 was overcome, and fluid remaining in the first fluid chamber 303 was delivered into the second fluid chamber 307 (FIGS. 6H and 6I).

In an alternative embodiment, a sacrificial valve 314 was placed at the junction of channel 305 and the second fluid chamber 308, which sacrificial valve was released to permit fluid flow through channel 305 and into the second fluid chamber 308. In such embodiments, fluid flow can be achieved at either $f_1$ or $f_2$ rotational velocity.

In embodiments comprising a sacrificial valve 313 in-line with capillary 308 at position 309 shown in FIG. 5, release of the sacrificial valve results in fluid flow into the third fluid chamber 310. In said embodiments, fluid flow was achieved at rotational speed $f_2$ with removal of the sacrificial valve.

In embodiments of the platforms of the invention comprising two-step assay arrays as described herein and not containing a sacrificial valve at position 310, capillary 309 filled along with filling of the second chamber 308 until the fluid reached capillary junction 309 at the junction between capillary 308 and the third fluid chamber 310; in such embodiments, the capillary junction has a depth of about 0.75 mm. At a third rotational speed $f_3$ of about 520 rpm, the fluid contained in the second chamber 308 was delivered into the third fluid chamber 310 (FIGS. 6H through 6K).

EXAMPLE 3

Blood Separation Array

A microsystems platform provided by the invention and specifically designed for separating vertebrate blood cells and components is illustrated in FIGS. 7 through 9.

The components of the blood separation array are shown in greater detail in FIG. 8. It will be understood by a comparison of FIGS. 7 and 8 that the center of the platform 11 is at the top of FIG. 8, and the edge or lateral extent of the platform is at the bottom of FIG. 8, illustrated by a curved line. Rotation of the blood separation array on platform disks of the invention can be in either direction, although rotation in a consistent, particular direction is preferred. Disk embodiments of the platforms of the invention were fashioned from machined acrylic. The overall disc dimensions included an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction with reagents was about 15 μL.

The components of the blood separation array were as follows. An entry port 401 having a depth in the platform surface of about 0.5 mm and lateral dimensions of about 0.5 cm was constructed on the platform, and designed to accommodate a volume of about 20 μL. This entry port was fluidly connected to an entry capillary 402, having a cross-sectional diameter of about 0.5 mm and having a depth of 0.5 mm; the length of this entry capillary was sufficient to contain a total volume of about 20 μL. Entry capillary 402 was further fluidly connected to a separation column 403 having a cross-sectional diameter of about 1.25 mm, a depth of about 0.75 mm, and a length of this separation column was sufficient to contain a total volume of about 15 μL. This separation column was also fluidly connected with a passage 411 to overflow chamber 404. Passage 411 had a cross-sectional diameter of about 1 mm, a depth of from about 0.5 mm, and a length of 2 mm. Overflow chamber 404 has a depth of about 0.5 mm.

A small capillary exit 406 was also fluidly connected with separation chamber 403, having a cross-sectional diameter of about 0.125 mm, a depth of about 0.125 mm, and a length of about 0.75 mm. This capillary was arranged to traverse a direction radially more proximal to the axis of rotation than the insertion point with separation column 403. This small capillary 406 terminated in a capillary junction 407 that was fluidly connected with capillary 408, extending in a radial direction to decant chamber 405. A sacrificial valve 413 is positioned in capillary 406 at the juncture with capillary junction 407. Capillary 408 had a cross-sectional diameter of about 0.25 mm, a depth of about 0.25 mm, and a length of about 3.5 mm. This capillary was arranged in a radially outward direction between capillary junction 407 and decant chamber 405. Passage 411 was positioned on separation column 403 to be significantly more proximal to the axis of rotation than the insertion point of small capillary 406.

Air displacement channels 409 that have dimensions of about 0.25 mm deep permitted venting of air displaced by fluid movement on the platform. Capillary junctions 410 that were about 0.75 mm deep were present in the air channels to prevent fluid flow into the air channels.

As illustrated in FIGS. 9A through 9H, in the use of this platform an imprecise volume (about 25 μL) of blood was applied to the entry port 401 (FIG. 9A). Blood entered the entry capillary 402 by capillary action, and stopped at the capillary junction between entry capillary 402 and the separation chamber 403 (FIGS. 9B and 9C).

At a first rotational speed $f_1$ of 150 rpm, blood flowed from the entry capillary 402 into separation chamber 403 (FIG. 9D). Blood continued to fill separation column 403 until blood reached the position of passage 411, whereupon excess blood flowed through passage 411 and into overflow chamber 404 (FIGS. 4E and 4F). Advantageously, small channel 406 had dimensions that prevent wicking of blood into the channel as blood flows past the insertion point of small channel 406 into separation column 403.

As shown in FIG. 9F, after sufficient time of rotation at the first non-zero rotational speed $f_1$, the excess blood has been transferred into overflow chamber 404 and the separation column 403 was filled with blood to the position of passage 411. Rotation at a second rotational speed $f_2$ of 1300 rpm, blood components were separated into red blood cell, white blood cell (i e., "buffy coat"), and plasma fractions (FIG. 9G). Advantageous dimensions of small capillary 406 permitted fluid flow of the plasma fraction through capillary 406 that was stopped at capillary junction 407. Fluid flow of plasma into decant chamber 405 resulted from fluid flow overcoming the capillary barrier 407 by rotation at a third rotational speed $f_3$ of about 1420 rpm (FIG. 9H).

EXAMPLE 4

Blood Separation Array: Alternative Embodiment

In an alternative embodiment, a blood separation disk of the invention is provided as shown in FIGS. 10 and 11. It will be understood that, as in Example 1, in FIG. 10, the arrangement of one separation array 15 on a disk 11 is shown; a multiplicity of such arrays can be advantageously arranged on a microsystems platform, most preferably a disk, of the invention, to provide a multi-use or multi-assay platform. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction with reagents is about 25 μL.

The components of this separation array are as follows. An entry port 501 having a depth in the platform surface from about 0.75 mm and lateral dimensions of from about 0.5 cm is constructed on the platform, and designed to accommodate a volume of about 20 μL. This entry port is fluidly connected with a first array of metering capillaries 502 and a second array of metering capillaries 503, wherein each of the capillaries has a cross-sectional diameter of about 0.5 mm. The length of the second metering capillary array 503 is longer than that of the first metering capillary array 502. The first metering capillary array 502 is fluidly connected with a ballast chamber 507, having a depth in the platform surface of about 0.75 mm and greater than the depth of the first metering capillary array 502, wherein the first metering capillary array 502 forms a capillary junction between the array and the ballast chamber. The second capillary array 503 is fluidly connected with capillary junction 506.

The entry port is also constructed to be fluidly connected with an overflow capillary 504 having a cross-sectional diameter of about 0.5 mm and proximal ends rounded with respect to entry port 501. The overflow capillary is fluidly connected with an overflow chamber 505 having a depth in the platform surface of about 0.75 mm, greater than the depth of the overflow capillary 504. Each of the overflow and fluid chambers is also connected with air ports or air channels, such as 514, that have dimensions of about 0.25 mm deep and permit venting of air displaced by fluid movement on the platform. Capillary junctions 516 that is about 0.75 mm deep are present in the air channels to prevent fluid flow into the air channels.

Entry port 501 is positioned on the platform from 1 cm to 20 cm from the center of rotation. Metering capillary array 502 extends from entry port 501 from about 0.6 cm. Metering capillary array 503 extends from entry port 501 from about 1.9 cm. The extent of the length of metering capillary array 503 is about 20% longer than metering capillary array 502, and the extent of the length of overflow capillary 504 is at least about 20% greater than the extent of the length of either the first metering capillary array 502 or the second metering capillary array 503. The position of ballast chamber 507 is about 2.8 cm from the center of rotation, the position of capillary junction 506 is about 3.8 cm from the center of rotation, and the position of overflow chamber 505 is thus about 5 cm from the axis of rotation.

The ballast chamber 507 acts as a capillary barrier that prevents fluid flow from the first metering capillary array 502 at a first, non-zero rotational speed $f_1$ sufficient to permit fluid flow comprising excess blood overflow from the entry port 501 through overflow capillary 504 and into overflow chamber 505. Capillary junction 506 is a capillary barrier that prevents fluid flow from the second metering capillary array 503 at said first, non-zero rotational speed $f_1$ sufficient to permit fluid flow comprising excess blood overflow from the entry port 501 through overflow capillary 504 and into overflow chamber 505. These capillary boundaries are constructed to be overcome at a second rotational speed $f_2$ (where $f_2 > f_1$).

Ballast chamber 507 is fluidly connected to capillary 510 that is 0.25 mm deep and has a cross-sectional diameter of about 0.65 mm and that extends about 5 cm and is connected to capillary junction 511. A sacrificial valve 518 is positioned at the exit of ballast chamber 507 at the juncture with capillary junction 511. Alternatively, capillary 510 is fluidly connected with a sacrificial valve 515. In said embodiments, fluid flow is achieved at rotational speed $f_2$ with removal of the sacrificial valve. Sacrificial valve 515 or capillary junction 511 are further fluidly connected with channel 512 which is about 0.25 mm deep and has a cross-sectional diameter of about 0.25 mm and that extends about 3 cm. Channel 512 is fluidly connected with separation chamber 509 at a point most distal from the axis of rotation.

Second metering capillary array 503 is fluidly connected with capillary junction 506, which is overcome at a rotational speed $f_2 > f_1$. Capillary junction 506 is further fluidly connected to channel 508, which is further fluidly connected to separation chamber 509. Channel 508 is about 0.25 mm deep and has a cross-sectional diameter of about 0.25 mm. Separation chamber 509 is about 0.75 mm deep and has a cross-sectional diameter of about 5 mm, and is positioned from about 40 cm from the center of rotation.

Separation chamber 509 is fluidly connected with decant channel 517 at a point close to the chamber's most axis-proximal extent. Decant channel 517 is about 0.25 mm deep and has a cross-sectional diameter of about 0.25 mm and extends about 4.3 cm to about 5 cm. Decant channel 517 is fluidly connected with decant chamber 514, which is about 0.75 mm deep and has a cross-sectional diameter of about 5 mm, and is positioned from about 50 cm to about 80 cm from the center of rotation.

As illustrated in FIGS. 12A through 12J, in the use of this platform an imprecise volume (about 25 μL of fluid) of blood is applied to the entry port 501 (FIG. 12A). Blood enters the each of the metering capillary arrays 502 and 503 and stops at the capillary junction between metering capillary array 502 and ballast chamber 507 and between metering capillary 503 and capillary junction 506 (FIGS. 12B and 12C). Blood also enters and fills overflow capillary 504, stopping at the capillary junction with overflow chamber 505.

At a first rotational speed $f_1$ of 45 rpm, blood flows from the entry port 501 through overflow capillary 504 and into overflow chamber 505 (FIGS. 12D and 12E). At a second rotational speed $f_2$ of 70 rpm, the capillary junction between the first metering capillary array 502 and ballast chamber 508 is overcome, and blood from the first metering capillary array fills ballast chamber 508 (FIG. 12F). Similarly, at second rotational speed $f_2$, capillary junction 506 is overcome, and blood from second metering capillary array 503 enters separation chamber 509 FIG. 12F). Advantageously, the volume of blood in second metering capillary array 503 is insufficient to fill separation chamber 509 to the level of insertion of decant channel 517.

By rotation at a third rotational speed $f_3$ of 1300 rpm, blood components in separation chamber 509 are separated into red blood cell, white blood cell (i.e., "buffy coat"), and plasma fractions (FIGS. 12G and 12H). Separation of blood components is not achieved in ballast chamber 507, due to its position on the platform, and the capillary junction 511 or sacrificial valve 515 are not overcome at third rotational speed $f_3$. Advantageously, the separated plasma does not extend to decant capillary 517.

Release of sacrificial valve 517, or rotation at a fourth rotational speed $f_4$ of rpm, results in flow of blood from ballast chamber 507 through channel 512 and into separation chamber 509 at the "bottom" or most axis-distal extent of the separation chamber (FIG. 12I). This results in filling of the separation chamber to a position equal to the insertion point of decant channel 517 (FIG. 12J). Plasma flow through decant channel 517 and into decant chamber 514 in an amount equal to the amount of blood contained in ballast chamber 507. Decant channel 517 is advantageously provided with dimensions that retard passage of unfractionated blood, or plasma contaminated with greater than 0.1–1% of blood cells in whole blood.

EXAMPLE 5

Mixing Arrays

A microsystems platform provided by the invention and specifically designed for performing mixing of equal volumes of different liquid samples is illustrated in FIG. 13. In the Figure, the arrangement of one assay array 15 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 14. Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume was about 50 $\mu$L.

The components of the mixing array were prepared as follows. Entry ports 601 having a depth in the platform surface of about 0.5 mm and lateral dimensions of about 1 cm to about 5 cm were constructed on the platform, and designed to accommodate a volume of about 5–50 $\mu$L. Each entry port was fluidly connected with one of a paired array of metering capillaries 602 having a square cross-sectional diameter of about 0.5 mm and proximal ends rounded with respect to entry port 601; the length of each metering capillary array was sufficient to contain a total volume of about 25 $\mu$L. Metering capillaries 602 were fluidly connected to a curved capillary barrier 603 having a depth in the platform surface of about 0.25 mm that was greater than the depth of metering capillaries 602. The capillary barrier 603 and other fluid components of the mixing array were also connected with air channels 608, that have dimensions of about 0.25 mm deep and permitted venting of air displaced by fluid movement on the platform. In addition, capillary junctions 609 that were about 0.75 mm deep were present in the air channels to prevent fluid backflow into the air channel.

Capillary barrier 603 was fluidly connected by a narrow capillary channel 604 to mixing chamber 605, which was fluidly connected with channel 610, which was further connected with mixed fluid receiving chamber 606. Alternatively, capillary 604 comprises a sacrificial valve 612. Capillary channel 604 was about 0.25 mm deep and had a cross-sectional diameter of about 0.25 mm and that extends about 0.2 cm. Mixing chamber 605 was about 0.75 mm deep and had a cross-sectional diameter of about 2 mm, and was positioned about 4 cm from the center of rotation. Capillary channel 610 was about 0.25 mm deep and had a cross-sectional diameter of about 0.25 mm and that extended from about 0.2 cm to about 30 cm. Mixing chamber 605 was constructed such that the insertion point of capillary channel 604 and the insertion point of capillary channel 610 were offset at opposite ends of the mixing chamber. As a consequence, fluid flowing through capillary channel 604 was forced to encounter the opposite wall of mixing chamber 605 before fluid flow can proceed through capillary channel 610. This results in the creation of turbulence in the mixed laminar fluid stream in capillary channel 604 caused by the conjoint flow of fluid from the first and second metering channels without appreciable mixing. The turbulence created by the structure of mixing chamber 605 was sufficient to disrupt laminar flow and cause fluid mixing in the chamber prior to continued fluid flow through capillary channel 610 and into mixed fluid receiving chamber 606. Mixed fluid receiving chamber 606 was about 0.75 mm deep and had a cross-sectional diameter of about 5 mm, and was positioned from about 1 cm to about 30 cm from the center of rotation.

As illustrated in FIGS. 15A through 15d, in the use of this platform an equal volume (ranging from 1–150 $\mu$L of fluid) of each of the fluids to be mixed was applied to the entry ports 601 (FIG. 15A). Fluid enters the each of the metering capillary arrays 602 and stops at capillary barrier 603.

At a first rotational speed $f_1$ of 90 rpm, the fluids from each capillary array flowed into and filled the capillary barrier 603 (FIG. 15B). In embodiments comprising a sacrificial valve 612, the valve prevented fluid flow into channel 604. Upon release of sacrificial valve 612 or rotation at first rotational speed $f_1$, fluid flow proceeded from capillary junction 603 through channel 604 and into mixing chamber 605 (FIG. 15C). Fluid flow within mixing chamber 605 was turbulent, in contrast to fluid flow through capillary barrier 603 or channel 604, which was primarily laminar, so that mixing occurs predominantly in mixing chamber 605. Fluid flow proceed through channel 610 and the mixed fluid solution was displaced into mixed fluid receiving chamber 606 (FIG. 15D).

EXAMPLE 6

Mixing Arrays: First Alternatives

An additional embodiment of the microsystems platform provided by the invention and specifically designed for performing mixing of equal volumes (FIGS. 17 through 18) or unequal volumes (FIGS. 19 through 21) of different liquid samples. In these Figures, the arrangement of one assay array 17 on a disk 11 is shown; a multiplicity of such arrays can be advantageously arranged on a microsystems platform, most preferably a disk, of the invention, to provide a multi-use or multi-assay platform.

Figure 17:
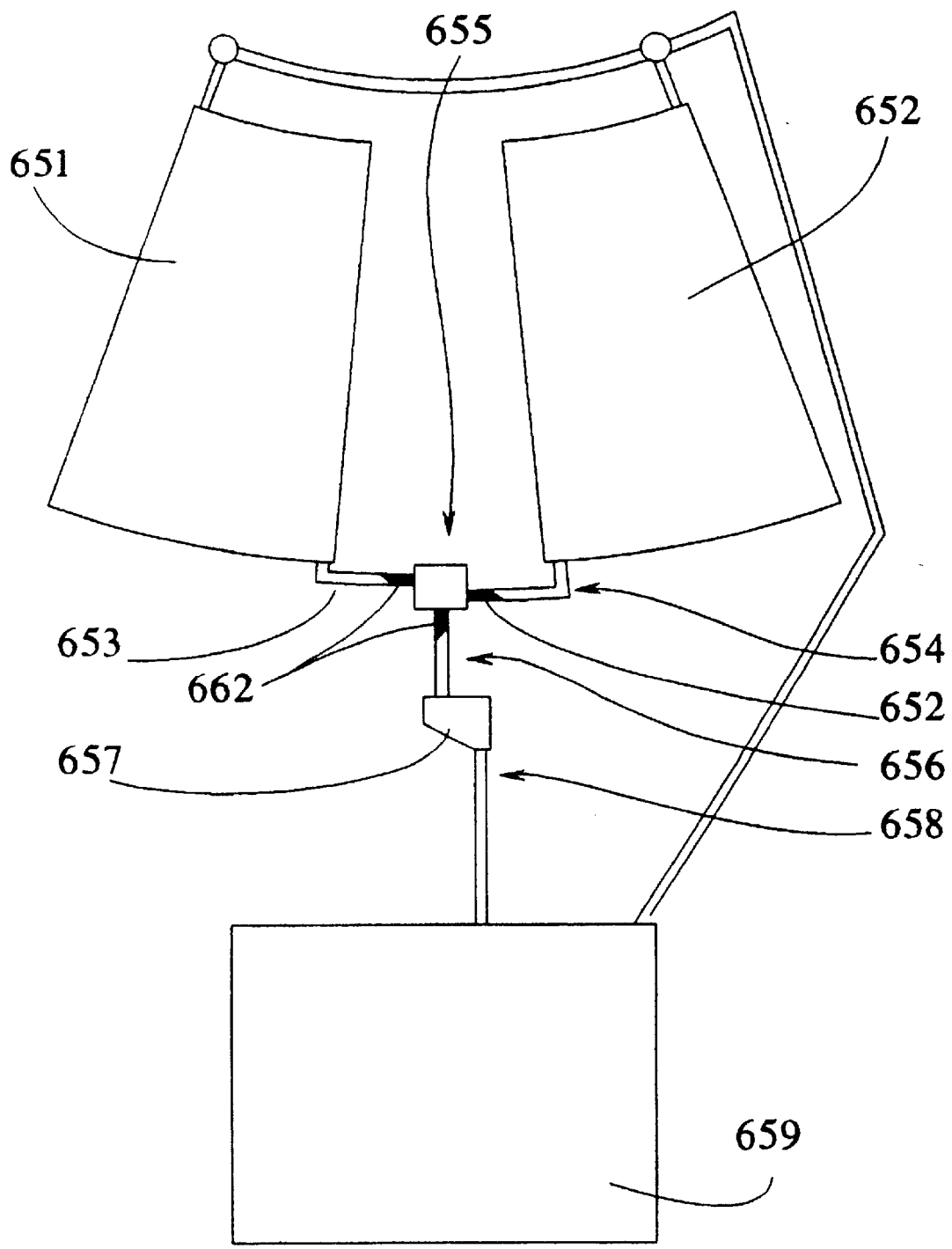

The components of the mixing array are shown in greater detail in FIGS. 17 and 20. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume is about 40 $\mu$L in each fluid reservoir.

The components of the mixing array are as follows. Mixing of equal volumes is illustrated in FIG. 17 and for unequal volumes in FIG. 20. (Components will be identified using the number from FIG. 17; equivalent structures are shown in FIG. 20 for unequal mixing and will be shown in parentheses). Fluid reservoirs 651 and 652 (701 and 702), each containing one of a pair of liquids to be mixed, are constructed on the platform, having a depth in the platform surface from about 0.75 mm and lateral dimensions of 1 cm, and wherein fluid reservoirs 651 and 652 are designed to accommodate equal volumes of fluid (about 50 $\mu$L); (for unequal volumesn fluid reservoir 701 is designed to accommodate a volume of about 45 $\mu$L, and fluid reservoir 702 is designed to accommodate a volume of about 5 $\mu$L, wherein the volume of fluid reservoir 702 is less than the volume of fluid reservoir 701.) In particular and in addition, the viscosity of the fluid in the fluid reservoirs may differ, so that mixing produces a mixed fluid of intermediate viscosity. Each fluid reservoir is fluidly connected with a capillary channel 653 and 654 (703 or 704) to capillary junction 655 (705). Each capillary channel is about 0.5 mm deep and having a cross-sectional diameter of about 0.5 mm and that extends about 5 cm. Capillary junction junction 655 (705) has a depth in the platform surface of about 0.75 mm that is greater than the depth of capillaries 652 and 653 (703 and 704). Alternatively, capillaries 652 and 653 (703 and 704) comprise a sacrificial valve 662 (712). Use of said sacrificial valves can be used in addition to or in place of capillary junction 655 (705).

The fluid components of the mixing array are also connected with air channels 660 (710), that have dimensions of about 0.25 mm deep and permit venting of air displaced by fluid movement on the platform. In addition, capillary junctions 661 (711) that are about 0.75 mm deep are present in the air channels to prevent fluid backflow into the air channel.

Capillary junction 655 (705) is fluidly connected by a narrow capillary channel 656 (706) to mixing chamber 657 (707), which is fluidly connected with channel 658 (708) which is further connected with mixed fluid receiving chamber 659 (709). Alternatively, capillary 656 (706) comprises a sacrificial valve 662 (712). Capillary channel 656 (706) is about 0.25 mm deep and having a cross-sectional diameter of from about 0.5 mm and that extends from about 0.2 cm to about 30 cm. Mixing chamber 657 (707) is about 0.25 mm deep and having a cross-sectional diameter of from about 0.75 mm, and is positioned from about 0.2 cm to about 30 cm from the center of rotation. Capillary channel 658 (708) is about 0.5 mm deep and has a cross-sectional diameter of about 5 mm and that extends from about 0.2 cm to about 30 cm. Capillary channel 656 (706) and capillary channel 658 (708) may be offset in their connection with the mixing chamber as previously described in Example 5, or the capillaries can be positioned in the mixing chamber at any convenient position, and Coriolis forces have be relied upon to facilitate mixing.

Capillary 658 (708) is fluidly connected with mixed fluid receiving chamber 659 (709). Mixed fluid receiving chamber 659 (709) is about 0.75 mm deep and having a cross-sectional diameter of about 5 mm from about, and is positioned from about 1 cm to about 30 cm from the center of rotation.

Figure 18A:
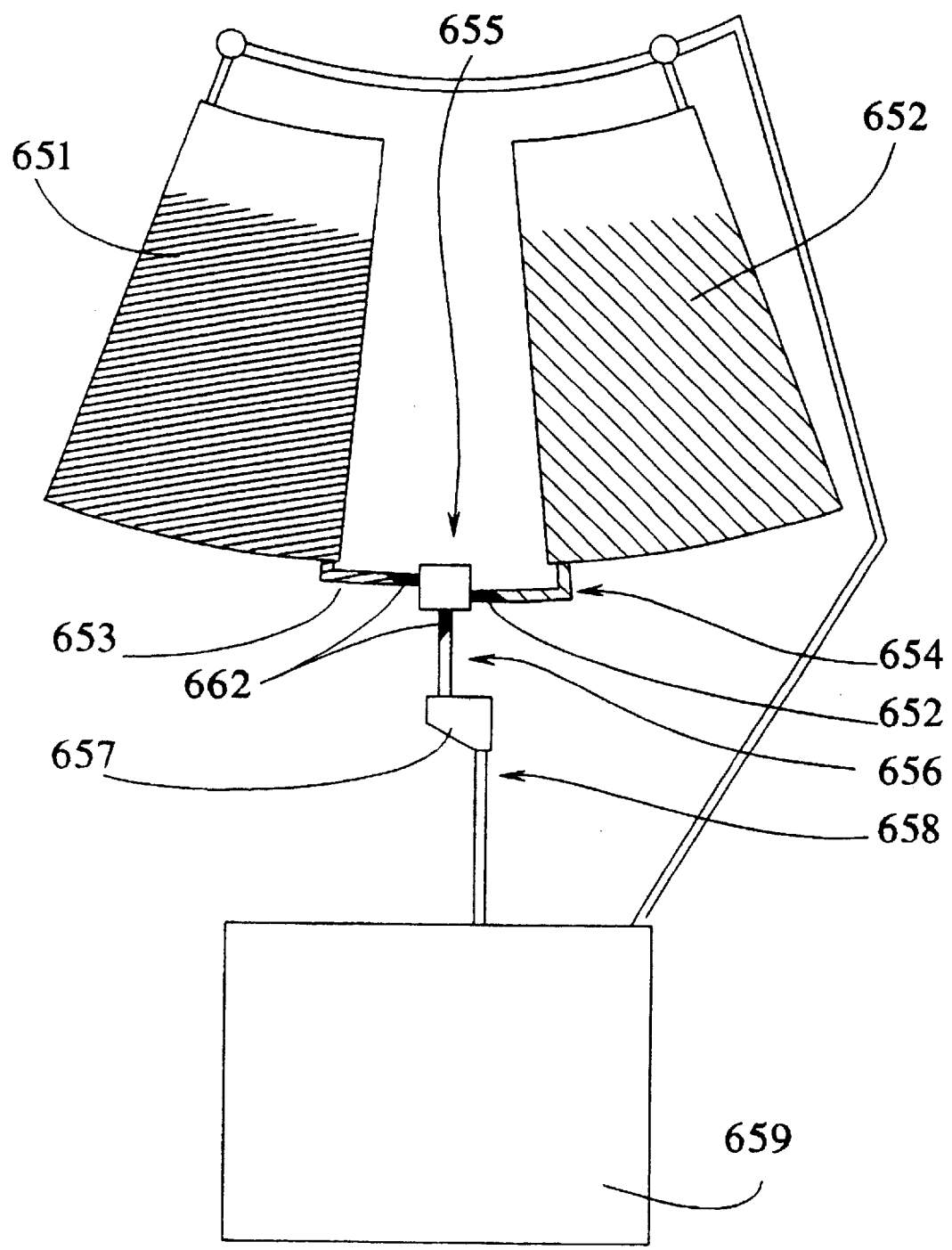
Figure 18B:
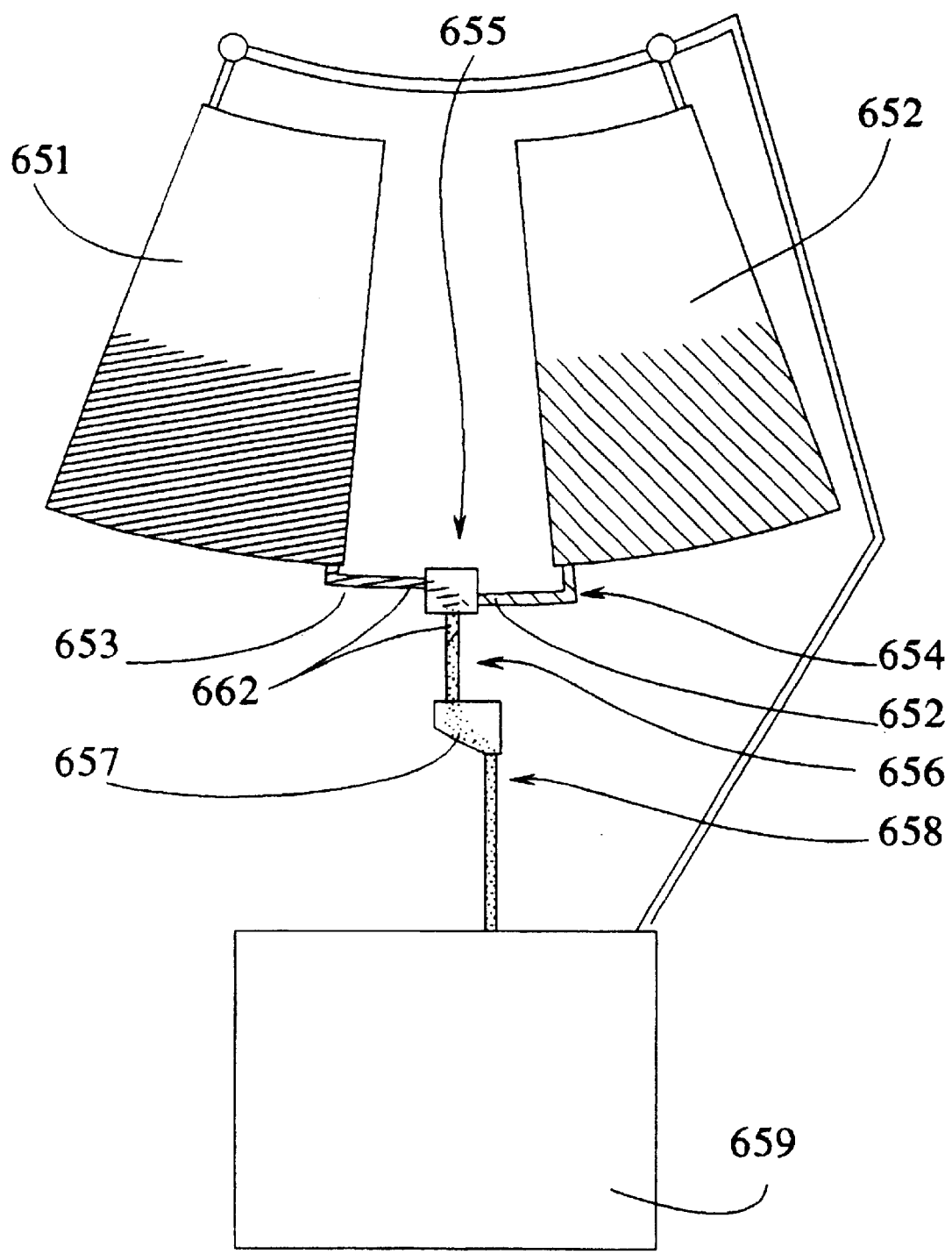
Figure 18C:
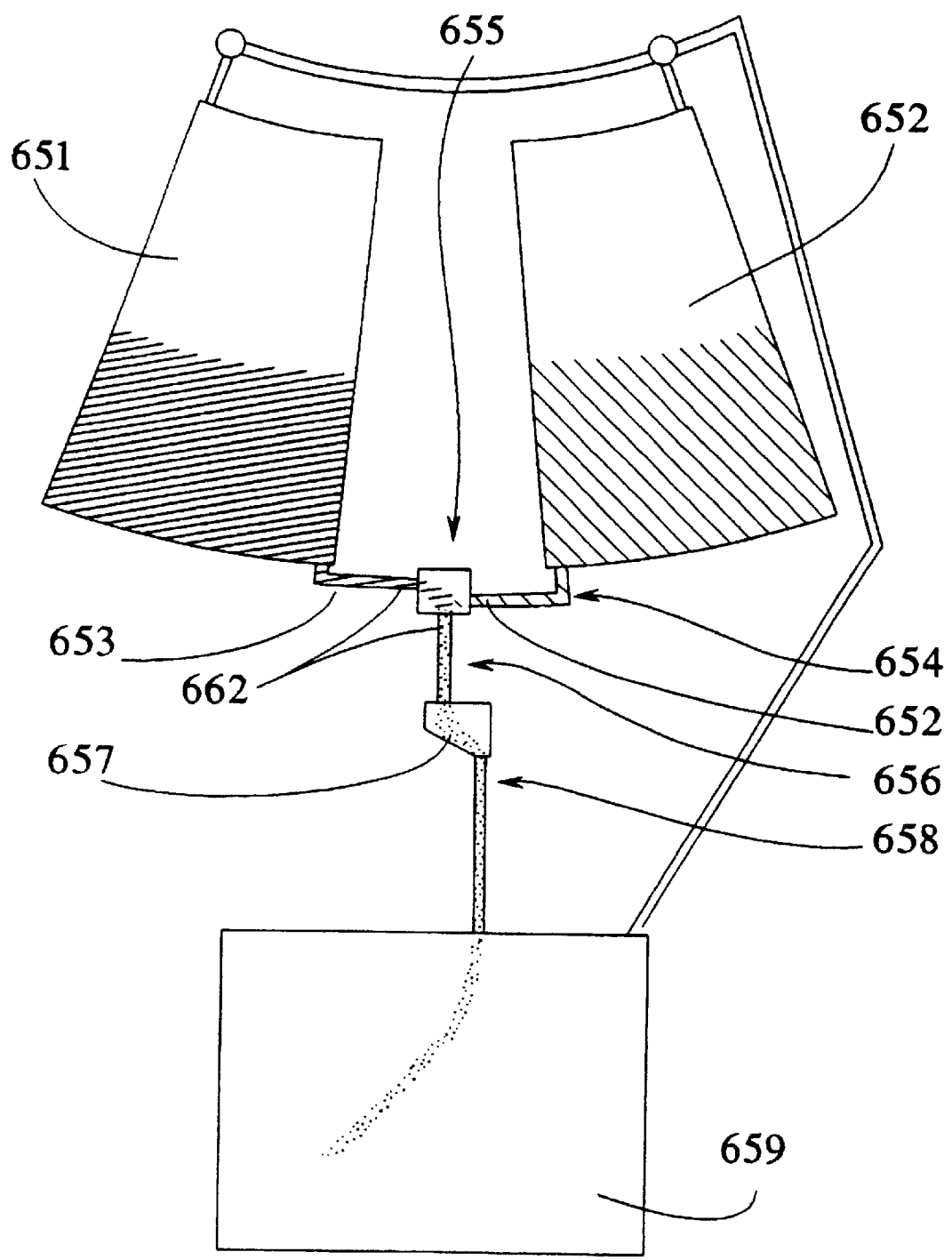
Figure 18D:
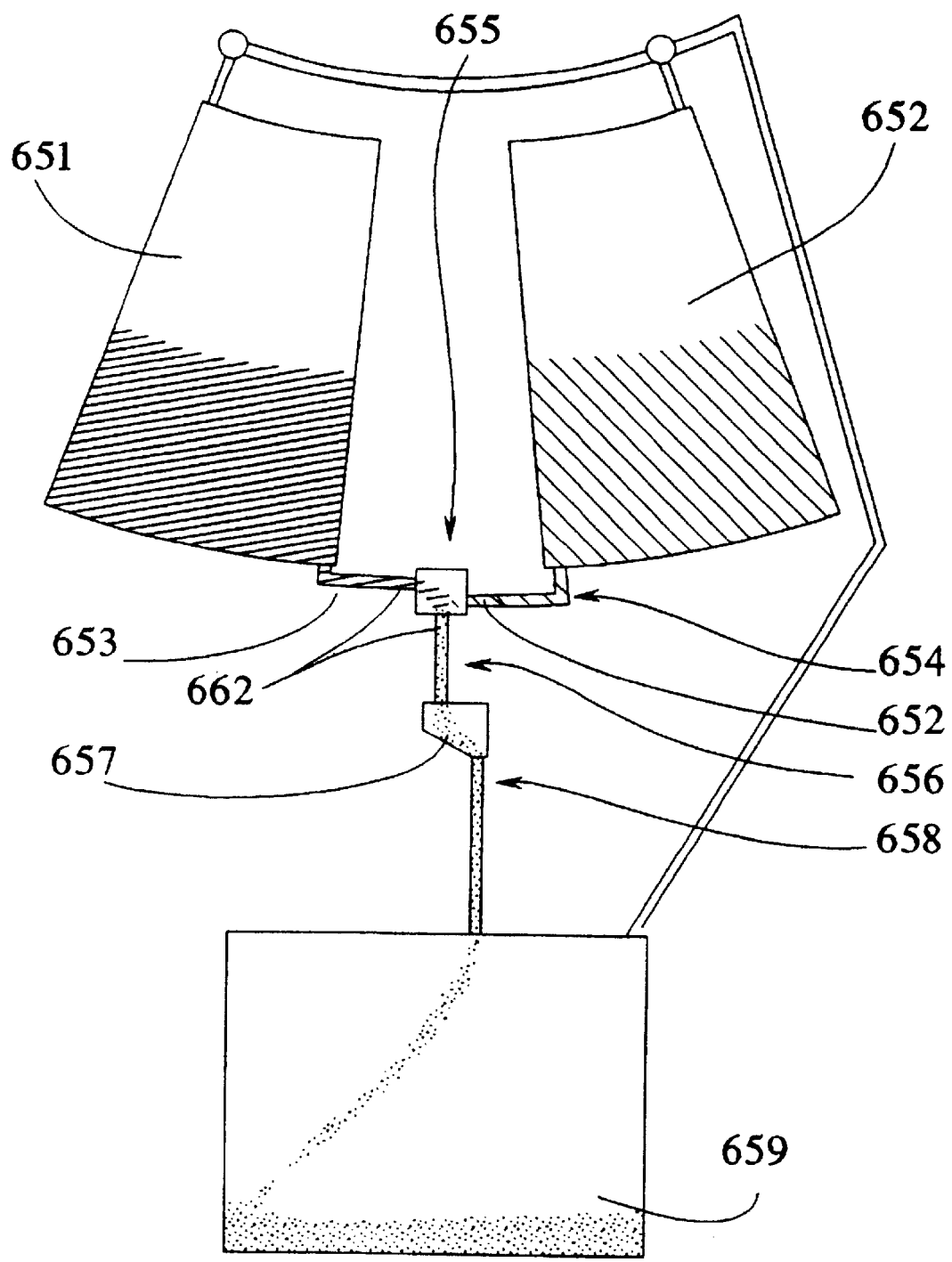
Figure 18E:
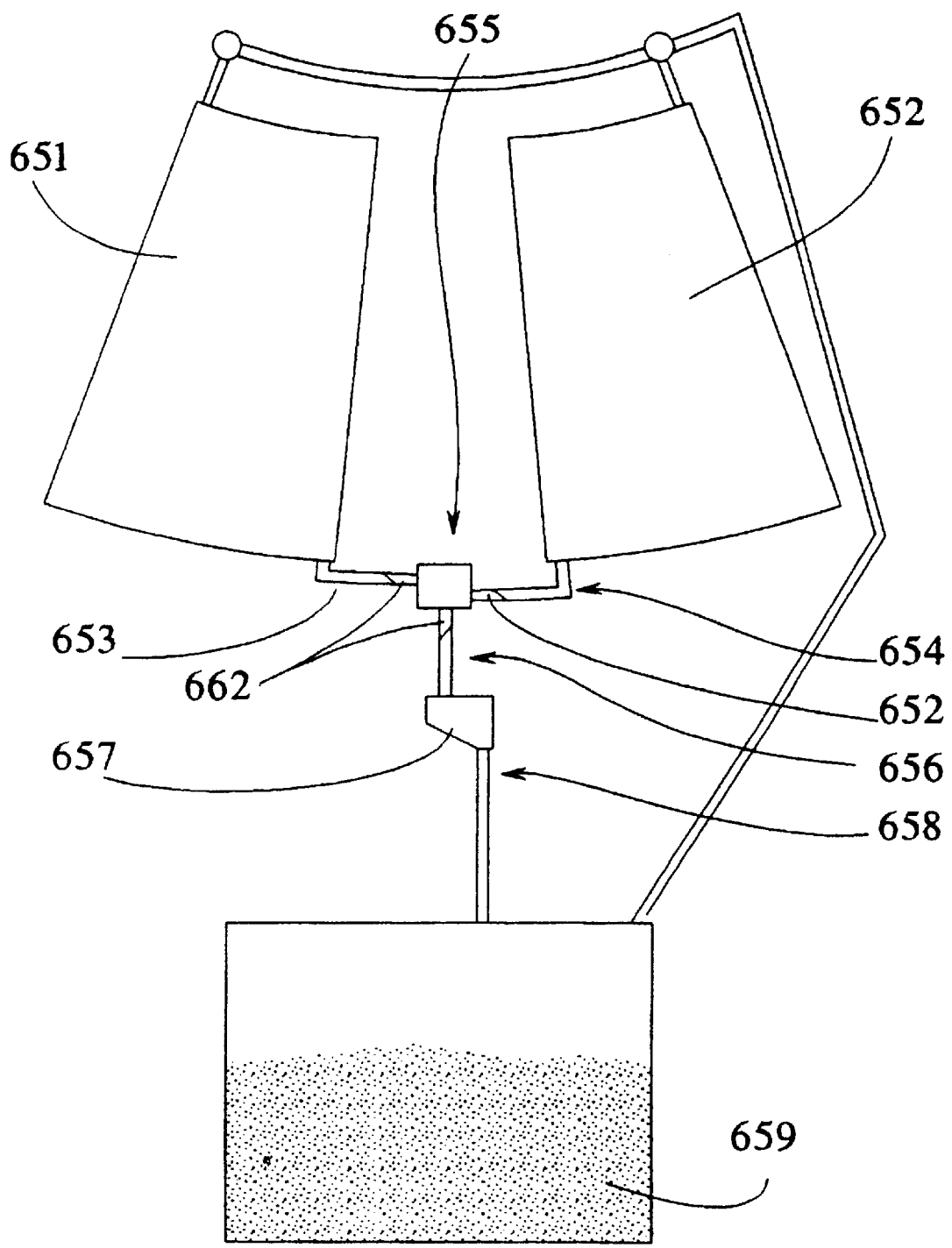

As illustrated in FIGS. 18E through 18E for mixing equal volumes, and in FIGS. 21A through 21E for mixing unequal volumes, in the use of this platform a volume of each of the fluids to be mixed is applied to the fluid reservoirs 651 and 652 (701 and 702) (FIGS. 18A and 21A). Fluid enters the each of the capillaries 653 and 654 (703 or 704) and stops at capillary junction 655 (705). Alternatively, the platforms of the invention are provided containing the fluids to be mixed already in fluid reservoirs 651 and 652 (701 and 702). In these embodiments, it is preferred that sacrificial valves 712 be provided in capillaries 653 and 654 (703 or 704), to prevent evaporation, wetting or leakage of fluid from the reservoirs prior to use.

At a first rotational speed $f_1$ of 100 rpm, the fluids from each capillary flows past capillary junction 655 (705) and through mixing chamber 657 (707) (FIGS. 18B and 18C and FIGS. 21B and 21C). In embodiments comprising a sacrificial valve 712, the valve prevents fluid flow into channels 653 and 654 (703 or 704). Upon release of sacrificial valve 712, fluid flow proceeds from capillary junction 655 (705) through channel 656 (706) and into mixing chamber 707 (FIGS. 18C and 21C). Fluid flow within mixing chamber 657 (707) is turbulent, in contrast to fluid flow through capillary barrier 655 (705) or channel 656 (706), which is primarily laminar, so that mixing occurs predominantly in mixing chamber 657 (707). Fluid flow proceed through channel 658 (708) and the mixed fluid solution is displaced into mixed fluid receiving chamber 659 (709) (FIGS. 18D and 18E and FIGS. 21D and 21E).

EXAMPLE 7

Mixing Arrays: Second Alternative

An additional embodiment of the microsystems platform provided by the invention and specifically designed for performing mixing of different volumes of liquid samples to form a gradient in the concentration of a species in which the two fluids differ; this embodiment is illustrated in FIG. 22. In the Figure, the arrangement of one assay array 18 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 23. Disk embodiments of the platforms of the invention are fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume is about 40 µL for each fluid reservoir.

The components of the mixing array are as follows. Fluid reservoirs 801 and 802, each containing one of a pair of liquids to be mixed, are constructed on the platform, having a depth in the platform surface from about 0.75 mm and lateral dimensions of 1 cm, and wherein fluid reservoir 801 is designed to accommodate a volume of about 40 µL, and fluid reservoir 802 is designed to accommodate a volume of about 40 µL, wherein the volume of fluid reservoir 802 is different than the volume of fluid reservoir 801. In particular and in addition, fluid reservoirs 801 and 802 are shaped so that the rate of fluid output in the two reservoirs differs between the reservoirs at a particular rotational speed, due to a change in the pressure "head" (related to the cross-sectional area of the fluid at each point in the reservoir), so that the proportion of fluid in the mixture from one of the reservoirs is at a maximum at the beginning of rotation and is at a minimum when the fluids from the reservoirs are completely mixed at the end of rotation, thus forming a gradient. Gradient should be approximately 40% of left reservoir and 60% of right reservoir fluid at beginning and reversed at end; aliquoting structure of other mixing array should provide a way to preserve this gradient.

Each fluid reservoir is fluidly connected with a capillary channel 803 or 804 to capillary junction 805. Each capillary channel is about 0.5 mm deep and having a cross-sectional diameter of about 0.5 mm and that extends about 5 cm. Capillary junction 805 has a depth in the platform surface of about 0.75 mm that is greater than the depth of capillaries 803 to 804. Alternatively, capillaries 803 or 804 comprise a sacrificial valve 812. Use of said sacrificial valves can be used in addition to or in place of capillary junction 805.

The fluid components of the mixing array are also connected with air channels 810, that have dimensions of about 0.25 mm deep and permit venting of air displaced by fluid movement on the platform. In addition, capillary junctions 811 that are about 0.75 mm deep are present in the air channels to prevent fluid backflow into the air channel.

Capillary junction 805 is fluidly connected by a narrow capillary channel 806 to mixing chamber 807, which is fluidly connected with channel 808, which is further connected with mixed fluid receiving chamber 809. Alternatively, capillary 806 comprises a sacrificial valve 812. Capillary channel 806 is about 0.5 mm deep and having a cross-sectional diameter of from about 0.5 mm and that extends from about 0.2 cm to about 30 cm. Mixing chamber 807 is about 0.75 mm deep and having a cross-sectional diameter of from about 0.75 mm, and is positioned from about 0.2 cm to about 30 cm from the center of rotation. Capillary channel 808 is about 0.5 mm deep and has a cross-sectional diameter of about 5 mm and that extends from about 0.2 cm to about 30 cm. Capillary channel 806 and capillary channel 808 may be offset in their connection with the mixing chamber as previously described in Example 5, or they can be positioned in the mixing chamber at any convenient position, and Coriolis forces have be relied upon to facilitate mixing.

Capillary 808 is fluidly connected with mixed fluid receiving chamber 809. Mixed fluid receiving chamber 809 is about 0.75 mm deep and having a cross-sectional diameter of about 5 mm from about, and is positioned from about 1 cm to about 30 cm from the center of rotation.

As illustrated in FIGS. 24A through 24E, in the use of this platform a volume (ranging from 5–45 μL of fluid) of each of the fluids to be mixed is applied to the fluid reservoirs 801 and 802 (FIG. 24A). Fluid enters the each of the capillaries 803 and 804 and stops at capillary junction 805. Alternatively, the platforms of the invention are provided containing the fluids to be mixed already in fluid reservoirs 801 and 802. In these embodiments, it is preferred that sacrificial valves 812 be provided in capillaries 803 and 804, to prevent evaporation, wetting or leakage of fluid from the reservoirs prior to use.

At a first rotational speed $f_1$ of 100 rpm, the fluids from each capillary flows past capillary junction 805 and through mixing chamber 807 (FIGS. 24B and 24C). In embodiments comprising a sacrificial valve 812, the valve prevents fluid flow into channels 803 and 804. Upon release of sacrificial valve 812, fluid flow proceeds from capillary junction 805 through channel 806 and into mixing chamber 807 (FIG. 24D). Fluid flow within mixing chamber 807 is turbulent, in contrast to fluid flow through capillary barrier 805 or channel 806, which is primarily laminar, so that mixing occurs predominantly in mixing chamber 807. Fluid flow proceed through channel 808 and the mixed fluid solution is displaced into mixed fluid receiving chamber 809 (FIGS. 24D and 24E).

EXAMPLE 8

Immunoassays

A microsystems platform provided by the invention and specifically designed for performing immunoassay is illustrated in FIG. 25. In the Figure, the arrangement of one assay array 19 on a disk 11 is shown; a multiplicity of such arrays can be advantageously arranged on a microsystems platform, most preferably a disk, of the invention, to provide a multi-use or multi-assay platform.

The components of the mixing array are shown in greater detail in FIG. 26. Disk embodiments of the platforms of the invention were fashioned from machined acrylic. The overall disc dimensions include an outer radius of about 6 cm and an inner radius of about 0.75 cm, wherein the disk is mounted on the spindle of a rotary device. The thickness of the disc ranged from about 0.9 mm to about 1.5 mm. The working fluid volume for reaction was about 10 μL.

The components of the mixing array were as follows. An entry port 901 having a depth in the platform surface of about 0.75 m and lateral dimensions of about 0.5 cm was constructed on the platform, and designed to accommodate a volume of about 10 μL, ranging from 2 μL to 20 μL. This entry port was fluidly connected with a metering capillary 902 having cross-sectional diameter of about 0.5 mm and having a depth of about 0.75 mm; the length of this metering capillary was sufficient to contain a total volume of about 10 μL. The metering capillary 902 was fluidly connected to capillary junction 904.

The entry port was also constructed to be fluidly connected with an overflow capillary 903 having a cross-sectional diameter of about 0.5 mm and proximal ends rounded with respect to entry port 901. The overflow capillary was fluidly connected with an overflow chamber 905 having a depth in the platform surface of about 0.75 mm, greater than the depth of the overflow capillary 903. Each of the overflow and fluid chambers was also connected with air ports or air channels, such as 523, that have dimensions of about 0.25 mm deep and permit venting of air displaced by fluid movement on the platform. Capillary junctions 524 that were about 0.75 mm deep were present in the air channels to prevent fluid flow into the air channels.

Entry port 901 was positioned on the platform 1.3 cm from the center of rotation. Metering capillary 902 extends 4.2 cm from entry port 9015. Overflow capillary 902 extends from entry port 901 from about 1 cm to about 20 cm. The extent of the length of overflow capillary 903 was 20% longer than metering capillary 902. The position of overflow chamber 905 was from about 1 cm to about 20 cm from the center of rotation, and the position of capillary junction 904 was 5 cm from the center of rotation.

Capillary junction 904 was fluidly connected with capillary channel 906, which in turn was fluidly connected with incubation chamber 910. Capillary channel 906 has a cross-sectional diameter of about 0.5 mm and extends about 1 cm. Incubation chamber 910 has a depth in the platform surface of about 0.75 mm, that was greater than the depth of capillary channel 906. Capillary channel 906 was also fluidly connected with channel 909 through capillary junction 907. Capillary junction 907 was constructed to prevent fluid flow of the sample backwards through the junction and into the wash buffer. Channel 909 has a cross-sectional diameter of about 0.5 mm and extends about 5 cm. Capillary junction 907 has a depth in the platform surface of about 0.75 mm, greater than the depth of the channel 909 or capillary channel 906. Incubation chamber 910 also contains a specific binding species, most preferably an antibody, specific for a component of the sample. This species was advantageously contained within incubation chamber 910 as a coating on the surface of the chamber, or attached to beads or other carrier within the chamber, or to a functionalized inner surface of the chamber.

Capillary junction 907 was further fluidly connected with wash buffer reservoir 516, having a depth in the platform surface of about 0.75 mm and positioned at a distance 3.7 cm from the axis of rotation.

Capillary junction 907 was further fluidly connected with reagent capillary 920, which was further fluidly connected with capillary junction 914, which was further fluidly connected with channel 926, and which was fluidly connected with reagent reservoir 917. Reagent capillary 920 has a cross-sectional diameter of about 0.25 mm and extended about 1 cm. Capillary junction 914 has a depth in the platform surface of about 0.25 mm and positioned at a distance of about 2.7 cm from the axis of rotation. Reagent capillary 926 has a cross-sectional diameter of about 0.25 mm and extends from about 0.2 cm to about 20 cm. Reagent reservoir 917 has a depth in the platform surface of about 0.75 mm and positioned at a distance of about 2.3 cm from the axis of rotation.

Incubation chamber 910 was fluidly connected at a point most distal to the axis of rotation to U-shaped capillary 921. U-shaped capillary 921 has a cross-sectional diameter of about 0.5 mm and extended about 1 cm. This capillary extends in a U-shape to a point that was at least as proximal to the axis of rotation than the most axis-proximal extent of incubation chamber 910. This to positioning of the U-shaped channel relative to incubation chamber 910 ensures that additional fluids flowing into incubation chamber 910 and displacing fluid therefrom will displace said fluid homogeneously, i.e., the first fluid in the chamber will be pushed out of the chamber whilst being replaced by the second fluid.

This U-shaped capillary was also fluidly connected with waste reservoir 915. Waste reservoir 915 has a depth in the platform surface of about 0.75 mm and positioned at a distance of about 4.5–5.7 cm from the axis of rotation.

In certain embodiments of the invention, sacrificial valves 922 can be positioned at the junction of capillary junction 904 and capillary channel 906, at the junction of capillary junction 907 and wash buffer capillary 908, or at the junction of reagent reservoir 918 and capillary junction 919.

As illustrated in FIGS. 27A through 27L, in the use of this platform reagent reservoir 916 and wash reservoir 915 were pre-loaded on the disk, and most preferably the disk contains sacrificial valves 922 at the junction of capillary junction 907 and wash buffer capillary 908, and at the junction of reagent reservoir 918 and capillary junction 919. An imprecise volume (ranging from 1–150 μL of fluid) of a fluid was applied to the entry port 901 (FIG. 27A). Fluid wicks into metering capillary 902 and stops at the capillary junction between metering capillary 902 and capillary junction 904 (FIGS. 27B and 27C). After sample loading by a user and filling of metering capillary 902 and overflow capillary 903 at no rotational speed, the platform was spun at a first rotational speed $f_1$ of 45 rpm.

Due to the greater distance of the end of overflow capillary 903 from the center of rotation than the end of metering capillary 902, fluid flows through overflow capillary 903 into overflow chamber 905 (FIG. 27D). The platform was spun until all excess fluid was evacuated from entry port 901 and into overflow chamber 905, except the fluid contained in metering capillary 902 (FIG. 27E).

At a second rotational speed $f_2$ of 65 rpm, the capillary junction 904 at the distal end of the metering capillary 902 was overcome, and sample from metering capillary 902 fills incubation chamber 910 (FIGS. 27F and 27G). A portion of the sample wicks into U-shaped capillary 914 to the level of the sample in incubation chamber 910 (FIG. 27G). The sample was incubated for a time sufficient for maximum saturation binding of the component in the sample that specifically bind to the specific binding species.

At a third rotational speed $f_3$ of 450 rpm, the capillary junction 908 was overcome, and wash buffer from reservoir 916 flows through capillary 909, capillary 906, and into incubation chamber 910. Wash buffer fluid flow forces the sample through U-shaped capillary 914 and into waste reservoir 915 (FIGS. 27H through 27J). Preferably, sacrificial valves 922 were released to permit wash buffer fluid flow.

Figure 27K:
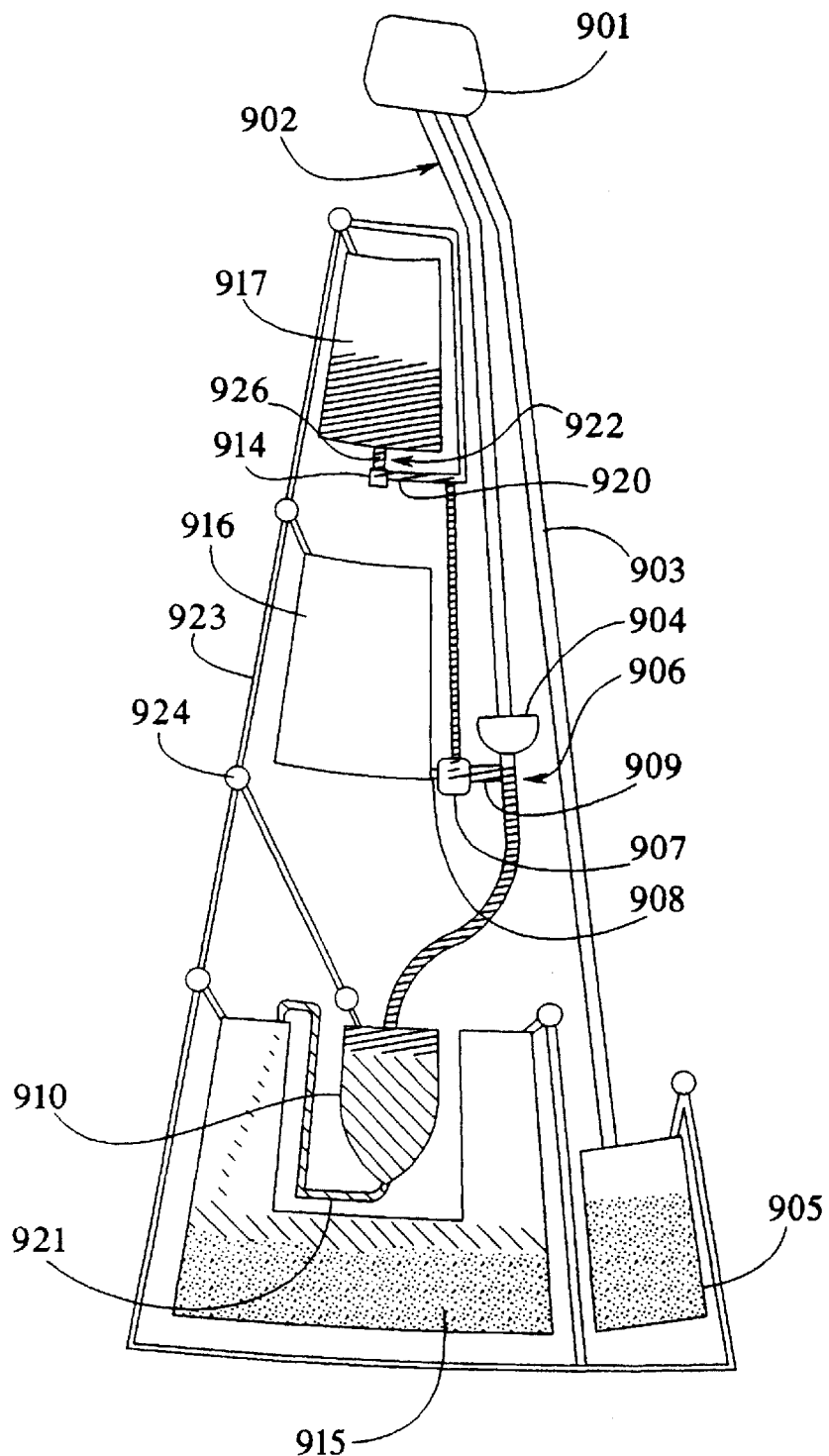
Figure 27L:
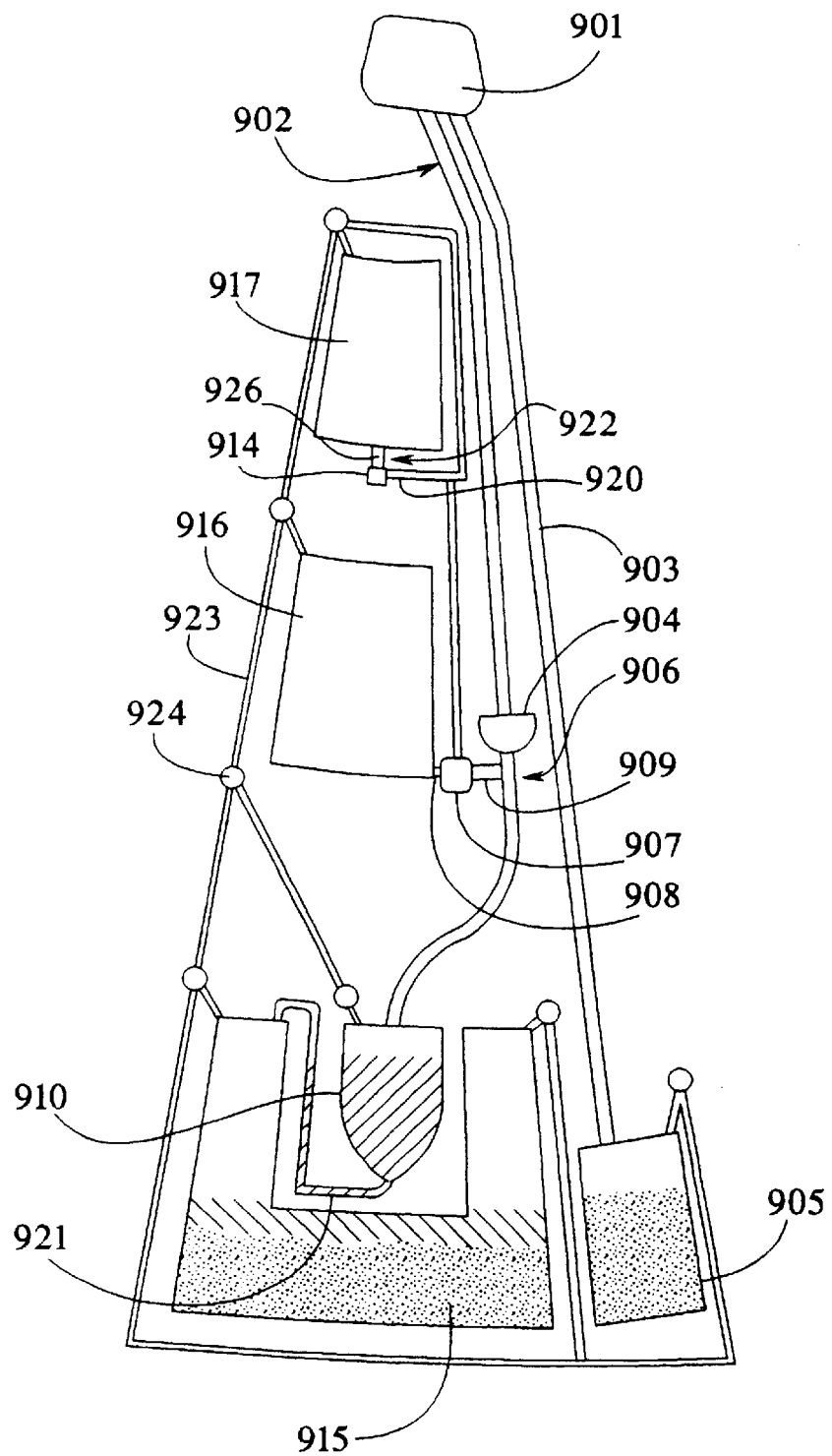

At a fourth rotational speed $f_4$ of 500 rpm, the capillary junction 919 was overcome, and reagent buffer from reservoir 917 flows through capillary 918, capillary 920, capillary junction 908, capillary 906, and into incubation chamber 910. Reagent buffer fluid flow forces the wash buffer through U-shaped capillary 914 and into waste reservoir 515 (FIGS. 27K through 27L). Preferably, sacrificial valves 922 were released to permit reagent buffer fluid flow.

The reagent buffer contained a chromogen or other developing agent for detection of specific binding in incubation chamber 910. The extent of specific immunoassay being was determined relative to the amount of chromogen produced in the assay.

EXAMPLE 9

Immunoassays

Use of nitrocellulose for immobilizing antigens for use with the immunoassay arrays described in Example 8 were demonstrated as follows.

Proof-of Principle

Visual blue signals have been developed resulting from formation of a three-membered sandwich immobilized on a nitrocellulose (NC) surface. This sandwich is composed of (a) a capture anti-TSH monoclonal antibody (MAB) adsorbed onto porous NC; (b) TSH antigen, and c) a complimentary anti-TSH MAB coated onto colloidal blue latex particles. The intensity of blue color immobilized at the capture site increases in a regular way with antigen (TSH) level, thus providing a method of the quantitative analysis of unknown specimens.

Capture MAB was immobilized on 8-μm NC by application of 2 μL spots at a concentration of 10 mg/mL. These spots spread to circles about ¼" in diameter. After brief incubation, the field surface of the NC was blocked in a bath of 1% BSA in PBS, followed by extensive washing with 0.1% BSA-PBS. The membrane was allowed to air dry prior to use. The spotted region was then cut into small squares and introduced into glass test tubes followed by 200 μL aliquots of serially diluted TSH standards in 50/50 horse serum/PBS-BSA buffer. After a brief incubation to wet the NC, 10 μL of a 0.309 micron diameter blue latex suspension coated with a complimentary MAB was added and mixed. After 5 min of gentle shaking, the disk was removed, washed under a PBS-BSA stream, and allowed to dry. By visual inspection, the color intensity was seen to vary in the expected way with TSH concentration.

Additional antibody labeled groups, such a colloidal gold, fluorescent or colored latex beads, can be used to detect antibody binding and accumulation.

Experimental: Competitive Immunoassay

A competitive assay for the monovalent thyroid hormone Thyroxine has been developed analogous to and complimenting the sandwich assay described above for TSH. Antigen was immobilized on 5 μm NC by application of 1.5 μL volumes of BSA-T4 (12.5 mg/mL) followed by blocking with 1% BSA in PBS and final washing with 0.1% BSA in PBS. Anti-thyroxine monoclonal antibody (MAB) was immobilized on Seradyne 0.309 μm blue latex beads by passive adsorption.

Antibody-coated beads were briefly incubated in test tubes with T4 in buffer over a wide hormone concentration range. Square pieces of nitrocellulose containing adsorbed capture antigen were then added to the test tubes and incubated for 10 minutes, during which time color developed on the NC. The squares were then washed with a small volume of buffer and color intensity visually noted as a function of T4 level.

A roughly monotonic increase in blue color intensity with decreasing T4 concentration was found, as expected for a competitive assay. Change in color intensity occurred over a low T4 concentration range, implying that a serum specimen can be diluted by about ten-fold for analysis; i.e., about 30 μL of serum per test can be used, diluted to 300 μL to produce detectable signal variation over the range of clinical diagnostic interest. A total assay time of about 20-?? minutes was determined without optimization, and low background and high signal intensity were obtained (without optimization). These results indicate that these procedures make it possible to detect immunoassay results at antigen and antibody concentrations useful for the detection of small amounts of antigen in complex mixtures, such as biological mixtures.

EXAMPLE 10

Preparation of Resistive Heater Elements

Resistive heater elements were prepared on the platforms of the invention as follows. Portions of the surface of a microsystems platform on which a resistive heater element are desired are screen printed with a resistive ink electrically coupled with a conductive ink to conduct electricity across the resistive ink in the presence of a direct current (DC) voltage drop across the extent of the resistive ink. Both the resistive ink and the conductive ink are screened printed using methods well known in the art (Gilleo, ibid.)

Figure 32:
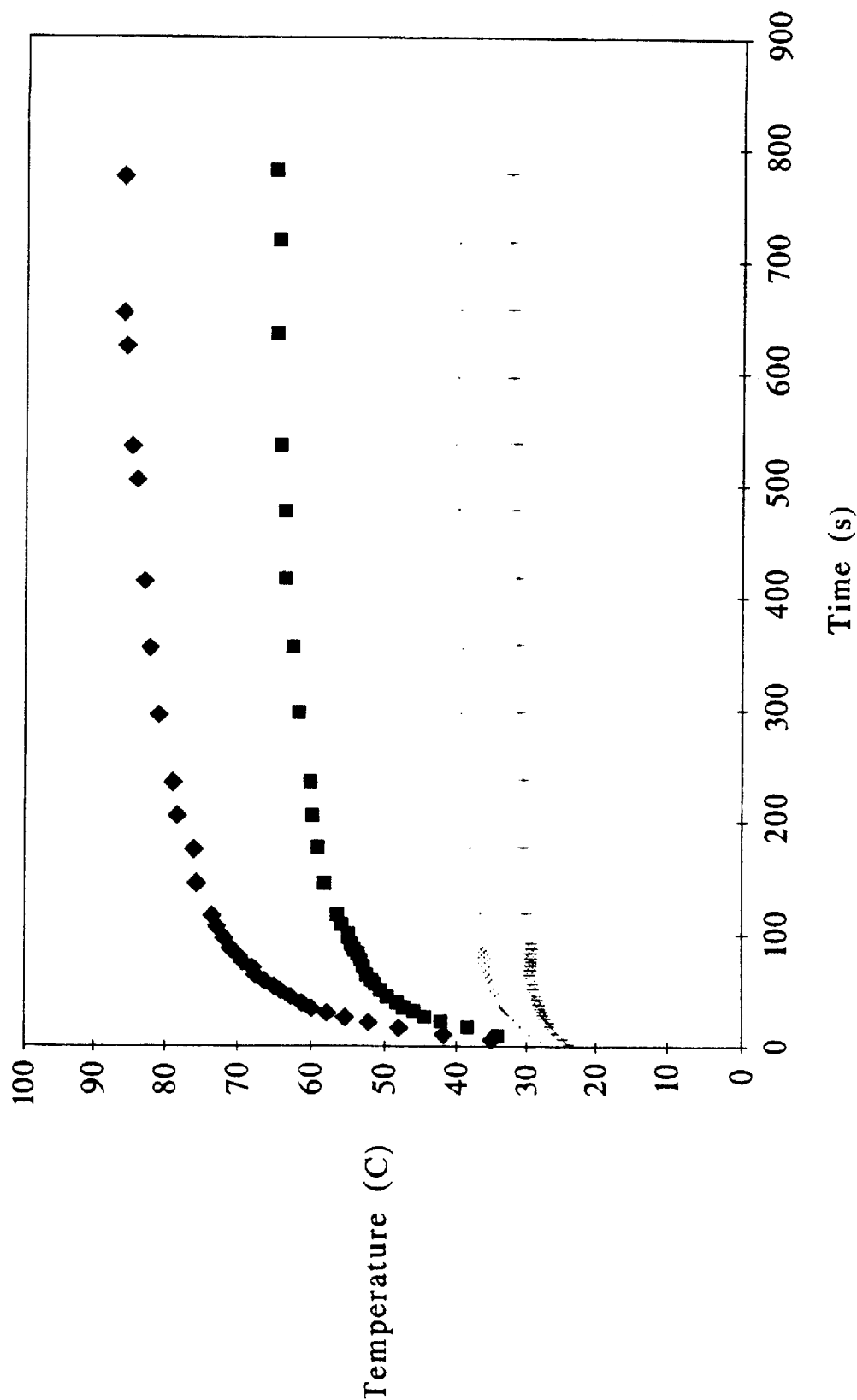
FIG. 32 is a graph showing the time dependence of temperature produced at a variety of voltages using a resistive heater element as described in Example 10.

Briefly, a conductive ink pattern, such as those illustrated in FIG. 30, was screened onto a heat stabilized polyester sheet substrate (ICI ST505), and cured at 110–120° C. for 10 minutes. A resistive ink was then screened over the cured conductive ink pattern and the composite cured for an additional 10 min at 110–120° C. Typically, the ink is laid down in a layer that is about 10 resistive polymer thick films to produce heat when an electrical potential is applied across a resistive polymer thick film element produced as described in Example 10. The capacity of a resistive polymer thick film element to be used as a heater is shown in FIG. 32. Circuits in the pattern shown in FIGS. 30 and 31 were screen-printed using Dupont 5028 silver paste as the conductive electrode combined with a 50:50 mixture of Dupont 7082 resistive ink blended with Dupont 7102 resistive ink to form the resistive heating element. A direct current (DC) voltage was applied across the electrical contacts 31 and 33 in FIG. 31 and the temperature at the surface of the heater measure using a thermistor probe. These experiments were performed "dry", that is, on a resistive heater element without application of a fluid on the platform, and stationary, that is, without rotation of the disc. FIG. 32 is a graph of the temperature produced as a function of time and applied (DC) voltage (voltage applied was 2V, 3V, 4V, 5V, and 6V, read bottom to top from the voltage that produced the lowest steady-state voltage through the highest steady-state voltage). This graph shows that the maximum temperature produced increased with both time and applied voltage, and that the maximum voltage reached a steady state within between 100–150 seconds, and that the maximum voltage achieved was about 85–90° C. These data have been converted into the graph shown in FIG. 33, which show a plot of the steady-state temperature obtained as a function of applied (DC) voltage. These results show that the steady-state temperature achieved increases in a parabolic fashion with increased applied voltage.

The dependence of maximum steady-state temperature on voltage was also determined using positive temperature coefficient (PTC) inks, specifically Dupont 7285 ink, in experiments performed as described above. The voltage dependence on temperature is linear over the voltage range tested, and the applied (DC) voltages were about ten-fold higher than the results obtained using blended resistive inks.

Figure 33:
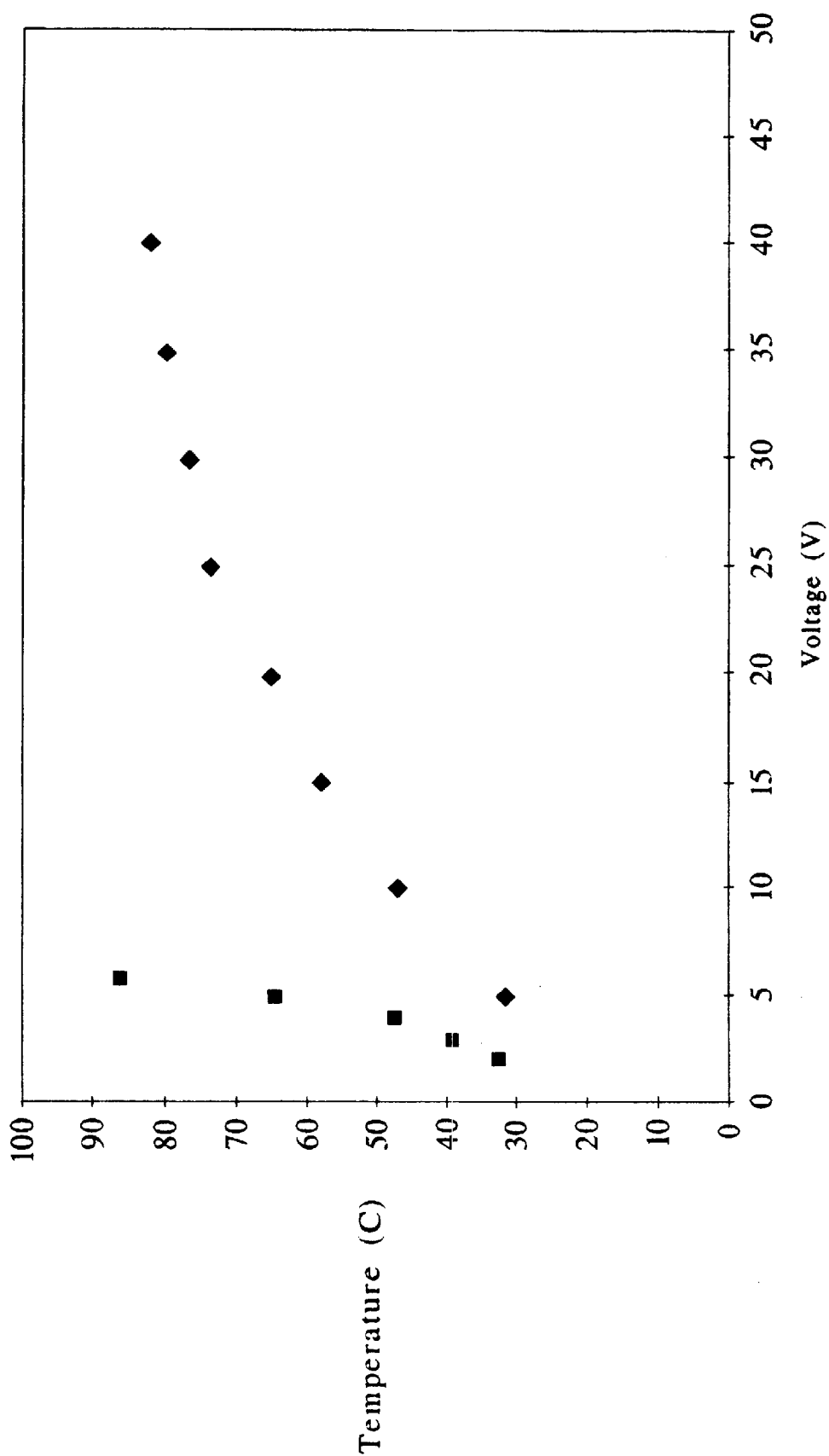
FIG. 33 is a graph showing the voltage dependence of temperature produced at a variety of voltages using a resistive heater element as described in Example 10.

These results are contrasted in FIG. 33 with the results obtained with PTC inks, which approach a steady state temperature with increasing voltage, as expected for a positive temperature controlled ink. The results obtained with PTC inks were obtained using a resistive heating element screen-printed in a patterns as shown in FIG. 31 using Dupont 7285 PTC ink.

Figure 34:
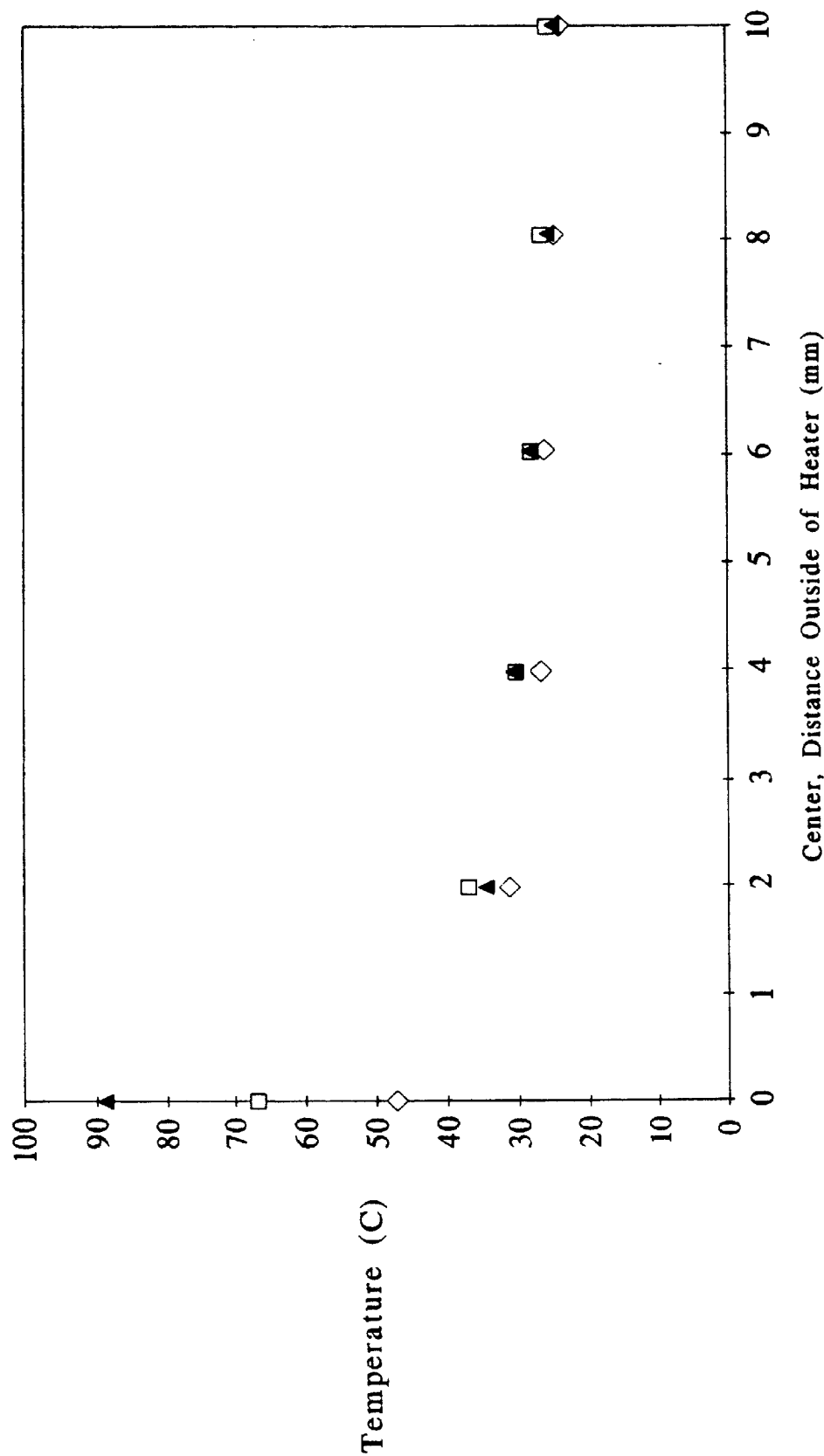
FIG. 34 is a graph showing the distance dependence on heating using a resistive heater element as described in Example 10.
Figure 35:
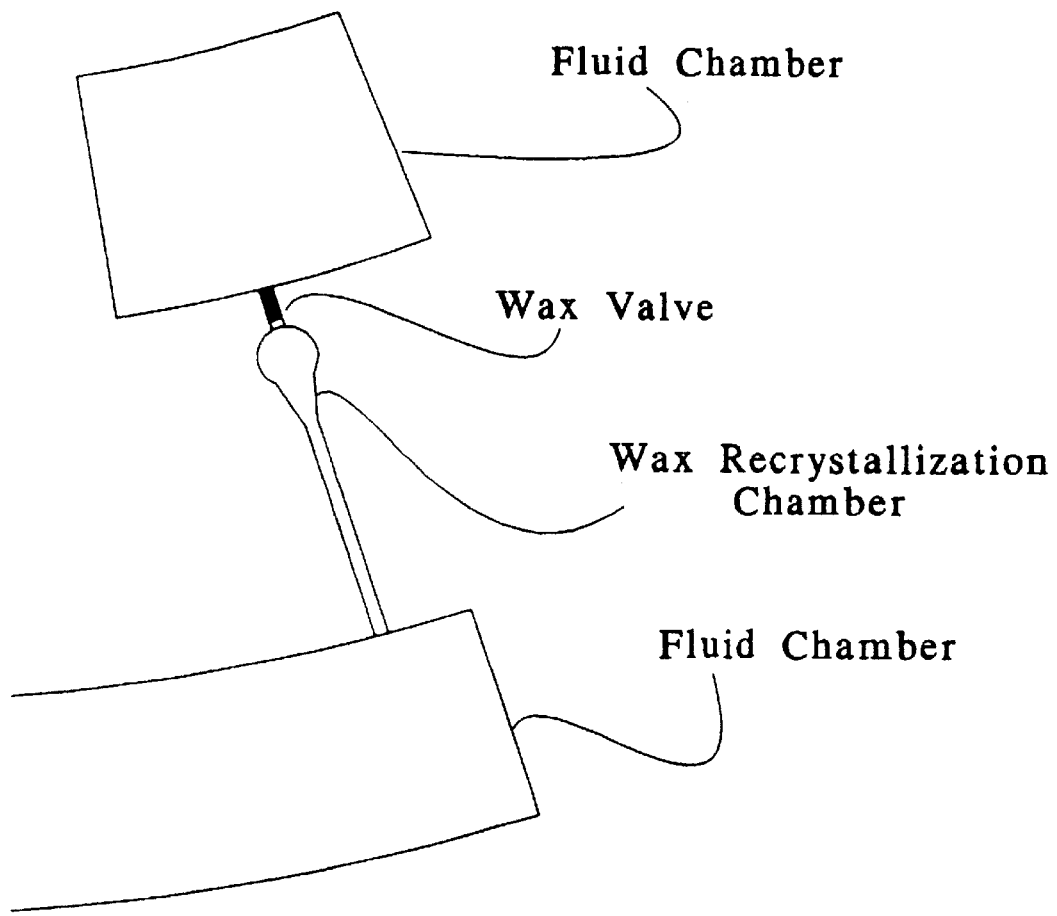
FIG. 35 illustrates screen-printing of a resistive heater element associated with wax valves as described in Example 11.
Figure 36A:
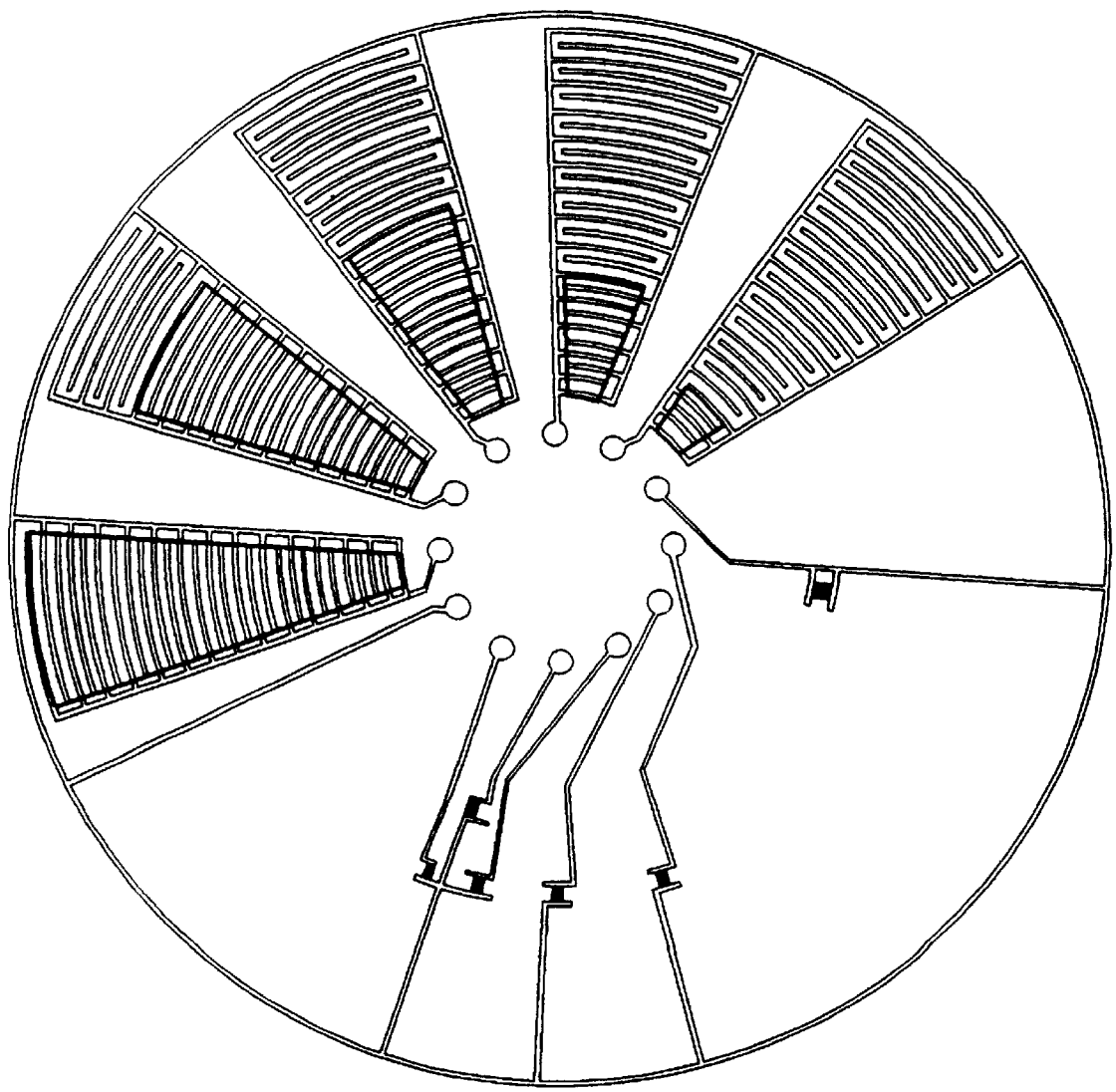
FIG. 36 illustrates screen-printing of a resistive heater element associated with wax valves as described in Example 11.
Figure 36B:
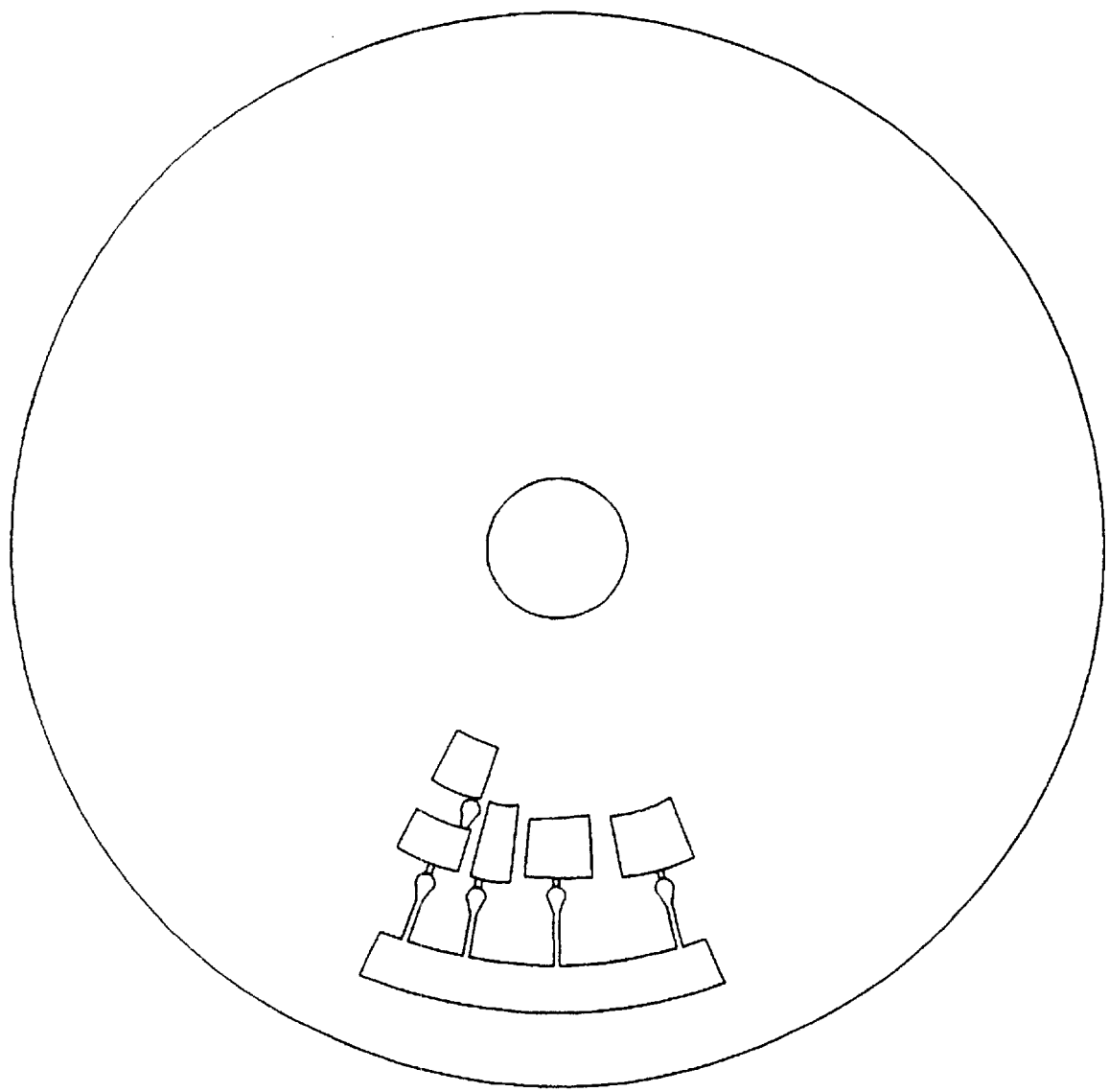
Figure 36C:
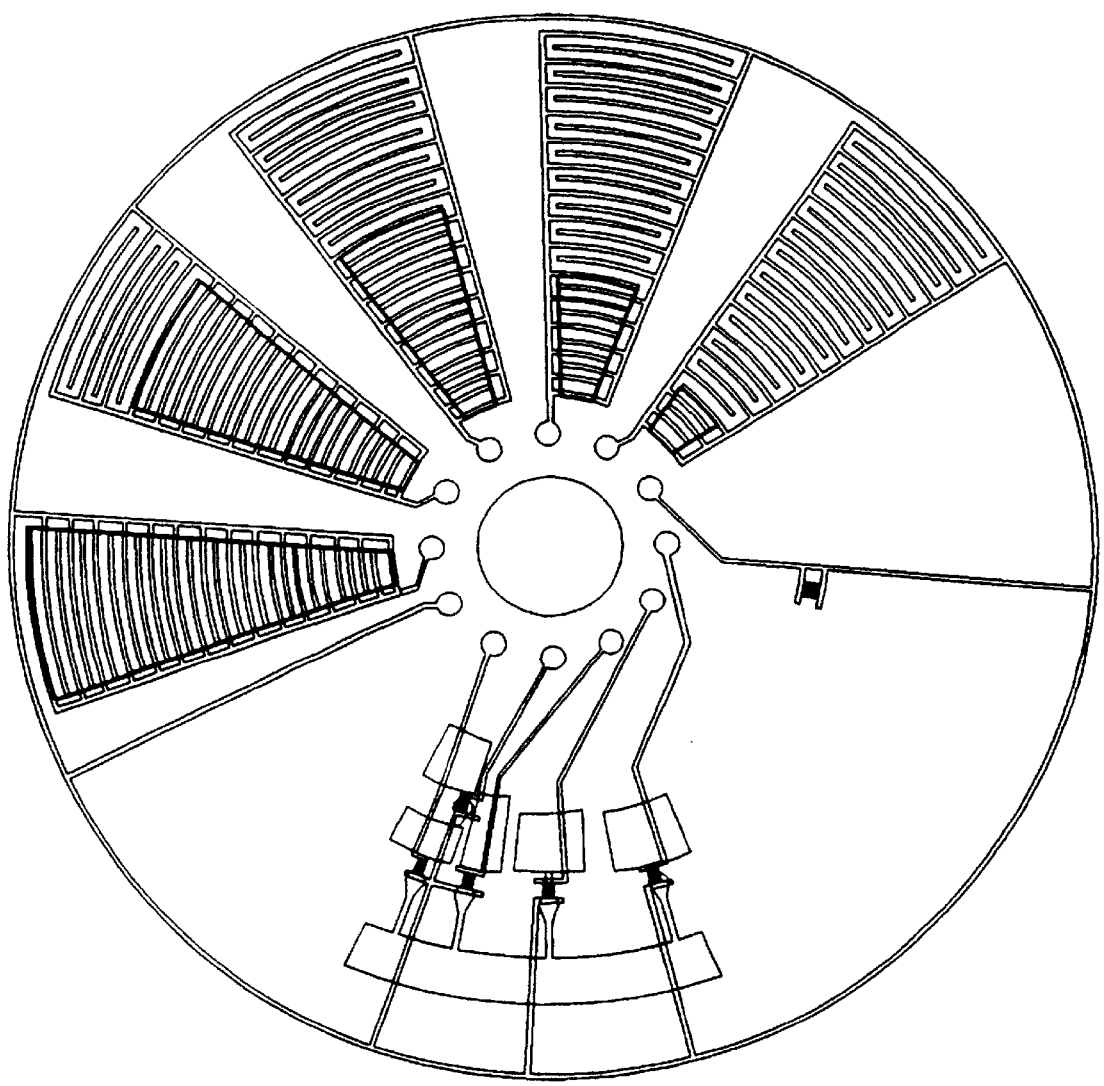
Figure 37:
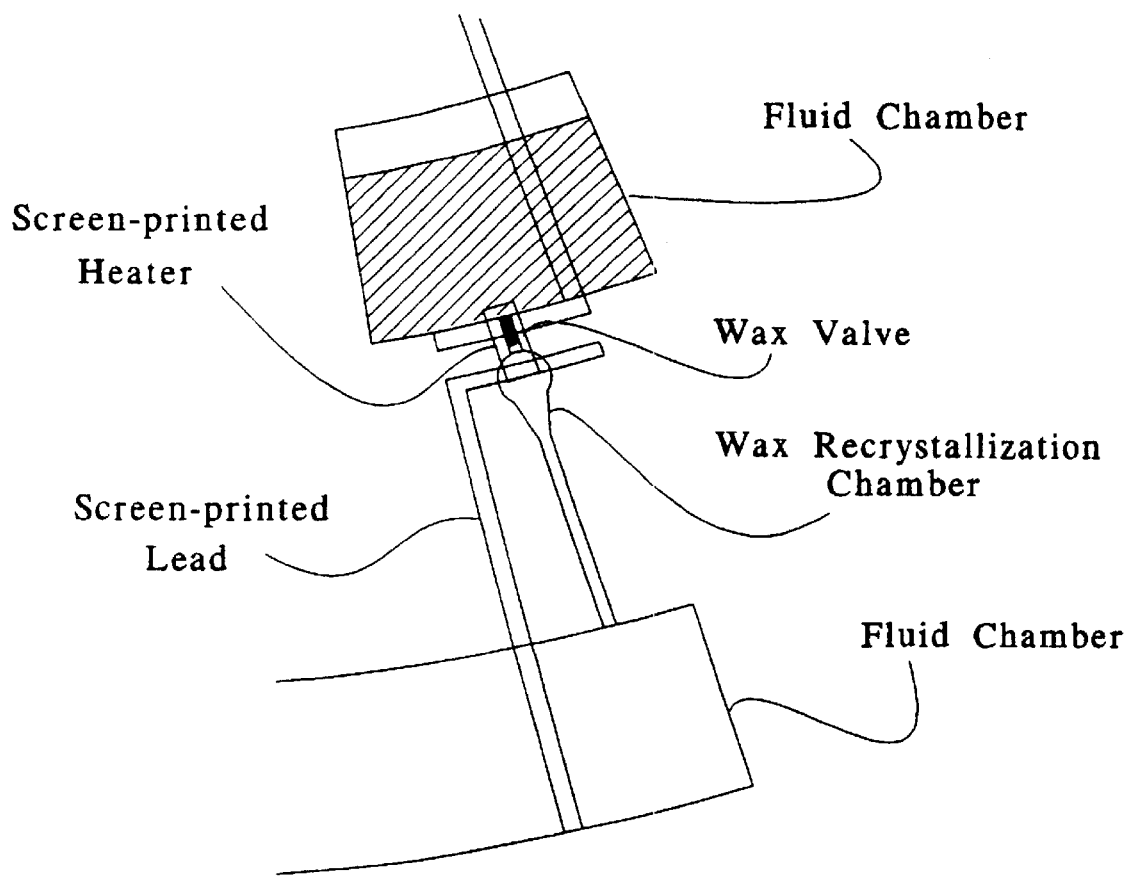
FIG. 37 illustrates screen-printing of a resistive heater element associated with wax valves as described in Example 11.
Figure 38A:
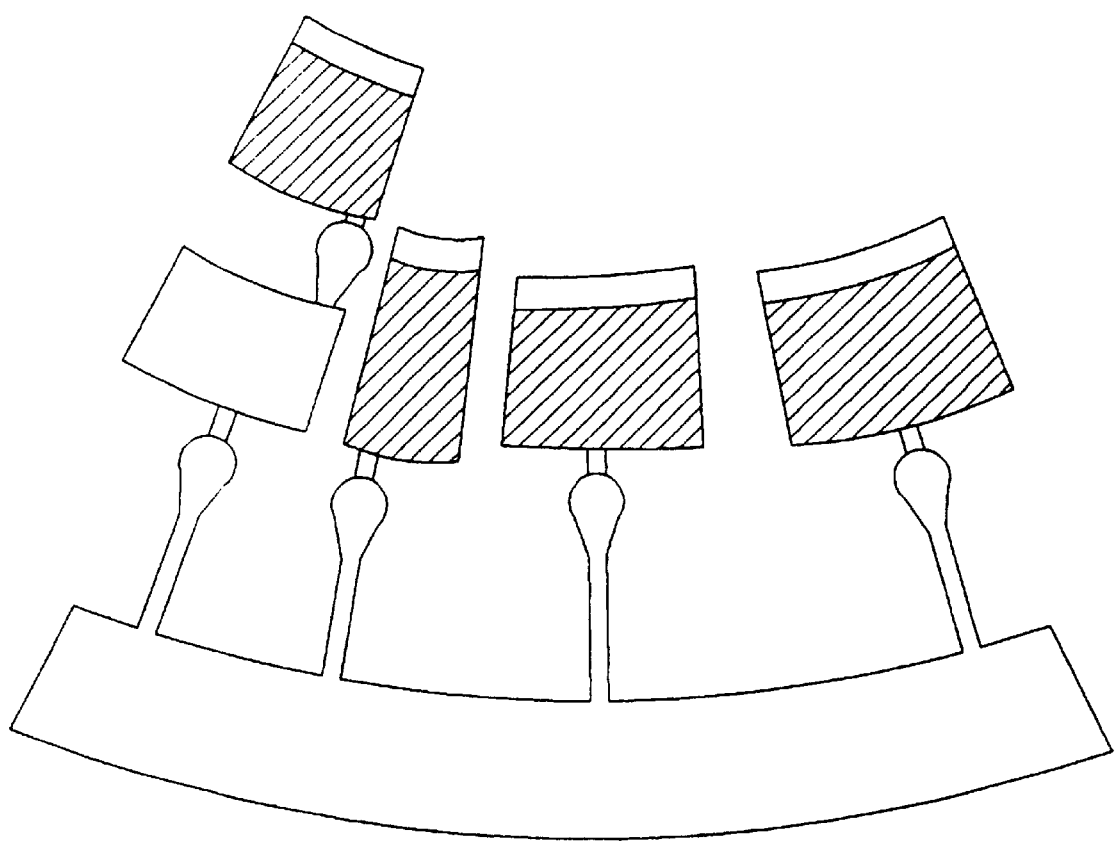
FIG. 38 illustrates the use of screen-printed resistive heater elements to melt wax valves and control fluid flow in a microfluidics array as described in Example 11.
Figure 38B:
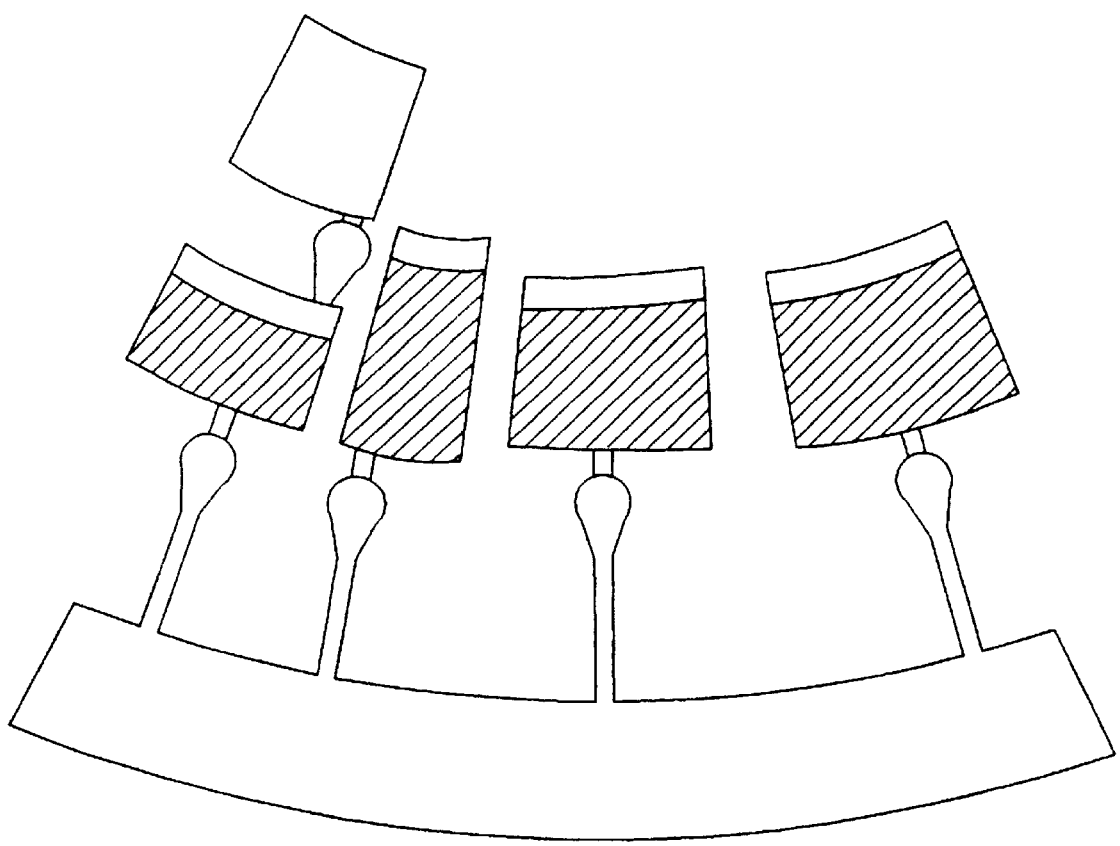
Figure 38C:
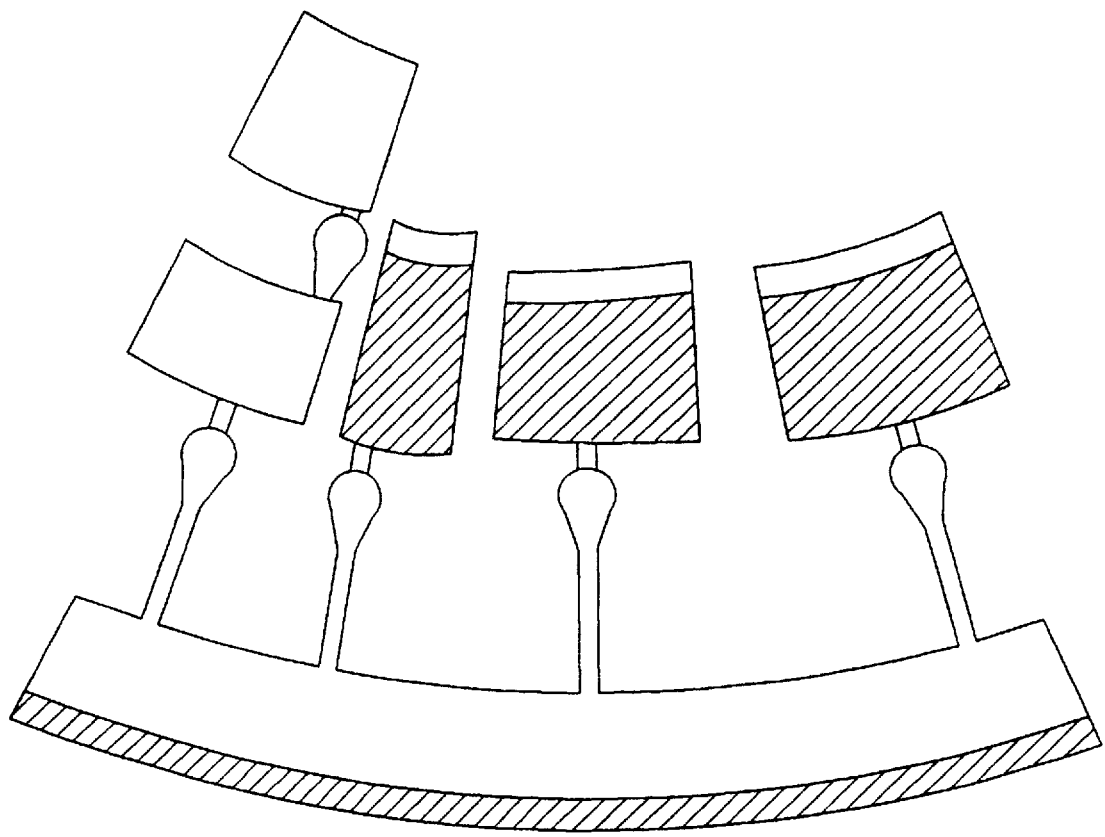
Figure 38D:
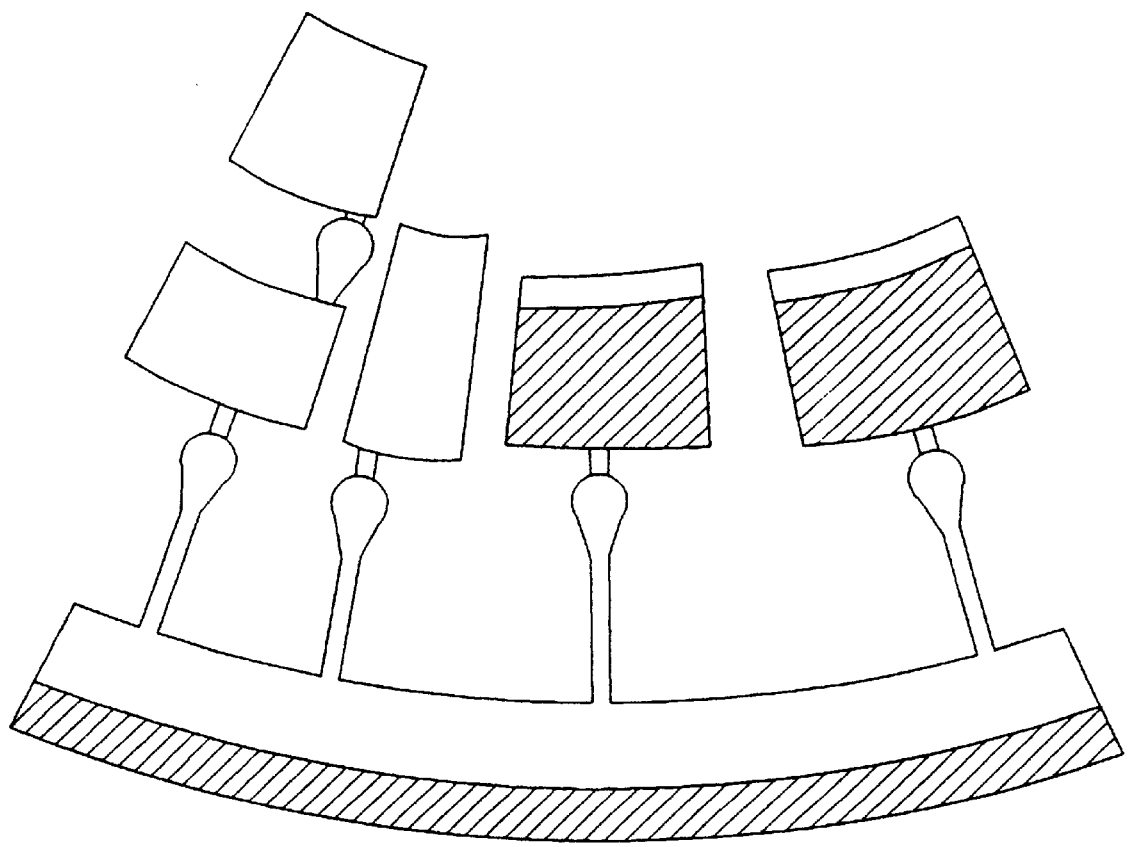
Figure 38E:
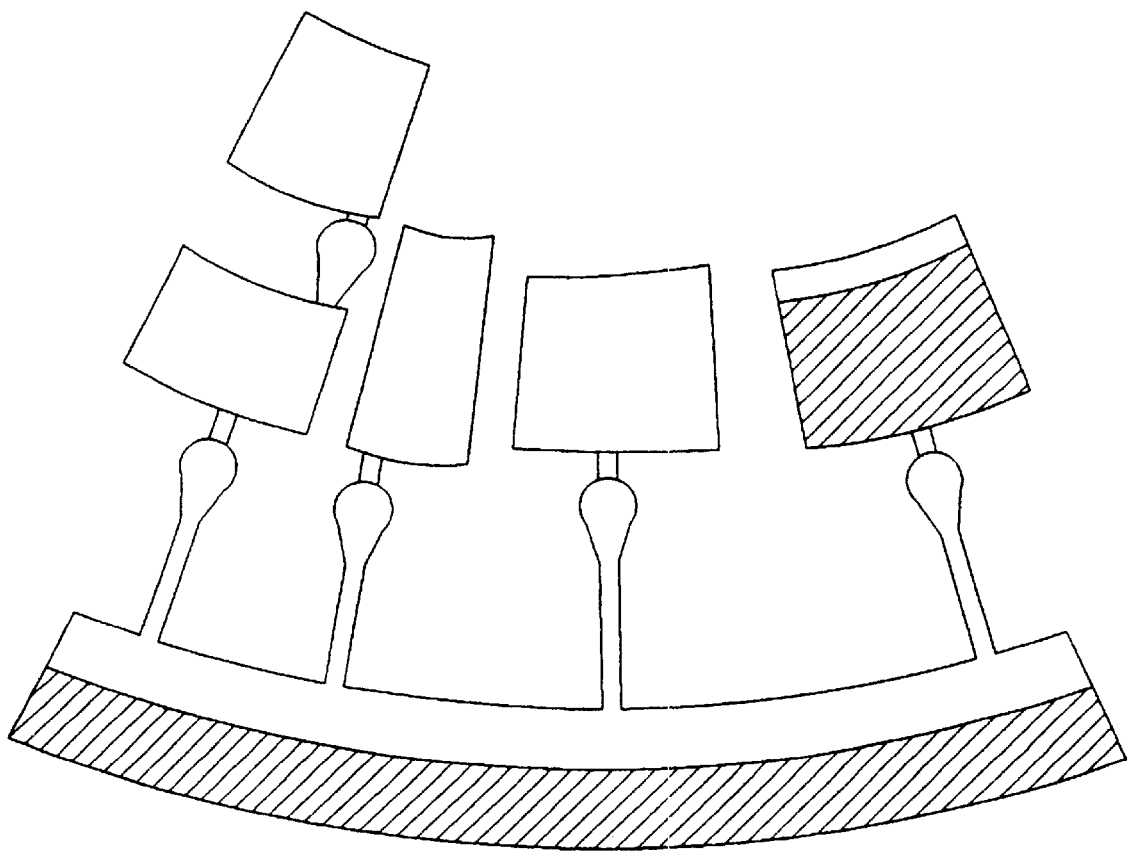
Figure 38F:
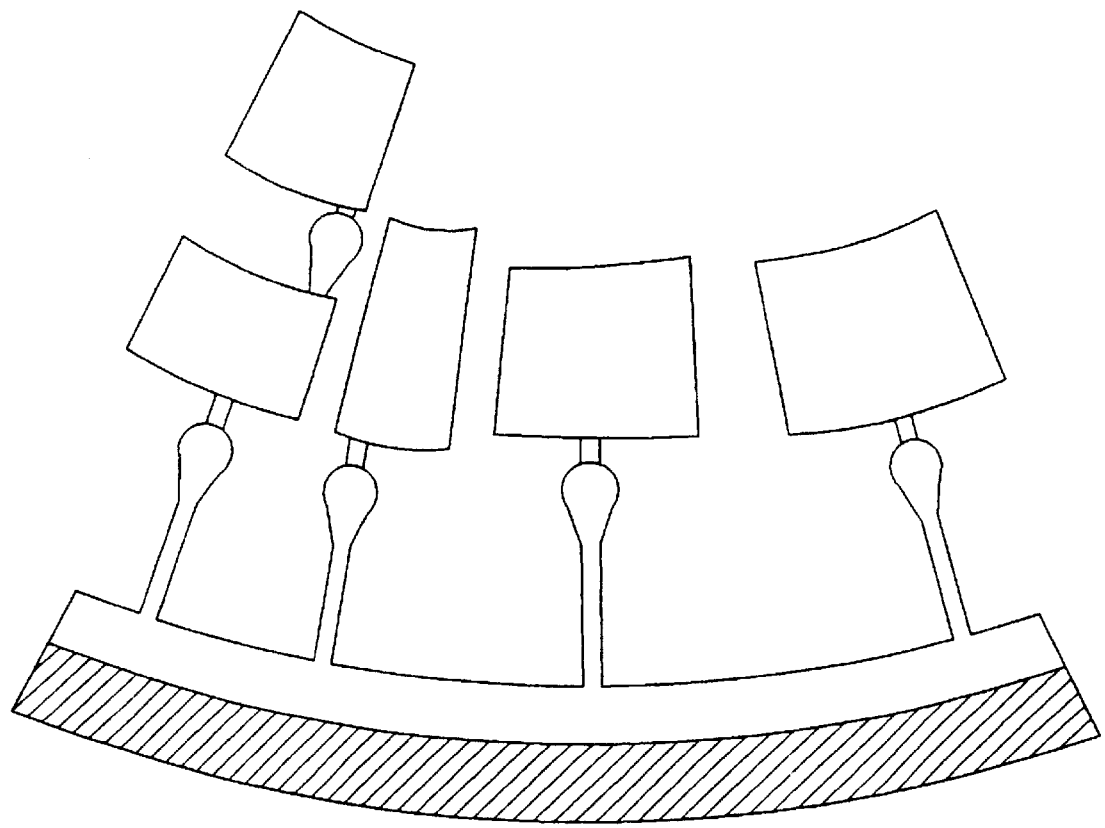

The temperature of the substrate at increasing distance from the resistive heater elements of the invention was determined. These results are shown in FIG. 34, where the temperature of the disk drops to ambient within 1–2 mm of the resistive heater. These results indicate that resistive heaters can be arrayed in close proximity without the activation of one of the heaters affecting either the adjacent heater or the platform component (such as a sacrificial valve) controlled by the adjacent

EXAMPLE 11

Use of Resistive Polymer Thick Films as Heater Elements

The use of resistive polymer thick films as heater elements depends on the capacity of resistive polymer thick films to produce heat when an electrical potential is applied across a resistive polymer thick film element produced as described in Example 10. The capacity of a resistive polymer thick film element to be used as a heater is shown in FIG. 32. Circuits in the pattern shown in FIGS. 30 and 31 were screen-printed using Dupont 5028 silver paste as the conductive electrode combined with a 50:50 mixture of Dupont 7082 resistive ink blended with Dupont 7102 resistive ink to form the resistive heating element. A direct current (DC) voltage was applied across the electrical contacts 31 and 33 in FIG. 31 and the temperature at the surface of the heater measure using a thermistor probe. These experiments were performed "dry", that is, on a resistive heater element without application of a fluid on the platform, and stationary, that is, without rotation of the disc. FIG. 32 is a graph of the temperature produced as a function of time and applied (DC) voltage (voltage applied was 2V, 3V, 4V, 5V, and 6V, read bottom to top from the voltage that produced the lowest steady-state voltage through the highest steady-state voltage). This graph shows that the maximum temperature produced increased with both time and applied voltage, and that the maximum voltage reached a steady state within between 100–150 seconds, and that the maximum voltage achieved was about 85–90° C. These data have been converted into the graph shown in FIG. 33, which show a plot of the steady-state temperature obtained as a function of applied (DC) voltage. These results show that the steady-state temperature achieved increases in a parabolic fashion with increased applied voltage.

The dependence of maximum steady-state temperature on voltage was also determined using positive temperature coefficient (PTC) inks, specifically Dupont 7285 ink, in experiments performed as described above. The voltage dependence on temperature is linear over the voltage range tested, and the applied (DC) voltages were about ten-fold higher than the results obtained using blended resistive inks.

These results are contrasted in FIG. 33 with the results obtained with PTC inks, which approach a steady state temperature with increasing voltage, as expected for a positive temperature controlled ink. The results obtained with PTC inks were obtained using a resistive heating element screen-printed in a patterns as shown in FIG. 31 using Dupont 7285 PTC ink.

The temperature of the substrate at increasing distance from the resistive heater elements of the invention was determined. These results are shown in FIG. 34, where the temperature of the disk drops to ambient within 1–2 mm of the resistive heater. These results indicate that resistive heaters can be arrayed in close proximity without the activation of one of the heaters affecting either the adjacent heater or the platform component (such as a sacrificial valve) controlled by the adjacent heater.

These results demonstrate the capacity of resistive elements prepared using polymer thick films according to the teachings of this invention to be used as resistive heater elements on synthetic substrates appropriate for the production of microsystems platforms of this invention.

EXAMPLE 12

Use of Resistive Heaters with Heat-Activated Valves

Resistive heater elements prepared using resistive polymer thick films as described in Examples 10 and 11 are advantageously used to activate heat-activated valves. Heat-activated valves include valves prepared by depositing a "wax" in a channel or capillary of the fluidics structures disclosed herein.

In preparing heat-activated wax valves, a small amount of molten wax is taken up in a preheated plastic pipette sip, and when the tip is applied to a capillary channel, the channel takes up some of the molten wax by capillary action. The wax valve forms when the wax cools and solidifies in the channel or capillary. Examples of particular hydrocarbons useful in preparing wax valves include the monodisperse alkanes eicosane ($T_m$=36.8° C.), tetracosane ($T_m$=54.0° C.), and octocosane ($T_m$=64.5° C.), as well as polydisperse waxes such as paraffin ($T_m$=54.4° C.). Experiments using these different waxes showed that paraffin is preferred over the monodisperse hydrocarbons because it is easier to work. Use of temperature-controlled dispensing tips could avoid this distinction and permit monodisperse hydrocarbons to be advantageously used as wax valves. clogging either the channel or any microfluidics structure downstream from the sacrificial valve site.

EXAMPLE 14

Use of Resistive Heaters with Heat-Activated Valves: Second Alternative

The use of the resistive heater itself as a sacrificial valve was demonstrated. It was observed that certain configurations of the resistive heaters of the invention were capable of melting the platform substrate when sufficient voltages were placed across the resistive heater. In this experiment, 15V (DC) was applied across the heaters shown in FIG. 31. After less than 1 second at this voltage, a hole developed within the resistive element itself, typically at its center, having an area of about 1 mm². These results suggested that the heater could be used as a sacrificial valve. In this embodiment, a platform comprising a chamber is prepared connected to a channel that terminates at a radius R from the center of rotation. This terminal part of the channel is then bonded to a heater circuit positioned just below the channel termination point. A second fluidics disk is prepared having a channel positioned at precisely the termination point of the first channel, and is then bonded to this heater circuit so that the beginning point of this second channel is positioned just below the resistive element. After bonding the platform layers together, the resistive element will be positioned between the two channels in different layers of the platform, so that heating through the element will conjoin the two channels and permit fluid flow from one chamber to the other at a different layer of the platform.

EXAMPLE 14

Use of Resistive Heaters to Heat a Fluid

Figure 39:
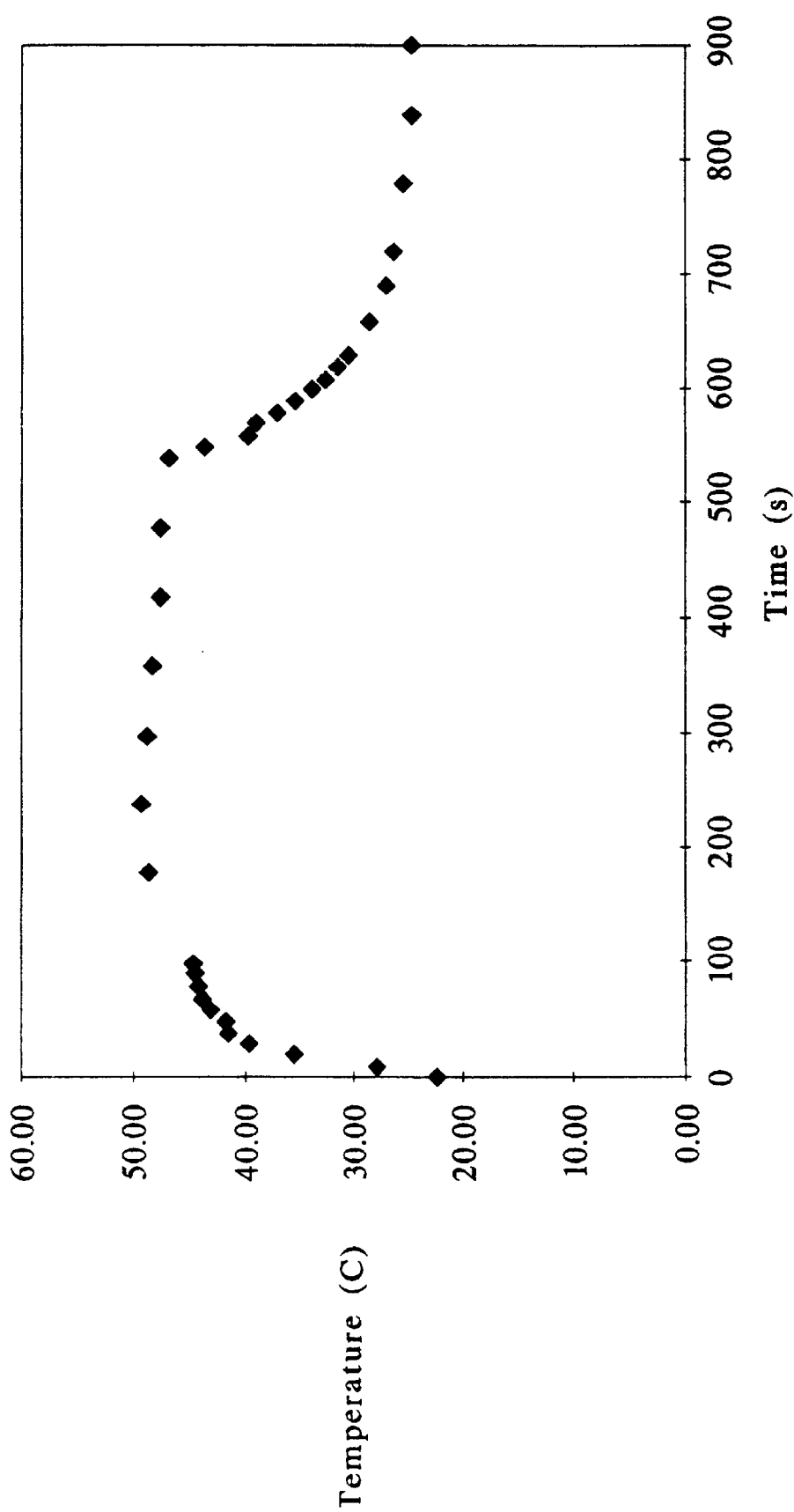
FIG. 39 is a graph showing that temperature can be cycled using a screen-printed resistive heater element as described in Example 14.

The resistive heaters of the invention are also used to heat a fluid in an incubation chamber or other microfluidics component of a platform of the invention. A DC voltage of 40V was applied between contacts 31 and 33 in a resistive heater produced as shown in FIG. 31, in which a fluid chamber containing about 65 μL of water was placed in thermal contact. A thermistor was also placed in the fluid chamber to monitor the temperature of the water, and the platform was rotated at about 500 rpm. These results are shown in FIG. 39. A steady-state temperature was obtained after about 200 seconds. After about 500 seconds, the heater was turned off while rotation of the platform continued. The results shown in FIG. 39 demonstrate that a resistive heater element of the invention was able to heat this water sample to about 50° C. and maintain this temperature for almost 10 minutes, and that convective cooling of the spinning platform reduced the temperature to melting of any of the adjacent wax valves, which are separated on the platform by about1–2 mm.

EXAMPLE 13

Use of Resistive Heaters with Heat-Activated Valves: First Alternative

In an alternative embodiment, heat-recoverable polymers were used as heat activated valves. In this experiment, heat recoverable tubing FP301H (obtained from 3M, Minneapolis, Minn.) was cut into a sheet and placed in a capillary channel on a microsystems platform of the invention. This capillary channel divided two fluid chambers, the interior-most one of which contained 25–50μL of fluid. The heat-recoverable polymer functioned as a fluid-tight valve, and no leakage of fluid was observed into the second fluid chamber. The disc was then heated to approximately 100° C. and the heat recoverable tubing was observed to shrink by approximately 50%, and liquid was observed to be transported through the channel to the second, exterior fluid chamber.

These results demonstrate that heat-recoverable polymers can be advantageously used as a sacrificial valve. A particular advantage of this type of valve when compared with a wax valve is that the polymer sheet is macroscopic object that is retained by the channel, most likely without clogging either the channel or any microfluidics structure downstream from the sacrificial valve site.

EXAMPLE 14

Use of Resistive Heaters with Heat-Activated Valves: Second Alternative

The use of the resistive heater itself as a sacrificial valve was demonstrated. It was observed that certain configurations of the resistive heaters of the invention were capable of melting the platform substrate when sufficient voltages were placed across the resistive heater. In this experiment, 15V (DC) was applied across the heaters shown in FIG. 31. After less than 1 second at this voltage, a hole developed within the resistive element itself, typically at its center, having an area of about 1 mm². These results suggested that the heater could be used as a sacrificial valve. In this embodiment, a platform comprising a chamber is prepared connected to a channel that terminates at a radius R from the center of rotation. This terminal part of the channel is then bonded to a heater circuit positioned just below the channel termination point. A second fluidics disk is prepared having a channel positioned at precisely the termination point of the first channel, and is then bonded to this heater circuit so that the beginning point of this second channel is positioned just below the resistive element. After bonding the platform layers together, the resistive element will be positioned between the two channels in different layers of the platform, so that heating through the element will conjoin the two channels and permit fluid flow from one chamber to the other at a different layer of the platform.

EXAMPLE 14

Use of Resistive Heaters to Heat a Fluid

The resistive heaters of the invention are also used to heat a fluid in an incubation chamber or other microfluidics component of a platform of the invention. A DC voltage of 40V was applied between contacts 31 and 33 in a resistive heater produced as shown in FIG. 31, in which a fluid chamber containing about 65 µL of water was placed in thermal contact. A thermistor was also placed in the fluid chamber to monitor the temperature of the water, and the platform was rotated at about 500 rpm. These results are shown in FIG. 39. A steady-state temperature was obtained after about 200 seconds. After about 500 seconds, the heater was turned off while rotation of the platform continued. The results shown in FIG. 39 demonstrate that a resistive heater element of the invention was able to heat this water sample to about 50° C. and maintain this temperature for almost 10 minutes, and that convective cooling of the spinning platform reduced the temperature to ambient within 1–2 minutes of the resistive heater shut-off.

This experiment also demonstrated that temperature can be rapidly cycled in a rotating platform by sequential activation of a resistive heater element.

EXAMPLE 14

Use of Resistive Heaters as Thermosensors

Because screen-printed PTC inks display a larger change in resistance with temperature than other inks, these inks can be used to measure temperature on a screen-printed circuit.

In this embodiment, the temperature-sensing device is screen-printed identically as a resistive heater element; however, rather than applying a voltage across the element to produce heat, the resistance of the element is sampled to determine whether resistance has increase as a result of heating. In one application, the resistive heater element itself could be used both as a heater and a temperature sensing device. In this use, the heater circuit is coupled to an external circuit that is switched between constant voltage and constant (small) current modes. In the constant voltage mode the element would heat up, and in the constant current mode the voltage drop would be measured and the temperature determined thereby.

In another application, a PTC ink is screen-printed over a portion to a resistive heater element. The resistive heater and PTC ink/thermosensor elements are joined to external circuitry using different sets of conductive leads; the external circuit delivers voltage to the resistive heater element and a small constant current to the thermosensor element. By measuring the voltage drop in the PTC ink element, the temperature of the resistive element is inferred. Coordination of these two circuits could be provided so that the thermosensor is used to regulate the temperature of the resistive heating element.

It should be understood that the foregoing disclosure emphasizes certain specific embodiments of the invention and that all modifications or alternatives equivalent thereto are within the spirit and scope of the invention.

We claim:

1. A microsystem platform, comprising a substrate having a first flat, planar surface and a second flat, planar surface opposite thereto, wherein the first surface comprises a multiplicity of microfluidics components embedded in said first surface and in fluidic contact, and a resistive heater element comprising in combination:

a) an electrically inert substrate capable of being screen printed with a conductive ink and a resistive ink;
   b) a conductive ink screen-printed in a pattern;
   c) a resistive ink screen-printed in a pattern over the conductive ink pattern wherein the resistive ink in electrical contact with the conductive ink and wherein an electrical potential applied across the conductive ink causes current to flow across the resistive ink wherein the resistive ink produces heat, wherein the resistive heater element is in thermal contact with at least one of the multiplicity of microfluidics components.

2. The microsystems platform of claim 1, wherein the conductive ink of the resistive heater element is a silver conductive ink selected from the group consisting of Dupont 5028, Dupont 5025, Acheson 423SS, Acheson 426SS and Acheson SS24890.

3. The microsystems platform of claim 1, wherein the resistive ink of the resistive heater element is selected from the group consisting of Dupont 7082, Dupont 7102, Dupont 7271, Dupont 7278 and Dupont 7285.

4. The microsystems platform of claim 1, wherein the resistive ink of the resistive heater element is a PTC ink.

5. A microsystems platform according to claim 1 wherein the resistive heater element further comprises d) a dielectric ink screen-printed over the resistive ink pattern and conductive ink pattern.

6. A microsystems platform according to claim 1, wherein one of the multiplicity of microfluidics components is a microchannel.

7. The microsystems platform of claim 6, wherein the microchannel further comprises a wax valve.

8. The microsystems platform of claim 7, wherein the resistive heater element is in thermal contact with the wax valve.

* * * * *